(12) United States Patent  
Weiss et al.

(10) Patent No.: US 10,472,356 B2  
(45) Date of Patent: Nov. 12, 2019

(54) BICYCLIC KETONE SULFONAMIDE COMPOUNDS

(71) Applicant: AMGEN INC., Thousand Oaks, CA (US)

(72) Inventors: Matthew Weiss, Boston, MA (US); Benjamin Charles Milgram, Cambridge, MA (US); Thomas Dineen, Somerville, MA (US); John Stellwagen, Beverly, MA (US); Angel Guzman-Perez, Belmont, MA (US); Alessandro Boezio, Somerville, MA (US); Issac E. Marx, Arlington, MA (US)

(73) Assignee: AMGEN INC., Thousand Oaks, CA (US)

( * ) Notice: Subject to any disclaimer, the term of this patent is extended or adjusted under 35 U.S.C. 154(b) by 84 days.

(21) Appl. No.: 15/554,801

(22) PCT Filed: Mar. 2, 2016

(86) PCT No.: PCT/US2016/020403  
§ 371 (c)(1),  
(2) Date: Aug. 31, 2017

(87) PCT Pub. No.: WO2016/141035  
PCT Pub. Date: Sep. 9, 2016

(65) Prior Publication Data  
US 2018/0051021 A1 Feb. 22, 2018

Related U.S. Application Data

(60) Provisional application No. 62/127,206, filed on Mar. 2, 2015.

(51) Int. Cl.  
*A61K 31/4375* (2006.01)  
*C07D 471/04* (2006.01)

(52) U.S. Cl.  
CPC .................. *C07D 471/04* (2013.01)

(58) Field of Classification Search  
CPC .......................... C07D 471/04; A61K 31/4375  
(Continued)

(56) References Cited

U.S. PATENT DOCUMENTS 5,077,429 A * 12/1991 Grohe ................. C07D 215/56  
544/128

FOREIGN PATENT DOCUMENTS

| WO | 2013/122897 A1 | 8/2013 |
| WO | 2013/134518 A1 | 9/2013 |
| WO | 2014/201206 A1 | 12/2014 |

OTHER PUBLICATIONS

S. M. Berge et al., Pharmaceutical Salts, J. Pharm Sci., vol. 66, No. 1, Jan. 1977.

(Continued)

*Primary Examiner* — Niloofar Rahmani  
(74) *Attorney, Agent, or Firm* — Elsa D. Lemoine

(57) ABSTRACT

The present invention provides compounds of Formula (I),

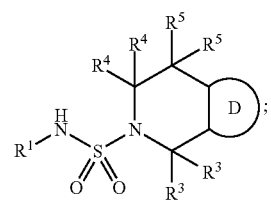

wherein:

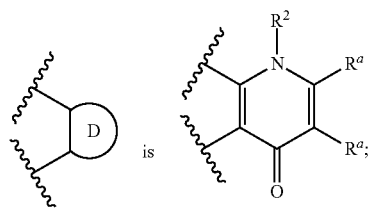

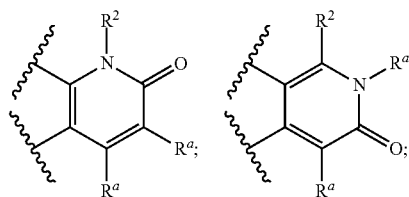

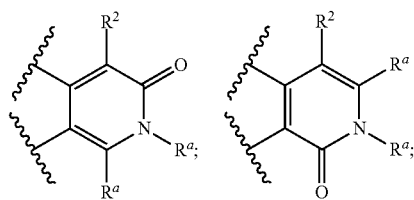

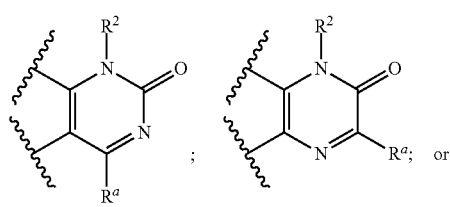

(Continued)

-continued

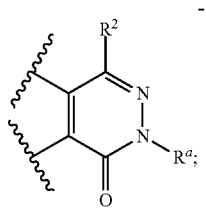

as defined in the specification, an enantiomer, diastereomer, atropisomer thereof, or a mixture thereof, or pharmaceutically acceptable salts thereof, that are inhibitors of voltage-gated sodium channels, in particular Nav 1.7. The compounds are useful for the treatment of diseases treatable by inhibition of sodium channels such as pain disorders, cough, or itch. Also provided are pharmaceutical compositions containing compounds of the present invention.

17 Claims, No Drawings

(58) Field of Classification Search
USPC .......................................................... 546/122
See application file for complete search history.

(56) References Cited

OTHER PUBLICATIONS

Chaplan, et al., Quantitative assessment of tactile allodynia in the rat paw, Journal of Neuroscience Methods, 53, 55-63, 1994.
Chung and Kim, Segmental Spinal Nerve Ligation Model of Neuropathic Pain, Methods in Molecular Medicine, vol. 99, 35-45, 1992.
Cox J.J., Reimann F, Nicholas A. K., et al. "An SCN9A channelopathy causes congenital inability to experience pain," Nature, vol. 444:894-898, 2006.
Dib-Hajj, et. al., The $Na_v1.7$ sodium channel: from molecule to man, Nature Reviews Neuroscience, 14, 49-62, 2013.
Dib-Hajj, et al., NaN, a novel voltage-gated Na channel, is expressed preferentially in peripheral sensory neurons and down-regulated after axotomy, Proc. Natl. Acad. Sci. USA, 95(15):8963-8968, 1998.
Do and Bean, Subthreshold Sodium Currents and Pacemaking of Subthalamic Neurons: Modulation by Slow Inactivation, Neuron 39 :109-120, 2003.
Drenth J. P. H., Morsche R. H. M., Guillet G., Taieb A., et al., "SCN9A mutations define primary erythermalgia as a neuropathic disorder of voltage gated sodium channels," J Invest Dermatol 124:1333-1338, 2005.
Ettinger and Argoff, Use of antiepileptic drugs for nonepileptic conditions: psychiatric disorders and chronic pain, Neurotherapeutics, 4:75-83, 2007.
Fertleman C. R., Baker M. D., Parker K. A., Moffatt S., et al., "SCN9A mutations in paroxysmal extreme pain disorder: allelic variants underlie distinct channel defects and phenotypes," Neuron 52:767-774, 2006.
Gillet L., et. al., Voltage-Gated sodium channel activity promotes cysteine cathepsin-dependent invasiveness and colony growth of human cancer cells, J Biol Chem, (epub) 2009.

Goldberg Y. P., MacFarlane J., MacDonald M. L., Thompson J., et al. "Loss-of-function mutations in the Nav1.7 gene underlie congenital indifference to pain in multiple human populations," Clin Genet vol. 71, Issue 4, pp. 311-319, 2007.
Goldin, A. L, "Resurgence of sodium channel research," Ann Rev Physiol 63:871-894, 2001.
Gonzalez, Termin, Wilson, Small Molecule Blockers of Voltage-gated Sodium Channels, Methods and Principles in Medicinal Chemistry, 29:168-192, 2006.
Hains, B.D., et al., Upregulation of Sodium Channel Nav1.3 and Functional Involvement in Neuronal Hyperexcitability Associated with Central Neuropathic Pain after Spinal Cord Injury, J. Neuroscience, 23(26): 8881-8892, 2003.
Bethany Halford, Changing the Channel, Cen. ACS. Org., 2014.
Hamann M, Meisler MH, Richter A., Motor disturbances in mice with deficiency of the sodium channel gene Scn8a show features of human dystonia, Exp Neurol 23, 184: 830-838, 2003.
Haufe V., et. al., The promiscuous nature of the cardiac sodium current, J Mol. Cell Cardiol. 42(3):469-477, 2007.
T. Higuchi; V. Stella; ACS Symposium Series, vol. 14, Pro-drugs as Novel Delivery Systems, 1975.
Hille B, Ion Channels of Excitable Membranes, Sinauer Associates, Inc.: Sunderland MA, $3^{rd}$ Ed. 2001.
Johannessen L. C., Antiepileptic drugs in non-epilepsy disorders: relations between mechanisms of action and clinical efficacy, CNS Drugs 22(1)27-47, 2008.
Kim D. Y., et. al., BACE1 regulates voltage gated sodium channels and neuronal activity, Nat. Cell. Biol. 9 (7):755-764, 2007.
Liu, H., et al., Mutations in Cardiac Sodium Channels, Am. J. Pharmacogenomics, 3(3): 173-179, 2003.
McKinney B. C, et. al., Exaggerated emotional behavior in mice heterozygous for the sodium channel Scn8a (Nav1.6), Genes Brain Behav., 7(6):629-638, 2008.
Morinville et al., Distribution of the voltage—gated sodium channel $Na_v$ 1.7 in the rat: Expression in the autonomic and endocrine systems, J Comp Neurol., 504:680-689, 2007.
Puopolo et al., Roles of Subthreshold Calcium Current and Sodium Current in Spontaneous Firing of Mouse Midbrain Dopamine Neurons, J. Neurosci. 27 :645-656, 2007.
Raymond, C.K., et al., Expression of Alternatively Spliced Sodium Channel—Subunit Genes: J. Biol.Chem, 279 (44):46234-46241, 2004.
Roche, Edward B. Bioreversible Carriers in Drug Design: Theory and Applications. Pergamon Press, 1987.
Tamaoka A., Paramyotonia congenita and skeletal sodium channelopathy, Internal Medicine, vol. 42, No. 9:769-770, 2003.
Waxman, Axonal conduction and injury in multiple sclerosis: the role of sodium channels, Nature Neurosci. 7 :932-941, 2006.
Wood, J. N. and Boorman, J. Voltage-gated sodium channel blockers; target validation and therapeutic potential, Curr. Top Med. Chem. 5:529-537, 2005.
Woodruff-Pak D. S., et. al., Inactivation of sodium channel Scn8A ($Na_v$ 1.6) in purkinje neurons impairs learning in Morris Water Maze and delay but not trace eyeblink classical conditioning, Behav. Neurosci. 120(2):229-240, 2006.
Yang Y., Wang Y., Li S, et al., Mutations in SCN9A, encoding a sodium channel alpha subunit, in patients with primary erythermalgia, J. Med. Genet. 41:171-174, 2004.
Yu, F.H., et al., Reduced sodium current in GABAergic interneurons in a mouse model of severe myoclonic epilepsy in infancy, Nat. Neuroscience, 9 (9) 1142-1149, 2006.

* cited by examiner

BICYCLIC KETONE SULFONAMIDE COMPOUNDS

CROSS REFERENCES TO RELATED APPLICATIONS

This application is a National Stage Application under 35 U.S.C. § 371 of International Application No. PCT/US2016/020403, having an international filing date of Mar. 2, 2016, which is claiming priority from U.S. Provisional Application No. 62/127,206, having a filing date of Mar. 2, 2015.

FIELD OF THE INVENTION

The present invention provides compounds that are inhibitors of voltage-gated sodium channels (Nav), in particular Nav 1.7, and are useful for the treatment of diseases treatable by inhibition of sodium channels such as pain disorders. Also provided are pharmaceutical compositions containing compounds of the present invention.

BACKGROUND OF THE INVENTION

A 2011 report of the institute of medicine estimates that 100 million adults in the US, roughly 30% of the population, suffer from chronic pain (*C & E News*, Bethany Halford, "Changing the Channel", published 3-24). Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingular cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland Mass., 3$^{rd}$ Ed. 2001). There are nine different isoforms of voltage-gated sodium channel (Nav 1.1-Nav 1.9), and they have distinct expression patterns in tissues including neurons and cardiac and skeletal muscle (Goldin, A. L, "Resurgence of sodium channel research," *Ann Rev Physiol* 63:871-894, 2001; Wood, J. N. and, Boorman, J. "Voltage-gated sodium channel blockers; target validation and therapeutic potential" *Curr. Top Med. Chem.* 5:529-537, 2005).

Nav1.1 and Nav1.2 are highly expressed in the brain (Raymond, C. K., et al., J. Biol. Chem. (2004) 279 (44): 46234-41) and are vital to normal brain function. Some loss of function due to Nav 1.1 mutations in humans, have resulted in epilepsy, presumably as these channels are expressed in inhibitory neurons (Yu, F. H., et al., Nat. Neuroscience (2006), 9 (9) 1142-1149). Navy 1.1 is also expressed in the peripheral nervous system and inhibition of Nav1.1 in the periphery may provide relief of pain. Hence, while inhibiting Nav 1.1 may provide use for treating pain, it may also be undesirable possibly leading to anxiety and over excitability. Nav1.3 is expressed primarily in the fetal central nervous system, and expression was found to be upregulated after nerve injury in rats (Hains, B. D., et al., J. Neuroscience (2030) 23(26):8881-8892). Nav1.4 is expressed primarily in skeletal muscle. Mutations of the gene and its' product have significant impact on muscle function, including paralysis (Tamaoka A., Internal Medicine (2003), (9):769-770). Nav1.5 is expressed mainly in cardiac myocytes, including atria, ventricles, the sino-atrial node, atrio-ventircular node and cardiac Purkinje fibers. The rapid upstroke of the cardiac action potential and the rapid impulse conduction through cardiac tissue is due to the opening of the Nav1.5 channel. Mutations of the Nav1.5 channel have resulted in arrhythmic syndromes, including QTc prolongation, Brugada syndrome (BS), sudden unexpected nocturnal death syndrome (SUNDS) and sudden infant death syndrome (SIDS) (Liu, H., et al., Am. J. Pharmacogenomics (2003), 3(3):173-179). Nav1.6 is widely distributed voltage-gated sodium channel expressed throughout the central and peripheral nervous system. Nav1.8 is expressed primarily in sensory ganglia of the peripheral nervous system, such as the dorsal root ganglia. There are no identified Nav1.8 mutations that produce varied pain responses in humans. Nav1.8 differs from most neuronal Nav isotypes in that it is insensitive to inhibition by tetrodotoxin. Nav1.9, similar to Nav1.8, is also a tetrodotoxin insensitive sodium channels expressed primarily in dorsal root ganglia neurons (Dib-Hajj, S. D., et al., Proc. Natl. Acad. Sci. USA (1998), 95(15):8963-8968).

Recent evidence from several independent genetic studies has shown that the tetrodotoxin-sensitive voltage-gated sodium ion channel Nav 1.7 (SCN9A) is required to sense pain. Rare genetic forms of severe chronic pain, Primary Erythromelalgia and Paroxysmal Extreme Pain Disorder, result from mutations that increase the activity of Nav 1.7 (Fertleman C. R., Baker M. D., Parker K. A., Moffatt S., et al., "SCN9A mutations in paroxysmal extreme pain disorder: allelic variants underlie distinct channel defects and phenotypes," *Neuron* 52:767-774, 2006; Yang Y., Wang Y., Li S, et al., "Mutations in SCN9A, encoding a sodium channel alpha subunit, in patients with primary erythermalgia," J. Med. Genet. 41:171-174, 2004; Drenth J. P. H., te Morsche R. H. M., Guillet G., Taieb A., et al., "SCN9A mutations define primary erythermalgia as a neuropathic disorder of voltage gated sodium channels," *J Invest Dermatol* 124:1333-1338). Conversely, two separate clinical studies have determined that the root cause of the genetic disorder Congenital Indifference to Pain (CIP) is a loss of function of Nav 1.7 via mutations that truncate the protein and destroy function (Cox J. J., Reimann F, Nicholas A. K., et al. "An SCN9A channelopathy causes congenital inability to experience pain," *Nature* 444:894-898, 2006; Goldberg Y. P., MacFarlane J., MacDonald M. L., Thompson J., et al. "Loss-of-function mutations in the Nav1.7 gene underlie congenital indifference to pain in multiple human populations," *Clin Genet* 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick or tendon pressure. Yet sensory, motor, autonomic, and other measured functions are normal, with the only reported abnormality being anosmia (inability to smell). These studies indicate that among the many possible targets in the pain pathway, Nav 1.7 governs one or more control points critical for pain perception.

Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway. Lidocaine is a local anesthetic doctors use for minor surgery. So is the dentists office staple novocaine. But these compounds don't distinguish between the various sodium channel subtypes, making them unsuitable for use as systemic pain killers. "If you give a drug that blocks Nav1.7 but also blocks Nav1.5, the patient will die of heart failure," says Glenn F. King, a professor at Australia's University of Queensland who studies venoms that block ion channels. "It will be a completely painless death, but the patient will die none the less." Thus, selectivity for Nav1.7 is desired, particularly over Nav1.5. Researchers have tailored their efforts to find a molecule that inhibitors or block the activity of only Nav1.7. To compound this problem, the identity, every location, every function and/or the tertiary structures of each subtype of voltage gated sodium channel proteins are not known or completely understood.

Consequently, a number of researchers are attempting to identify small molecule inhibitors of Nav1.7. For example, Chafeev et al disclose spiro-oxindole compound for the treatment and/or prevention of sodium channel-mediated diseases, such as pain, in U.S. Pat. No. 8,101,647. International Publications WO 2013/134518 and WO 2014/201206 disclose sulfonamide derivatives which are different from the sulfonamide derivatives of the present invention. Thus, there is a need to identify Nav1.7 inhibitors selective over at least Nav1.5 to treat pain. The present invention provides compounds that are selective inhibitors of Nav 1.7. over at least Nav1.5.

SUMMARY OF THE INVENTION

In embodiment 1, the present invention provides a compound of Formula (I), an enantiomer, diastereoisomer, atropisomer thereof, or a mixture thereof, or a pharmaceutically acceptable salt thereof,

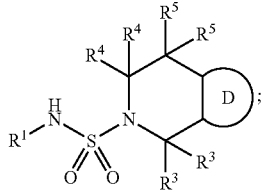

I

Wherein the group:

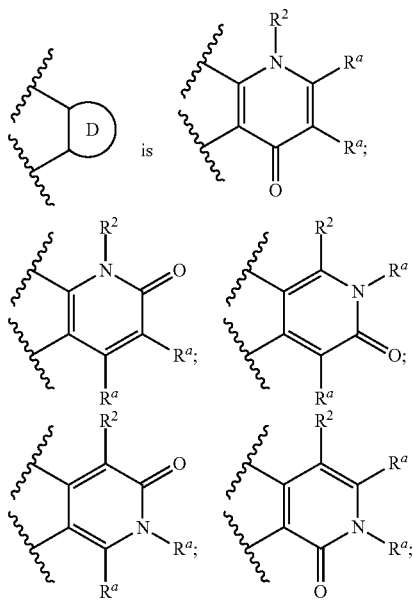

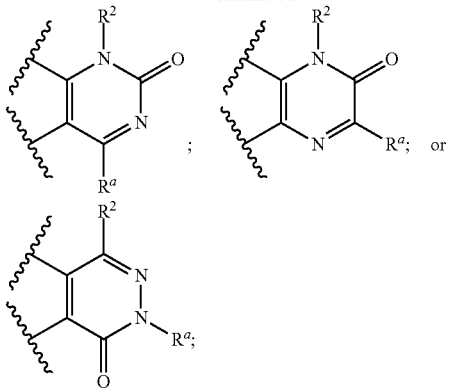

$R^1$ is a 5-, 6-, 7-, 8-, 9-, or 10-membered aryl or heteroaryl, or a 3-, 4-, 5-, 6-, 7-, 8-, 9-, or 10-membered cycloalkyl or heterocycloalkyl group, wherein the heteroaryl or heterocycloalkyl group can have from 1 to 3 heteroatoms independently selected from O, N or S, or a carbon atom in the cycloalkyl or heterocycloalkyl group can be part of a $C=O$ group, and the aryl, heteroaryl, cycloalkyl, or heterocycloalkyl group is substituted with 0, 1, 2, 3, or 4 substituents independently selected from halo, —CN, —$C_{1-6}$alkyl, halo$C_{1-6}$alkyl, —OH, —O—$C_{1-6}$alkyl, —O-halo$C_{1-6}$alkyl, —C(=O)O$R^a$, or —(C$R^bR^b$)$_n$N$R^aR^a$;

$R^2$ is $C_{1-6}$alkyl, or a 5-, 6-, 7-, 8-, 9-, or 10-membered aryl or heteroaryl, or a 3-, 4-, 5-, 6-, 7-, 8-, 9-, or 10-membered cycloalkyl or heterocycloalkyl group, where the heteroaryl or heterocycloalkyl group can have from 1 to 3 heteroatoms independently selected from O, N or S, or a carbon atom in the cycloalkyl or heterocycloalkyl group can be part of a $C=O$ group, and the alkyl, aryl, heteroaryl, cycloalkyl or heterocycloalkyl group is substituted with from 1 to 5 $R^6$ substituents independently selected from halo, —CN, —$C_{1-6}$alkyl, halo$C_{1-6}$alkyl, —OH, —O—$C_{1-6}$alkyl, —O-halo$C_{1-6}$alkyl, —(C$R^bR^b$)$_m$A, —$C_{2-6}$alkenyl-A, —$C_{2-6}$alkynyl-A, or —O(C$R^bR^b$)-A;

$R^3$ is independently selected from H, —$C_{1-6}$alkyl, halo-$C_{1-6}$alkyl, or halo;

$R^4$ is independently selected from H, —$C_{1-6}$alkyl, halo-$C_{1-6}$alkyl, or halo;

$R^5$ is independently selected from H, —$C_{1-6}$alkyl, halo-$C_{1-6}$alkyl, or halo;

A is a 4 to 9 membered aryl, heteroaryl, or heterocycloalkyl group, or a 3-, 4-, 5-, 6-, 7-, 8-, 9-, or 10-membered cycloalkyl group, where the heteroaryl or heterocycloalkyl group can have from 1 to 3 heteroatoms independently selected from O, N or S; and the aryl, heteroaryl, heterocycloalkyl, or cycloalkyl group is substituted with 0, 1, 2, 3, or 4 $R^7$ substituents independently selected from halo, —N$R^aR^a$, —$C_{1-6}$alkyl, —O$C_{1-6}$alkyl, —(C$R^bR^b$)$_m$OH, hydroxy$C_{1-6}$alkyl, —CF$_3$, —CHF$_2$, —CH$_2$F, —OCF$_3$, —OCHF$_2$, —OCH$_2$F, —CN, —C(=O)N$R^aR^a$, —O—(C$R^bR^b$)$_m$B or —(C$R^bR^b$)$_m$B;

B is a 5 to 6 membered aryl, heteroaryl, or heterocycloalkyl group, or a 3 to 5 membered cycloalkyl group, where the heteroaryl or heterocycloalkyl group can have from 1 to 3 heteroatoms independently selected from O, N or S; and the aryl, heteroaryl, cycloalkyl or heterocycloalkyl group is substituted with 0, 1, 2, 3, or 4 $R^8$ substituents independently selected from halo, —N$R^aR^a$, —$C_{1-6}$alkyl, —O$C_{1-6}$alkyl, hydroxy$C_{1-6}$alkyl, —CF$_3$, —CHF$_2$, —CH$_2$F, —OCF$_3$, —OCHF$_2$, —OCH$_2$F, —CN or —C(=O)N$R^aR^a$;

each $R^a$ is independently H, halo, —CN, —NR$^c$R$^c$, —OH, —C$_{1-6}$alkyl, —C$_{1-6}$haloalkyl, —OC$_{1-6}$haloalkyl, or —OC$_{1-6}$alkyl;

each $R^b$ is independently H, halo, —CN, —NR$^c$R$^c$, —OH, —C$_{1-6}$alkyl, —C$_{1-6}$haloalkyl, —OC$_{1-6}$haloalkyl, or —OC$_{1-6}$alkyl;

each $R^c$ is independently H or —C$_{1-6}$alkyl;

each n is independently 0, 1, 2, 3 or 4; and each m is independently 0, 1, 2, 3 or 4.

In embodiment 1a, the present invention provides compounds of Formula (I)-a, an enantiomer, diastereoisomer, atropisomer thereof, or a mixture thereof, or a pharmaceutically acceptable salt thereof, wherein

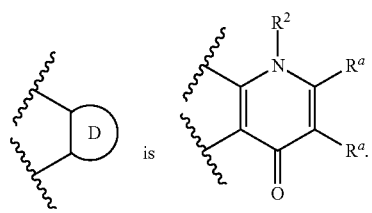

(I-a)

In embodiment 1b, the present invention provides compounds of Formula (I)-b, an enantiomer, diastereoisomer, atropisomer thereof, or a mixture thereof, or a pharmaceutically acceptable salt thereof, wherein

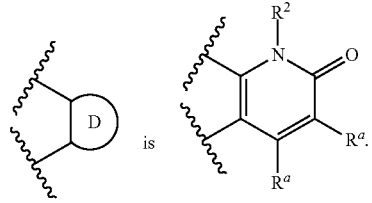

(I-b)

In embodiment 1c, the present invention provides compounds of Formula (I)-c, an enantiomer, diastereoisomer, atropisomer thereof, or a mixture thereof, or a pharmaceutically acceptable salt thereof, wherein

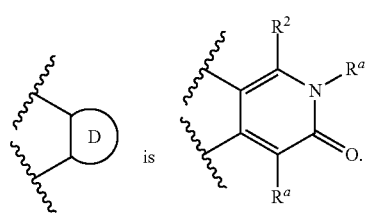

(I-c)

In embodiment 1d, the present invention provides compounds of Formula (I)-d, an enantiomer, diastereoisomer, atropisomer thereof, or a mixture thereof, or a pharmaceutically acceptable salt thereof, wherein

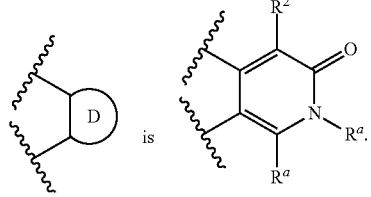

(I-d)

In embodiment 1e, the present invention provides compounds of Formula (I)-e, an enantiomer, diastereoisomer, atropisomer thereof, or a mixture thereof, or a pharmaceutically acceptable salt thereof, wherein

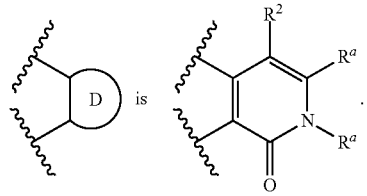

(I-e)

In embodiment 1f, the present invention provides compounds of Formula (I)-f, an enantiomer, diastereoisomer, atropisomer thereof, or a mixture thereof, or a pharmaceutically acceptable salt thereof, wherein

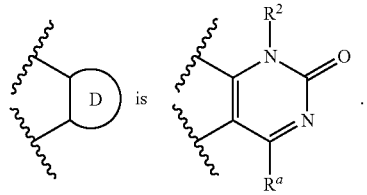

(I-f)

In embodiment 1g, the present invention provides compounds of Formula (I)-g, an enantiomer, diastereoisomer, atropisomer thereof, or a mixture thereof, or a pharmaceutically acceptable salt thereof, wherein

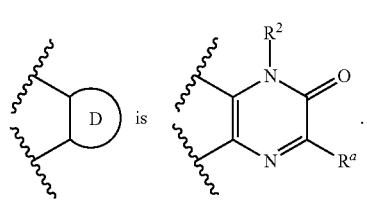

(I-g)

In embodiment 1h, the present invention provides compounds of Formula (I)-h, an enantiomer or diastereoisomer thereof, or a mixture thereof, or a pharmaceutically acceptable salt thereof, wherein

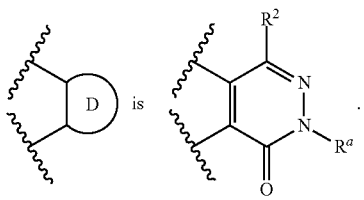 (I-h)

In embodiment 1i, the present invention provides a compound of Formula (I), an enantiomer, diastereoisomer, atropisomer thereof, or a mixture thereof, or a pharmaceutically acceptable salt thereof:

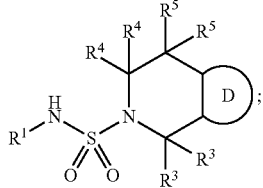 I

Wherein the group:

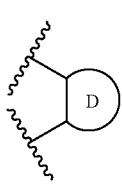 is 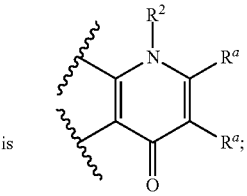

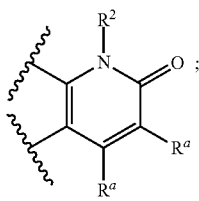 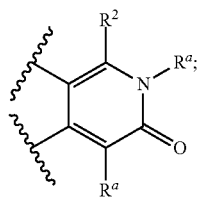

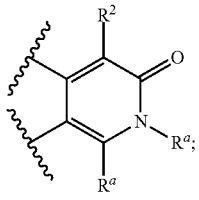 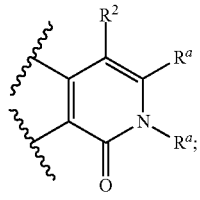

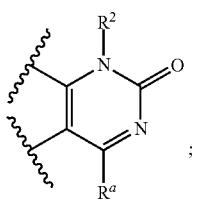 ; 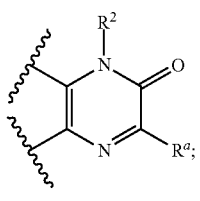 or

-continued

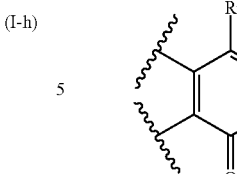

$R^1$ is a 5-, 6-, 7-, 8-, 9-, or 10-membered aryl or heteroaryl, or a 3-, 4-, 5-, 6-, 7-, 8-, 9-, or 10-membered cycloalkyl or heterocycloalkyl group, wherein the heteroaryl or heterocycloalkyl group can have from 1 to 3 heteroatoms independently selected from O, N or S, or a carbon atom in the cycloalkyl or heterocycloalkyl group can be part of a C=O group, and the aryl, heteroaryl, cycloalkyl, or heterocycloalkyl group is substituted with 0, 1, 2, 3, or 4 substituents independently selected from halo, —CN, —$C_{1-6}$alkyl, halo$C_{1-6}$alkyl, —OH, —O—$C_{1-6}$alkyl, —O-halo$C_{1-6}$alkyl, —C(=O)OR$^a$, or —(CR$^b$R$^b$)$_n$NR$^a$R$^a$;

$R^2$ is $C_{1-6}$alkyl, or a 5-, 6-, 7-, 8-, 9-, or 10-membered aryl or heteroaryl, or a 3-, 4-, 5-, 6-, 7-, 8-, 9-, or 10-membered cycloalkyl or heterocycloalkyl group, where the heteroaryl or heterocycloalkyl group can have from 1 to 3 heteroatoms independently selected from O, N or S, or a carbon atom in the cycloalkyl or heterocycloalkyl group can be part of a C=O group, and the alkyl, aryl, heteroaryl, cycloalkyl or heterocycloalkyl group is optionally substituted with from 1 to 5 $R^6$ substituents independently selected from halo, —CN, —$C_{1-6}$alkyl, halo$C_{1-6}$alkyl, —OH, —O—$C_{1-6}$alkyl, —O-halo$C_{1-6}$alkyl, —(CR$^b$R$^b$)$_m$A, —$C_{2-6}$alkenyl-A, —$C_{2-6}$alkynyl-A, or —O(CR$^b$R$^b$)$_m$-A;

Each of $R^3$, $R^4$, and $R^5$ is independently selected from H, —$C_{1-6}$alkyl, halo$C_{1-6}$alkyl, or halo;

A is a 4 to 9 membered aryl, heteroaryl, or heterocycloalkyl group, or a 3-, 4-, 5-, 6-, 7-, 8-, 9-, or 10-membered cycloalkyl group, where the heteroaryl or heterocycloalkyl group can have from 1 to 3 heteroatoms independently selected from O, N or S; and the aryl, heteroaryl, heterocycloalkyl, or cycloalkyl group is substituted with 0, 1, 2, 3, or 4 $R^7$ substituents independently selected from halo, —NR$^a$R$^a$, —$C_{1-6}$alkyl, —O—$C_{1-6}$alkyl, —(CR$^b$R$^b$)$_m$OH, hydroxy$C_{1-6}$alkyl, halo$C_{1-6}$alkyl, —O-halo$C_{1-6}$alkyl, —CN, —C(=O)NR$^a$R$^a$, —O—(CR$^b$R$^b$)$_m$B or —(CR$^b$R$^b$)$_m$B;

B is a 5 to 6 membered aryl, heteroaryl, or heterocycloalkyl group, or a 3 to 5 membered cycloalkyl group, where the heteroaryl or heterocycloalkyl group can have from 1 to 3 heteroatoms independently selected from O, N or S; and the aryl, heteroaryl, cycloalkyl or heterocycloalkyl group is substituted with 0, 1, 2, 3, or 4 $R^8$ substituents independently selected from halo, —NR$^a$R$^a$, —$C_{1-6}$alkyl, —O$C_{1-6}$alkyl, hydroxy$C_{1-6}$alkyl, —CF$_3$, —CHF$_2$, —CH$_2$F, —OCF$_3$, —OCHF$_2$, —OCH$_2$F, —CN or —C(=O)NR$^a$R$^a$;

each R$^a$ and R$^b$ is independently H, halo, —CN, —NR$^c$R$^c$, —OH, —$C_{1-6}$alkyl, —$C_{1-6}$haloalkyl, —O$C_{1-6}$haloalkyl, or —O$C_{1-6}$alkyl;

each R$^c$ is independently H or —$C_{1-6}$alkyl;

each n is independently 0, 1, 2, 3 or 4; and each m is independently 0, 1, 2, 3 or 4.

In embodiment 2, the present invention provides compounds in accordance with any one of embodiments 1, 1a-1i, an enantiomer, diastereoisomer, atropisomer thereof, or a mixture thereof, or pharmaceutically acceptable salts thereof, wherein each $R^2$ is a 6 membered aryl or 6 membered heteroaryl group.

In embodiment 2a, the present invention provides compounds in accordance with any one of embodiments 1, 1a-1i, an enantiomer, diastereoisomer, atropisomer thereof, or a mixture thereof, or pharmaceutically acceptable salts thereof, wherein each $R^2$ is phenyl.

In embodiment 2b, the present invention provides compounds in accordance with any one of embodiments 1, 1a-1i, an enantiomer, diastereoisomer, atropisomer thereof, or a mixture thereof, or pharmaceutically acceptable salts thereof, wherein each $R^2$ is pyridinyl.

In embodiment 3, the present invention provides compounds in accordance with any one of embodiments 1, 1a-1i, 2, 2a-2b, an enantiomer, diastereoisomer, atropisomer thereof, or a mixture thereof, or pharmaceutically acceptable salts thereof, wherein each $R^2$ is substituted with from 1 to 3 $R^6$ substituents independently selected from —$OC_{1-6}$alkyl, halo, —$C_{1-6}$alkyl, halo$C_{1-6}$alkyl, —$(CR^bR^b)_m$-A, or —$C_{2-6}$alkynyl-A.

In embodiment 3a, the present invention provides compounds in accordance with embodiment 3, an enantiomer, diastereoisomer, atropisomer thereof, or a mixture thereof, or pharmaceutically acceptable salts thereof, wherein in said $R^6$—$(CR^bR^b)_m$-A group, A is a ring selected from phenyl, pyridyl, or pyrimidinyl, wherein the ring is substituted with 0, 1, 2, 3, or 4 $R^7$ substituents independently selected from chloro, fluoro, methyl, methoxy, —$CF_3$, —$CHF_2$, —$CH_2F$, —$OCF_3$, —$OCHF_2$, —$OCH_2F$, or —CN; each $R^b$ is independently H or —$C_{1-6}$alkyl; and m is 0 or 1.

In embodiment 3b, the present invention provides compounds in accordance with embodiment 3, an enantiomer, diastereoisomer, atropisomer thereof, or a mixture thereof, or pharmaceutically acceptable salts thereof, wherein in said $R^6$—$C_{2-6}$alkynyl-A group, A is a $C_{3-8}$cycloalkyl ring, such as cyclopentyl or cyclohexyl ring, substituted with 0, 1, 2, 3, or 4 $R^7$ substituents selected from chloro, fluoro, methyl, methoxy, —$CF_3$, —$CHF_2$, —$CH_2F$, —$OCF_3$, —$OCHF_2$, —$OCH_2F$, or —CN.

In embodiment 3c, the present invention provides compounds in accordance with embodiment 3, an enantiomer, diastereomer, atropisomer thereof, or a mixture thereof, or a pharmaceutically acceptable salt thereof, wherein in said $R^6$—$(CR^bR^b)_m$-A group, A is a ring selected from phenyl, pyridyl, or pyrimidinyl, wherein the ring is substituted with 0, 1, 2, 3, or 4 $R^7$ substituents independently selected from chloro, fluoro, methyl, methoxy, —$CF_3$, —$CHF_2$, —$CH_2F$, —$OCF_3$, —$OCHF_2$, —$OCH_2F$, —$OCH_2CF_3$, or —CN; each $R^b$ is independently H or —$C_{1-6}$alkyl; and m is 0 or 1.

In embodiment 4, the present invention provides compounds in accordance with any one of embodiments 1, 1a-1i, 2, 2a-2b, 3, 3a-3c, an enantiomer, diastereoisomer, atropisomer thereof, or a mixture thereof, or pharmaceutically acceptable salts thereof, wherein $R^2$ is phenyl or pyridinyl ring substituted with 3 $R^6$ substituents comprising:

(a) ortho to ring D: $R^6$ is selected from methyl, methoxy or ethoxy;

(b) meta to ring D: $R^6$ is selected from methyl, F, or Cl; and (c) para to ring D: $R^6$ is selected from phenyl or pyridyl ring substituted with 0, 1, 2, 3, or 4 $R^1$ substituents selected from F, Cl, methyl, cyclopropyl, methoxy, ethoxy, —$CF_3$, —$CHF_2$, —$CH_2F$, —$OCF_3$, —$OCHF_2$, —$OCH_2F$, or —CN.

In embodiment 4a, the present invention provides compounds in accordance with embodiment 4, an enantiomer, diastereoisomer, atropisomer thereof, or a mixture thereof, or pharmaceutically acceptable salts thereof, wherein said $R^6$ ortho to ring D is methoxy.

In embodiment 4b, the present invention provides compounds in accordance with embodiment 4, an enantiomer, diastereoisomer, atropisomer thereof, or a mixture thereof, or pharmaceutically acceptable salts thereof, wherein said $R^6$ meta to ring D is F or Cl.

In embodiment 4c, the present invention provides compounds in accordance with embodiment 4, an enantiomer, diastereoisomer, atropisomer thereof, or a mixture thereof, or pharmaceutically acceptable salts thereof, wherein said $R^6$ para to ring D is phenyl substituted with 1 to 3 $R^7$ substituents selected from F, Cl, methyl, cyclopropyl, methoxy, or —$CF_3$.

In embodiment 4d, the present invention provides compounds in accordance with any one of embodiments 1, 1a-1i, 2, 2a-2b, 3, 3a-3c, an enantiomer, diastereoisomer, atropisomer thereof, or a mixture thereof, or pharmaceutically acceptable salts thereof, wherein $R^2$ is phenyl or pyridinyl ring substituted with 3 $R^6$ substituents comprising:

(a) ortho to ring D: $R^6$ is selected from methyl, methoxy or ethoxy;

(b) meta to ring D: $R^6$ is selected from absent, methyl, F, or Cl; and (c) para to ring D: $R^6$ is selected from halo, phenyl ring, or pyridyl ring; wherein each of said phenyl ring or pyridyl ring is substituted with 0, 1, 2, 3, or 4 $R^7$ substituents selected from F, Cl, methyl, cyclopropyl, methoxy, ethoxy, —$CF_3$, —$CHF_2$, —$CH_2F$, —$OCF_3$, —$OCHF_2$, —$OCH_2F$, or —CN.

In embodiment 5, the present invention provides compounds in accordance with embodiments 1, 1a-1i, 2, 2a-2b, 3, 4a-4d, an enantiomer, diastereoisomer, atropisomer thereof, or a mixture thereof, or pharmaceutically acceptable salts thereof, wherein $R^2$ is phenyl ring.

In embodiment 5a, the present invention provides compounds in accordance with embodiment 5, an enantiomer, diastereoisomer, atropisomer thereof, or a mixture thereof, or pharmaceutically acceptable salts thereof, wherein said compound of formula (I) has the formula:

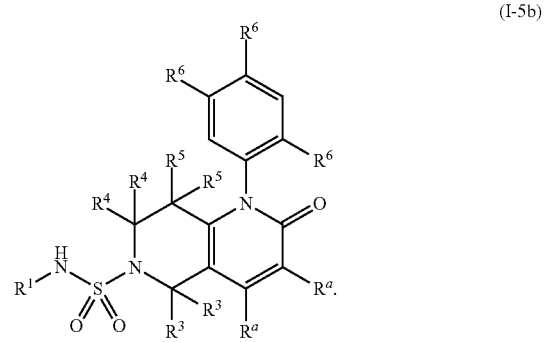

(I-5b)

In embodiment 5b, the present invention provides compounds in accordance with embodiments 1, 1a-1i, 2, 2a-2b, 3, 3a-3c, 4a-4d, an enantiomer, diastereoisomer, atropisomer thereof, or a mixture thereof, or pharmaceutically acceptable salts thereof, wherein $R^2$ is pyridinyl ring.

In embodiment 6, the present invention provides compounds in accordance with embodiments 1, 1a-1i, 2, 2a-2b, 3, 3a-3c, 4a-4d, 5, 5a-5b, an enantiomer, atropisomer thereof, or a mixture thereof, or pharmaceutically acceptable salts thereof, wherein each of $R^3$, $R^4$, and $R^5$ is independently selected from H or methyl.

In embodiment 7, the present invention provides compounds in accordance with embodiments 1, 1a-1i, 2, 2a-2b, 3, 3a-3c, 4a-4d, 5, 5a-5b, 6, an enantiomer, diastereoisomer, atropisomer thereof, or a mixture thereof, or pharmaceutically acceptable salts thereof, wherein $R^1$ is a 5 to 6 membered heteroaryl group.

In embodiment 7a, the present invention provides compounds in accordance with embodiment 7, an enantiomer, diastereoisomer, atropisomer thereof, or a mixture thereof, or pharmaceutically acceptable salts thereof, wherein said $R^1$ is isoxazolyl, thiazolyl, thiadiazolyl, pyridazinyl, pyridyl, or pyrimidinyl ring, wherein the ring is unsubstituted or is substituted with 0, 1, 2, 3, or 4 substituents independently selected from halo or —$C_{1-6}$alkyl.

In embodiment 7b, the present invention provides compounds in accordance with embodiment 7, an enantiomer, diastereoisomer, atropisomer thereof, or a mixture thereof, or pharmaceutically acceptable salts thereof, wherein said $R^1$ is

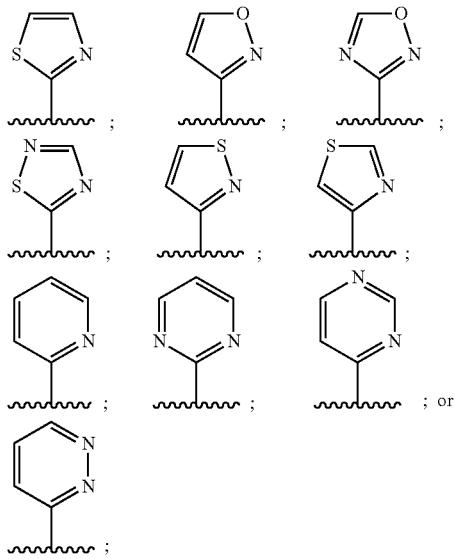

wherein the ring is unsubstituted or is substituted with 0, 1, 2, 3, or 4 substituents independently selected from halo or —$C_{1-6}$alkyl.

In embodiment 7c, the present invention provides compounds in accordance with embodiment 7, an enantiomer, diastereoisomer, atropisomer thereof, or a mixture thereof, or pharmaceutically acceptable salts thereof, wherein said $R^1$ is unsubstituted

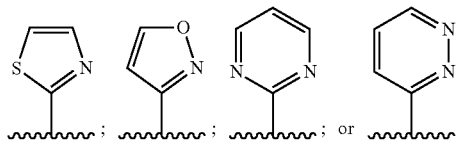

In embodiment 7d, the present invention provides compounds in accordance with embodiment 7, an enantiomer, diastereoisomer, atropisomer thereof, or a mixture thereof, or pharmaceutically acceptable salts thereof, wherein $R^1$ is

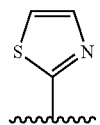

unsubstituted or substituted with from 1 to 3 substituents independently selected from halo or —$C_{1-6}$alkyl.

In embodiment 7e, the present invention provides compounds in accordance with embodiment 7, an enantiomer, diastereoisomer, atropisomer thereof, or a mixture thereof, or pharmaceutically acceptable salts thereof, wherein $R^1$ is

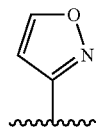

unsubstituted or substituted with from 1 to 3 substituents independently selected from halo or —$C_{1-6}$alkyl.

In embodiment 7g, the present invention provides compounds in accordance with embodiment 7, an enantiomer, diastereoisomer, atropisomer thereof, or a mixture thereof, or pharmaceutically acceptable salts thereof, wherein $R^1$ is

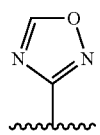

unsubstituted or substituted with from 1 to 3 substituents independently selected from halo or —$C_{1-6}$alkyl.

In embodiment 7h, the present invention provides compounds in accordance with embodiment 7, an enantiomer, diastereoisomer, atropisomer thereof, or a mixture thereof, or pharmaceutically acceptable salts thereof, wherein $R^1$ is

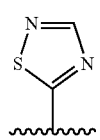 [SMILES: *c1ncns1]

unsubstituted or substituted with from 1 to 3 substituents independently selected from halo or —$C_{1-6}$alkyl.

In embodiment 7i, the present invention provides compounds in accordance with embodiment 7, an enantiomer, diastereoisomer, atropisomer thereof, or a mixture thereof, or pharmaceutically acceptable salts thereof, wherein $R^1$ is

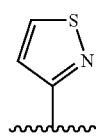 [SMILES: *c1ccsn1]

unsubstituted or substituted with from 1 to 4 substituents independently selected from halo or —$C_{1-6}$alkyl.

In embodiment 7i, the present invention provides compounds in accordance with embodiment 7, an enantiomer, diastereoisomer, atropisomer thereof, or a mixture thereof, or pharmaceutically acceptable salts thereof, wherein R¹ is

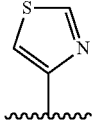

unsubstituted or substituted with from 1 to 4 substituents independently selected from halo or —C$_{1-6}$alkyl.

In embodiment 7j, the present invention provides compounds in accordance with embodiment 7, an enantiomer, diastereoisomer, atropisomer thereof, or a mixture thereof, or pharmaceutically acceptable salts thereof, wherein R¹ is

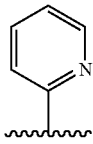

unsubstituted or substituted with from 1 to 4 substituents independently selected from halo or —C$_{1-6}$alkyl.

In embodiment 7k, the present invention provides compounds in accordance with embodiment 7, an enantiomer, diastereoisomer, atropisomer thereof, or a mixture thereof, or pharmaceutically acceptable salts thereof, wherein R¹ is

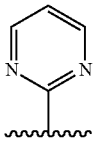

unsubstituted or substituted with from 1 to 4 substituents independently selected from halo or —C$_{1-6}$alkyl.

In embodiment 7l, the present invention provides compounds in accordance with embodiment 7, an enantiomer, diastereoisomer, atropisomer thereof, or a mixture thereof, or pharmaceutically acceptable salts thereof, wherein R¹ is

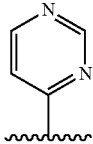

unsubstituted or substituted with from 1 to 4 substituents independently selected from halo or —C$_{1-6}$alkyl.

In embodiment 7m, the present invention provides compounds in accordance with embodiment 7, an enantiomer, diastereoisomer, atropisomer thereof, or a mixture thereof, or pharmaceutically acceptable salts thereof, wherein R¹ is

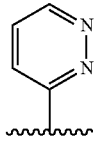

unsubstituted or substituted with from 1 to 4 substituents independently selected from halo or —C$_{1-6}$alkyl.

In embodiment 8, the present invention provides a compound, an enantiomer, diastereoisomer, atropisomer thereof, or a mixture thereof, or pharmaceutically acceptable salts thereof, selected from:
Rac-1-(4'-chloro-2-fluoro-5-methoxy-3'-methyl-4-biphenylyl)-2-oxo-N-4-pyrimidinyl-1,5,7,8-tetrahydro-1,6-naphthyridine-6(2H)-sulfonamide;
P-1-(4'-chloro-2-fluoro-5-methoxy-3'-methyl-4-biphenylyl)-2-oxo-N-4-pyrimidinyl-1,5,7,8-tetrahydro-1,6-naphthyridine-6(2H)-sulfonamide;
M-1-(4'-chloro-2-fluoro-5-methoxy-3'-methyl-4-biphenylyl)-2-oxo-N-4-pyrimidinyl-1,5,7,8-tetrahydro-1,6-naphthyridine-6(2H)-sulfonamide;
Rac-1-(4'-chloro-2-fluoro-3',5-dimethoxy-4-biphenylyl)-2-oxo-N-3-pyridazinyl-1,5,7,8-tetrahydro-1,6-naphthyridine-6(2H)-sulfonamide;
P-1-(4'-chloro-2-fluoro-3',5-dimethoxy-4-biphenylyl)-2-oxo-N-3-pyridazinyl-1,5,7,8-tetrahydro-1,6-naphthyridine-6(2H)-sulfonamide;
M-1-(4'-chloro-2-fluoro-3',5-dimethoxy-4-biphenylyl)-2-oxo-N-3-pyridazinyl-1,5,7,8-tetrahydro-1,6-naphthyridine-6(2H)-sulfonamide;
Rac-(5R)—N-3-isoxazolyl-5-methyl-2-oxo-1-(2,3',5'-trifluoro-5-methoxy-4-biphenylyl)-1,5,7,8-tetrahydro-1,6-naphthyridine-6(2H)-sulfonamide;
P-(5R)—N-3-isoxazolyl-5-methyl-2-oxo-1-(2,3',5'-trifluoro-5-methoxy-4-biphenylyl)-1,5,7,8-tetrahydro-1,6-naphthyridine-6(2H)-sulfonamide;
M-(5R)—N-3-isoxazolyl-5-methyl-2-oxo-1-(2,3',5'-trifluoro-5-methoxy-4-biphenylyl)-1,5,7,8-tetrahydro-1,6-naphthyridine-6(2H)-sulfonamide;
Rac-(5 S)—N-3-isoxazolyl-5-methyl-2-oxo-1-(2,3',5'-trifluoro-5-methoxy-4-biphenylyl)-1,5,7,8-tetrahydro-1,6-naphthyridine-6(2H)-sulfonamide;
P-(5 S)—N-3-isoxazolyl-5-methyl-2-oxo-1-(2,3',5'-trifluoro-5-methoxy-4-biphenylyl)-1,5,7,8-tetrahydro-1,6-naphthyridine-6(2H)-sulfonamide;
M-(5S)—N-3-isoxazolyl-5-methyl-2-oxo-1-(2,3',5'-trifluoro-5-methoxy-4-biphenylyl)-1,5,7,8-tetrahydro-1,6-naphthyridine-6(2H)-sulfonamide;
Rac-(7S)—N-3-isoxazolyl-7-methyl-2-oxo-1-(2,3',5'-trifluoro-5-methoxy-4-biphenylyl)-1,5,7,8-tetrahydro-1,6-naphthyridine-6(2H)-sulfonamide;
P-(7S)—N-3-isoxazolyl-7-methyl-2-oxo-1-(2,3',5'-trifluoro-5-methoxy-4-biphenylyl)-1,5,7,8-tetrahydro-1,6-naphthyridine-6(2H)-sulfonamide;
M-(7S)—N-3-isoxazolyl-7-methyl-2-oxo-1-(2,3',5'-trifluoro-5-methoxy-4-biphenylyl)-1,5,7,8-tetrahydro-1,6-naphthyridine-6(2H)-sulfonamide;
Rac-(7R)—N-3-isoxazolyl-7-methyl-2-oxo-1-(2,3',5'-trifluoro-5-methoxy-4-biphenylyl)-1,5,7,8-tetrahydro-1,6-naphthyridine-6(2H)-sulfonamide;
P-(7R)—N-3-isoxazolyl-7-methyl-2-oxo-1-(2,3',5'-trifluoro-5-methoxy-4-biphenylyl)-1,5,7,8-tetrahydro-1,6-naphthyridine-6(2H)-sulfonamide;

M-(7R)—N-3-isoxazolyl-7-methyl-2-oxo-1-(2,3',5'-trifluoro-5-methoxy-4-biphenylyl)-1,5,7,8-tetrahydro-1,6-naphthyridine-6(2H)-sulfonamide;
Rac-1-(3'-chloro-2,5'-difluoro-5-methoxy-4-biphenylyl)-N-(6-methyl-4-pyrimidinyl)-2-oxo-1,5,7,8-tetrahydro-1,6-naphthyridine-6(2H)-sulfonamide;
P-1-(3'-chloro-2,5'-difluoro-5-methoxy-4-biphenylyl)-N-(6-methyl-4-pyrimidinyl)-2-oxo-1,5,7,8-tetrahydro-1,6-naphthyridine-6(2H)-sulfonamide;
M-1-(3'-chloro-2,5'-difluoro-5-methoxy-4-biphenylyl)-N-(6-methyl-4-pyrimidinyl)-2-oxo-1,5,7,8-tetrahydro-1,6-naphthyridine-6(2H)-sulfonamide;
Rac-1-(3'-chloro-2,5'-difluoro-5-methoxy-4-biphenylyl)-2-oxo-N-1,2,4-thiadiazol-5-yl-1,5,7,8-tetrahydro-1,6-naphthyridine-6(2H)-sulfonamide;
P-1-(3'-chloro-2,5'-difluoro-5-methoxy-4-biphenylyl)-2-oxo-N-1,2,4-thiadiazol-5-yl-1,5,7,8-tetrahydro-1,6-naphthyridine-6(2H)-sulfonamide;
M-1-(3'-chloro-2,5'-difluoro-5-methoxy-4-biphenylyl)-2-oxo-N-1,2,4-thiadiazol-5-yl-1,5,7,8-tetrahydro-1,6-naphthyridine-6(2H)-sulfonamide;
Rac-1-(3'-chloro-2,5'-difluoro-5-methoxy-4-biphenylyl)-N-(2-methyl-4-pyrimidinyl)-2-oxo-1,5,7,8-tetrahydro-1,6-naphthyridine-6(2H)-sulfonamide;
P-1-(3'-chloro-2,5'-difluoro-5-methoxy-4-biphenylyl)-N-(2-methyl-4-pyrimidinyl)-2-oxo-1,5,7,8-tetrahydro-1,6-naphthyridine-6(2H)-sulfonamide;
M-1-(3'-chloro-2,5'-difluoro-5-methoxy-4-biphenylyl)-N-(2-methyl-4-pyrimidinyl)-2-oxo-1,5,7,8-tetrahydro-1,6-naphthyridine-6(2H)-sulfonamide;
Rac-1-(3'-chloro-5'-fluoro-3-methoxy-4-biphenylyl)-N-3-isoxazolyl-2-oxo-1,5,7,8-tetrahydro-1,6-naphthyridine-6(2H)-sulfonamide;
P-1-(3'-chloro-5'-fluoro-3-methoxy-4-biphenylyl)-N-3-isoxazolyl-2-oxo-1,5,7,8-tetrahydro-1,6-naphthyridine-6(2H)-sulfonamide;
M-1-(3'-chloro-5'-fluoro-3-methoxy-4-biphenylyl)-N-3-isoxazolyl-2-oxo-1,5,7,8-tetrahydro-1,6-naphthyridine-6(2H)-sulfonamide;
Rac-1-(3'-chloro-5'-fluoro-3-methoxy-4-biphenylyl)-2-oxo-N-3-pyridazinyl-1,5,7,8-tetrahydro-1,6-naphthyridine-6(2H)-sulfonamide;
P-1-(3'-chloro-5'-fluoro-3-methoxy-4-biphenylyl)-2-oxo-N-3-pyridazinyl-1,5,7,8-tetrahydro-1,6-naphthyridine-6(2H)-sulfonamide;
M-1-(3'-chloro-5'-fluoro-3-methoxy-4-biphenylyl)-2-oxo-N-3-pyridazinyl-1,5,7,8-tetrahydro-1,6-naphthyridine-6(2H)-sulfonamide;
Rac-1-(5'-chloro-2-fluoro-5-methoxy-2'-methyl-4-biphenylyl)-N-3-isoxazolyl-2-oxo-1,5,7,8-tetrahydro-1,6-naphthyridine-6(2H)-sulfonamide;
P-1-(5'-chloro-2-fluoro-5-methoxy-2'-methyl-4-biphenylyl)-N-3-isoxazolyl-2-oxo-1,5,7,8-tetrahydro-1,6-naphthyridine-6(2H)-sulfonamide;
M-1-(5'-chloro-2-fluoro-5-methoxy-2'-methyl-4-biphenylyl)-N-3-isoxazolyl-2-oxo-1,5,7,8-tetrahydro-1,6-naphthyridine-6(2H)-sulfonamide;
Rac-N-(5-fluoro-2-pyrimidinyl)-2-oxo-1-(2,3',5'-trifluoro-5-methoxy-4-biphenylyl)-1,5,7,8-tetrahydro-1,6-naphthyridine-6(2H)-sulfonamide;
P—N-(5-fluoro-2-pyrimidinyl)-2-oxo-1-(2,3',5'-trifluoro-5-methoxy-4-biphenylyl)-1,5,7,8-tetrahydro-1,6-naphthyridine-6(2H)-sulfonamide;
M-N-(5-fluoro-2-pyrimidinyl)-2-oxo-1-(2,3',5'-trifluoro-5-methoxy-4-biphenylyl)-1,5,7,8-tetrahydro-1,6-naphthyridine-6(2H)-sulfonamide;
Rac-1-(3'-chloro-2,5'-difluoro-5-methoxy-4-biphenylyl)-2-oxo-N-2-pyridinyl-1,5,7,8-tetrahydro-1,6-naphthyridine-6(2H)-sulfonamide;
P-1-(3'-chloro-2,5'-difluoro-5-methoxy-4-biphenylyl)-2-oxo-N-2-pyridinyl-1,5,7,8-tetrahydro-1,6-naphthyridine-6(2H)-sulfonamide;
M-1-(3'-chloro-2,5'-difluoro-5-methoxy-4-biphenylyl)-2-oxo-N-2-pyridinyl-1,5,7,8-tetrahydro-1,6-naphthyridine-6(2H)-sulfonamide;
Rac-1-(3'-chloro-2,5'-difluoro-5-methoxy-4-biphenylyl)-N-(5-fluoro-2-pyridinyl)-2-oxo-1,5,7,8-tetrahydro-1,6-naphthyridine-6(2H)-sulfonamide;
P-1-(3'-chloro-2,5'-difluoro-5-methoxy-4-biphenylyl)-N-(5-fluoro-2-pyridinyl)-2-oxo-1,5,7,8-tetrahydro-1,6-naphthyridine-6(2H)-sulfonamide;
M-1-(3'-chloro-2,5'-difluoro-5-methoxy-4-biphenylyl)-N-(5-fluoro-2-pyridinyl)-2-oxo-1,5,7,8-tetrahydro-1,6-naphthyridine-6(2H)-sulfonamide;
Rac-1-(3'-chloro-2,5'-difluoro-5-methoxy-4-biphenylyl)-N-(6-fluoro-2-pyridinyl)-2-oxo-1,5,7,8-tetrahydro-1,6-naphthyridine-6(2H)-sulfonamide;
P-1-(3'-chloro-2,5'-difluoro-5-methoxy-4-biphenylyl)-N-(6-fluoro-2-pyridinyl)-2-oxo-1,5,7,8-tetrahydro-1,6-naphthyridine-6(2H)-sulfonamide;
M-1-(3'-chloro-2,5'-difluoro-5-methoxy-4-biphenylyl)-N-(6-fluoro-2-pyridinyl)-2-oxo-1,5,7,8-tetrahydro-1,6-naphthyridine-6(2H)-sulfonamide;
Rac-N-(6-fluoro-2-pyridinyl)-2-oxo-1-(2,3',5'-trifluoro-5-methoxy-4-biphenylyl)-1,5,7,8-tetrahydro-1,6-naphthyridine-6(2H)-sulfonamide;
P—N-(6-fluoro-2-pyridinyl)-2-oxo-1-(2,3',5'-trifluoro-5-methoxy-4-biphenylyl)-1,5,7,8-tetrahydro-1,6-naphthyridine-6(2H)-sulfonamide;
M-N-(6-fluoro-2-pyridinyl)-2-oxo-1-(2,3',5'-trifluoro-5-methoxy-4-biphenylyl)-1,5,7,8-tetrahydro-1,6-naphthyridine-6(2H)-sulfonamide;
Rac-1-(4'-chloro-2-fluoro-3',5-dimethoxy-4-biphenylyl)-N-3-isoxazolyl-2-oxo-1,5,7,8-tetrahydro-1,6-naphthyridine-6(2H)-sulfonamide;
P-1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide;
M-1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide;
P-1-(4'-chloro-2-fluoro-3',5-dimethoxy-4-biphenylyl)-N-3-isoxazolyl-2-oxo-1,5,7,8-tetrahydro-1,6-naphthyridine-6(2H)-sulfonamide;
M-1-(4'-chloro-2-fluoro-3',5-dimethoxy-4-biphenylyl)-N-3-isoxazolyl-2-oxo-1,5,7,8-tetrahydro-1,6-naphthyridine-6(2H)-sulfonamide;
Rac-1-(2-fluoro-5-methoxy-3'-(trifluoromethyl)-4-biphenylyl)-N-3-isoxazolyl-2-oxo-1,5,7,8-tetrahydro-1,6-naphthyridine-6(2H)-sulfonamide;
P-1-(2-fluoro-5-methoxy-3'-(trifluoromethyl)-4-biphenylyl)-N-3-isoxazolyl-2-oxo-1,5,7,8-tetrahydro-1,6-naphthyridine-6(2H)-sulfonamide;
M-1-(2-fluoro-5-methoxy-3'-(trifluoromethyl)-4-biphenylyl)-N-3-isoxazolyl-2-oxo-1,5,7,8-tetrahydro-1,6-naphthyridine-6(2H)-sulfonamide;
Rac-N-1,2,4-oxadiazol-3-yl-2-oxo-1-(2,3',5'-trifluoro-5-methoxy-4-biphenylyl)-1,5,7,8-tetrahydro-1,6-naphthyridine-6(2H)-sulfonamide;
P—N-1,2,4-oxadiazol-3-yl-2-oxo-1-(2,3',5'-trifluoro-5-methoxy-4-biphenylyl)-1,5,7,8-tetrahydro-1,6-naphthyridine-6(2H)-sulfonamide;

M-N-1,2,4-oxadiazol-3-yl-2-oxo-1-(2,3',5'-trifluoro-5-methoxy-4-biphenylyl)-1,5,7,8-tetrahydro-1,6-naphthyridine-6(2H)-sulfonamide;

Rac-1-(3'-chloro-2,5'-difluoro-5-methoxy-4-biphenylyl)-N-3-isoxazolyl-2-oxo-1,5,7,8-tetrahydro-1,6-naphthyridine-6(2H)-sulfonamide;

P-1-(3'-chloro-2,5'-difluoro-5-methoxy-4-biphenylyl)-N-3-isoxazolyl-2-oxo-1,5,7,8-tetrahydro-1,6-naphthyridine-6(2H)-sulfonamide;

M-1-(3'-chloro-2,5'-difluoro-5-methoxy-4-biphenylyl)-N-3-isoxazolyl-2-oxo-1,5,7,8-tetrahydro-1,6-naphthyridine-6(2H)-sulfonamide;

Rac-1-(3'-(difluoromethoxy)-2-fluoro-5-methoxy-4-biphenylyl)-N-3-isoxazolyl-2-oxo-1,5,7,8-tetrahydro-1,6-naphthyridine-6(2H)-sulfonamide;

P-1-(3'-(difluoromethoxy)-2-fluoro-5-methoxy-4-biphenylyl)-N-3-isoxazolyl-2-oxo-1,5,7,8-tetrahydro-1,6-naphthyridine-6(2H)-sulfonamide;

M-1-(3'-(difluoromethoxy)-2-fluoro-5-methoxy-4-biphenylyl)-N-3-isoxazolyl-2-oxo-1,5,7,8-tetrahydro-1,6-naphthyridine-6(2H)-sulfonamide;

Rac-N-3-isoxazolyl-2-oxo-1-(2,3',4'-trifluoro-5-methoxy-4-biphenylyl)-1,5,7,8-tetrahydro-1,6-naphthyridine-6(2H)-sulfonamide;

P—N-3-isoxazolyl-2-oxo-1-(2,3',4'-trifluoro-5-methoxy-4-biphenylyl)-1,5,7,8-tetrahydro-1,6-naphthyridine-6(2H)-sulfonamide;

M-N-3-isoxazolyl-2-oxo-1-(2,3',4'-trifluoro-5-methoxy-4-biphenylyl)-1,5,7,8-tetrahydro-1,6-naphthyridine-6(2H)-sulfonamide;

Rac-1-(2,3'-difluoro-5-methoxy-4'-methyl-4-biphenylyl)-N-3-isoxazolyl-2-oxo-1,5,7,8-tetrahydro-1,6-naphthyridine-6(2H)-sulfonamide;

P-1-(2,3'-difluoro-5-methoxy-4'-methyl-4-biphenylyl)-N-3-isoxazolyl-2-oxo-1,5,7,8-tetrahydro-1,6-naphthyridine-6(2H)-sulfonamide;

M-1-(2,3'-difluoro-5-methoxy-4'-methyl-4-biphenylyl)-N-3-isoxazolyl-2-oxo-1,5,7,8-tetrahydro-1,6-naphthyridine-6(2H)-sulfonamide;

Rac-1-(2,4'-difluoro-5-methoxy-3'-methyl-4-biphenylyl)-N-3-isoxazolyl-2-oxo-1,5,7,8-tetrahydro-1,6-naphthyridine-6(2H)-sulfonamide;

P-1-(2,4'-difluoro-5-methoxy-3'-methyl-4-biphenylyl)-N-3-isoxazolyl-2-oxo-1,5,7,8-tetrahydro-1,6-naphthyridine-6(2H)-sulfonamide;

M-1-(2,4'-difluoro-5-methoxy-3'-methyl-4-biphenylyl)-N-3-isoxazolyl-2-oxo-1,5,7,8-tetrahydro-1,6-naphthyridine-6(2H)-sulfonamide;

Rac-1-(5-fluoro-2-methoxy-4-(2-methoxy-5-(trifluoromethyl)-3-pyridinyl)phenyl)-N-3-isoxazolyl-2-oxo-1,5,7,8-tetrahydro-1,6-naphthyridine-6(2H)-sulfonamide;

P-1-(5-fluoro-2-methoxy-4-(2-methoxy-5-(trifluoromethyl)-3-pyridinyl)phenyl)-N-3-isoxazolyl-2-oxo-1,5,7,8-tetrahydro-1,6-naphthyridine-6(2H)-sulfonamide;

M-1-(5-fluoro-2-methoxy-4-(2-methoxy-5-(trifluoromethyl)-3-pyridinyl)phenyl)-N-3-isoxazolyl-2-oxo-1,5,7,8-tetrahydro-1,6-naphthyridine-6(2H)-sulfonamide;

Rac-1-(4'-chloro-2-fluoro-5-methoxy-3'-methyl-4-biphenylyl)-N-3-isoxazolyl-2-oxo-1,5,7,8-tetrahydro-1,6-naphthyridine-6(2H)-sulfonamide;

P-1-(4'-chloro-2-fluoro-5-methoxy-3'-methyl-4-biphenylyl)-N-3-isoxazolyl-2-oxo-1,5,7,8-tetrahydro-1,6-naphthyridine-6(2H)-sulfonamide;

M-1-(4'-chloro-2-fluoro-5-methoxy-3'-methyl-4-biphenylyl)-N-3-isoxazolyl-2-oxo-1,5,7,8-tetrahydro-1,6-naphthyridine-6(2H)-sulfonamide;

Rac-N-3-isoxazolyl-2-oxo-1-(2,3',5'-trifluoro-5-methoxy-4-biphenylyl)-1,5,7,8-tetrahydro-1,6-naphthyridine-6(2H)-sulfonamide;

P—N-3-isoxazolyl-2-oxo-1-(2,3',5'-trifluoro-5-methoxy-4-biphenylyl)-1,5,7,8-tetrahydro-1,6-naphthyridine-6(2H)-sulfonamide;

M-N-3-isoxazolyl-2-oxo-1-(2,3',5'-trifluoro-5-methoxy-4-biphenylyl)-1,5,7,8-tetrahydro-1,6-naphthyridine-6(2H)-sulfonamide;

Rac-N-3-isoxazolyl-1-(2-methoxy-4-(trifluoromethyl)phenyl)-2-oxo-1,5,7,8-tetrahydro-1,6-naphthyridine-6(2H)-sulfonamide;

P—N-3-isoxazolyl-1-(2-methoxy-4-(trifluoromethyl)phenyl)-2-oxo-1,5,7,8-tetrahydro-1,6-naphthyridine-6(2H)-sulfonamide;

M-N-3-isoxazolyl-1-(2-methoxy-4-(trifluoromethyl)phenyl)-2-oxo-1,5,7,8-tetrahydro-1,6-naphthyridine-6(2H)-sulfonamide;

Rac-N-3-isoxazolyl-1-(2-methoxyphenyl)-2-oxo-1,5,7,8-tetrahydro-1,6-naphthyridine-6(2H)-sulfonamide;

P—N-3-isoxazolyl-1-(2-methoxyphenyl)-2-oxo-1,5,7,8-tetrahydro-1,6-naphthyridine-6(2H)-sulfonamide;

M-N-3-isoxazolyl-1-(2-methoxyphenyl)-2-oxo-1,5,7,8-tetrahydro-1,6-naphthyridine-6(2H)-sulfonamide;

Rac-2-oxo-N-2-pyrimidinyl-1-(2,3',4'-trifluoro-5-methoxy-4-biphenylyl)-1,5,7,8-tetrahydro-1,6-naphthyridine-6(2H)-sulfonamide;

P-2-oxo-N-2-pyrimidinyl-1-(2,3',4'-trifluoro-5-methoxy-4-biphenylyl)-1,5,7,8-tetrahydro-1,6-naphthyridine-6(2H)-sulfonamide;

M-2-oxo-N-2-pyrimidinyl-1-(2,3',4'-trifluoro-5-methoxy-4-biphenylyl)-1,5,7,8-tetrahydro-1,6-naphthyridine-6(2H)-sulfonamide;

Rac-1-(2,4'-difluoro-5-methoxy-3'-methyl-4-biphenylyl)-2-oxo-N-2-pyrimidinyl-1,5,7,8-tetrahydro-1,6-naphthyridine-6(2H)-sulfonamide;

P-1-(2,4'-difluoro-5-methoxy-3'-methyl-4-biphenylyl)-2-oxo-N-2-pyrimidinyl-1,5,7,8-tetrahydro-1,6-naphthyridine-6(2H)-sulfonamide;

M-1-(2,4'-difluoro-5-methoxy-3'-methyl-4-biphenylyl)-2-oxo-N-2-pyrimidinyl-1,5,7,8-tetrahydro-1,6-naphthyridine-6(2H)-sulfonamide;

Rac-1-(4'-chloro-2-fluoro-5-methoxy-3'-methyl-4-biphenylyl)-2-oxo-N-2-pyrimidinyl-1,5,7,8-tetrahydro-1,6-naphthyridine-6(2H)-sulfonamide;

P-1-(4'-chloro-2-fluoro-5-methoxy-3'-methyl-4-biphenylyl)-2-oxo-N-2-pyrimidinyl-1,5,7,8-tetrahydro-1,6-naphthyridine-6(2H)-sulfonamide;

M-1-(4'-chloro-2-fluoro-5-methoxy-3'-methyl-4-biphenylyl)-2-oxo-N-2-pyrimidinyl-1,5,7,8-tetrahydro-1,6-naphthyridine-6(2H)-sulfonamide;

Rac-1-(4'-chloro-2-fluoro-5-methoxy-3'-methyl-4-biphenylyl)-2-oxo-N-2-pyrimidinyl-1,5,7,8-tetrahydro-1,6-naphthyridine-6(2H)-sulfonamide;

P-1-(4'-chloro-2-fluoro-5-methoxy-3'-methyl-4-biphenylyl)-2-oxo-N-2-pyrimidinyl-1,5,7,8-tetrahydro-1,6-naphthyridine-6(2H)-sulfonamide;

M-1-(4'-chloro-2-fluoro-5-methoxy-3'-methyl-4-biphenylyl)-2-oxo-N-2-pyrimidinyl-1,5,7,8-tetrahydro-1,6-naphthyridine-6(2H)-sulfonamide;

Rac-1-(3'-chloro-2,5'-difluoro-5-methoxy-4-biphenylyl)-2-oxo-N-2-pyrimidinyl-1,5,7,8-tetrahydro-1,6-naphthyridine-6(2H)-sulfonamide;

P-1-(3'-chloro-2,5'-difluoro-5-methoxy-4-biphenylyl)-2-oxo-N-2-pyrimidinyl-1,5,7,8-tetrahydro-1,6-naphthyridine-6(2H)-sulfonamide;

M-1-(3'-chloro-2,5'-difluoro-5-methoxy-4-biphenylyl)-2-oxo-N-2-pyrimidinyl-1,5,7,8-tetrahydro-1,6-naphthyridine-6(2H)-sulfonamide;
Rac-2-oxo-N-3-pyridazinyl-1-(2,3',4'-trifluoro-5-methoxy-4-biphenylyl)-1,5,7,8-tetrahydro-1,6-naphthyridine-6(2H)-sulfonamide;
P-2-oxo-N-3-pyridazinyl-1-(2,3',4'-trifluoro-5-methoxy-4-biphenylyl)-1,5,7,8-tetrahydro-1,6-naphthyridine-6(2H)-sulfonamide;
M-2-oxo-N-3-pyridazinyl-1-(2,3',4'-trifluoro-5-methoxy-4-biphenylyl)-1,5,7,8-tetrahydro-1,6-naphthyridine-6(2H)-sulfonamide;
Rac-1-(4'-chloro-2-fluoro-5-methoxy-3'-methyl-4-biphenylyl)-2-oxo-N-3-pyridazinyl-1,5,7,8-tetrahydro-1,6-naphthyridine-6(2H)-sulfonamide;
P-1-(4'-chloro-2-fluoro-5-methoxy-3'-methyl-4-biphenylyl)-2-oxo-N-3-pyridazinyl-1,5,7,8-tetrahydro-1,6-naphthyridine-6(2H)-sulfonamide;
M-1-(4'-chloro-2-fluoro-5-methoxy-3'-methyl-4-biphenylyl)-2-oxo-N-3-pyridazinyl-1,5,7,8-tetrahydro-1,6-naphthyridine-6(2H)-sulfonamide;
Rac-1-(4-(cyclopentylethynyl)-5-fluoro-2-methoxyphenyl)-N-3-isoxazolyl-2-oxo-1,5,7,8-tetrahydro-1,6-naphthyridine-6(2H)-sulfonamide;
P-1-(4-(cyclopentylethynyl)-5-fluoro-2-methoxyphenyl)-N-3-isoxazolyl-2-oxo-1,5,7,8-tetrahydro-1,6-naphthyridine-6(2H)-sulfonamide;
M-1-(4-(cyclopentylethynyl)-5-fluoro-2-methoxyphenyl)-N-3-isoxazolyl-2-oxo-1,5,7,8-tetrahydro-1,6-naphthyridine-6(2H)-sulfonamide;
Rac-1-(4'-chloro-3'-cyano-2-fluoro-5-methoxy-4-biphenylyl)-N-3-isoxazolyl-2-oxo-1,5,7,8-tetrahydro-1,6-naphthyridine-6(2H)-sulfonamide;
P-1-(4'-chloro-3'-cyano-2-fluoro-5-methoxy-4-biphenylyl)-N-3-isoxazolyl-2-oxo-1,5,7,8-tetrahydro-1,6-naphthyridine-6(2H)-sulfonamide;
M-1-(4'-chloro-3'-cyano-2-fluoro-5-methoxy-4-biphenylyl)-N-3-isoxazolyl-2-oxo-1,5,7,8-tetrahydro-1,6-naphthyridine-6(2H)-sulfonamide;
Rac-1-(6-(3-chloro-5-fluorophenyl)-5-fluoro-2-methoxy-3-pyridinyl)-N-3-isoxazolyl-2-oxo-1,5,7,8-tetrahydro-1,6-naphthyridine-6(2H)-sulfonamide;
P-1-(6-(3-chloro-5-fluorophenyl)-5-fluoro-2-methoxy-3-pyridinyl)-N-3-isoxazolyl-2-oxo-1,5,7,8-tetrahydro-1,6-naphthyridine-6(2H)-sulfonamide;
M-1-(6-(3-chloro-5-fluorophenyl)-5-fluoro-2-methoxy-3-pyridinyl)-N-3-isoxazolyl-2-oxo-1,5,7,8-tetrahydro-1,6-naphthyridine-6(2H)-sulfonamide;
Rac-1-(6-(3-chloro-5-fluorophenyl)-5-fluoro-2-methoxy-3-pyridinyl)-2-oxo-N-3-pyridazinyl-1,5,7,8-tetrahydro-1,6-naphthyridine-6(2H)-sulfonamide;
P-1-(6-(3-chloro-5-fluorophenyl)-5-fluoro-2-methoxy-3-pyridinyl)-2-oxo-N-3-pyridazinyl-1,5,7,8-tetrahydro-1,6-naphthyridine-6(2H)-sulfonamide;
M-1-(6-(3-chloro-5-fluorophenyl)-5-fluoro-2-methoxy-3-pyridinyl)-2-oxo-N-3-pyridazinyl-1,5,7,8-tetrahydro-1,6-naphthyridine-6(2H)-sulfonamide;
Rac-1-(3'-chloro-2,5'-difluoro-5-methoxy-4-biphenylyl)-2-oxo-N-3-pyridazinyl-1,5,7,8-tetrahydro-1,6-naphthyridine-6(2H)-sulfonamide;
P-1-(3'-chloro-2,5'-difluoro-5-methoxy-4-biphenylyl)-2-oxo-N-3-pyridazinyl-1,5,7,8-tetrahydro-1,6-naphthyridine-6(2H)-sulfonamide;
M-1-(3'-chloro-2,5'-difluoro-5-methoxy-4-biphenylyl)-2-oxo-N-3-pyridazinyl-1,5,7,8-tetrahydro-1,6-naphthyridine-6(2H)-sulfonamide;
Rac-1-(4'-chloro-2-fluoro-5-methoxy-3'-methyl-4-biphenylyl)-2-oxo-N-1,3-thiazol-2-yl-1,5,7,8-tetrahydro-1,6-naphthyridine-6(2H)-sulfonamide;
P-1-(4'-chloro-2-fluoro-5-methoxy-3'-methyl-4-biphenylyl)-2-oxo-N-1,3-thiazol-2-yl-1,5,7,8-tetrahydro-1,6-naphthyridine-6(2H)-sulfonamide;
M-1-(4'-chloro-2-fluoro-5-methoxy-3'-methyl-4-biphenylyl)-2-oxo-N-1,3-thiazol-2-yl-1,5,7,8-tetrahydro-1,6-naphthyridine-6(2H)-sulfonamide;
Rac-1-(4'-chloro-2-fluoro-5-methoxy-3'-methyl-4-biphenylyl)-N-(6-methyl-4-pyrimidinyl)-2-oxo-1,5,7,8-tetrahydro-1,6-naphthyridine-6(2H)-sulfonamide;
P-1-(4'-chloro-2-fluoro-5-methoxy-3'-methyl-4-biphenylyl)-N-(6-methyl-4-pyrimidinyl)-2-oxo-1,5,7,8-tetrahydro-1,6-naphthyridine-6(2H)-sulfonamide;
M-1-(4'-chloro-2-fluoro-5-methoxy-3'-methyl-4-biphenylyl)-N-(6-methyl-4-pyrimidinyl)-2-oxo-1,5,7,8-tetrahydro-1,6-naphthyridine-6(2H)-sulfonamide;
Rac-1-(2,3'-difluoro-5-methoxy-5'-(trifluoromethyl)-4-biphenylyl)-2-oxo-N-3-pyridazinyl-1,5,7,8-tetrahydro-1,6-naphthyridine-6(2H)-sulfonamide;
P-1-(2,3'-difluoro-5-methoxy-5'-(trifluoromethyl)-4-biphenylyl)-2-oxo-N-3-pyridazinyl-1,5,7,8-tetrahydro-1,6-naphthyridine-6(2H)-sulfonamide;
M-1-(2,3'-difluoro-5-methoxy-5'-(trifluoromethyl)-4-biphenylyl)-2-oxo-N-3-pyridazinyl-1,5,7,8-tetrahydro-1,6-naphthyridine-6(2H)-sulfonamide;
Rac-1-(3'-cyclopropyl-2-fluoro-5-methoxy-4-biphenylyl)-2-oxo-N-3-pyridazinyl-1,5,7,8-tetrahydro-1,6-naphthyridine-6(2H)-sulfonamide;
P-1-(3'-cyclopropyl-2-fluoro-5-methoxy-4-biphenylyl)-2-oxo-N-3-pyridazinyl-1,5,7,8-tetrahydro-1,6-naphthyridine-6(2H)-sulfonamide;
M-1-(3'-cyclopropyl-2-fluoro-5-methoxy-4-biphenylyl)-2-oxo-N-3-pyridazinyl-1,5,7,8-tetrahydro-1,6-naphthyridine-6(2H)-sulfonamide;
Rac-1-(2'-chloro-2-fluoro-5-methoxy-5'-methyl-4-biphenylyl)-2-oxo-N-3-pyridazinyl-1,5,7,8-tetrahydro-1,6-naphthyridine-6(2H)-sulfonamide;
P-1-(2'-chloro-2-fluoro-5-methoxy-5'-methyl-4-biphenylyl)-2-oxo-N-3-pyridazinyl-1,5,7,8-tetrahydro-1,6-naphthyridine-6(2H)-sulfonamide;
M-1-(2'-chloro-2-fluoro-5-methoxy-5'-methyl-4-biphenylyl)-2-oxo-N-3-pyridazinyl-1,5,7,8-tetrahydro-1,6-naphthyridine-6(2H)-sulfonamide;
Rac-1-(3'-chloro-2-fluoro-5-methoxy-4'-methyl-4-biphenylyl)-2-oxo-N-3-pyridazinyl-1,5,7,8-tetrahydro-1,6-naphthyridine-6(2H)-sulfonamide;
P-1-(3'-chloro-2-fluoro-5-methoxy-4'-methyl-4-biphenylyl)-2-oxo-N-3-pyridazinyl-1,5,7,8-tetrahydro-1,6-naphthyridine-6(2H)-sulfonamide;
M-1-(3'-chloro-2-fluoro-5-methoxy-4'-methyl-4-biphenylyl)-2-oxo-N-3-pyridazinyl-1,5,7,8-tetrahydro-1,6-naphthyridine-6(2H)-sulfonamide;
Rac-1-(2-fluoro-5-methoxy-3'-(trifluoromethyl)-4-biphenylyl)-2-oxo-N-3-pyridazinyl-1,5,7,8-tetrahydro-1,6-naphthyridine-6(2H)-sulfonamide;
P-1-(2-fluoro-5-methoxy-3'-(trifluoromethyl)-4-biphenylyl)-2-oxo-N-3-pyridazinyl-1,5,7,8-tetrahydro-1,6-naphthyridine-6(2H)-sulfonamide;
M-1-(2-fluoro-5-methoxy-3'-(trifluoromethyl)-4-biphenylyl)-2-oxo-N-3-pyridazinyl-1,5,7,8-tetrahydro-1,6-naphthyridine-6(2H)-sulfonamide;
Rac-2-oxo-N-3-pyridazinyl-1-(2,3',4',5'-tetrafluoro-5-methoxy-4-biphenylyl)-1,5,7,8-tetrahydro-1,6-naphthyridine-6(2H)-sulfonamide;

P-2-oxo-N-3-pyridazinyl-1-(2,3',4',5'-tetrafluoro-5-methoxy-4-biphenylyl)-1,5,7,8-tetrahydro-1,6-naphthyridine-6(2H)-sulfonamide;

M-2-oxo-N-3-pyridazinyl-1-(2,3',4',5'-tetrafluoro-5-methoxy-4-biphenylyl)-1,5,7,8-tetrahydro-1,6-naphthyridine-6(2H)-sulfonamide;

Rac-1-(4'-chloro-2,3'-difluoro-5-methoxy-4-biphenylyl)-2-oxo-N-3-pyridazinyl-1,5,7,8-tetrahydro-1,6-naphthyridine-6(2H)-sulfonamide;

P-1-(4'-chloro-2,3'-difluoro-5-methoxy-4-biphenylyl)-2-oxo-N-3-pyridazinyl-1,5,7,8-tetrahydro-1,6-naphthyridine-6(2H)-sulfonamide;

M-1-(4'-chloro-2,3'-difluoro-5-methoxy-4-biphenylyl)-2-oxo-N-3-pyridazinyl-1,5,7,8-tetrahydro-1,6-naphthyridine-6(2H)-sulfonamide;

Rac-1-(3'-chloro-2,4'-difluoro-5-methoxy-4-biphenylyl)-2-oxo-N-3-pyridazinyl-1,5,7,8-tetrahydro-1,6-naphthyridine-6(2H)-sulfonamide;

P-1-(3'-chloro-2,4'-difluoro-5-methoxy-4-biphenylyl)-2-oxo-N-3-pyridazinyl-1,5,7,8-tetrahydro-1,6-naphthyridine-6(2H)-sulfonamide;

M-1-(3'-chloro-2,4'-difluoro-5-methoxy-4-biphenylyl)-2-oxo-N-3-pyridazinyl-1,5,7,8-tetrahydro-1,6-naphthyridine-6(2H)-sulfonamide;

Rac-1-(3'-chloro-2,2'-difluoro-5-methoxy-4-biphenylyl)-2-oxo-N-3-pyridazinyl-1,5,7,8-tetrahydro-1,6-naphthyridine-6(2H)-sulfonamide;

P-1-(3'-chloro-2,2'-difluoro-5-methoxy-4-biphenylyl)-2-oxo-N-3-pyridazinyl-1,5,7,8-tetrahydro-1,6-naphthyridine-6(2H)-sulfonamide;

M-1-(3'-chloro-2,2'-difluoro-5-methoxy-4-biphenylyl)-2-oxo-N-3-pyridazinyl-1,5,7,8-tetrahydro-1,6-naphthyridine-6(2H)-sulfonamide;

Rac-1-(4-(5-chloro-6-methoxy-3-pyridinyl)-5-fluoro-2-methoxyphenyl)-2-oxo-N-3-pyridazinyl-1,5,7,8-tetrahydro-1,6-naphthyridine-6(2H)-sulfonamide;

P-1-(4-(5-chloro-6-methoxy-3-pyridinyl)-5-fluoro-2-methoxyphenyl)-2-oxo-N-3-pyridazinyl-1,5,7,8-tetrahydro-1,6-naphthyridine-6(2H)-sulfonamide;

M-1-(4-(5-chloro-6-methoxy-3-pyridinyl)-5-fluoro-2-methoxyphenyl)-2-oxo-N-3-pyridazinyl-1,5,7,8-tetrahydro-1,6-naphthyridine-6(2H)-sulfonamide;

Rac-1-(2-chloro-3',4'-difluoro-5-methoxy-4-biphenylyl)-N-3-isoxazolyl-2-oxo-1,5,7,8-tetrahydro-1,6-naphthyridine-6(2H)-sulfonamide;

P-1-(2-chloro-3',4'-difluoro-5-methoxy-4-biphenylyl)-N-3-isoxazolyl-2-oxo-1,5,7,8-tetrahydro-1,6-naphthyridine-6(2H)-sulfonamide;

M-1-(2-chloro-3',4'-difluoro-5-methoxy-4-biphenylyl)-N-3-isoxazolyl-2-oxo-1,5,7,8-tetrahydro-1,6-naphthyridine-6(2H)-sulfonamide;

Rac-1-(2,4'-dichloro-3',5-dimethoxy-4-biphenylyl)-N-3-isoxazolyl-2-oxo-1,5,7,8-tetrahydro-1,6-naphthyridine-6(2H)-sulfonamide;

P-1-(2,4'-dichloro-3',5-dimethoxy-4-biphenylyl)-N-3-isoxazolyl-2-oxo-1,5,7,8-tetrahydro-1,6-naphthyridine-6(2H)-sulfonamide;

M-1-(2,4'-dichloro-3',5-dimethoxy-4-biphenylyl)-N-3-isoxazolyl-2-oxo-1,5,7,8-tetrahydro-1,6-naphthyridine-6(2H)-sulfonamide;

Rac-1-(2,3'-dichloro-5'-fluoro-5-methoxy-4-biphenylyl)-N-3-isoxazolyl-2-oxo-1,5,7,8-tetrahydro-1,6-naphthyridine-6(2H)-sulfonamide;

P-1-(2,3'-dichloro-5'-fluoro-5-methoxy-4-biphenylyl)-N-3-isoxazolyl-2-oxo-1,5,7,8-tetrahydro-1,6-naphthyridine-6(2H)-sulfonamide;

M-1-(2,3'-dichloro-5'-fluoro-5-methoxy-4-biphenylyl)-N-3-isoxazolyl-2-oxo-1,5,7,8-tetrahydro-1,6-naphthyridine-6(2H)-sulfonamide;

Rac-1-(2-chloro-5-methoxy-3'-(trifluoromethyl)-4-biphenylyl)-N-3-isoxazolyl-2-oxo-1,5,7,8-tetrahydro-1,6-naphthyridine-6(2H)-sulfonamide;

P-1-(2-chloro-5-methoxy-3'-(trifluoromethyl)-4-biphenylyl)-N-3-isoxazolyl-2-oxo-1,5,7,8-tetrahydro-1,6-naphthyridine-6(2H)-sulfonamide;

M-1-(2-chloro-5-methoxy-3'-(trifluoromethyl)-4-biphenylyl)-N-3-isoxazolyl-2-oxo-1,5,7,8-tetrahydro-1,6-naphthyridine-6(2H)-sulfonamide;

Rac-1-(3'-chloro-4-methoxy-4'-methyl-3-biphenylyl)-2-oxo-N-3-pyridazinyl-1,5,7,8-tetrahydro-1,6-naphthyridine-6(2H)-sulfonamide;

P-1-(3'-chloro-4-methoxy-4'-methyl-3-biphenylyl)-2-oxo-N-3-pyridazinyl-1,5,7,8-tetrahydro-1,6-naphthyridine-6(2H)-sulfonamide;

M-1-(3'-chloro-4-methoxy-4'-methyl-3-biphenylyl)-2-oxo-N-3-pyridazinyl-1,5,7,8-tetrahydro-1,6-naphthyridine-6(2H)-sulfonamide;

Rac-1-(4'-chloro-4-methoxy-3'-methyl-3-biphenylyl)-2-oxo-N-3-pyridazinyl-1,5,7,8-tetrahydro-1,6-naphthyridine-6(2H)-sulfonamide;

P-1-(4'-chloro-4-methoxy-3'-methyl-3-biphenylyl)-2-oxo-N-3-pyridazinyl-1,5,7,8-tetrahydro-1,6-naphthyridine-6(2H)-sulfonamide;

M-1-(4'-chloro-4-methoxy-3'-methyl-3-biphenylyl)-2-oxo-N-3-pyridazinyl-1,5,7,8-tetrahydro-1,6-naphthyridine-6(2H)-sulfonamide;

Rac-1-(3'-chloro-4-methoxy-2'-methyl-3-biphenylyl)-2-oxo-N-3-pyridazinyl-1,5,7,8-tetrahydro-1,6-naphthyridine-6(2H)-sulfonamide;

P-1-(3'-chloro-4-methoxy-2'-methyl-3-biphenylyl)-2-oxo-N-3-pyridazinyl-1,5,7,8-tetrahydro-1,6-naphthyridine-6(2H)-sulfonamide;

M-1-(3'-chloro-4-methoxy-2'-methyl-3-biphenylyl)-2-oxo-N-3-pyridazinyl-1,5,7,8-tetrahydro-1,6-naphthyridine-6(2H)-sulfonamide;

Rac-1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide;

P-1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide;

M-1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide;

Rac-1-(4-bromo-5-fluoro-2-methoxyphenyl)-2-oxo-N-2-pyrimidinyl-1,5,7,8-tetrahydro-1,6-naphthyridine-6(2H)-sulfonamide;

P-1-(4-bromo-5-fluoro-2-methoxyphenyl)-2-oxo-N-2-pyrimidinyl-1,5,7,8-tetrahydro-1,6-naphthyridine-6(2H)-sulfonamide;

M-1-(4-bromo-5-fluoro-2-methoxyphenyl)-2-oxo-N-2-pyrimidinyl-1,5,7,8-tetrahydro-1,6-naphthyridine-6(2H)-sulfonamide;

Rac-1-(4-bromo-5-fluoro-2-methoxyphenyl)-2-oxo-N-3-pyridazinyl-1,5,7,8-tetrahydro-1,6-naphthyridine-6(2H)-sulfonamide;

P-1-(4-bromo-5-fluoro-2-methoxyphenyl)-2-oxo-N-3-pyridazinyl-1,5,7,8-tetrahydro-1,6-naphthyridine-6(2H)-sulfonamide;

M-1-(4-bromo-5-fluoro-2-methoxyphenyl)-2-oxo-N-3-pyridazinyl-1,5,7,8-tetrahydro-1,6-naphthyridine-6(2H)-sulfonamide;

(Rac)-1-(5'-chloro-2-fluoro-2',5-dimethoxy-[1,1'-biphenyl]-4-yl)-2-oxo-N-(pyridazin-3-yl)-1,2,7,8-tetrahydro-1,6-naphthyridine-6(5H)-sulfonamide;
P-1-(5'-chloro-2-fluoro-2',5-dimethoxy-[1,1'-biphenyl]-4-yl)-2-oxo-N-(pyridazin-3-yl)-1,2,7,8-tetrahydro-1,6-naphthyridine-6(5H)-sulfonamide;
M-1-(5'-chloro-2-fluoro-2',5-dimethoxy-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(4-(5-chloro-2-methoxypyridin-3-yl)-5-fluoro-2-methoxyphenyl)-2-oxo-N-(pyridazin-3-yl)-1,2,7,8-tetrahydro-1,6-naphthyridine-6(5H)-sulfonamide;
P-1-(4-(5-chloro-2-methoxypyridin-3-yl)-5-fluoro-2-methoxyphenyl)-2-oxo-N-(pyridazin-3-yl)-1,2,7,8-tetrahydro-1,6-naphthyridine-6(5H)-sulfonamide;
M-1-(4-(5-chloro-2-methoxypyridin-3-yl)-5-fluoro-2-methoxyphenyl)-2-oxo-N-(pyridazin-3-yl)-1,2,7,8-tetrahydro-1,6-naphthyridine-6(5H)-sulfonamide;
(Rac)-1-(4'-chloro-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
P-1-(4'-chloro-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
M-1-(4'-chloro-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(3'-chloro-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
P-1-(3'-chloro-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
M-1-(3'-chloro-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(3'-chloro-2-fluoro-4',5-dimethoxy-[1,1'-biphenyl]-4-yl)-2-oxo-N-(pyridazin-3-yl)-1,2,7,8-tetrahydro-1,6-naphthyridine-6(5H)-sulfonamide;
P-1-(3'-chloro-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
M-1-(3'-chloro-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(5-fluoro-2-methoxy-4-(2-methoxy-5-(trifluoromethyl)pyridin-3-yl)phenyl)-2-oxo-N-(pyridazin-3-yl)-1,2,7,8-tetrahydro-1,6-naphthyridine-6(5H)-sulfonamide;
P-1-(3'-chloro-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
M-1-(3'-chloro-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(3'-chloro-2-fluoro-2',5-dimethoxy-[1,1'-biphenyl]-4-yl)-2-oxo-N-(pyridazin-3-yl)-1,2,7,8-tetrahydro-1,6-naphthyridine-6(5H)-sulfonamide;
P-1-(3'-chloro-2-fluoro-2',5-dimethoxy-[1,1'-biphenyl]-4-yl)-2-oxo-N-(pyridazin-3-yl)-1,2,7,8-tetrahydro-1,6-naphthyridine-6(5H)-sulfonamide;
M-1-(3'-chloro-2-fluoro-2',5-dimethoxy-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(2-fluoro-5-methoxy-3'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;
P-1-(2-fluoro-5-methoxy-3'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;
M-1-(2-fluoro-5-methoxy-3'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(2-fluoro-5-methoxy-4'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;
P-1-(2-fluoro-5-methoxy-4'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;
M-1-(2-fluoro-5-methoxy-4'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(2-fluoro-5-methoxy-3'-(2,2,2-trifluoroethoxy)-[1,1'-biphenyl]-4-yl)-2-oxo-N-(pyridazin-3-yl)-1,2,7,8-tetrahydro-1,6-naphthyridine-6(5H)-sulfonamide;
P-1-(2-fluoro-5-methoxy-3'-(2,2,2-trifluoroethoxy)-[1,1'-biphenyl]-4-yl)-2-oxo-N-(pyridazin-3-yl)-1,2,7,8-tetrahydro-1,6-naphthyridine-6(5H)-sulfonamide;
M-1-(2-fluoro-5-methoxy-3'-(2,2,2-trifluoroethoxy)-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(3'-chloro-2-fluoro-5-methoxy-5'-methyl-[1,1'-biphenyl]-4-yl)-2-oxo-N-(pyridazin-3-yl)-1,2,7,8-tetrahydro-1,6-naphthyridine-6(5H)-sulfonamide;
P-1-(3'-chloro-2-fluoro-5-methoxy-5'-methyl-[1,1'-biphenyl]-4-yl)-2-oxo-N-(pyridazin-3-yl)-1,2,7,8-tetrahydro-1,6-naphthyridine-6(5H)-sulfonamide;
M-1-(3'-chloro-2-fluoro-5-methoxy-5'-methyl-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(3'-chloro-2-fluoro-5,5'-dimethoxy-[1,1'-biphenyl]-4-yl)-2-oxo-N-(pyridazin-3-yl)-1,2,7,8-tetrahydro-1,6-naphthyridine-6(5H)-sulfonamide;
P-1-(3'-chloro-2-fluoro-5,5'-dimethoxy-[1,1'-biphenyl]-4-yl)-2-oxo-N-(pyridazin-3-yl)-1,2,7,8-tetrahydro-1,6-naphthyridine-6(5H)-sulfonamide;
M-1-(3'-chloro-2-fluoro-5,5'-dimethoxy-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(2,4'-difluoro-5-methoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;
P-1-(2,4'-difluoro-5-methoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;
M-1-(2,4'-difluoro-5-methoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(3'-(difluoromethyl)-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
P-1-(3'-(difluoromethyl)-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
M-1-(3'-(difluoromethyl)-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;
(Rac)-1-(2,4'-difluoro-5-methoxy-3'-methyl-[1,1'-biphenyl]-4-yl)-2-oxo-N-(pyridazin-3-yl)-1,2,7,8-tetrahydro-1,6-naphthyridine-6(5H)-sulfonamide;
P-1-(2,4'-difluoro-5-methoxy-3'-methyl-[1,1'-biphenyl]-4-yl)-2-oxo-N-(pyridazin-3-yl)-1,2,7,8-tetrahydro-1,6-naphthyridine-6(5H)-sulfonamide;

M-1-(2,4'-difluoro-5-methoxy-3'-methyl-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(2-fluoro-2',5-dimethoxy-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

P-1-(2-fluoro-2',5-dimethoxy-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

M-1-(2-fluoro-2',5-dimethoxy-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(2-fluoro-5-methoxy-3'-methyl-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

P-1-(2-fluoro-5-methoxy-3'-methyl-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

M-1-(2-fluoro-5-methoxy-3'-methyl-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(2-fluoro-3',5-dimethoxy-5'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;

P-1-(2-fluoro-3',5-dimethoxy-5'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;

M-1-(2-fluoro-3',5-dimethoxy-5'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(3'-chloro-2-fluoro-5-methoxy-5'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;

P-1-(3'-chloro-2-fluoro-5-methoxy-5'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;

M-1-(3'-chloro-2-fluoro-5-methoxy-5'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(2-fluoro-5-methoxy-3'-methyl-5'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;

P-1-(2-fluoro-5-methoxy-3'-methyl-5'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;

M-1-(2-fluoro-5-methoxy-3'-methyl-5'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;

(Rac)-2-oxo-N-(pyridazin-3-yl)-1-(2,3',4'-trifluoro-5,5'-dimethoxy-[1,1'-biphenyl]-4-yl)-1,2,7,8-tetrahydro-1,6-naphthyridine-6(5H)-sulfonamide;

P-2-oxo-N-(pyridazin-3-yl)-1-(2,3',4'-trifluoro-5,5'-dimethoxy-[1,1'-biphenyl]-4-yl)-1,2,7,8-tetrahydro-1,6-naphthyridine-6(5H)-sulfonamide;

M-2-oxo-N-(pyridazin-3-yl)-1-(2,3',4'-trifluoro-5,5'-dimethoxy-[1,1'-biphenyl]-4-yl)-1,2,7,8-tetrahydro-1,6-naphthyridine-6(5H)-sulfonamide;

(Rac)-1-(5-fluoro-2-methoxy-4-(6-methoxy-5-(trifluoromethyl)pyridin-3-yl)phenyl)-2-oxo-N-(pyridazin-3-yl)-1,2,7,8-tetrahydro-1,6-naphthyridine-6(5H)-sulfonamide;

P-1-(5-fluoro-2-methoxy-4-(6-methoxy-5-(trifluoromethyl)pyridin-3-yl)phenyl)-2-oxo-N-(pyridazin-3-yl)-1,2,7,8-tetrahydro-1,6-naphthyridine-6(5H)-sulfonamide;

M-1-(5-fluoro-2-methoxy-4-(6-methoxy-5-(trifluoromethyl)pyridin-3-yl)phenyl)-2-oxo-N-(pyridazin-3-yl)-1,2,7,8-tetrahydro-1,6-naphthyridine-6(5H)-sulfonamide;

(Rac)-1-(2,4'-difluoro-5-methoxy-3'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;

P-1-(2,4'-difluoro-5-methoxy-3'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;

M-1-(2,4'-difluoro-5-methoxy-3'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(2-fluoro-4',5-dimethoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

P-1-(2-fluoro-4',5-dimethoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

M-1-(2-fluoro-4',5-dimethoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(2-fluoro-3',5-dimethoxy-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

P-1-(2-fluoro-3',5-dimethoxy-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

M-1-(2-fluoro-3',5-dimethoxy-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(3'-(difluoromethyl)-2,5'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;

P-1-(3'-(difluoromethyl)-2,5'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;

M-1-(3'-(difluoromethyl)-2,5'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(3'-(difluoromethyl)-2,4'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;

P-1-(3'-(difluoromethyl)-2,4'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;

M-1-(3'-(difluoromethyl)-2,4'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(3'-(difluoromethyl)-2,4',5'-trifluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;

P-1-(3'-(difluoromethyl)-2,4',5'-trifluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;

M-1-(3'-(difluoromethyl)-2,4',5'-trifluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(4'-(difluoromethyl)-2,3'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;

P-1-(4'-(difluoromethyl)-2,3'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;

M-1-(4'-(difluoromethyl)-2,3'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide;

(Rac)-2-oxo-N-(pyrimidin-4-yl)-1-(2,3',5'-trifluoro-5-methoxy-[1,1'-biphenyl]-4-yl)-1,2,7,8-tetrahydro-1,6-naphthyridine-6(5H)-sulfonamide;

P-2-oxo-N-(pyrimidin-4-yl)-1-(2,3',5'-trifluoro-5-methoxy-[1,1'-biphenyl]-4-yl)-1,2,7,8-tetrahydro-1,6-naphthyridine-6(5H)-sulfonamide;

M-2-oxo-N-(pyrimidin-4-yl)-1-(2,3',5'-trifluoro-5-methoxy-[1,1'-biphenyl]-4-yl)-1,2,7,8-tetrahydro-1,6-naphthyridine-6(5H)-sulfonamide;

(Rac)-1-(3'-chloro-2-fluoro-5,5'-dimethoxy-[1,1'-biphenyl]-4-yl)-N-(isoxazol-3-yl)-2-oxo-1,2,7,8-tetrahydro-1,6-naphthyridine-6(5H)-sulfonamide;

P-1-(3'-chloro-2-fluoro-5,5'-dimethoxy-[1,1'-biphenyl]-4-yl)-N-(isoxazol-3-yl)-2-oxo-1,2,7,8-tetrahydro-1,6-naphthyridine-6(5H)-sulfonamide;

M-1-(3'-chloro-2-fluoro-5,5'-dimethoxy-[1,1'-biphenyl]-4-yl)-N-(isoxazol-3-yl)-2-oxo-1,2,7,8-tetrahydro-1,6-naphthyridine-6(5H)-sulfonamide;

(Rac)-1-(2-fluoro-3',5,5'-trimethoxy-[1,1'-biphenyl]-4-yl)-N-(isoxazol-3-yl)-2-oxo-1,2,7,8-tetrahydro-1,6-naphthyridine-6(5H)-sulfonamide;

P-1-(2-fluoro-3',5,5'-trimethoxy-[1,1'-biphenyl]-4-yl)-N-(isoxazol-3-yl)-2-oxo-1,2,7,8-tetrahydro-1,6-naphthyridine-6(5H)-sulfonamide;

M-1-(2-fluoro-3',5,5'-trimethoxy-[1,1'-biphenyl]-4-yl)-N-(isoxazol-3-yl)-2-oxo-1,2,7,8-tetrahydro-1,6-naphthyridine-6(5H)-sulfonamide;

(Rac)-1-(2-chloro-5-methoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

P-1-(2-chloro-5-methoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

M-1-(2-chloro-5-methoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(2-chloro-4'-fluoro-5-methoxy-3'-methyl-[1,1'-biphenyl]-4-yl)-2-oxo-N-(pyridazin-3-yl)-1,2,7,8-tetrahydro-1,6-naphthyridine-6(5H)-sulfonamide;

P-1-(2-chloro-4'-fluoro-5-methoxy-3'-methyl-[1,1'-biphenyl]-4-yl)-2-oxo-N-(pyridazin-3-yl)-1,2,7,8-tetrahydro-1,6-naphthyridine-6(5H)-sulfonamide;

M-1-(2-chloro-4'-fluoro-5-methoxy-3'-methyl-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(4'-fluoro-5-methoxy-2,3'-dimethyl-[1,1'-biphenyl]-4-yl)-2-oxo-N-(pyridazin-3-yl)-1,2,7,8-tetrahydro-1,6-naphthyridine-6(5H)-sulfonamide;

P-1-(4'-fluoro-5-methoxy-2,3'-dimethyl-[1,1'-biphenyl]-4-yl)-2-oxo-N-(pyridazin-3-yl)-1,2,7,8-tetrahydro-1,6-naphthyridine-6(5H)-sulfonamide;

M-1-(4'-fluoro-5-methoxy-2,3'-dimethyl-[1,1'-biphenyl]-4-yl)-2-oxo-N-(pyridazin-3-yl)-1,2,7,8-tetrahydro-1,6-naphthyridine-6(5H)-sulfonamide;

(Rac)-1-(5-fluoro-2-methoxy-4-(3,3,3-trifluoropropyl)phenyl)-N-(isoxazol-3-yl)-2-oxo-1,2,7,8-tetrahydro-1,6-naphthyridine-6(5H)-sulfonamide;

P-1-(5-fluoro-2-methoxy-4-(3,3,3-trifluoropropyl)phenyl)-N-(isoxazol-3-yl)-2-oxo-1,2,7,8-tetrahydro-1,6-naphthyridine-6(5H)-sulfonamide;

M-1-(5-fluoro-2-methoxy-4-(3,3,3-trifluoropropyl)phenyl)-N-(isoxazol-3-yl)-2-oxo-1,2,7,8-tetrahydro-1,6-naphthyridine-6(5H)-sulfonamide;

(Rac)-1-(5-fluoro-2-methoxy-4-(3,3,3-trifluoropropyl)phenyl)-2-oxo-N-(pyridazin-3-yl)-1,2,7,8-tetrahydro-1,6-naphthyridine-6(5H)-sulfonamide;

P-1-(5-fluoro-2-methoxy-4-(3,3,3-trifluoropropyl)phenyl)-2-oxo-N-(pyridazin-3-yl)-1,2,7,8-tetrahydro-1,6-naphthyridine-6(5H)-sulfonamide;

M-1-(5-fluoro-2-methoxy-4-(3,3,3-trifluoropropyl)phenyl)-2-oxo-N-(pyridazin-3-yl)-1,2,7,8-tetrahydro-1,6-naphthyridine-6(5H)-sulfonamide;

(Rac)-1-(5-chloro-2-methoxy-4-(3,3,3-trifluoropropyl)phenyl)-2-oxo-N-(pyridazin-3-yl)-1,2,7,8-tetrahydro-1,6-naphthyridine-6(5H)-sulfonamide;

P-1-(5-chloro-2-methoxy-4-(3,3,3-trifluoropropyl)phenyl)-2-oxo-N-(pyridazin-3-yl)-1,2,7,8-tetrahydro-1,6-naphthyridine-6(5H)-sulfonamide;

M-1-(5-chloro-2-methoxy-4-(3,3,3-trifluoropropyl)phenyl)-2-oxo-N-(pyridazin-3-yl)-1,2,7,8-tetrahydro-1,6-naphthyridine-6(5H)-sulfonamide;

(Rac)-1-(4-bromo-5-fluoro-2-methoxyphenyl)-2-oxo-N-(pyrimidin-4-yl)-1,2,7,8-tetrahydro-1,6-naphthyridine-6(5H)-sulfonamide;

P-1-(4-bromo-5-fluoro-2-methoxyphenyl)-2-oxo-N-(pyrimidin-4-yl)-1,2,7,8-tetrahydro-1,6-naphthyridine-6(5H)-sulfonamide;

M-1-(4-bromo-5-fluoro-2-methoxyphenyl)-2-oxo-N-(pyrimidin-4-yl)-1,2,7,8-tetrahydro-1,6-naphthyridine-6(5H)-sulfonamide;

(Rac)-1-(4-bromo-5-chloro-2-methoxyphenyl)-2-oxo-N-(pyridazin-3-yl)-1,2,7,8-tetrahydro-1,6-naphthyridine-6(5H)-sulfonamide;

P-1-(4-bromo-5-chloro-2-methoxyphenyl)-2-oxo-N-(pyridazin-3-yl)-1,2,7,8-tetrahydro-1,6-naphthyridine-6(5H)-sulfonamide; and M-1-(4-bromo-5-chloro-2-methoxyphenyl)-2-oxo-N-(pyridazin-3-yl)-1,2,7,8-tetrahydro-1,6-naphthyridine-6(5H)-sulfonamide.

In embodiment 9, the present invention provides a compound, an enantiomer, diastereoisomer, atropisomer thereof, or a mixture thereof, or pharmaceutically acceptable salts thereof, selected from:

P-1-(4'-chloro-2-fluoro-3',5-dimethoxy-4-biphenylyl)-2-oxo-N-3-pyridazinyl-1,5,7,8-tetrahydro-1,6-naphthyridine-6(2H)-sulfonamide;

P-1-(4'-chloro-2-fluoro-3',5-dimethoxy-4-biphenylyl)-N-3-isoxazolyl-2-oxo-1,5,7,8-tetrahydro-1,6-naphthyridine-6(2H)-sulfonamide;

Rac-1-(2-fluoro-5-methoxy-3'-(trifluoromethyl)-4-biphenylyl)-N-3-isoxazolyl-2-oxo-1,5,7,8-tetrahydro-1,6-naphthyridine-6(2H)-sulfonamide;

P-1-(2-fluoro-5-methoxy-3'-(trifluoromethyl)-4-biphenylyl)-N-3-isoxazolyl-2-oxo-1,5,7,8-tetrahydro-1,6-naphthyridine-6(2H)-sulfonamide;

P-1-(3'-chloro-2,5'-difluoro-5-methoxy-4-biphenylyl)-N-3-isoxazolyl-2-oxo-1,5,7,8-tetrahydro-1,6-naphthyridine-6(2H)-sulfonamide;

Rac-1-(5-fluoro-2-methoxy-4-(2-methoxy-5-(trifluoromethyl)-3-pyridinyl)phenyl)-N-3-isoxazolyl-2-oxo-1,5,7,8-tetrahydro-1,6-naphthyridine-6(2H)-sulfonamide;

P-1-(4'-chloro-2-fluoro-5-methoxy-3'-methyl-4-biphenylyl)-N-3-isoxazolyl-2-oxo-1,5,7,8-tetrahydro-1,6-naphthyridine-6(2H)-sulfonamide;

P-1-(4'-chloro-2-fluoro-5-methoxy-3'-methyl-4-biphenylyl)-2-oxo-N-2-pyrimidinyl-1,5,7,8-tetrahydro-1,6-naphthyridine-6(2H)-sulfonamide;

P-2-oxo-N-3-pyridazinyl-1-(2,3',4'-trifluoro-5-methoxy-4-biphenylyl)-1,5,7,8-tetrahydro-1,6-naphthyridine-6(2H)-sulfonamide;

P-1-(4'-chloro-2-fluoro-5-methoxy-3'-methyl-4-biphenylyl)-2-oxo-N-3-pyridazinyl-1,5,7,8-tetrahydro-1,6-naphthyridine-6(2H)-sulfonamide;

P-1-(3'-chloro-2,5'-difluoro-5-methoxy-4-biphenylyl)-2-oxo-N-3-pyridazinyl-1,5,7,8-tetrahydro-1,6-naphthyridine-6(2H)-sulfonamide;
Rac-1-(4'-chloro-2-fluoro-5-methoxy-3'-methyl-4-biphenylyl)-2-oxo-N-1,3-thiazol-2-yl-1,5,7,8-tetrahydro-1,6-naphthyridine-6(2H)-sulfonamide;
P-1-(2,3'-difluoro-5-methoxy-5'-(trifluoromethyl)-4-biphenylyl)-2-oxo-N-3-pyridazinyl-1,5,7,8-tetrahydro-1,6-naphthyridine-6(2H)-sulfonamide;
P-1-(3'-cyclopropyl-2-fluoro-5-methoxy-4-biphenylyl)-2-oxo-N-3-pyridazinyl-1,5,7,8-tetrahydro-1,6-naphthyridine-6(2H)-sulfonamide;
P-1-(2-fluoro-5-methoxy-3'-(trifluoromethyl)-4-biphenylyl)-2-oxo-N-3-pyridazinyl-1,5,7,8-tetrahydro-1,6-naphthyridine-6(2H)-sulfonamide;
P-2-oxo-N-3-pyridazinyl-1-(2,3',4',5'-tetrafluoro-5-methoxy-4-biphenylyl)-1,5,7,8-tetrahydro-1,6-naphthyridine-6(2H)-sulfonamide;
P-1-(2,4'-dichloro-3',5-dimethoxy-4-biphenylyl)-N-3-isoxazolyl-2-oxo-1,5,7,8-tetrahydro-1,6-naphthyridine-6(2H)-sulfonamide;
P-1-(2,3'-dichloro-5'-fluoro-5-methoxy-4-biphenylyl)-N-3-isoxazolyl-2-oxo-1,5,7,8-tetrahydro-1,6-naphthyridine-6(2H)-sulfonamide;
P-1-(2-chloro-5-methoxy-3'-(trifluoromethyl)-4-biphenylyl)-N-3-isoxazolyl-2-oxo-1,5,7,8-tetrahydro-1,6-naphthyridine-6(2H)-sulfonamide; and
P-1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide.

In embodiment 9a, the present invention provides a compound, an enantiomer, diastereoisomer, atropisomer thereof, or a mixture thereof, or pharmaceutically acceptable salts thereof, selected from:
1-(4'-chloro-2-fluoro-3',5-dimethoxy-4-biphenylyl)-2-oxo-N-3-pyridazinyl-1,5,7,8-tetrahydro-1,6-naphthyridine-6(2H)-sulfonamide;
1-(4'-chloro-2-fluoro-3',5-dimethoxy-4-biphenylyl)-N-3-isoxazolyl-2-oxo-1,5,7,8-tetrahydro-1,6-naphthyridine-6(2H)-sulfonamide;
1-(2-fluoro-5-metoxy-3'-(trifluoromethyl)-4-biphenylyl)-N-3-isoxazolyl-2-oxo-1,5,7,8-tetrahydro-1,6-naphthyridine-6(2H)-sulfonamide;
1-(3'-chloro-2,5'-difluoro-5-methoxy-4-biphenylyl)-N-3-isoxazolyl-2-oxo-1,5,7,8-tetrahydro-1,6-naphthyridine-6(2H)-sulfonamide;
1-(5-fluoro-2-methoxy-4-(2-methoxy-5-(trifluoromethyl)-3-pyridinyl)phenyl)-N-3-isoxazolyl-2-oxo-1,5,7,8-tetrahydro-1,6-naphthyridine-6(2H)-sulfonamide;
1-(4'-chloro-2-fluoro-5-methoxy-3'-methyl-4-biphenylyl)-N-3-isoxazolyl-2-oxo-1,5,7,8-tetrahydro-1,6-naphthyridine-6(2H)-sulfonamide;
1-(4'-chloro-2-fluoro-5-methoxy-3'-methyl-4-biphenylyl)-2-oxo-N-2-pyrimidinyl-1,5,7,8-tetrahydro-1,6-naphthyridine-6(2H)-sulfonamide;
2-oxo-N-3-pyridazinyl-1-(2,3',4'-trifluoro-5-methoxy-4-biphenylyl)-1,5,7,8-tetrahydro-1,6-naphthyridine-6(2H)-sulfonamide;
1-(4'-chloro-2-fluoro-5-methoxy-3'-methyl-4-biphenylyl)-2-oxo-N-3-pyridazinyl-1,5,7,8-tetrahydro-1,6-naphthyridine-6(2H)-sulfonamide;
1-(3'-chloro-2,5'-difluoro-5-methoxy-4-biphenylyl)-2-oxo-N-3-pyridazinyl-1,5,7,8-tetrahydro-1,6-naphthyridine-6(2H)-sulfonamide;
1-(4'-chloro-2-fluoro-5-methoxy-3'-methyl-4-biphenylyl)-2-oxo-N-1,3-thiazol-2-yl-1,5,7,8-tetrahydro-1,6-naphthyridine-6(2H)-sulfonamide;
1-(2,3'-difluoro-5-methoxy-5'-(trifluoromethyl)-4-biphenylyl)-2-oxo-N-3-pyridazinyl-1,5,7,8-tetrahydro-1,6-naphthyridine-6(2H)-sulfonamide;
1-(3'-cyclopropyl-2-fluoro-5-methoxy-4-biphenylyl)-2-oxo-N-3-pyridazinyl-1,5,7,8-tetrahydro-1,6-naphthyridine-6(2H)-sulfonamide;
1-(2-fluoro-5-methoxy-3'-(trifluoromethyl)-4-biphenylyl)-2-oxo-N-3-pyridazinyl-1,5,7,8-tetrahydro-1,6-naphthyridine-6(2H)-sulfonamide;
2-oxo-N-3-pyridazinyl-1-(2,3',4',5'-tetrafluoro-5-methoxy-4-biphenylyl)-1,5,7,8-tetrahydro-1,6-naphthyridine-6(2H)-sulfonamide;
1-(2,4'-dichloro-3',5-dimethoxy-4-biphenylyl)-N-3-isoxazolyl-2-oxo-1,5,7,8-tetrahydro-1,6-naphthyridine-6(2H)-sulfonamide;
1-(2,3'-dichloro-5'-fluoro-5-methoxy-4-biphenylyl)-N-3-isoxazolyl-2-oxo-1,5,7,8-tetrahydro-1,6-naphthyridine-6(2H)-sulfonamide;
1-(2-chloro-5-methoxy-3'-(trifluoromethyl)-4-biphenylyl)-N-3-isoxazolyl-2-oxo-1,5,7,8-tetrahydro-1,6-naphthyridine-6(2H)-sulfonamide; and
1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide.

In embodiment 10, the present invention provides a compound, an enantiomer, diastereoisomer, atropisomer thereof, or a mixture thereof, or pharmaceutically acceptable salts thereof, recited in embodiments 8 and 9-9a.

In embodiment 11, the present invention provides a P atropisomer of each individual compound, independently, or a mixture thereof, or pharmaceutically acceptable salts thereof, recited in embodiments 8 and 9-9a.

In embodiment 12, the present invention provides an M atropisomer of each individual compound, independently, or a mixture thereof, or pharmaceutically acceptable salts thereof, recited in embodiments 8 and 9-9a.

In embodiment 13, the present invention provides pharmaceutical compositions comprising a compound, an enantiomer, diastereoisomer, atropisomer thereof, or a mixture thereof, or pharmaceutically acceptable salts thereof, in accordance with any one of embodiments 1, 1a-1i, 2, 2a-2b, 3, 4a-4d, 5, 5a-5b, 6, 7, 7a-7m, 8, 9-9a, 10, 11, 12, and a pharmaceutically acceptable excipient.

In embodiment 14, the present invention provides methods of treating pain, cough, or itch, the methods comprising administering to a patient in need thereof a therapeutically effective amount of a compound, an enantiomer, diastereoisomer, atropisomer thereof, or a mixture thereof, or pharmaceutically acceptable salts thereof, in accordance with any one of embodiments 1, 1a-1i, 2, 2a-2b, 3, 4a-4d, 5, 5a-5b, 6, 7, 7a-7m, 8, 9-9a, 10, 11, 12, or a pharmaceutically acceptable salt thereof.

In embodiment 15, the present invention provides methods of embodiment 14 wherein the pain is selected from chronic pain, acute pain, neuropathic pain, pain associated with rheumatoid arthritis, pain associated with osteoarthritis, pain associated with cancer, cancer, or pain associated with diabetes.

In embodiment 16, the present invention provides methods of embodiment 30 wherein the cough is selected from post viral cough, viral cough, or acute viral cough. See Dib-Hajj. et. al., "The Nav1.7 sodium channel: from molecule to man", *Nature Reviews Neuroscience* (2013), 14, 49-62.

In embodiment 17, the invention provides a method of preparing a compound of Formula (I) as described above. In a sub embodiment, said method is as described in any of Scheme A below.

In embodiment 18, the invention provides an intermediate compound used in the method of preparing a compound of Formula (I) as described above. In a sub embodiment, said intermediate compound is as described in Scheme A below.

DETAILED DESCRIPTION OF THE INVENTION

The present invention provides compounds of Formula (I), as defined above, an enantiomer, diastereoisomer, atropisomer thereof, or a mixture thereof, or pharmaceutically acceptable salts thereof. The present invention also provides pharmaceutical compositions comprising a compound of Formula (I), compound, an enantiomer, diastereoisomer, atropisomer thereof, or a mixture thereof, or pharmaceutically acceptable salts thereof, and methods of treating diseases and/or conditions, such as pain, using compounds of Formula (I), compound, an enantiomer, diastereoisomer, atropisomer thereof, or a mixture thereof, or pharmaceutically acceptable salts thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "halo$C_{1-6}$alkyl" means a straight or branched alkyl chain having one to six carbons and substituted with one or more halo groups. Representative examples of halo$C_{1-6}$alkyl groups include methyl bromide (—$CH_2Br$), 2-fluoroethyl, 3-chloropropyl, 2,3-dichloropropyl (—$CH_2CH(Cl)CH_2Cl$), 3-iodoisopropyl, 4-fluorobutyl and the like. Typical alkyl groups are alkyl groups having from 1 to 8 carbon atoms, which groups are commonly represented as $C_{1-8}$alkyl.

The term "hydroxy$C_{1-6}$alkyl" means a straight or branched alkyl chain having one to six carbons and substituted with one or more hydroxyl groups. Representative examples of hydroxy$C_{1-6}$alkyl groups include hydroxymethyl (—$CH_2OH$), 2-hydroxyethyl, 3-hydroxypropyl, 2,3-dihydroxypropyl (—$CH_2CH(OH)CH_2OH$), 3-hydroxyisopropyl, 4-hydroxybutyl and the like. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. Common cycloalkyl groups are $C_{3-8}$ cycloalkyl groups.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is —$CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heterotaoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heterotaoms are particularly common.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "unsubstituted" means a hydrogen atom on a molecule or group. The term "substituted" means that a hydrogen atom on a molecule or group is replaced with a group or atom. Typical substituents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring.

The term "oxo", when used as a substituent, means the =O group, which is typically attached to a carbon atom.

A group or atom that replaces a hydrogen atom is also called a substituent.

Any particular molecule or group can have one or more substituent depending on the number of hydrogen atoms that can be replaced.

The symbol "-" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptoms of a particular disease or condition, or prevents or delays the onset of one of more symptoms of a particular disease or condition.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered by a tablet, while another is administered by injection or orally as a syrup. All combinations, delivery methods and administration sequences are contemplated.

The compounds of the present invention may be used in the manufacture of a medicament for the treatment of a disease and/or condition mediated by Nav 1.7, such as pain, chronic cough or itch.

Pain is typically divided into primary types: chronic and acute pain based on the duration of the pain. Typically, chronic pain lasts for longer than 3 months. Examples of chronic pain include pain associated with rheumatoid arthritis, osteoarthritis, lumbosacral radiculopathy or cancer. Chronic pain also includes idiopathic pain, which is pain that has no identified cause. An example of idiopathic pain is fibromyalgia.

Another type of pain is nociceptive pain. Nociceptive pain is caused by stimulation of peripheral nerve fibers that respond to highly noxious events such as thermal, mechanical or chemical stimuli.

Still another type of pain is neuropathic pain. Neuropathic pain is pain that is caused by damage or disease affecting a part of the nervous system. Phantom limb pain is a type of neuropathic pain. In phantom limb pain, the body detects pain from a part of a body that no longer exists. For example, a person who has had a leg amputated may feel leg pain even though the leg no longer exists.

In one embodiment of the methods of treatment provided by the present invention using the compounds of Formula (I), or pharmaceutically acceptable salts thereof, the disease is chronic pain. In another aspect, the chronic pain is associated with, but are not limited to, post-herpetic neuralgia (shingles), rheumatoid arthritis, osteoarthritis, diabetic neuropathy, complex regional pain syndrome (CRPS), cancer or chemotherapy-induced pain, chronic back pain, phantom limb pain, trigeminal neuralgia, HIV-induced neuropathy, cluster headache disorders, and migraine, primary erythromelalgia, and paroxysmal extreme pain disorder. Other indications for Nav 1.7 inhibitors include, but are not limited to, depression (Morinville et al., *J Comp Neurol.*, 504:680-689 (2007)), bipolar and other CNS disorders (Ettinger and Argoff, *Neurotherapeutics,* 4:75-83 (2007)), epilepsy: ibid., and Gonzalez, Termin, Wilson, *Methods and Principles in Medicinal Chemistry,* 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2): 830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J Mol. Cell Cardiol.* 42(3):469-477, 2007), schizophrenia, neuroprotection after stroke, drug and alcohol abuse (Johannessen L. C., *CNS Drugs* 22(1)27-47, 2008), Alzheimer's (Kim D. Y., et. al., *Nat. Cell. Biol.* 9(7):755-764, 2007), and cancer (Gillet L., et. al., *J Biol Chem* 2009, January 28 (epub)).

Another aspect of the invention relates to a method of treating acute and/or chronic inflammatory and neuropathic pain, dental pain, general headache, migraine, cluster headache, mixed-vascular and non-vascular syndromes, tension headache, general inflammation, arthritis, rheumatic diseases, rheumatoid arthritis, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain. Another preferred type of pain to be treated is chronic inflammatory pain.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cycloxogenase inhibitors and opiod analgesics.

The compounds of the present invention may also be used to treat diabetes, obesity and/or to facilitate weight loss.

The compounds of the present invention may be used in combination with other pharmaceutically active compounds. It is noted that the term "pharmaceutically active compounds" can include biologics, such as proteins, antibodies and peptibodies.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed by said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, cocrystyals, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$) alkanoyloxymethyl, 1-(alkanoyloxy)ethyl having from 4 to 9 carbon atoms, 1-methyl-1-(alkanoyloxy)ethyl having from 5, 6, 7, 8, 9, or 10 carbon atoms, alkoxycarbonyloxymethyl having from 3 to 6 carbon atoms, 1-(alkoxycarbonyloxy) ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

In addition, if a compound of the present invention comprises a sulfonamide moiety, a prodrug can be formed by replacement of the sulfonamide N(H) with a group such as —CH$_2$P(O)(O($C_1$-$C_6$)alkyl)$_2$ or —CH$_2$OC(O)($C_1$-$C_6$) alkyl.

The compounds of the present invention also include tautomeric forms of prodrugs.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers.

The compounds of general formula (I) may also exist in the form of atropisomers. Atropisomers are compounds with identical structural formulae, but which have a particular spatial configuration resulting from a restricted rotation around a single bond, due to a major steric hindrance on either side of this single bond. Atropisomerism is independent of the presence of stereogenic elements, such as an asymmetric carbon. The terms "P atropisomer" or "M atropisomer" are used herein in order to be able to clearly name two atropisomers of the same pair. For example, the following compound of Example 28 having the structure below can be separated into the pair of atropisomers Example 28-P and Example 28-M via a chiral column:

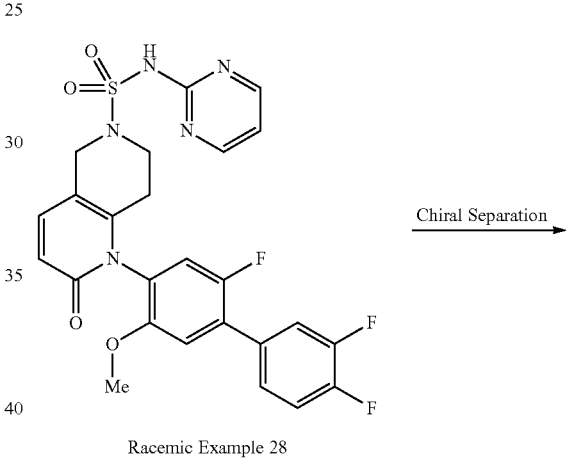

Racemic Example 28

Chiral Separation →

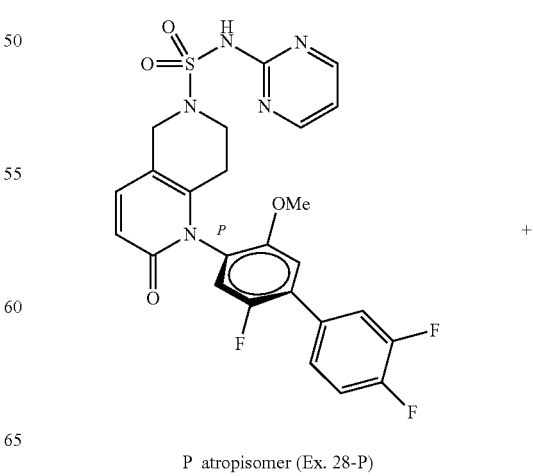

P atropisomer (Ex. 28-P)       +

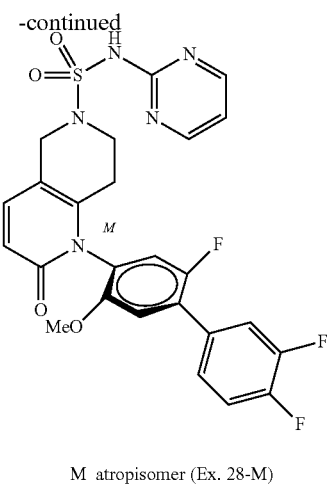

M atropisomer (Ex. 28-M)

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention. Other examples of tautomerism are as follows:

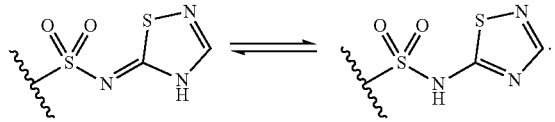 [SMILES: *S(=O)(=O)/N=c1/[nH]cns1 ; *S(=O)(=O)Nc1ncns1]

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{31}$P, $^{32}$P, $^{35}$S, $^{18}$F, and $^{36}$Cl. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents and other publications recited herein are hereby incorporated by reference in their entirety.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: Agilent Zorbax Eclipse XDB-C8 4.6×150 mm, 5 μm, 5 to 100% CH$_3$CN in H$_2$O with 0.1% TFA for 15 min at 1.5 mL/min; System B: Zorbax SB-C8, 4.6×75 mm, 10 to 90% CH$_3$CN in H$_2$O with 0.1% formic acid for 12 min at 1.0 mL/min) (Agilent Technologies, Santa Clara, Calif.). Silica gel chromatography was generally performed with prepacked silica gel cartridges (Biotage, Uppsala, Sweden or Teledyne-Isco, Lincoln, Nebr.). $^1$H NMR spectra were recorded on a Bruker AV-400 (400 MHz) spectrometer (Bruker Corporation, Madison, Wis.) or a Varian (Agilent Technologies, Santa Clara, Calif.) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, Calif.) LC/MS with UV detection at 254 nm and 215 nm and a low resonance electrospray mode (ESI).

The following abbreviations may be used herein:

| | |
|---|---|
| AmPhos | 4-(di-tert-butylphosphino)-N,N-dimethylaniline |
| AcCl | acetyl chloride |
| CAN | acetonitrile |
| AcOH | acetic acid |
| aq or aq. | Aqueous |
| BOC or Boc | tert-butyloxycarbonyl |
| DAST | diethylaminosulfur trifluoride |
| DCM | dichloromethane |
| DMAP | 4-dimethylaminopyridine |
| DMB | dimethoxybenzyl |
| DME | dimethoxyethane |
| DMF | N,N-dimethylformamide |
| DMSO | dimethyl sulfoxide |
| Dppf, DPPF or dppf | 1,1'-bis(diphenylphosphino)ferrocene |
| ESI or ES | electrospray ionization |
| Et | Ethyl |
| Et$_2$O | diethyl ether |
| TEA or Et$_3$N | triethylamine |
| EtOAc | ethyl acetate |
| eq or eq. | equivalent |
| G | Grams |
| h or hr | Hour |
| HPLC | high pressure liquid chromatography |
| iPr | isopropyl |
| iPr$_2$Net | N-ethyl diisopropylamine (Hunig's base) |
| KOAc | potassium acetate |
| KHMDS | potasium hexamethyldisilazide |
| LC MS, LCMS, LC-MS or LC/MS | liquid chromatography mass spectroscopy |
| LHMDS or LiHMDS | lithium hexamethyldisilazide |
| m/z | mass divided by charge |
| Me | methyl |
| MeOH | methanol |
| MeCN or CAN | acetonitrile |
| Mg | milligrams |
| Min | minutes |
| mL | milliliters |
| MPLC | medium pressure liquid chromatography |
| MS | mass spectra |
| NaHMDS | sodium hexamethyldisilazide |
| NBS | N-bromosuccinimide |
| NCS | N-chlorosuccinimide |
| n-BuLi | n-butyllithium |
| NMR | nuclear magnetic resonance |
| Pd$_2$(dba)$_3$ | tris(dibenzylideneacetone)dipalladium(0) |
| Ph | Phenyl |
| PMB | p-methoxybenzyl |
| Pr or PR or PG | protecting group |
| RBF or round bottomed flask | round bottom flask |
| RT or rt | room temperature |
| SCX | strong cation exchange |
| SEM | 2-(trimethylsilyl)ethoxymethyl |
| SFC | supercritical fluid chromatography |
| TBAF | tetra-n-butylammonium fluoride |
| t-BuOH | tert-butanol |
| TIPS-Cl | triisopropylsilyl chloride |
| TFA | trifluoroacetic acid |
| THF | tetrahydrofuran |
| UV | ultraviolet |
| Xantphos | 4,5-bis(diphenylphosphino)-9,9-dimethylxanthene |
| X-Phos | 2-dicyclohexylphosphino-2',4',6'-triisopropyl-1,1'-biphenyl |

General Synthetic Scheme

Compounds of the present invention can be made by the methods depicted in the general reaction schemes shown below.

Unless otherwise stated, starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) and subgenus thereof, i.e., Formulae (Ia) and (Ib), as defined in the Summary of the Invention can be prepared as illustrated and described below.

Scheme A

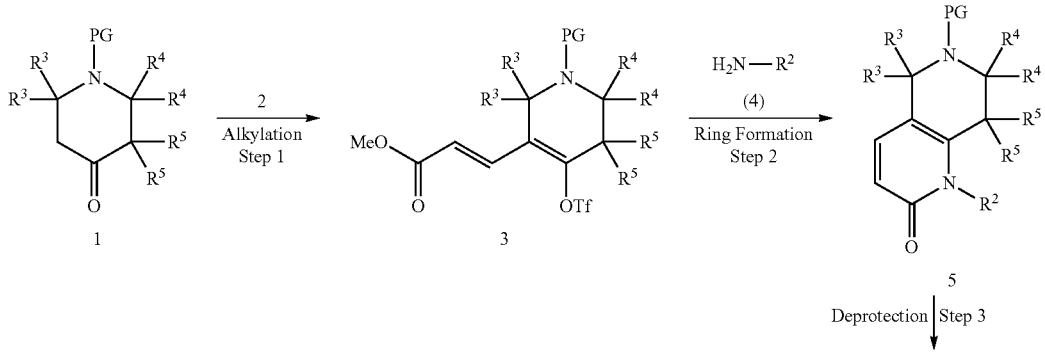

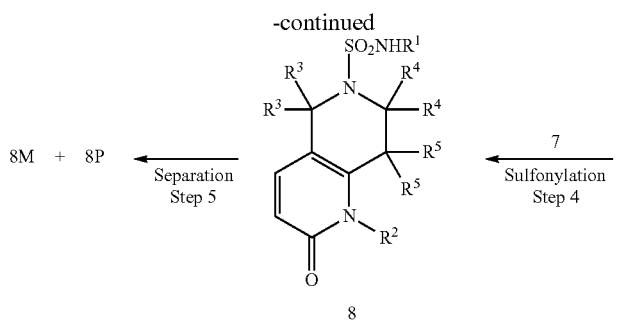 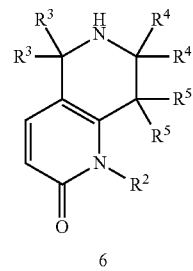

Step 1:

Alkylation Step. In step 1, a ketone, such as starting material 1, wherein $R^3$, $R^4$, and $R^5$ are as defined in the summary of the inventions, such as H or methyl, and PG is an amino protecting group, such as tert-Butyloxycarbonyl (BOC) group or Benzyl (Bn) group, can be reacted with compound 2, such as methyl 3-methoxyacrylate, in the presence of a base, such as t-BuOK, in an organic solvent, such as a polar ethereal solvent, such as THF, at −78° C. to room temperature, to form intermediate compound 3.

Step 2:

Ring Formation Step. Intermediate compound 3 can be reacted with an amine reagent 4 in the presence of a catalyst, such as tris(dibenzylideneacetone)dipalladium (0), in the presence of a base, such as cesium carbonate in various solvents, such as toluene, 1,4-dioxane, THF, or DME, at an elevated temperature, such as from room temperature to 100° C., to form compound 5.

Step 3:

Deprotection Step. Compound 5 can be reacted with a deprotecting agent, for example a tert-butyloxycarbonyl protecting group (Boc) removal agent, such as trifluoroacetic acid, in a solvent such as THF, methylene chloride, $CCl_4$, or neat, at ambient temperature, or alternatively a benzyl protecting group (Bn) removal agent, such as hydrogenolysis with palladium in the presence of carbon and hydrogen gas, in a solvent, such as ethyl acetate, methanol, ethanol, or THF, to form compound 6.

Step 4:

Sulfonylation step: Compound 6 can be reacted with a sulfonamide intermediate compound 7, such as N-(isoxazol-3-yl)-2-oxooxazolidine-3-sulfonamide, in the presence of a base, such as diisopropylethylamine or triethylamine, in various solvents, such as acetonitrile or benzonitrile, at an elevated temperature, such as 130° C., to form a racemic compound 8.

Step 5:

Separation step: Racemic compound 8 can be separated via chiral column, such as chiral SFC separation ((S,S) Whelk-O column, in a solvent, such as 35% methanol, into a pair of atropisomers 8P and 8M.

CrossCoupling Step:

Within Scheme A, compound 8 may contain further substitutions. Such compound 8 can be prepared by adding a Cross-Coupling Step within Scheme A In one embodiment, such Cross-Coupling Step can be performed in the preparation of the amino reagent compound 4. A compound 4 having formula

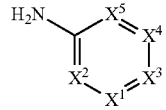

(4-1); wherein $X^1$ is CH or N; $X^2$ is CH or $CR^6$ (for example, wherein $R^6$ is methyl, ethoxy, or methoxy); $X^3$ is CH or $CR^6$ (for example, wherein $R^6$ is halo, or $haloC_{1-6}alkyl$); $X^4$ is CH or $CR^6$ (for example, wherein $R^6$ is F, Cl, Br, methyl, or $—CH_2F$); and $X^5$ is CH or $CR^6$ (for example, wherein $R^6$ is F, Cl, Br, or methyl); are commercially available or can be prepared according to methods known to those skilled in the art.

Compound of formula 4-1, as described above, wherein $X^3$ is CH or $CR^6$ (for example, wherein $R^6$ is $—(CR^bR^b)_mA$, or $—C_{2-6}alkynyl-A$), hereinafter compound 4-2, can be prepared by performing a Cross-Coupling Step as follows:

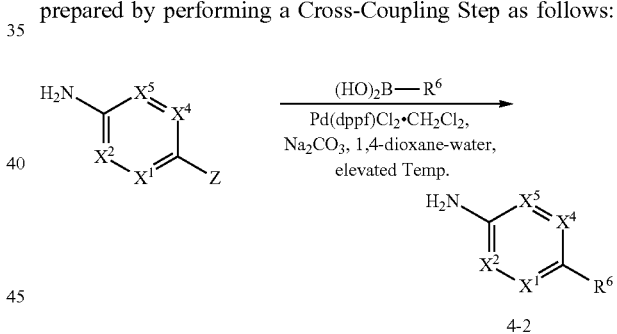

Similarly, Compound of formula 4-1, as described above, wherein $X^4$ is CH or $CR^6$ (for example, wherein $R^6$ is $—(CR^bR^b)_mA$, or $—C_{2-6}alkynyl-A$), hereinafter compound 4-3, can be prepared by performing a Cross-Coupling Step as follows:

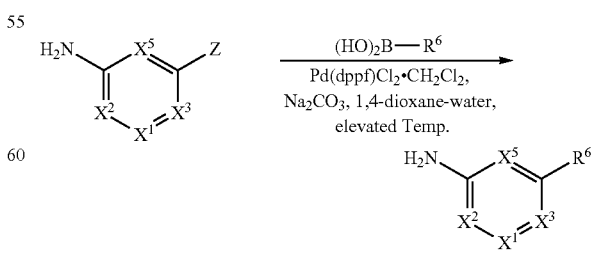

Specifically, in the preparation of Compounds of formula 4-2 and 4-3, as described above, a starting material having formula NH$_2$—R$^2$, wherein R$^2$ is

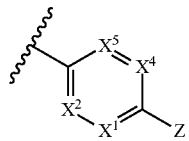 or 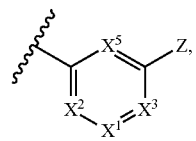

wherein X$^1$, X$^2$, X$^3$, X$^4$, and X$^5$ are as described in the Compound of formula 4-1, and Z can be halo, such as bromo, can be reacted with a coupling reagent, such as a boronic acid or ester reagent of formula (OH)$_2$—B—(CR$^b$R$^b$)$_m$A or (OH)$_2$—B—C$_{2-6}$alkynyl-A, respectively, wherein B is boron, and A, R$^b$, and m are as defined in the summary of the invention, in the presence of a catalyst, such as 1,1'-bis(diphenylphosphino)ferrocene palladium(II)dichloride dichloromethane adduct, in the presence of a base, such as aqueous sodium carbonate solution, in a solvent such as dioxane/water, or DMF, at an elevated temperature, such as 50° C. or 80° C., to form a Compound of formula 4-2 or 4-3.

In another embodiment, such Cross-Coupling Step can be performed after any of Steps 2, 3, 4, or 5 in Scheme A. For Example, such Cross Coupling Step can be performed after Step 3 (Deprotection Step) before Step 4 (Sulfonylation Step) of Scheme A as follows:

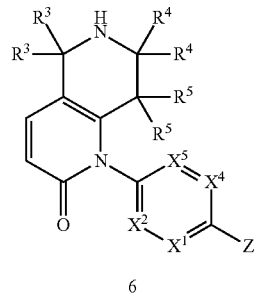

6

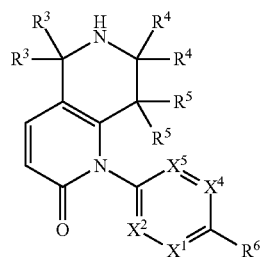

6-1

Specifically, Compound 6, which is a product of Step 3 of Scheme A, wherein X$^1$, X$^2$, X$^4$, and X$^5$ are as described in the Compound of formula 4-1, and X$^3$ is C—Z, wherein Z is halo, such as bromo, can be reacted with a coupling reagent, such as a boronic acid or ester reagent of formula (OH)$_2$—B—(CR$^b$R$^b$)$_m$A or (OH)$_2$—B—C$_{2-6}$alkynyl-A, respectively, wherein B is boron, and A, R$^b$, and m are as defined in the summary of the invention, in the presence of a catalyst, such as 1,1'-bis(diphenylphosphino)ferrocene palladium(II)dichloride dichloromethane adduct, in the presence of a base, such as aqueous sodium carbonate solution, in a solvent such as dioxane/water, or DMF, at an elevated temperature, such as 50° C. or 80° C., to form a compound 6-1 wherein X$^3$ is CR$^6$, wherein R$^6$ is (CR$^b$R$^b$)$_m$A, or —C$_{2-6}$alkynyl-A.

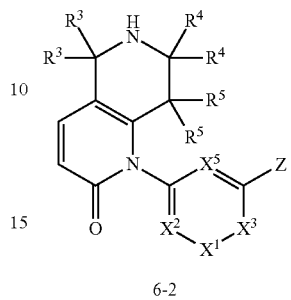

6-2

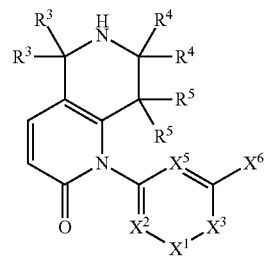

6-3

Alternatively, Compound 6-2, which is a product of Step 3 of Scheme A, wherein X$^1$, X$^2$, X$^3$, and X$^5$ are as described in the Compound of formula 4-1, and X$^4$ is C—Z, wherein Z is halo, such as bromo, can be reacted with a coupling reagent, such as a boronic acid or ester reagent of formula (OH)$_2$—B—(CR$^b$R$^b$)$_m$A or (OH)$_2$—B—C$_{2-6}$alkynyl-A, respectively, wherein B is boron, and A, R$^b$, and m are as defined in the summary of the invention, in the presence of a catalyst, such as 1,1'-bis(diphenylphosphino)ferrocene palladium(II)dichloride dichloromethane adduct, in the presence of a base, such as aqueous sodium carbonate solution, in a solvent such as dioxane/water, or DMF, at an elevated temperature, such as 50° C. or 80° C., to form a compound 6-3 wherein X$^4$ is CR$^6$, wherein R$^6$ is (CR$^b$R$^b$)$_m$A, or —C$_{2-6}$alkynyl-A.

Alternatively, such Cross-Coupling Step can be performed after Step 4 (Sulfonylation Step) before Step 5 (Separation Step) of Scheme A as follows:

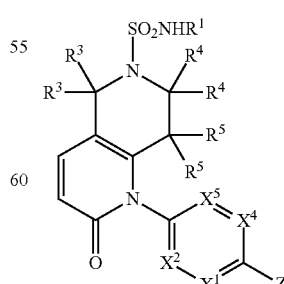

8

-continued

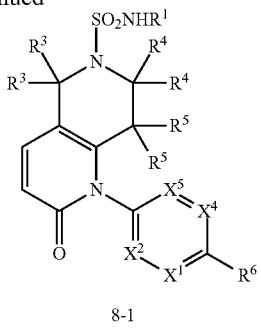

8-1

Specifically, Compound 8, which is a product of Step 4 of Scheme A, wherein $X^1$, $X^2$, $X^4$, and $X^5$ are as described in the Compound of formula 4-1, and $X^3$ is C—Z, wherein Z is halo, such as bromo, can be reacted with a coupling reagent, such as a boronic acid or ester reagent of formula $(OH)_2$—B—$(CR^bR^b)_m$A or $(OH)_2$—B—$C_{2-6}$alkynyl-A, respectively, wherein B is boron, and A, $R^b$, and m are as defined in the summary of the invention, in the presence of a catalyst, such as 1,1'-bis(diphenylphosphino)ferrocene palladium(II)dichloride dichloromethane adduct, in the presence of a base, such as aqueous sodium carbonate solution, in a solvent such as dioxane/water, or DMF, at an elevated temperature, such as 50° C. or 80° C., to form a compound 8-1 wherein $X^3$ is $CR^6$, wherein $R^6$ is $(CR^bR^b)_m$A, or —$C_{2-6}$alkynyl-A.

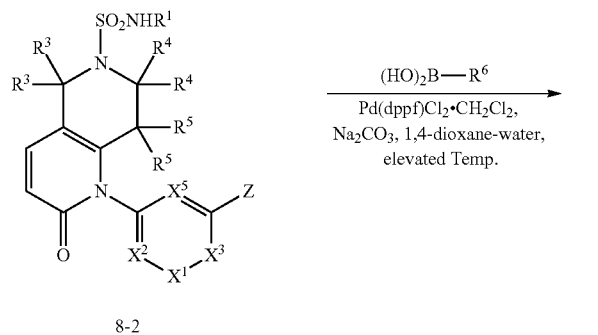

8-2

Alternatively, Compound 8-2, which is a product of Step 4 of Scheme A, wherein $X^1$, $X^2$, $X^3$, and $X^5$ are as described in the Compound of formula 4-1, and $X^4$ is C—Z, wherein Z is halo, such as bromo, can be reacted with a coupling reagent, such as a boronic acid or ester reagent of formula $(OH)_2$—B—$(CR^bR^b)_m$A or $(OH)_2$—B—$C_{2-6}$alkynyl-A, respectively, wherein B is boron, and A, $R^b$, and m are as defined in the summary of the invention, in the presence of a catalyst, such as 1,1'-bis(diphenylphosphino)ferrocene palladium(II)dichloride dichloromethane adduct, in the presence of a base, such as aqueous sodium carbonate solution, in a solvent such as dioxane/water, or DMF, at an elevated temperature, such as 50° C. or 80° C., to form a compound 8-3 wherein $X^4$ is $CR^6$, wherein $R^6$ is $(CR^bR^b)_m$A, or —$C_{2-6}$alkynyl-A.

Yet alternatively, such Cross-Coupling Step can be performed after Step 5 (Separation Step) of Scheme A as follows:

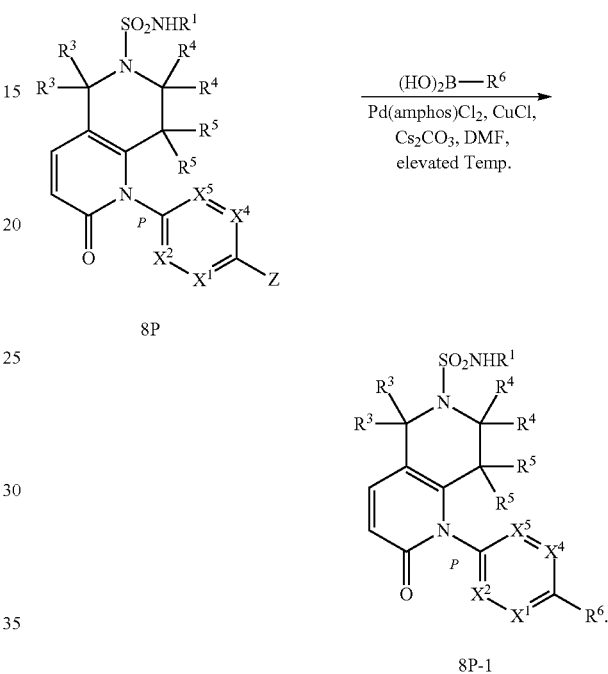

Specifically, Compound 8P, which is the product of Step 5 of Scheme A, wherein $X^1$, $X^2$, $X^4$, and $X^5$ are as described in the Compound of formula 4-1, and $X^3$ is C—Z, wherein Z is halo, such as bromo, can be reacted with a coupling reagent, such as a boronic acid or ester reagent of formula $(OH)_2$—B—$(CR^bR^b)_m$A or $(OH)_2$—B—$C_{2-6}$alkynyl-A, respectively, wherein B is boron, and A, $R^b$, and m are as defined in the summary of the invention, in the presence of a catalyst, such as 1,1-bis[(di-t-butyl-p-methylaminophenyl] palladium(II) chloride and CuCl, in the presence of a base, such as cesium carbonate, in a solvent such as dioxane/water at an elevated temperature, such as 50° C., to form a compound 8P-1 wherein $X^3$ is $CR^6$, wherein $R^6$ is $(CR^bR^b)_m$A, or —$C_{2-6}$alkynyl-A.

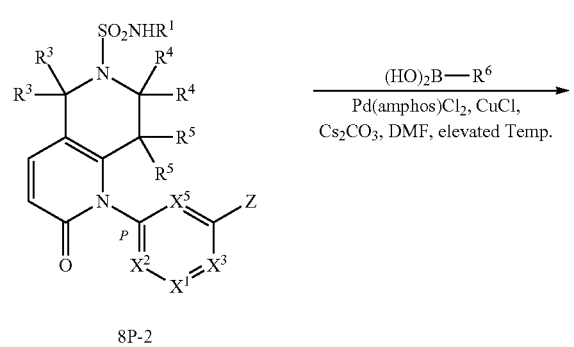

8P-2

-continued

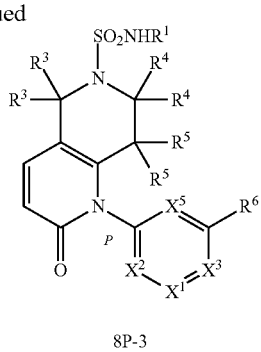

8P-3

Alternatively, Compound 8P-2, which is a product of Step 5 of Scheme A, wherein $X^1$, $X^2$, $X^3$, and $X^5$ are as described in the Compound of formula 4-1, and $X^4$ is C—Z, wherein Z is halo, such as bromo, can be reacted with a coupling reagent, such as a boronic acid or ester reagent of formula $(OH)_2$—B—$(CR^bR^b)_m$A or $(OH)_2$—B—$C_{2-6}$alkynyl-A, respectively, wherein B is boron, and A, $R^b$, and m are as defined in the summary of the invention, in the presence of a catalyst, such as 1,1'-bis(diphenylphosphino)ferrocene palladium(II)dichloride dichloromethane adduct, in the presence of a base, such as aqueous sodium carbonate solution, in a solvent such as dioxane/water, or DMF, at an elevated temperature, such as 50° C., to form a compound 8P-3 wherein $X^4$ is $CR^6$, wherein $R^6$ is $(CR^bR^b)_m$A, or —$C_{2-6}$alkynyl-A.

Preparation of Compound of Formula 3:
According to Generic Scheme A, Compounds of formula 3 were prepared as follows:

Preparation 3a: (E)-Tert-Butyl 3-(3-Methoxy-3-Oxoprop-1-En-1-Yl)-4-(((Trifluoromethyl) Sulfonyl)Oxy)-5,6-Dihydropyridine-1(2H)-Carboxylate

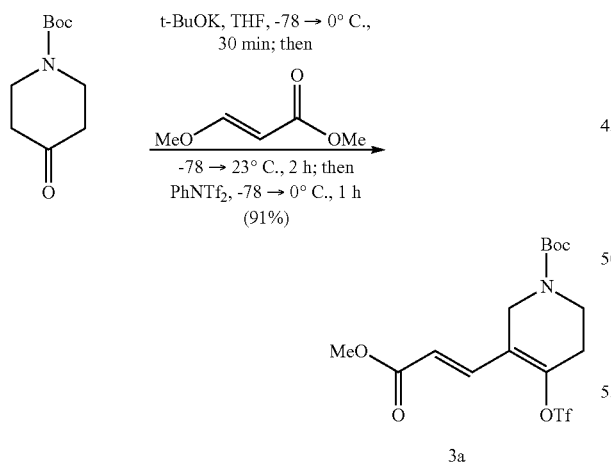

A 1-L round-bottom flask was charged with tert-butyl 4-oxopiperidine-1-carboxylate (Sigma Aldrich, 20.0 g, 100 mmol) and purged with nitrogen. THF (57 ml) was introduced, and the resultant solution cooled to −78° C. in a dry ice-acetone bath. A solution of potassium tert-butoxide (1.6 M in THF, 80 mL, 128 mmol, 1.28 equiv) was added to the reaction mixture via syringe over 5 min. Following addition, the reaction mixture was allowed to warm to 0° C. in an ice-water bath. After 30 min, the peach colored reaction mixture was cooled to −78° C. Methyl 3-methoxyacrylate (22.8 mL, 212 mmol, 2.11 equiv) was added dropwise to the reaction mixture via syringe over 5 min. Following addition, the reaction mixture was allowed to warm to ambient temperature. After 2 h, the resultant red reaction mixture was cooled was cooled to −78° C. N-phenyl bis-trifluoromethane sulfonimide (56.7 g, 159 mmol, 1.58 equiv) was added to the vigorously stirred, cooled reaction mixture in one portion and the resultant reaction mixture was subsequently allowed to warm to 0° C. in an ice-water bath. After 1 h, saturated aqueous sodium bicarbonate solution (200 mL) and EtOAc (200 mL) were added to the reaction mixture, and the layers were separated. The aqueous layer was extracted with EtOAc (3×150 mL), the combined organic layers were dried over anhydrous sodium sulfate, filtered, and concentrated under reduced pressure. The residue was purified by flash column chromatography in two portions (340-g silica gel Biotage column, eluent: gradient, 0 to 30% EtOAc in heptane with 1% $Et_3N$ as an additive) to afford (E)-tert-butyl 3-(3-methoxy-3-oxoprop-1-en-1-yl)-4-(((trifluoromethyl)sulfonyl)oxy)-5,6-dihydropyridine-1(2H)-carboxylate (38.0 g, 91 mmol, 91% yield) as a off-white solid. $^1$H NMR (400 MHz, DMSO-$d_6$) δ ppm 7.45 (d, J=16.07 Hz, 1H) 6.22 (d, J=16.07 Hz, 1H) 4.23 (s, 2H) 3.65-3.81 (m, 3H) 3.32 (s, 2H) 2.62 (d, J=5.91 Hz, 2H) 1.42 (s, 9H). m/z (ESI) 438.0 $(M+Na)^+$.

Preparation of Compound of Formula 4:
According to Generic Scheme A, Compounds of formula 4 were prepared as follows:

Preparation 4a: 2,3',5'-Trifluoro-5-Methoxy-[1,1'-Biphenyl]-4-Amine

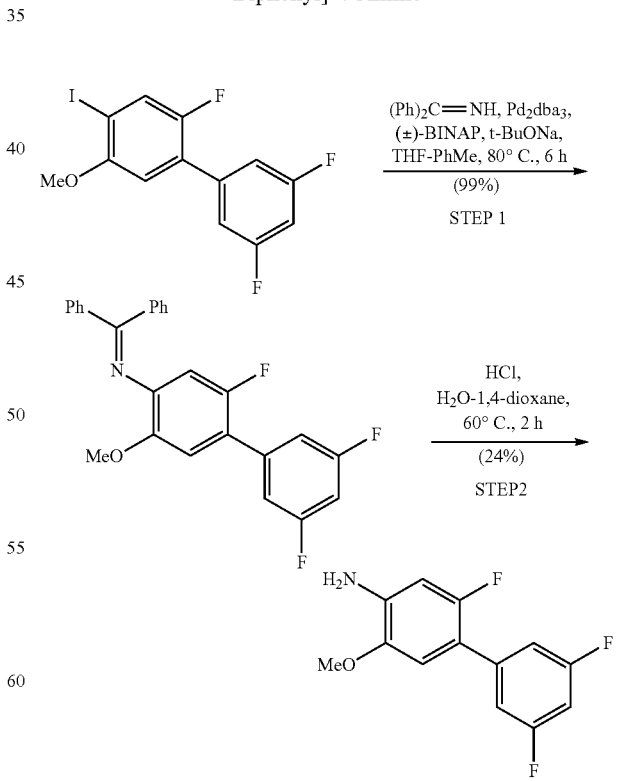

Step 1: N-(Diphenylmethylene)-2,3',5'-Trifluoro-5-Methoxy-[1,1'-Biphenyl]-4-Amine A 200-mL round-bottom flask was charged with tris(dibenzylideneacetone)di-palladium(0)-chloroform adduct (0.14 g, 0.14 mmol), (+/−)-2,2'-bis(diphenylphosphino)-1,1'-binaphthalene (0.26 g, 0.41 mmol) and purged with nitrogen. THF (54.9 ml) was introduced and the resultant reaction mixture stirred at ambient temperature for 30 min before a solution of benzophenone imine (2.77 ml, 16.5 mmol), sodium tert-butoxide (2.35 ml, 19.2 mmol), and 2,3',5'-trifluoro-4-iodo-5-methoxy-1,1'-biphenyl (5.00 g, 13.7 mmol) in toluene (36.0 mL) was added dropwise via cannula over 5 min. The reaction vessel was equipped with a reflux condenser and warmed to reflux in an oil bath. After 6 h, the reaction mixture was allowed to cool to ambient temperature and the reaction mixture was filtered through a pad of Celite®, which was subsequently washed with EtOAc (2×50 ml). The solvent was removed under reduced pressure and the residue purified by flash column chromatography (100-g Biotage column, eluent: gradient, 0 to 30% EtOAc in heptane) to afford N-(diphenylmethylene)-2,3',5'-trifluoro-5-methoxy-[1,1'-biphenyl]-4-amine (5.7 g, 13.7 mmol, 99% yield) as a yellow oil, which was used without further purification. m/z (ESI) 418.2 (M+H)+.

Step 2: 2,3',5'-Trifluoro-5-Methoxy-[1,1'-Biphenyl]-4-Amine

A 100-mL round-bottom flask was charged with N-(diphenylmethylene)-2,3',5'-trifluoro-5-methoxy-[1,1'-biphenyl]-4-amine (5.7 g, 13.7 mmol), 1,4-dioxane (30 mL), and aqueous HCl solution (1.0 M, 13.7 mL, 13.7 mmol) and the mixture was warmed 60° C. After 2 h, the reaction mixture was allowed to cool to ambient temperature and transferred to a 500 mL Erlenmeyer flask. An aqueous solution of sodium carbonate (1.9 M, 50 mL) was introduced. The mixture was extracted with EtOAc (3×50 mL). The combined organic layers were washed with brine (100 mL), dried over anhydrous sodium sulfate, filtered, concentrated under reduced pressure, and purified by flash column chromatography (100-g silica gel Biotage column, eluent: gradient, 0 to 50% EtOAc in heptane) to afford 2,3',5'-trifluoro-5-methoxy-[1,1'-biphenyl]-4-amine (825 mg, 3.26 mmol, 23.7% yield) as a tan amorphous solid. 1H NMR (400 MHz, DMSO-d6) δ ppm 7.20-7.28 (m, 2H) 7.13 (tt, J=9.36, 2.36 Hz, 1H) 6.95 (d, J=7.46 Hz, 1H) 6.50 (d, J=13.06 Hz, 1H) 3.83 (s, 3H). m/z (ESI) 254.2. (M+H)+.

Preparation 4b: 3'-Chloro-4-Methoxy-4'-Methyl-[1,1'-Biphenyl]-3-Amine

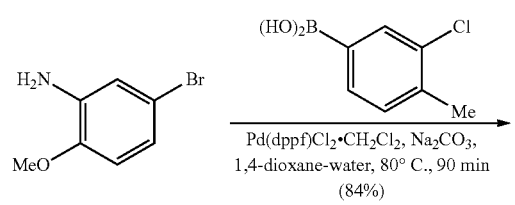

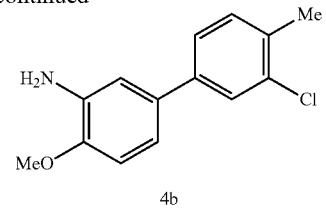

4b

A 50-mL round-bottom flask was charged with 5-bromo-2-methoxy aniline (Alfa Aesar, 1.00 g, 4.95 mmol), 3-chloro-4-methylphenylboronic acid (Acros, 1.69 g, 9.90 mmol), 1,1'-bis(diphenylphosphino)ferrocene palladium(II) dichloride dichloromethane adduct (0.81 g, 0.99 mmol), and purged with nitrogen. 1,4-Dioxane (37.1 ml) and an aqueous sodium carbonate solution (1.9 M, 12.4 mL) were introduced and the reaction mixture was warmed to 80° C. After 90 min, the reaction mixture was allowed to cool to ambient temperature and diluted with aqueous HCl solution (1.0 M, 25 mL) and EtOAc (25 mL). The layers were separated and the aqueous layer extracted with additional EtOAc (2×25 mL). The combined organic layers were washed with brine (50 mL), dried over anhydrous magnesium sulfate, filtered, concentrated under reduced pressure and purified by flash column chromatography (100-g silica gel Biotage column, eluent: gradient, 0 to 40% EtOAc in heptane with DCM as a 5% additive) to afford 3'-chloro-4-methoxy-4'-methyl-[1,1'-biphenyl]-3-amine (1.03 g, 4.16 mmol, 84.0% yield) as a tan solid. 1H NMR (400 MHz, DMSO-d6) δ=7.53 (d, J=1.8 Hz, 1H), 7.44-7.33 (m, 2H), 6.95 (d, J=2.0 Hz, 1H), 6.90-6.80 (m, 2H), 4.93-4.72 (m, 2H), 3.91-3.71 (m, 3H), 2.42-2.25 (m, 3H). m/z (ESI) 248.0 (M+H)+.

Preparation 4c: 4'-Chloro-4-Methoxy-3'-Methyl-[1,1'-Biphenyl]-3-Amine

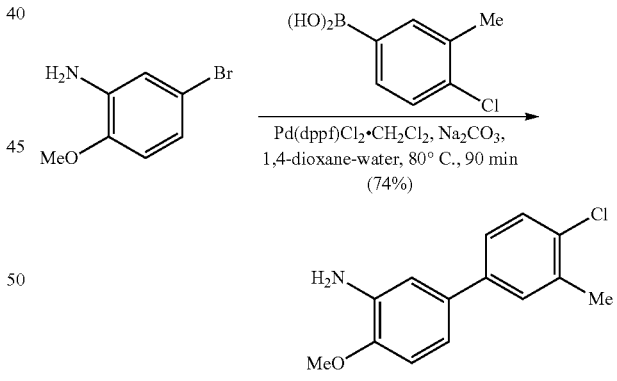

4c

A 50-mL round-bottom flask was charged with 5-bromo-2-methoxy aniline (Alfa Aesar, 1.00 g, 4.95 mmol), 3-chloro-4-methylphenylboronic acid (Alfa Aesar, 1.69 g, 9.90 mmol), 1,1'-bis(diphenylphosphino)ferrocene palladium(II)dichloride dichloromethane adduct (0.81 g, 0.99 mmol), and purged with nitrogen. 1,4-Dioxane (37.1 ml) and an aqueous sodium carbonate solution (1.9 M, 12.4 mL) were introduced and the reaction mixture was warmed to 80° C. After 90 min, the reaction mixture was allowed to cool to ambient temperature and diluted with aqueous HCl solution (1.0 M, 25 mL) and EtOAc (25 mL). The layers were separated and the aqueous layer extracted with additional EtOAc (2×25 mL). The combined organic layers were washed with brine (50 mL), dried over anhydrous magnesium sulfate, filtered, concentrated under reduced pressure and purified by flash column chromatography (100-g silica gel Biotage column, eluent: gradient, 0 to 40% EtOAc in heptane with DCM as a 5% additive) to afford 4'-chloro-4-methoxy-3'-methyl-[1,1'-biphenyl]-3-amine (0.91 g, 3.65 mmol, 73.8% yield) as a tan solid. $^1$H NMR (400 MHz, DMSO-d$_6$) δ=7.51 (d, J=2.2 Hz, 1H), 7.46-7.39 (m, 1H), 7.38-7.32 (m, 1H), 6.93 (d, J=2.2 Hz, 1H), 6.89-6.79 (m, 2H), 4.98-4.68 (m, 2H), 3.92-3.64 (m, 3H), 2.38 (s, 3H). m/z (ESI) 248.0 (M+H)$^+$.

Preparation 4d: 3'-Chloro-4-Methoxy-2'-Methyl-[1,1'-Biphenyl]-3-Amine

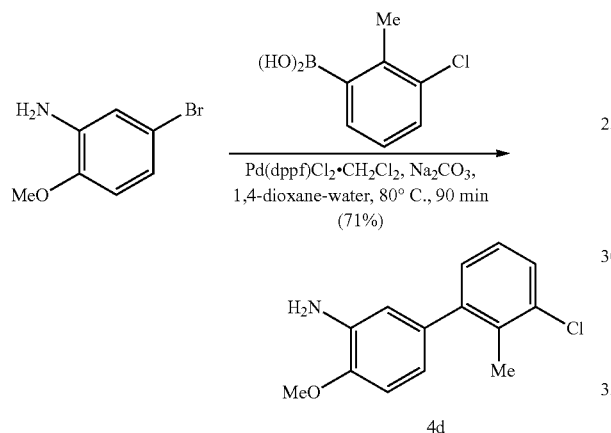

A 50-mL round-bottom flask was charged with 5-bromo-2-methoxy aniline (Alfa Aesar, 259 mg, 1.28 mmol), (3-chloro-2-methylphenyl)boronic acid (Combi-Blocks Inc., 240 mg, 1.41 mmol), 1,1'-bis(diphenylphosphino)ferrocene palladium(II)dichloride dichloromethane adduct (209 mg, 0.26 mmol), and purged with nitrogen. 1,4-Dioxane (9.60 ml) and an aqueous sodium carbonate solution (1.9 M, 3.20 mL) were introduced and the reaction mixture was warmed to 80° C. After 90 min, the reaction mixture was allowed to cool to ambient temperature and diluted with aqueous HCl solution (1.0 M, 25 mL) and EtOAc (25 mL). The layers were separated and the aqueous layer extracted with additional EtOAc (2×25 mL). The combined organic layers were washed with brine (50 mL), dried over anhydrous magnesium sulfate, filtered, concentrated under reduced pressure and purified by flash column chromatography (100-g silica gel Biotage column, eluent: gradient, 0 to 40% EtOAc in heptane with DCM as a 5% additive) to afford 3'-chloro-4-methoxy-2'-methyl-[1,1'-biphenyl]-3-amine (226 mg, 0.91 mmol, 71.3% yield) as a tan solid. $^1$H NMR (400 MHz, DMSO-d$_6$) δ=7.39 (dd, J=1.0, 8.0 Hz, 1H), 7.22 (t, J=7.8 Hz, 1H), 7.12 (dd, J=1.0, 7.6 Hz, 1H), 6.85 (d, J=8.2 Hz, 1H), 6.58 (d, J=2.2 Hz, 1H), 6.46 (dd, J=2.2, 8.1 Hz, 1H), 4.90-4.72 (m, 2H), 3.96-3.66 (m, 3H), 2.34-2.07 (m, 3H). m/z (ESI) 248.2 (M+H)$^+$.

Preparation of Compound of Formula 6:

According to Generic Scheme A, Compounds of formula 6 were prepared as follows:

Preparation 6a: (Rac)-1-(6-(3-Chloro-5-Fluorophenyl)-5-Fluoro-2-Methoxypyridin-3-Yl)-5,6,7,8-Tetrahydro-1,6-Naphthyridin-2(1H)-One

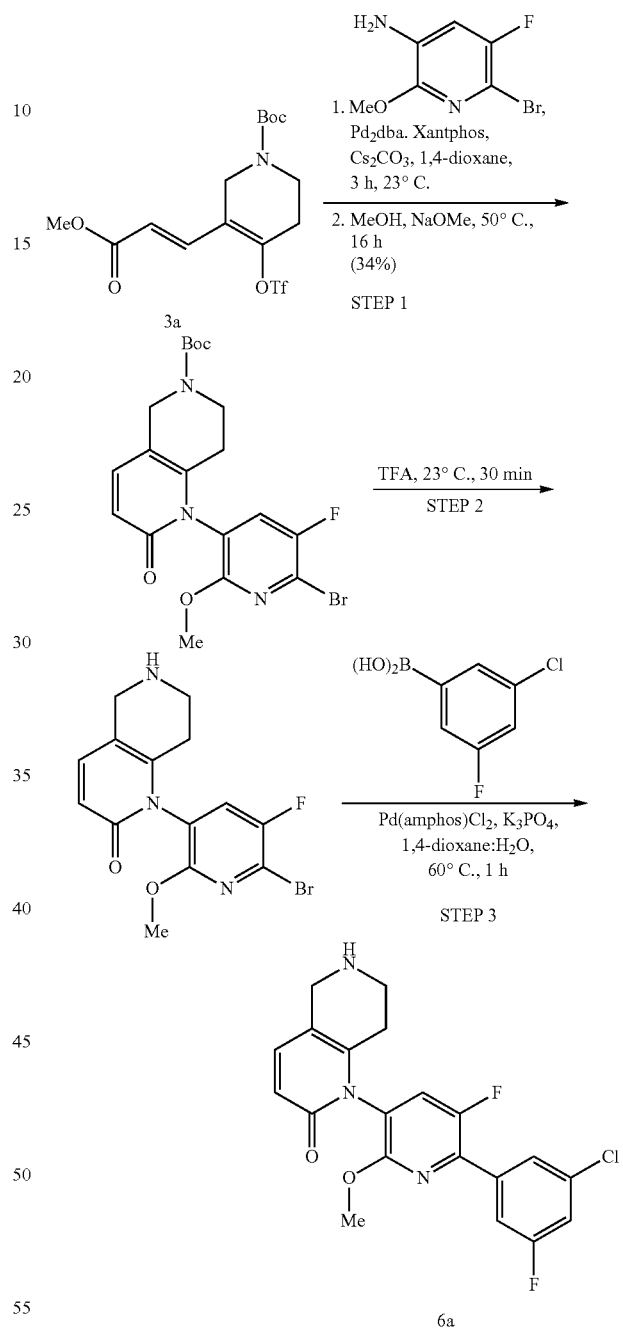

Step 1: (Rac)-Tert-Butyl 1-(6-Bromo-5-Fluoro-2-Methoxypyridin-3-Yl)-2-Oxo-1,2,7,8-Tetrahydro-1,6-Naphthyridine-6(5H)-Carboxylate A vial was charged with (E)-tert-butyl 3-(3-methoxy-3-oxoprop-1-en-1-yl)-4-(((trifluoromethyl)sulfonyl)oxy)-5,6-dihydropyridine-1(2H)-carboxylate (Preparation 3a, 2.15 g, 5.18 mmol), 6-bromo-5-fluoro-2-methoxypyridin-3-amine (1.26 g, 5.70 mmol), xantphos (0.38 g, 0.65 mmol), tris (dibenzylideneacetone)dipalladium(0) (0.24 g, 0.26 mmol), and cesium carbonate (5.05 g, 15.5 mmol). The vial was flushed with Ar (g), then 1,4-dioxane (25.9 ml) was added. The vial was sealed and stirred vigorously at ambient temperature. After 3 h, the reaction mixture was filtered through Celite with the aid of EtOAc, and the filtrate was concentrated under reduced pressure. The residue was dissolved in MeOH (52 mL) and sodium methoxide (25 wt % solution in methanol (0.58 ml, 2.59 mmol). A reflux condenser was attached to the flask, and the mixture was heated to 50° C. After 16 h, the reaction mixture was concentrated under reduced pressure and the residue was purified by chromatography on silica gel (100-g SNAP Ultra column with 20-70% of a 3:1 EtOAc/EtOH mixture in heptane with 10% DCM) to give an impure solid. This material was repurified by chromatography on silica gel (100-g SNAP Ultra column with 0-50% of a 3:1 EtOAc/EtOH mixture in heptane with 10% DCM) to give (Rac)-tert-butyl 1-(6-bromo-5-fluoro-2-methoxypyridin-3-yl)-2-oxo-1,2,7,8-tetrahydro-1,6-naphthyridine-6(5H)-carboxylate (807 mg, 1.78 mmol, 34.3% yield) as a tan foam. m/z (ESI) 454.0 (M+H)$^+$.

Step 2: (Rac)-1-(6-Bromo-5-Fluoro-2-Methoxypyridin-3-Yl)-5,6,7,8-Tetrahydro-1,6-Naphthyridin-2(1H)-One 2,2,2-Trifluoroacetate A round-bottom flask was charged with (Rac)-tert-butyl 1-(6-bromo-5-fluoro-2-methoxypyridin-3-yl)-2-oxo-1,2,7,8-tetrahydro-1,6-naphthyridine-6(5H)-carboxylate (0.81 g, 1.77 mmol) and trifluroacetic acid (5.91 ml) at ambient temperature. After 1 h, the mixture was concentrated under reduced pressure, and the residue was dried under high vac to give (Rac)-1-(6-bromo-5-fluoro-2-methoxypyridin-3-yl)-5, 6,7,8-tetrahydro-1, 6-naphthyridin-2(1H)-one 2,2,2-trifluoroacetate (0.95 g) as a tan solid contaminated with trifluoroacetic acid. m/z (ESI) 354.9 (M+H)$^+$.

Step 3: (Rac)-1-(6-(3-Chloro-5-Fluorophenyl)-5-Fluoro-2-Methoxypyridin-3-Yl)-5,6,7,8-Tetrahydro-1,6-Naphthyridin-2(1H)-One A vial was charged with (Rac)-1-(6-bromo-5-fluoro-2-methoxypyridin-3-yl)-5,6,7,8-tetrahydro-1,6-naphthyridin-2(1H)-one 2,2,2-trifluoroacetate (228 mg, 0.49 mmol), (3-chloro-5-fluorophenyl)boronic acid (102 mg, 0.59 mmol), 1,1-bis[(di-t-butyl-p-methylaminophenyl]palladium (II) chloride (34.5 mg, 0.05 mmol), and potassium phosphate (310 mg, 1.46 mmol). The vial was flushed with argon (g), then 1,4-dioxane (1.95 mL) and water (487 µL) were added. The vial was sealed and heated to 60° C. for 1 h in a Biotage Initiator microwave reactor. The mixture was extracted with EtOAc (4×). The combined organic extracts were concentrated. The residue was purified by chromatography on silica gel (50-g SNAP Ultra column with 0-10% MeOH/DCM) to give (Rac)-1-(6-(3-chloro-5-fluorophenyl)-5-fluoro-2-methoxypyridin-3-yl)-5,6,7,8-tetrahydro-1, 6-naphthyridin-2(1H)-one (246 mg) as a light-yellow solid that was determined to be 80-90% pure by LCMS analysis. m/z (ESI) 404.2 (M+H)$^+$.

Preparation of Compound of Formula 7:
According to Generic Scheme A, Compounds of formula 7 were prepared as follows:

Preparation 7a: N-(4-Methoxybenzyl)-N-(Pyrimidin-4-Yl)-1H-Imidazole-1-Sulfonamide

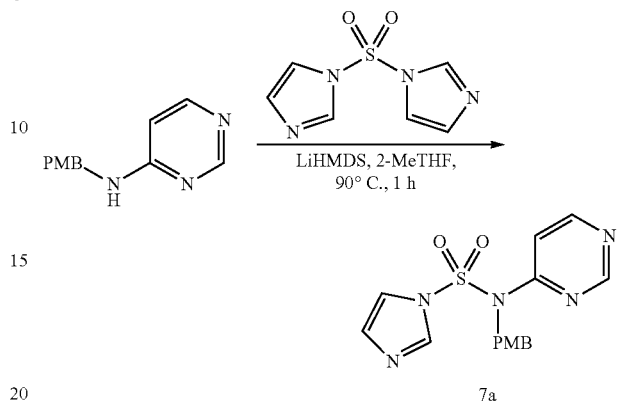

A 20-mL vial was charged with N-(4-methoxybenzyl) pyrimidin-4-amine (prepared analogous to Intermediate A, pages 43-44 of WO2013122897, wherein 1,2,4-thiadiazol-5-amine was replaced with pyrimidin-4-amine and 2,4-dimethoxybenzaldehyde was replaced with 4-methoxybenzaldehyde) (500 mg, 2.32 mmol) and 1,1'-sulfonylbis(1H-imidazole) (1.84 g, 9.29 mmol) then purged with nitrogen. 2-Methyltetrahydrofuran (10.0 mL) and a solution of lithium hexamethyldisilazide in THF (1.0 M, 6.97 mL, 6.97 mmol) were added via syringe to the stirred reaction mixture. The vial was sealed with a Teflon coated cap and the reaction was warmed to 90° C. and stirred vigorously. After 1 h, the red reaction mixture was allowed to cool to ambient temperature. The reaction mixture was diluted with water (25 mL) and EtOAc (25 mL). The layers were separated and the aqueous layer extracted with additional EtOAc (2×25 mL). The combined organic layers were washed with brine (50 mL), dried over anhydrous magnesium sulfate, filtered, concentrated under reduced pressure and purified by flash column chromatography (100-g silica gel Biotage column, eluent: gradient, 20 to 80% 3:1 EtOAc/EtOH in heptane with DCM as a 10% additive) to afford N-(4-methoxybenzyl)-N-(pyrimidin-4-yl)-1H-imidazole-1-sulfonamide (Preparation 7a, 1.12 g, 3.24 mmol, 140% yield) as a yellow solid (50% purity by LCMS) mixed with 1,1'-sulfonylbis(1H-imidazole). m/z (ESI) 346.2 (M+H)$^+$.

Preparation 7b: N-(4-Methoxybenzyl)-N-(1,2,4-Thiadiazol-5-Yl)-1H-Imidazole-1-Sulfonamide

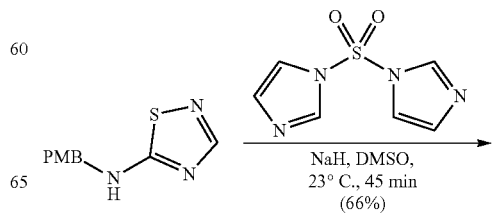

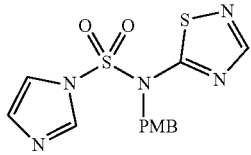

7b

A 100-mL round-bottom flask was charged with N-(4-methoxybenzyl)-1,2,4-thiadiazol-5-amine (1.0 g, 4.52 mmol) and 1,1'-sulfonylbis(1H-imidazole) (1.791 g, 9.04 mmol) then purged with nitrogen. Dimethyl sulfoxide (20.0 mL) was introduced followed by sodium hydride (0.11 g, 4.52 mmol). The resultant green reaction mixture was stirred vigorously at ambient temperature. After 45 minutes, the reaction mixture was poured into water (300 mL) and the white precipitate was collected by vacuum filtration. The precipitate was dried in vacuo to provide N-(4-methoxybenzyl)-N-(1,2,4-thiadiazol-5-yl)-1H-imidazole-1-sulfonamide (1.05 g, 2.99 mmol, 66.1% yield) as a white powder. m/z (ESI) 352.0 (M+H)$^+$.

Preparation 7c:
N-(Isoxazol-3-Yl)-2-Oxooxazolidine-3-Sulfonamide

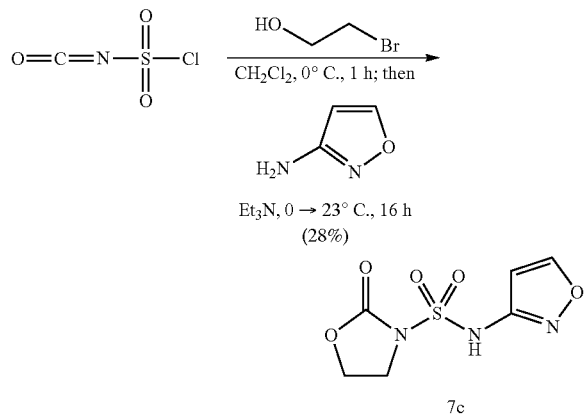

7c

A 1-L round-bottom flask was charged with dichloromethane (376 ml) and chlorosulfonyl isocyanate (9.82 ml, 113 mmol). The reaction mixture was cooled to 0° C. in an ice-water bath before 2-bromoethanol (8.0 mL, 113 mmol) was added dropwise via addition funnel over 20 min. After 1 h, a solution of isoxazol-3-amine (8.40 ml, 113 mmol), triethylamine (47.1 ml, 339 mmol) in DCM (50 mL) was added dropwise over 20 min via addition funnel. After the addition was complete, the cooling bath was removed and the reaction mixture was warmed to ambient temperature. After 16 h, the reaction mixture was concentrated under reduced pressure to give a yellow oily solid. The residue diluted with aqueous HCl solution (1.0 M, 250 mL) and extracted with DCM (4×150 mL). The combined organic layers were dried over magnesium sulfate, filtered, and concentrated under reduced pressure to give a yellow solid. The solid was triturated in DCM (25 mL) and heptane (2 mL). The resulting suspension was filtered, and the collected solid was washed with heptane and DCM to afford N-(isoxazol-3-yl)-2-oxooxazolidine-3-sulfonamide (7.24 g, 31.0 mmol, 27.5% yield) as a free-flowing white solid. $^1$H NMR (400 MHz, DMSO-d$_6$) δ ppm 11.77-12.81 (m, 1H) 8.84 (d, J=1.76 Hz, 1H) 6.37 (d, J=1.87 Hz, 1H) 4.38-4.49 (m, 2H) 4.13 (dd, J=9.12, 6.74 Hz, 2H). m/z (ESI) 234.0 (M+H)$^+$.

Preparation 7d: N-(5-Fluoropyrimidin-2-Yl)-2-Oxooxazolidine-3-Sulfonamide

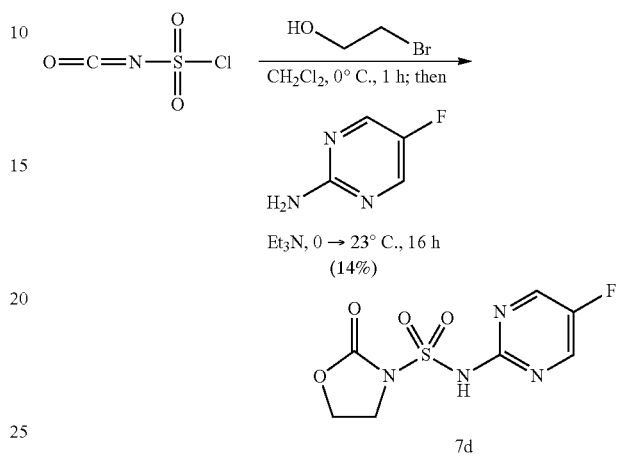

7d

A 500-mL round-bottom flask was charged with dichloromethane (100 ml) and chlorosulfonyl isocyanate (1.82 ml, 21.0 mmol). The reaction mixture was cooled to 0° C. in an ice-water bath before 2-bromoethanol (1.49 mL, 21.0 mmol) was added dropwise via syringe over 5 min. After 1 h, 5-fluoropyrimidin-2-amine (2.37 g, 21.0 mmol) and triethylamine (8.33 ml, 59.9 mmol) were introduced. After the addition was complete, the cooling bath was removed and the reaction mixture was warmed to ambient temperature. After 48 h, the reaction mixture was concentrated under reduced pressure to give a yellow oily solid. The residue diluted with aqueous HCl solution (2.0 M, 150 mL) and extracted with DCM (4×100 mL). The combined organic layers were dried over magnesium sulfate, filtered, and concentrated under reduced pressure to give a yellow solid. The solid was triturated in DCM (25 mL) and heptane (2 mL). The resulting suspension was filtered, and the collected solid was washed with heptane and DCM to afford N-(5-fluoropyrimidin-2-yl)-2-oxooxazolidine-3-sulfonamide (711 mg, 2.71 mmol, 13.6% yield) as an off-white solid. $^1$H NMR (400 MHz, DMSO-d$_6$) δ ppm 11.77-12.81 (m, 1H) 8.84 (d, J=1.76 Hz, 1H) 6.37 (d, J=1.87 Hz, 1H) 4.38-4.49 (m, 2H) 4.13 (dd, J=9.12, 6.74 Hz, 2H) m/z (ESI) 261.2 (M−H)$^-$.

Preparation 7e: N-(4-Methoxybenzyl)-N-(6-Methylpyrimidin-4-Yl)-1H-Imidazole-1-Sulfonamide

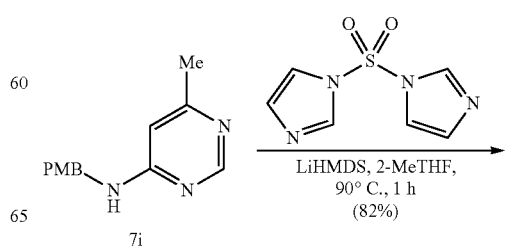

7i

-continued

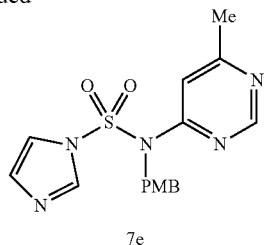

7e

A 20-mL vial was charged with N-(4-methoxybenzyl)-6-methylpyrimidin-4-amine (Preparation 7i, 500 mg, 2.181 mmol) and 1,1'-sulfonylbis(1H-imidazole) (864 mg, 4.36 mmol) then purged with nitrogen. 2-Methyltetrahydrofuran (10.0 mL) and a solution of lithium hexamethyldisilazide in THF (1.0 M, 4.27 mL, 4.27 mmol) were added via syringe to the stirred reaction mixture. The vial was sealed with a Teflon coated cap and the reaction was warmed to 90° C. and stirred vigorously. After 1 h, the red reaction mixture was allowed to cool to ambient temperature. The reaction mixture was diluted with water (25 mL) and EtOAc (25 mL). The layers were separated and the aqueous layer extracted with additional EtOAc (2×25 mL). The combined organic layers were washed with brine (50 mL), dried over anhydrous magnesium sulfate, filtered, concentrated under reduced pressure and purified by flash column chromatography (100-g silica gel Biotage column, eluent: gradient, 20 to 80% 3:1 EtOAc/EtOH in heptane with DCM as a 10% additive) to afford N-(4-methoxybenzyl)-N-(6-methylpyrimidin-4-yl)-1H-imidazole-1-sulfonamide (0.64 g, 1.78 mmol, 82% yield) as a reddish oil. m/z (ESI) 360.2 (M+H)$^+$.

Preparation 7f:
2-Oxo-N-(Pyridazin-3-Yl)Oxazolidine-3-Sulfonamide

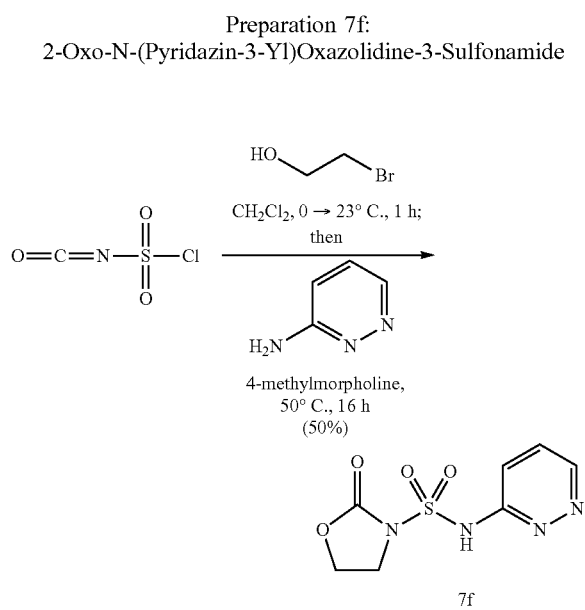

7f

A 2-L round-bottom flask was charged with MeCN (600 ml) and chlorosulfonyl isocyanate (13.7 ml, 158 mmol)). The reaction mixture was cooled to 0° C. in an ice-water bath before 2-bromoethanol (11.2 ml, 158 mmol) was added dropwise via syringe over 20 min. After 30 min, the yellow solution was allowed to warm to ambient temperature. After 1 h, pyridazin-3-amine (15 g, 158 mmol) and 4-methylmorpholine (69.4 ml, 631 mmol) were added in single portions to the stirred reaction mixture. The reaction vessel was equipped with a reflux adaptor. After 5 min, the reaction mixture was warmed to 50° C. After 16 h, the reaction mixture was allowed to cool to ambient temperature and the solvent was removed under reduced pressure. Aqueous HCl solution (0.5 M, 900 mL) and DCM (500 mL) were introduced and the layers were separated. The aqueous layer was further extracted with DCM (4×300 mL). The combined organic layers were dried over magnesium sulfate, filtered, and concentrated under reduced pressure to give a tan solid. The solid was triturated in DCM (50 mL) and heptane 5 mL). The resulting suspension was filtered, and the collected solid was washed with heptane and DCM to afford 2-oxo-N-(pyridazin-3-yl)oxazolidine-3-sulfonamide (19.3 g, 39.7 mmol, 50.2% yield) as a tan solid. 1H NMR (400 MHz, DMSO-d6) δ ppm 8.45 (d, J=3.11 Hz, 1H) 8.16 (d, J=9.54 Hz, 1H) 7.84 (dd, J=9.59, 4.20 Hz, 1H) 4.28-4.41 (m, 2H) 3.97 (t, J=7.83 Hz, 2H). m/z (ESI) 245.0 (M−H)$^+$.

Preparation 7g:
2-Oxo-N-(Pyrimidin-2-Yl)Oxazolidine-3-Sulfonamide

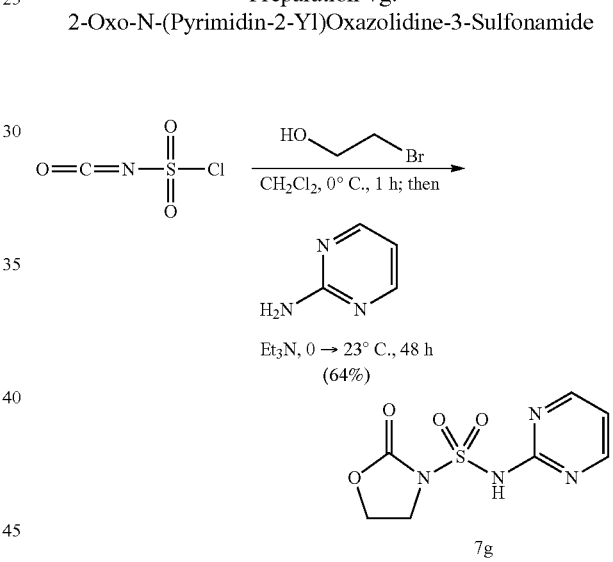

7g

A 500-mL round-bottom flask was charged with dichloromethane (100 ml) and chlorosulfonyl isocyanate (2.47 mL, 28.4 mmol). The reaction mixture was cooled to 0° C. in an ice-water bath before 2-bromoethanol (2.01 ml, 28.4 mmol) was added dropwise via addition funnel over 20 min. After 1 h, 2-aminopyrimidine (2.70 g, 28.4 mmol) was added in a single portion. A solution of triethylamine (11.3 ml, 81.0 mmol) and DCM (50 mL) were added dropwise over 20 min via addition funnel. After the addition was complete, the cooling bath was removed and the reaction mixture was warmed to ambient temperature. After 48 h, the reaction mixture was concentrated under reduced pressure to give a yellow oily solid. The residue was suspended in aqueous HCl solution (2.0 M, 150 mL), filtered, and the collected solid was washed with water (3×50 mL) to afford 2-oxo-N-(pyrimidin-2-yl)oxazolidine-3-sulfonamide (4.21 g, 17.2 mmol, 63.8% yield) as an off-white solid. m/z (ESI) 245.0 (M+H)+.

Preparation 7h: N-(4-Methoxybenzyl)-N-(Thiazol-2-Yl)-1H-Imidazole-1-Sulfonamide

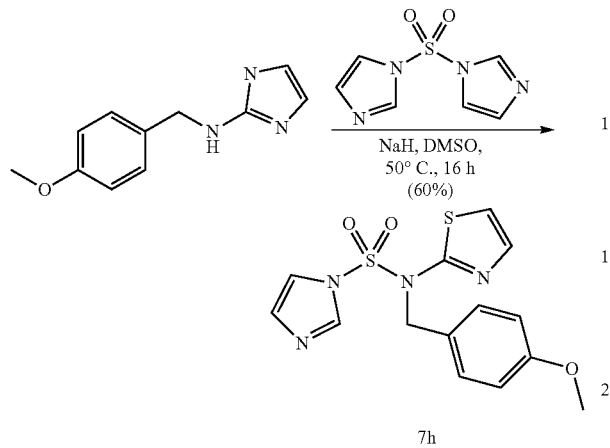

A 40-mL vial was charged with N-(4-methoxybenzyl)thiazol-2-amine (prepared analogous to Intermediate A, pages 43-44 of WO2013122897, wherein 1,2,4-thiadiazol-5-amine was replaced with thiazol-2-amine and 2,4-dimethoxybenzaldehyde was replaced with 4-methoxybenzaldehyde) (1 g, 4.54 mmol) and 1,1'-sulfonylbis(1H-imidazole) (0.99 g, 4.99 mmol) then purged with nitrogen. Dimethyl sulfoxide (20 mL) was introduced followed by sodium hydride (60% dispersion in mineral oil, 0.11 g, 2.72 mmol). The vial was sealed with a Teflon coated cap and the reaction was warmed to 50° C. and stirred vigorously. After 16 h, the reaction mixture was allowed to cool to ambient temperature. The reaction mixture was carefully diluted with water (25 mL) and EtOAc (25 mL). The layers were separated and the aqueous layer extracted with additional EtOAc (2×25 mL). The combined organic layers were dried over anhydrous magnesium sulfate, filtered, concentrated under reduced pressure and purified by flash column chromatography (100-g silica gel Biotage column, eluent: gradient, 20 to 80% 3:1 EtOAc/EtOH in heptane with DCM as a 10% additive) to afford N-(4-methoxybenzyl)-N-(thiazol-2-yl)-1H-imidazole-1-sulfonamide (0.96 g, 1.65 mmol, 60.4% yield) as a yellow oil. m/z (ESI) 351.0 (M+H)⁺.

Preparation 7i: N-(4-Methoxybenzyl)-6-Methylpyrimidin-4-Amine

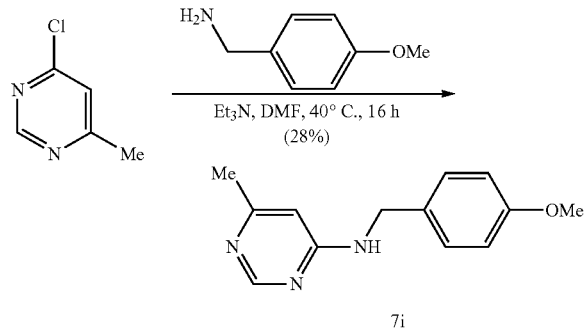

A 40-mL vial was charged with a solution of 4-chloro-6-methyl-pyrimidine (1 g, 7.78 mmol), triethylamine (1.63 mL, 11.7 mmol), and N,N-dimethylformamide (10 mL). 4-methoxybenzylamine (1.51 mL, 11.7 mmol) was introduced, the vial was sealed with a Teflon coated cap, and the reaction mixture was warmed to 40° C. After 16 hours, the reaction mixture was allowed to cool to ambient temperature and diluted with water (25 mL) and EtOAc (25 mL). The layers were separated and the aqueous layer extracted with additional EtOAc (2×25 mL). The combined organic layers were dried over anhydrous magnesium sulfate, filtered, concentrated under reduced pressure and purified by flash column chromatography (50-g silica gel Biotage column, eluent: gradient, 50 to 100% 3:1 EtOAc/EtOH in heptane) to afford N-(4-methoxybenzyl)-6-methylpyrimidin-4-amine (0.50 g, 2.18 mmol, 28.0% yield) as an off-white solid. m/z (ESI) 230.2 (M+H)⁺.

Preparation 7j: N-(4-Methoxybenzyl)-N-(2-Methylpyrimidin-4-Yl)-1H-Imidazole-1-Sulfonamide

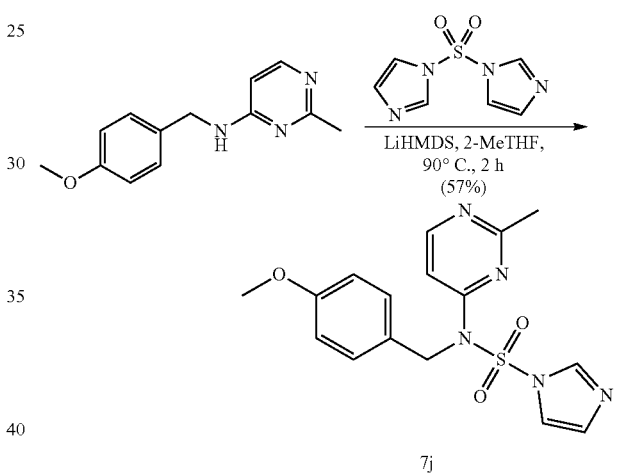

A 20-mL vial was charged with N-(4-methoxybenzyl)-2-methylpyrimidin-4-amine (prepared analogous to Intermediate A, pages 43-44 of WO2013122897, wherein 1,2,4-thiadiazol-5-amine was replaced with 2-methylpyrimidin-4-amine and 2,4-dimethoxybenzaldehyde was replaced with 4-methoxybenzaldehyde) (864 mg, 4.36 mmol) then purged with nitrogen. 2-Methyltetrahydrofuran (10.0 mL) and a solution of lithium hexamethyldisilazide in THF (1.0 M, 4.27 mL, 4.27 mmol) were added via syringe to the stirred reaction mixture. The vial was sealed with a Teflon coated cap and the reaction was warmed to 90° C. and stirred vigorously. After 2 h, the red reaction mixture was allowed to cool to ambient temperature. The reaction mixture was diluted with water (25 mL) and EtOAc (25 mL). The layers were separated and the aqueous layer extracted with additional EtOAc (2×25 mL). The combined organic layers were washed with brine (50 mL), dried over anhydrous magnesium sulfate, filtered, concentrated under reduced pressure and purified by flash column chromatography (100-g silica gel Biotage column, eluent: gradient, 20 to 80% 3:1 EtOAc/EtOH in heptane with DCM as a 10% additive) to afford N-(4-methoxybenzyl)-N-(2-methylpyrimidin-4-yl)-1H-imidazole-1-sulfonamide (450 mg, 1.25 mmol, 57.4% yield) as a light-yellow solid. m/z (ESI) 360.2 (M+H)⁺.

Preparation of Compound of Formula 8:

Note: According to Generic Scheme A, Compounds of formula 8 are final compounds, and are described in the Examples section below. Compounds of Preparations 8a-8f are described below as preparations, because while they are final compounds, they were also used as intermediate compounds in the Examples section below.

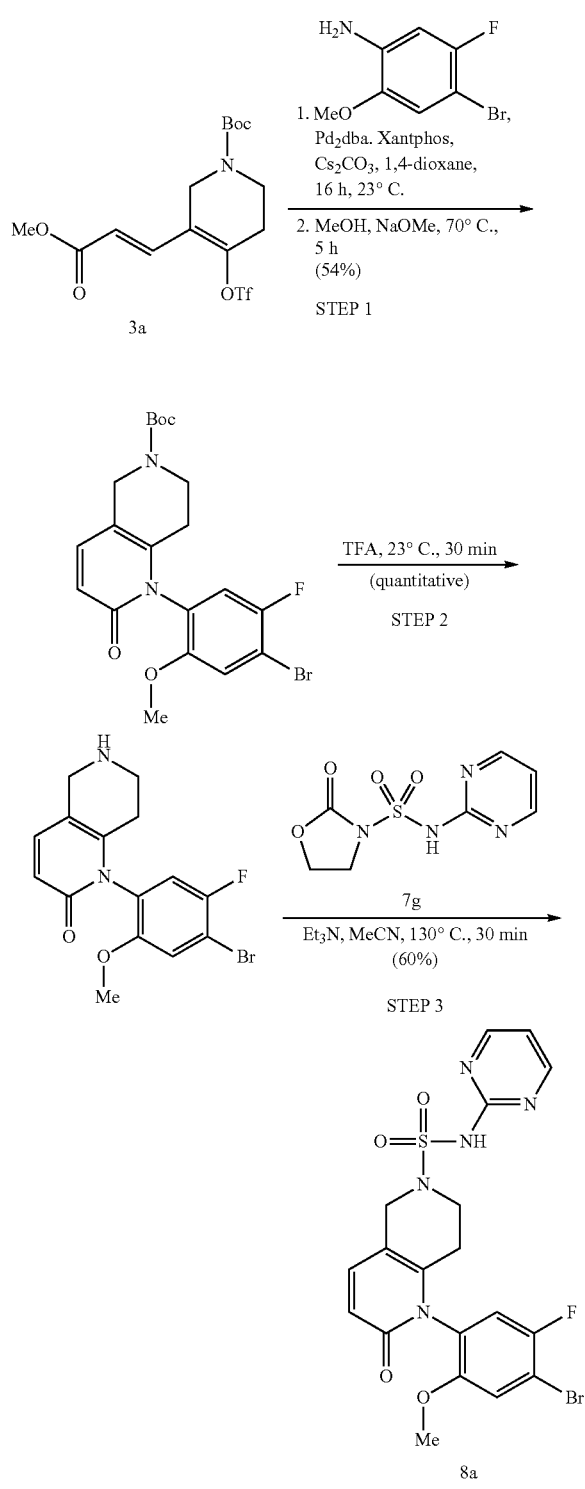

Preparation 8a: (Rac)-1-(4-Bromo-5-Fluoro-2-Methoxyphenyl)-2-Oxo-N-(Pyrimidin-2-Yl)-1,2,7,8-Tetrahydro-1,6-Naphthyridine-6(5H)-Sulfonamide Step 1: (Rac)-tert-Butyl 1-(4-Bromo-5-Fluoro-2-Methoxyphenyl)-2-Oxo-1,2,7,8-Tetrahydro-1,6-Naphthyridine-6(5H)-Carboxylate A 500-mL round-bottom flask was charged with (E)-tert-butyl 3-(3-methoxy-3-oxoprop-1-en-1-yl)-4-(((trifluoromethyl)sulfonyl)oxy)-5,6-dihydropyridine-1(2H)-carboxylate (Preparation 3a, 10.4 g, 25.0 mmol), xantphos (1.81 g, 3.13 mmol), cesium carbonate (24.4 g, 75.0 mmol), 4-bromo-5-fluoro-2-methoxyaniline (Alfa Aesar, 6.06 g, 27.5 mmol), tris(dibenzylideneacetone)dipalladium (0) (1.15 g, 1.25 mmol) and 1,4-dioxane (125 mL) then sparged with nitrogen for 15 min. The reaction mixture stirred vigorously for 20 h at ambient temperature. The reaction mixture was subsequently vacuum filtered through a 1.0 cm plug of silica gel and the pad was rinsed with EtOAc (3×150 mL). The filtrate was concentrated under reduced pressure to give a brown foam that was used immediately without further purification.

The brown foam was diluted with MeOH (250 mL) and transferred to a 350-mL pressure vessel equipped with a stir bar. The reaction vessel was subsequently charged with sodium methoxide (25 wt. % in MeOH, 2.79 ml, 12.5 mmol) and sealed with a Teflon cap equipped with a pressure-relief valve. The reaction vessel was placed in a 70° C. oil bath and stirred vigorously. After 5 h, the reaction mixture was allowed to cool to ambient temperature, transferred to a 1-L round-bottom flask with additional MeOH and concentrated under reduced pressure. The brown oil was redissolved in DCM (150 mL) and filtered through a pad of Celite® (3 cm) to facilitate loading the material onto a column. The Celite® pad was rinsed with DCM (3×50 mL). The brown filtrate was concentrated under reduced pressure and purified by flash column chromatography (340-g Biotage column, eluent: gradient, 5 to 70% 3:1 EtOAc/EtOH in heptane with DCM as a 10% additive) to afford (Rac)-tert-butyl 1-(4-bromo-5-fluoro-2-methoxyphenyl)-2-oxo-1,2,7,8-tetrahydro-1,6-naphthyridine-6(5H)-carboxylate (6.1 g, 13.5 mmol, 53.7% yield) as a tan foam.

Step 2: (Rac)-1-(4-Bromo-5-Fluoro-2-Methoxyphenyl)-5,6,7,8-Tetrahydro-1,6-Naphthyridin-2(1H)-One A 100-mL round-bottom flask was charged with (Rac)-tert-butyl 1-(4-bromo-5-fluoro-2-methoxyphenyl)-2-oxo-1,2,7,8-tetrahydro-1,6-naphthyridine-6(5H)-carboxylate (1.50 g, 3.31 mmol) and trifluoroaceticacid (33.1 mL) then stirred for 30 min at ambient temperature. The reaction mixture was concentrated under reduced pressure, dissolved in DCM (50 mL) and carefully poured into saturated aqueous sodium bicarbonate solution (50 mL). The layers were separated and the aqueous layer extracted with additional DCM (3×50 mL). The combined organic layers were dried over anhydrous magnesium sulfate, filtered, concentrated under reduced pressure to afford (Rac)-1-(4-bromo-5-fluoro-2-methoxyphenyl)-5,6,7,8-tetrahydro-1,6-naphthyridin-2(1H)-one (1.27 g, 3.60 mmol, quantitative) as a tan foam which was used without further purification. $^1$H NMR (400 MHz, DMSO-$d_6$) δ ppm 7.55 (d, J=6.32 Hz, 1H) 7.42 (d, J=8.60 Hz, 1H) 7.25 (d, J=9.43 Hz, 1H) 6.31 (d, J=9.33 Hz, 1H) 3.76 (s, 3H) 3.52-3.65 (m, 2H) 2.80 (t, J=5.86 Hz, 2H) 2.05-2.21 (m, 1H) 1.76-1.96 (m, 1H). m/z (ESI) 355.0 (M+H)⁺.

Step 3: (Rac)-1-(4-Bromo-5-Fluoro-2-Methoxyphenyl)-2-Oxo-N-(Pyrimidin-2-Yl)-1,2,7,8-Tetrahydro-1,6-Naphthyridine-6(5H)-Sulfonamide A microwave vial was charged with (Rac)-1-(4-bromo-5-fluoro-2-methoxyphenyl)-5,6,7,8-tetrahydro-1,6-naphthyridin-2(1H)-one (520 mg, 1.473 mmol), 2-oxo-N-(pyrimidin-2-yl)oxazolidine-3-sulfonamide (Preparation 7g, 899 mg, 3.68 mmol), and acetonitrile (7.4 mL) to give a suspension. Triethylamine (2.05 mL, 14.7 mmol) was added, resulting in the formation of a yellow solution. The vial was sealed and heated in a Biotage Initiator microwave reactor for 30 min at 130° C. The mixture was concentrated. The residue was taken up in 1N aq. HCl and DCM. The layers were separated, and the aq. layer was extracted with DCM (2×). The combined organic extracts were dried over sodium sulfate, filtered, and concentrated. The residue was purified by chromatography on silica gel (50-g SNAP Ultra column, 20-70% of 3:1 EtOAc/EtOH in heptane with 10% DCM). The major spot was collected with a small amount of a lower spot to give (Rac)-1-(4-bromo-5-fluoro-2-methoxyphenyl)-2-oxo-N-(pyrimidin-2-yl)-1,2,7,8-tetrahydro-1,6-naphthyridine-6(5H)-sulfonamide (451 mg, 0.884 mmol, 60.0% yield) as an off-white solid that was 90% pure by ¹H NMR. ¹H NMR (400 MHz, DMSO-d₆) δ ppm 10.99-11.59 (m, 1H) 8.52 (d, J=4.90 Hz, 2H) 7.53 (d, J=6.22 Hz, 1H) 7.29-7.46 (m, 2H) 7.08 (t, J=4.89 Hz, 1H) 6.35 (d, J=9.43 Hz, 1H) 4.25-4.39 (m, 2H) 3.69 (s, 3H) 3.41-3.52 (m, 2H) 2.28-2.37 (m, 1H) 1.98-2.10 (m, 1H) 1.17 (t, J=7.10 Hz, 1H). m/z (ESI) 510.0 (M+H)⁺.

Preparation 8b: (Rac)-; (P)-; and (M)-1-(4-Bromo-5-Fluoro-2-Methoxyphenyl)-2-Oxo-N-(Pyridazin-3-Yl)-1,2,7,8-Tetrahydro-1,6-Naphthyridine-6(5H)-Sulfonamide

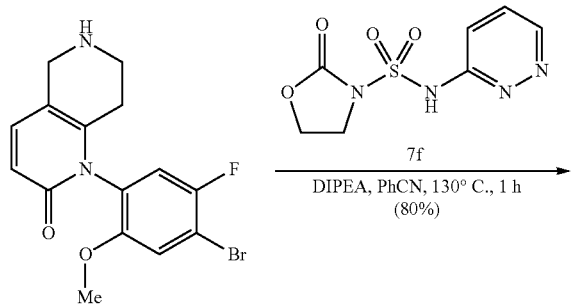

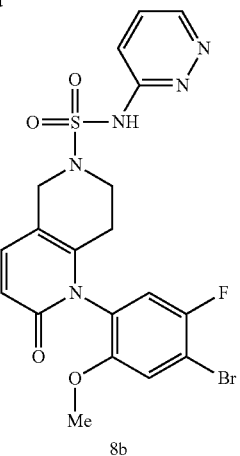

A 250-mL sealed tube was charged with 1-(4-bromo-5-fluoro-2-methoxyphenyl)-5,6,7,8-tetrahydro-1,6-naphthyridin-2(1H)-one (See Preparation 8a, step 2, 5.65 g, 16.0 mmol), 2-oxo-N-(pyridazin-3-yl)oxazolidine-3-sulfonamide (Preparation 7f, 5.86 g, 24.0 mmol), N,N-diisopropylethylamine (19.5 ml, 112 mmol), and benzonitrile (32.0 ml). The reaction vessel was sealed and warmed to 130° C. After 1 h, the reaction was cooled to ambient temperature and transferred to a 250-mL round-bottomed flask and concentrated under reduced pressure (1 mbar at 80-90° C.). The resultant black oil was diluted with DCM (200 mL) and washed with a solution of aqueous HCl (1.0 M, 100 mL). The aqueous layer was back-extracted with DCM (3×50 mL). The combined organic layers were dried over magnesium sulfate, filtered, concentrated under reduced pressure, and purified (200-g silica gel Grace, 0 to 10% MeOH in DCM) to afford 1-(4-bromo-5-fluoro-2-methoxyphenyl)-2-oxo-N-(pyridazin-3-yl)-1,2,7,8-tetrahydro-1,6-naphthyridine-6(5H)-sulfonamide (6.53 g, 12.80 mmol, 80% yield) as a brown solid. ¹H NMR (400 MHz, DMSO-d₆) δ=7.66 (dd, J=4.1, 9.6 Hz, 1H), 7.56 (d, J=6.3 Hz, 1H), 7.45 (d, J=8.6 Hz, 1H), 7.37 (d, J=9.4 Hz, 1H), 6.36 (d, J=9.3 Hz, 1H), 4.15-3.97 (m, 2H), 3.76 (s, 3H), 3.29-3.18 (m, 2H), 2.40 (td, J=5.7, 17.0 Hz, 1H), 2.10 (td, J=5.5, 17.4 Hz, 1H). m/z (ESI) 510.0 (M+H)⁺.

Separation Step: Racemic product of Preparation 8b was subjected to chiral SFC (Regis Whelk-O (s,s), 50% methanol) to give (Preparation 8b-P, 1.78 g, 3.49 mmol, 21.8% yield) (peak 1) and (Preparation 8b-M, 1.99 g, 3.90 mmol, 24.4% yield) (peak 2) as tan solids.

Preparation 8c: (Rac); —(P)-; and (M) 1-(4-Bromo-5-Chloro-2-Methoxyphenyl)-N-(Isoxazol-3-Yl)-2-Oxo-1,2,7,8-Tetrahydro-1,6-Naphthyridine-6(5H)-Sulfonamide

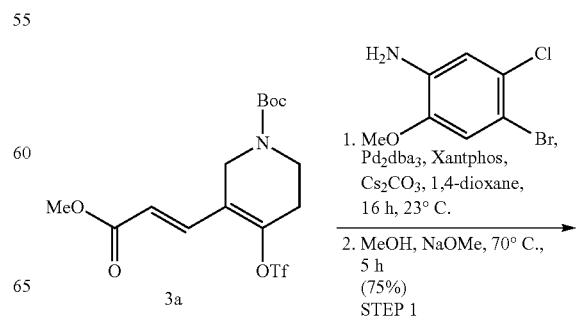

-continued

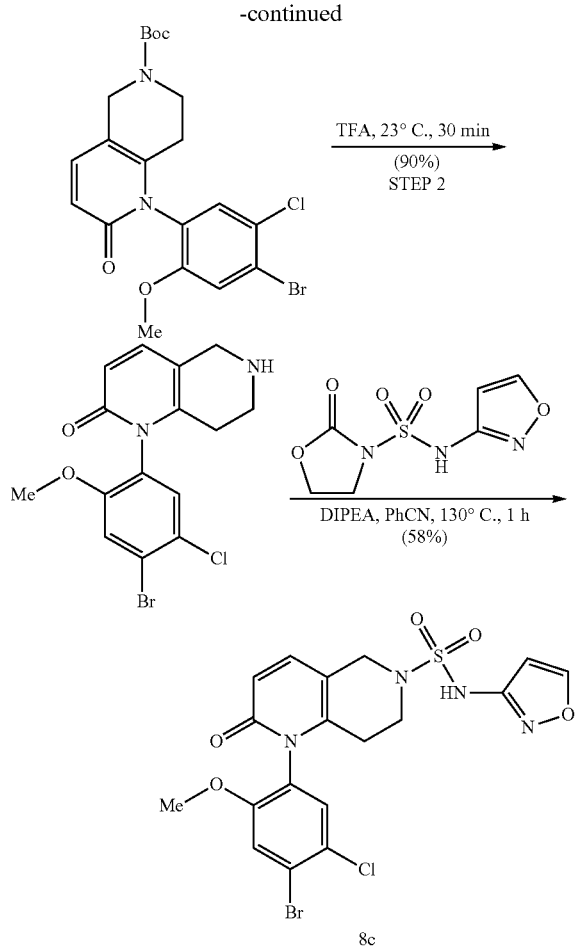

Step 1: (Rac)-tert-Butyl 1-(4-Bromo-5-Chloro-2-Methoxyphenyl)-2-Oxo-1,2,7,8-Tetrahydro-1,6-Naphthyridine-6(5H)-Carboxylate A 500-mL round-bottom flask was charged with (E)-tert-butyl 3-(3-methoxy-3-oxoprop-1-en-1-yl)-4-(((trifluoromethyl)sulfonyl)oxy)-5,6-dihydropyridine-1(2H)-carboxylate (Preparation 3a, (10.8 g, 26.0 mmol), xantphos (1.88 g, 3.25 mmol), cesium carbonate (25.4 g, 78.0 mmol), 4-bromo-5-chloro-2-methoxyaniline (6.15 g, 26.0 mmol), tris(dibenzylideneacetone)dipalladium (0) (1.19 g, 1.30 mmol) and 1,4-dioxane (130 mL) then sparged with nitrogen for 15 min. The reaction mixture stirred vigorously for 20 h at ambient temperature. The reaction mixture was subsequently vacuum filtered through a 1.0 cm plug of silica gel and the pad was rinsed with EtOAc (3×150 mL). The filtrate was concentrated under reduced pressure to give a brown foam that was used immediately without further purification.

The product was diluted with MeOH (260 mL) and transferred to a 350-mL pressure vessel equipped with a stir bar. The reaction vessel was subsequently charged with sodium methoxide (25 wt. % in MeOH, 2.97 ml, 13.00 mmol) and sealed with a Teflon cap equipped with a pressure-relief valve. The reaction vessel was placed in a 70° C. oil bath and stirred vigorously. After 5 h, the reaction mixture was allowed to cool to ambient temperature, transferred to a 1-L round-bottom flask with additional MeOH and concentrated under reduced pressure. The brown oil was redissolved in DCM (150 mL) and filtered through a pad of Celite® (3 cm) to facilitate loading the material onto a column. The Celite® pad was rinsed with DCM (3×50 mL). The brown filtrate was concentrated under reduced pressure and purified by flash column chromatography (340-g Biotage column, eluent: gradient, 5 to 35% 3:1 EtOAc/EtOH in heptane with DCM as a 10% additive) to afford (Rac)-tert-butyl 1-(4-bromo-5-chloro-2-methoxyphenyl)-2-oxo-1,2,7,8-tetrahydro-1,6-naphthyridine-6(5H)-carboxylate (9.12 g, 19.4 mmol, 74.7% yield) as a tan solid.

Step 2: (Rac)-1-(4-Bromo-5-Chloro-2-Methoxyphenyl)-5,6,7,8-Tetrahydro-1,6-Naphthyridin-2(1H)-One A 100-mL round-bottom flask was charged with (Rac)-tert-butyl 1-(4-bromo-5-chloro-2-methoxyphenyl)-2-oxo-1,2,7,8-tetrahydro-1,6-naphthyridine-6(5H)-carboxylate (4.5 g, 9.58 mmol) and trifluoroacetic acid (47.9 mL) then stirred for 30 min at ambient temperature. The reaction mixture was concentrated under reduced pressure, dissolved in DCM (100 mL) and carefully poured into saturated aqueous sodium bicarbonate solution (100 mL). The layers were separated and the aqueous layer extracted with additional DCM (4×25 mL). The combined organic layers were dried over anhydrous magnesium sulfate, filtered, concentrated under reduced pressure to afford (Rac)-1-(4-bromo-5-chloro-2-methoxyphenyl)-5,6,7,8-tetrahydro-1,6-naphthyridin-2(1H)-one (3.2 g, 8.66 mmol, 90% yield) as a tan foam which was used without further purification. $^1$H NMR (400 MHz, DMSO-$d_6$) δ=7.62 (s, 1H), 7.56 (s, 1H), 7.25 (d, J=9.3 Hz, 1H), 6.31 (d, J=9.3 Hz, 1H), 3.78 (s, 3H), 3.68-3.51 (m, 2H), 2.80 (t, J=5.8 Hz, 2H), 2.11 (td, J=5.4, 17.1 Hz, 1H), 1.88 (td, J=5.5, 17.1 Hz, 1H). m/z (ESI) 369.0 (M+H)$^+$.

Step 3: (Rac)-1-(4-Bromo-5-Chloro-2-Methoxyphenyl)-N-(Isoxazol-3-Yl)-2-Oxo-1,2,7,8-Tetrahydro-1,6-Naphthyridine-6(5H)-Sulfonamide A 75-mL sealed tube was charged with (Rac)-1-(4-bromo-5-chloro-2-methoxyphenyl)-5,6,7,8-tetrahydro-1,6-naphthyridin-2(1H)-one (2.72 g, 7.36 mmol), N-(isoxazol-3-yl)-2-oxooxazolidine-3-sulfonamide (Preparation 7c, 3.6 g, 15.44 mmol), (8.96 ml, 51.5 mmol), and benzonitrile (14.7 mL). The reaction vessel was sealed and warmed to 130° C. After 1 h, the reaction was cooled to ambient temperature and transferred to a 250-mL round-bottomed flask and concentrated under reduced pressure (1 mbar at 80-90° C.). The resultant black oil was diluted with DCM (200 mL) and washed with a solution of aqueous HCl (1.0 M, 100 mL). The aqueous layer was back-extracted with DCM (3×50 mL). The combined organic layers were dried over magnesium sulfate, filtered, concentrated under reduced pressure, and purified (100-g silica gel Biotage column, eluent: gradient, 0 to 5% MeOH in DCM) to afford (Rac)-1-(4-bromo-5-chloro-2-methoxyphenyl)-N-(isoxazol-3-yl)-2-oxo-1,2,7,8-tetrahydro-1,6-naphthyridine-6(5H)-sulfonamide as a tan solid (4.05 g, 79% purity by $^1$H NMR). $^1$H NMR (400 MHz, DMSO-$d_6$) δ ppm 8.74 (d, J=1.76 Hz, 1H) 7.62 (s, 1H) 7.52 (s, 1H) 7.32 (d, J=9.43 Hz, 1H) 6.39 (d, J=1.76 Hz, 1H) 6.35 (d, J=9.43 Hz, 1H) 4.17-4.25 (m, 2H) 3.76 (s, 3H) 3.35-3.43 (m, 2H) 2.30-2.46 (m, 1H) 1.96-2.11 (m, 1H). m/z (ESI) 515.0 (M+H)$^+$. Separation Step: Racemic product of Preparation 8c was subjected to chiral SFC (Regis Whelk-O (s,s), 40% methanol) to give (Preparation 8c-P, 1.05 g, 2.04 mmol, 27.7% yield) (peak 1) and (Preparation 8c-M, 1.13 g, 2.19 mmol, 29.8% yield) (peak 2) as tan solids.

Preparation 8d: (Rac)-1-(4-Bromo-5-Fluoro-2-Methoxyphenyl)-N-(Isoxazol-3-Yl)-2-Oxo-1,2,7,8-Tetrahydro-1,6-Naphthyridine-6(5H)-Sulfonamide

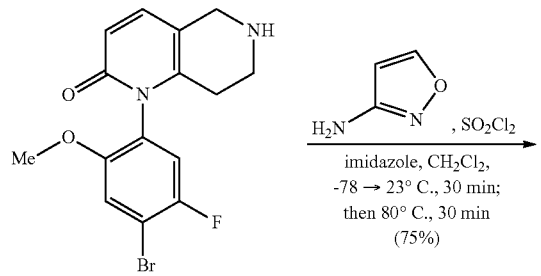

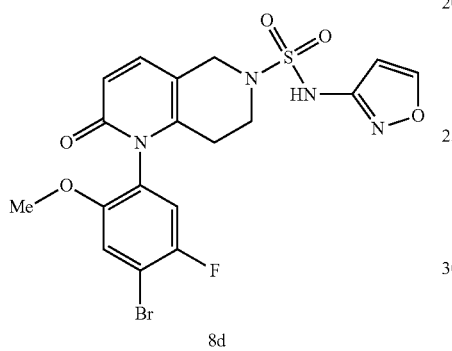

A 40-mL vial was charged with imidazole (922 mg, 13.6 mmol) and 3-aminoisoxazole (320 µL, 4.34 mmol) then purged with nitrogen. CH$_2$Cl$_2$ (10 mL) was introduced and the reaction mixture was cooled to −78° C. in a dry ice-acetone bath. Sulfuryl chloride (352.0 µL, 4.32 mmol) was added dropwise via syringe to the reaction mixture. Following addition, the cold bath was removed and the resultant mixture was allowed to warm to ambient temperature. After 30 minutes, (Rac)-1-(4-bromo-5-fluoro-2-methoxyphenyl)-5,6,7,8-tetrahydro-1,6-naphthyridin-2(1H)-one (See Preparation 8a, step 2, 957 mg, 2.71 mmol) was introduced in a single portion followed by CH$_2$Cl$_2$ (10.0 mL). The vial was sealed with a PTFE lined cap and the reaction mixture was warmed to 80° C. After 30 min, the reaction mixture was cooled to ambient temperature and diluted with an aqueous solution of citric acid (1.0 M, 25 mL), brine (25 mL) and EtOAc (50 mL). The layers were separated and the aqueous layer was extracted with EtOAc (3×25 mL). The combined organic layers were dried over anhydrous magnesium sulfate, filtered, and concentrated under reduced pressure and purified (100-g silica gel SNAP Ultra column, 0 to 50% 3:1 EtOAc/EtOH in heptane with DCM as a 10% additive) to afford (Rac)-1-(4-bromo-5-fluoro-2-methoxyphenyl)-N-(isoxazol-3-yl)-2-oxo-1,2,7,8-tetrahydro-1,6-naphthyridine-6(5H)-sulfonamide (1.01 g, 2.023 mmol, 74.7% yield) as a yellow solid. $^1$H NMR (400 MHz, DMSO-d$_6$) δ ppm 11.13 (s, 1H) 8.73 (d, J=1.76 Hz, 1H) 7.55 (d, J=6.22 Hz, 1H) 7.37 (d, J=8.60 Hz, 1H) 7.32 (d, J=9.54 Hz, 1H) 6.38 (d, J=1.76 Hz, 1H) 6.34 (d, J=9.43 Hz, 1H) 4.12-4.30 (m, 2H) 3.73 (s, 3H) 3.32-3.44 (m, 2H) 2.33-2.44 (m, 1H) 2.03 (dt, J=17.62, 5.75 Hz, 1H). m/z (ESI) 499.0 (M+H)$^+$.

Preparation 8e: (Rac)-1-(4-Bromo-5-Chloro-2-Methoxyphenyl)-2-Oxo-N-(Pyridazin-3-Yl)-1,2,7,8-Tetrahydro-1,6-Naphthyridine-6(5H)-Sulfonamide

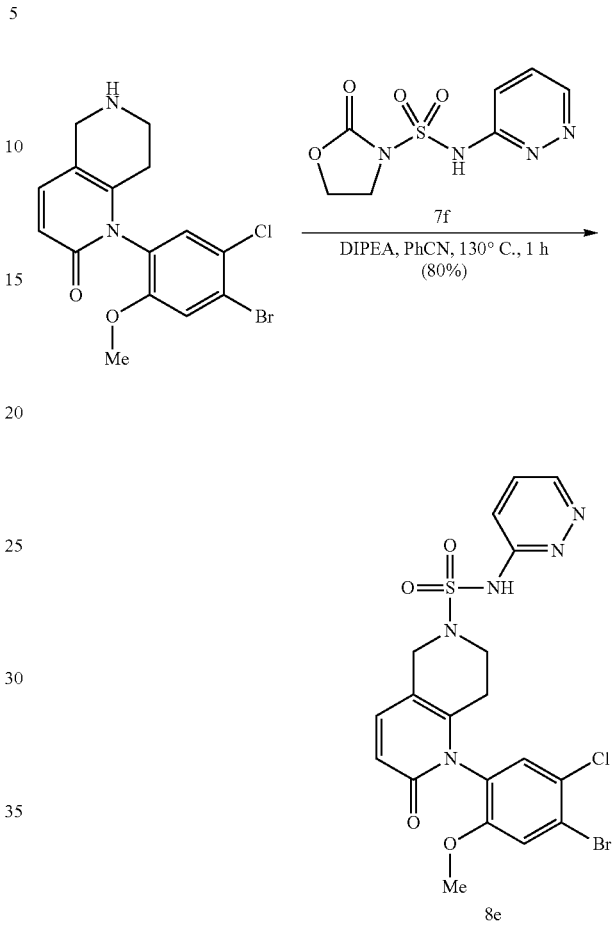

A 125-mL sealed tube was charged with 1-(4-bromo-5-chloro-2-methoxyphenyl)-5,6,7,8-tetrahydro-1,6-naphthyridin-2(1H)-one (See Preparation 8c, step 2, 6.00 g, 16.2 mmol), 2-oxo-N-(pyridazin-3-yl)oxazolidine-3-sulfonamide (7.93 g, 32.5 mmol) (Preparation 7f, 5.86 g, 24.0 mmol), N,N-diisopropylethylamine (19.8 ml, 114 mmol), and benzonitrile (32.5 ml). The reaction vessel was sealed and warmed to 130° C. After 1 h, the reaction was cooled to ambient temperature and transferred to a 250-mL round-bottomed flask and concentrated under reduced pressure (1 mbar at 80-90° C.). The resultant black oil was diluted with DCM (200 mL) and washed with a solution of aqueous HCl (1.0 M, 100 mL). The aqueous layer was back-extracted with DCM (3×50 mL). The combined organic layers were dried over magnesium sulfate, filtered, concentrated under reduced pressure, and purified (200-g silica gel Grace, 0 to 10% MeOH in DCM) to afford (Rac)-1-(4-bromo-5-chloro-2-methoxyphenyl)-2-oxo-N-(pyridazin-3-yl)-1,2,7,8-tetrahydro-1,6-naphthyridine-6(5H)-sulfonamide (3 g, 5.69 mmol, 35.1% yield) as a brown solid. $^1$H NMR (400 MHz, DMSO-d$_6$) δ=14.22 (br. s., 1H), 7.84 (dd, J=4.2, 9.6 Hz, 1H), 7.70-7.58 (m, 3H), 7.37 (d, J=9.5 Hz, 1H), 6.36 (d, J=9.4 Hz, 1H), 4.05 (d, J=11.2 Hz, 2H), 3.79 (s, 3H), 3.22 (br. s., 2H), 2.47-2.27 (m, 1H), 2.18-2.02 (m, 1H). m/z (ESI) 526.0 (M+H)$^+$.

Preparations 8f: (Rac); (P)-; and (M)-1-(4-Bromo-5-Fluoro-2-Methoxyphenyl)-2-Oxo-N-(Pyrimidin-4-Yl)-1,2,7,8-Tetrahydro-1,6-Naphthyridine-6(5H)-Sulfonamide

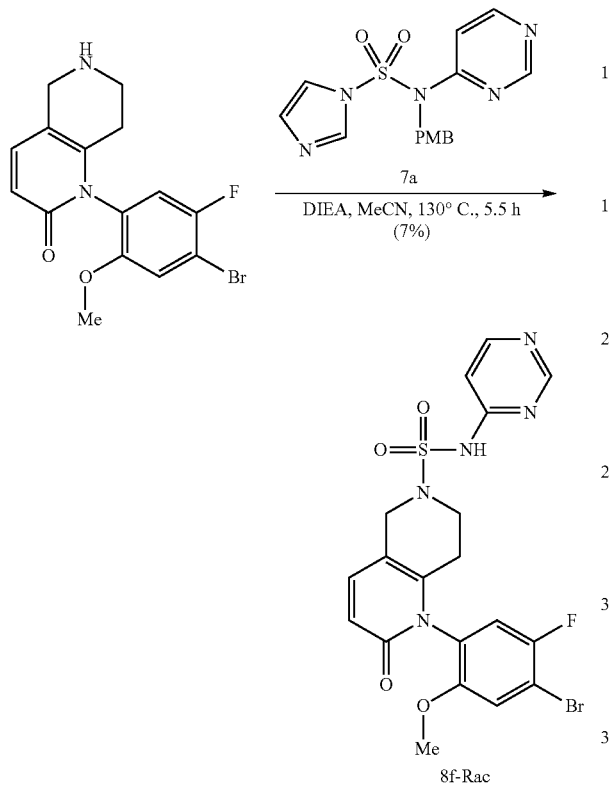

8f-Rac

A 20-mL vial was charged with N-(4-methoxybenzyl)-N-(pyrimidin-4-yl)-1H-imidazole-1-sulfonamide (Preparative 7a, 978 mg, 2.83 mmol), 1-(4-bromo-5-fluoro-2-methoxyphenyl)-5,6,7,8-tetrahydro-1,6-naphthyridin-2(1H)-one (500 mg, 1.42 mmol), acetonitrile (7.10 mL), and N-ethyl-N-isopropylpropan-2-amine (1.73 mL, 9.91 mmol). The vial was sealed with a PTFE lined cap and heated to 130° C. After 5 h 30 min, the resultant brown reaction mixture was cooled to ambient temperature and diluted with EtOAc (10 mL) and washed with 1M HCl (20 mL). The aqueous layer was extracted with EtOAc (3×15 mL). The combined organic layers were dried over magnesium sulfate, filtered, concentrated under reduced pressure, diluted with DMSO and filtered through a 0.45 micron filter. The filtrate was purified by reverse phase HPLC in 2 separate injections (XBridge Prep Shield RP18 19×100 mm Mobile phase: 0.1% formic acid in water/acetonitrile Flow rate: 40 ml/min Inj: 1500 uL Gradient: 12 min 25-90%). The fractions containing product were frozen and lyophilized to afford The fraction containing the desired product were combined and lyophilized to afford (Rac)-1-(4-bromo-5-fluoro-2-methoxyphenyl)-2-oxo-N-(pyrimidin-4-yl)-1,2,7,8-tetrahydro-1,6-naphthyridine-6(5H)-sulfonamide (50 mg, 0.098 mmol, 6.9% yield) as a tan solid. $^1$H NMR (400 MHz, DMSO-$d_6$) δ ppm 8.61 (br. s., 1H) 8.33 (br. s., 1H) 7.56 (d, J=6.22 Hz, 1H) 7.31-7.45 (m, 2H) 6.97 (br. s., 1H) 6.36 (d, J=9.43 Hz, 1H) 4.20 (d, J=11.92 Hz, 2H) 3.73 (s, 3H) 2.28-2.45 (m, 1H) 1.98-2.18 (m, 1H). m/z (ESI) 511.0 (M+H)+.

Separation Step: Racemic 8f-Rac was subjected to chiral SFC (Regis Whelk-O (s,s), 40% methanol) to give Preparation 8f-P (peak 1) and Preparation 8f-M (peak 2) as an off-white solids.

Example 1

(Rac)-; (P)-; and (M)-1-(4'-Chloro-2-Fluoro-5-Methoxy-3'-Methyl-[1,1'-Biphenyl]-4-Yl)-2-Oxo-N-(Pyrimidin-4-Yl)-1,2,7,8-Tetrahydro-1,6-Naphthyridine-6(5H)-Sulfonamide

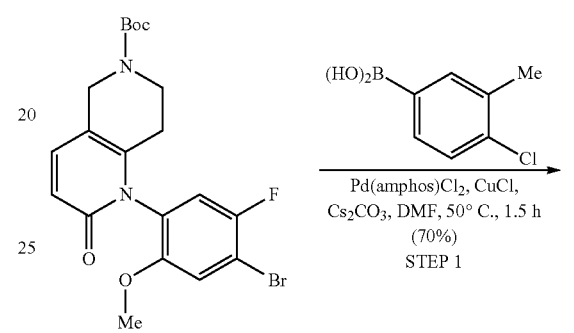

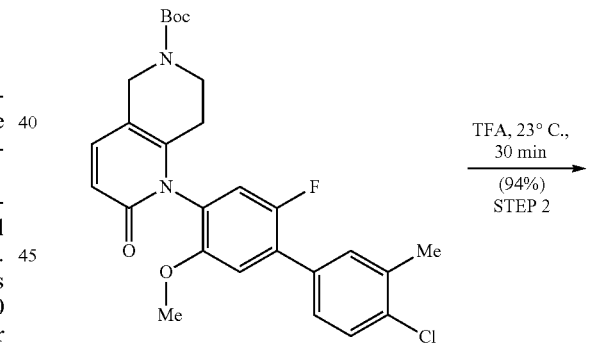

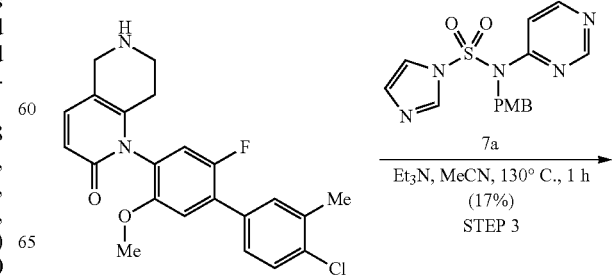

-continued

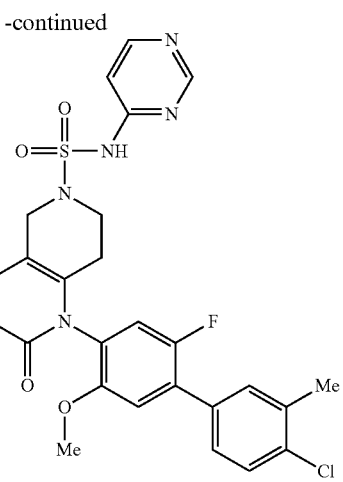

Step 1: (Rac)-tert-Butyl 1-(4'-Chloro-2-Fluoro-5-Methoxy-3'-Methyl-[1,1'-Biphenyl]-4-Yl)-2-Oxo-1,2,7,8-Tetrahydro-1,6-Naphthyridine-6(5H)-Carboxylate A 50-mL round-bottom flask was charged with (Rac)-tert-butyl 1-(4-bromo-5-fluoro-2-methoxyphenyl)-2-oxo-1,2,7,8-tetrahydro-1,6-naphthyridine-6(5H)-carboxylate (See Preparation 8a, step 1, 528 mg, 1.17 mmol), (4-chloro-3-methylphenyl)boronic acid (Sigma Aldrich, 595 mg, 3.49 mmol), cesium carbonate (1.52 g, 4.66 mmol), copper chloride (346 mg, 3.49 mmol), 1,1-bis[(di-t-butyl-p-methylaminophenyl]palladium(II) chloride (165 mg, 0.23 mmol), then purged with nitrogen. DMF (5.82 mL) was introduced and the resultant orange reaction mixture was warmed to 50° C. After 1.5 h, the reaction mixture was allowed to cool to ambient temperature and diluted with a 1:1 mixture of saturated aqueous solution of ethylenediaminetetraacetic acid and water (25 mL) and EtOAc (15 mL). The mixture was filtered through a pad of Celite® then rinsed with EtOAc (2×10 mL). The layers were separated and the aqueous layer was extracted with EtOAc (3×5 mL). The combined organic layers were washed with brine (25 mL), dried over anhydrous magnesium sulfate, filtered, and concentrated under reduced pressure and purified by flash column chromatography (25-g silica gel Biotage column, eluent: gradient, 0 to 50% 3:1 EtOAc/EtOH in heptane with DCM as a 10% additive) to afford (Rac)-tert-butyl 1-(4'-chloro-2-fluoro-5-methoxy-3'-methyl-[1,1'-biphenyl]-4-yl)-2-oxo-1,2,7,8-tetrahydro-1,6-naphthyridine-6(5H)-carboxylate (407 mg, 0.82 mmol, 70.0% yield) as a tan solid. m/z (ESI) 499.0 (M+H)$^+$.

Step 2: (Rac)-1-(4'-Chloro-2-Fluoro-5-Methoxy-3'-Methyl-[1,1'-Biphenyl]-4-Yl)-5,6,7,8-Tetrahydro-1,6-Naphthyridin-2(1H)-One A 50-mL round-bottom flask was charged with (Rac)-tert-butyl 1-(4'-chloro-2-fluoro-5-methoxy-3'-methyl-[1,1'-biphenyl]-4-yl)-2-oxo-1,2,7,8-tetrahydro-1,6-naphthyridine-6(5H)-carboxylate (407 mg, 0.82 mmol) and trifluoroacetic acid (8.16 mL) then stirred for 30 min at ambient temperature. The reaction mixture was concentrated under reduced pressure, dissolved in DCM (25 mL) and carefully poured into saturated aqueous sodium bicarbonate solution (25 mL). The layers were separated and the aqueous layer extracted with additional DCM (3×25 mL). The combined organic layers were dried over anhydrous magnesium sulfate, filtered, concentrated under reduced pressure to afford (Rac)-1-(4'-chloro-2-fluoro-5-methoxy-3'-methyl-[1,1'-biphenyl]-4-yl)-5,6,7,8-tetrahydro-1,6-naphthyridin-2(1H)-one (307 mg, 0.77 mmol, 94% yield) as a tan foam which was used without further purification. m/z (ESI) 399.2 (M+H)$^+$.

Step 3: (Rac)-1-(4'-Chloro-2-Fluoro-5-Methoxy-3'-Methyl-[1,1'-Biphenyl]-4-Yl)-2-Oxo-N-(Pyrimidin-4-Yl)-1,2,7,8-Tetrahydro-1,6-Naphthyridine-6(5H)-Sulfonamide A 3-mL vial was charged with N-(4-methoxybenzyl)-N-(pyrimidin-4-yl)-1H-imidazole-1-sulfonamide (Preparative 7a, 260 mg, 0.75 mmol), 1-(4'-chloro-2-fluoro-5-methoxy-3'-methyl-[1,1'-biphenyl]-4-yl)-5,6,7,8-tetrahydro-1,6-naphthyridin-2(1H)-one (100 mg, 0.251 mmol), acetonitrile (1.25 ml), and triethylamine (245 µL, 1.76 mmol). The vial was sealed with a PTFE lined cap and heated to 130° C. After 1 h, the resultant brown reaction mixture was cooled to ambient temperature and diluted to 3 mL total volume with DMSO and filtered through a 0.4 micron filter. The filtrate was purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-70%). The fractions containing product were frozen and lyophilized to afford 1-(4'-chloro-2-fluoro-5-methoxy-3'-methyl-[1,1'-biphenyl]-4-yl)-2-oxo-N-(pyrimidin-4-yl)-1,2,7,8-tetrahydro-1,6-naphthyridine-6(5H)-sulfonamide (23.0 mg, 0.04 mmol, 16.5% yield) as an off-white solid. $^1$H NMR (400 MHz, DMSO-d$_6$) δ=8.60 (br. s., 1H), 7.66 (s, 1H), 7.60-7.55 (m, 1H), 7.52-7.47 (m, 1H), 7.42-7.35 (m, 1H), 7.28 (d, J=7.2 Hz, 2H), 6.38 (d, J=9.4 Hz, 1H), 4.22 (d, J=10.9 Hz, 2H), 3.84-3.71 (m, 4H), 3.39 (br. s., 2H), 2.47-2.31 (m, 4H), 2.22-2.05 (m, 1H). m/z (ESI) 556.0 (M+H)$^+$.

Separation Step: Racemic product of Example 1 was subjected to chiral SFC (Regis Whelk-O (s,s), 50% methanol) to give Example 1-P (peak 1) as an off white solid.

(M)-1-(4'-Chloro-2-Fluoro-5-Methoxy-3'-Methyl-[1,1'-Biphenyl]-4-Yl)-2-Oxo-N-(Pyrimidin-4-Yl)-1,2,7,8-Tetrahydro-1,6-Naphthyridine-6(5H)-Sulfonamide (Example 1-M) was not isolated in this example.

Example 2

(Rac)-; (P)-; and (M)-1-(4'-Chloro-2-Fluoro-3',5-Dimethoxy)-[1,1']-Biphenyl-4-yl)-5,6,7,8-Tetrahydro-1,6-Naphthyridin-2(1H)-One

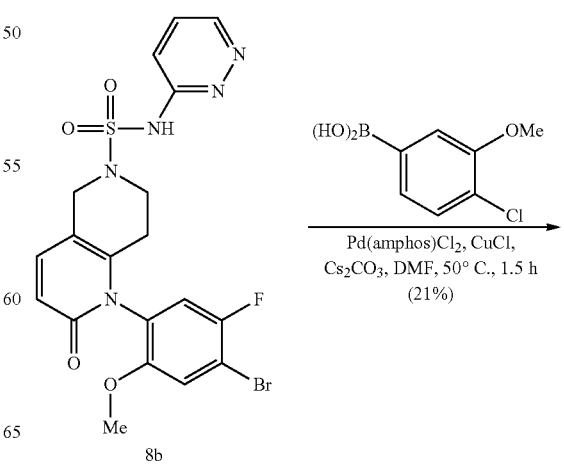

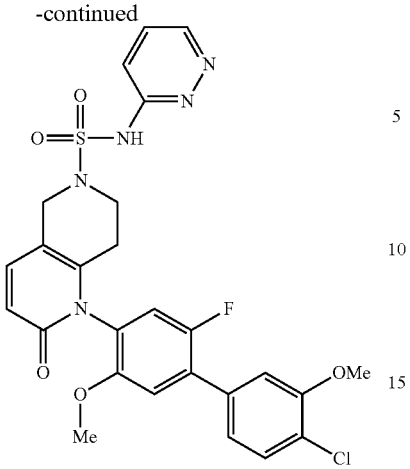

A 3-mL vial was charged with (Rac)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b, 100 mg, 0.20 mmol), (Matrix Scientific, 4-chloro-3-methoxyphenyl)boronic acid (110 mg, 0.59 mmol), cesium carbonate (255 mg, 0.784 mmol), copper chloride (58.2 mg, 0.588 mmol), and 1,1-bis[(di-t-butyl-p-methylaminophenyl]palladium(II) chloride (27.7 mg, 0.039 mmol), then purged with nitrogen. DMF (980 μL) was introduced, the vial was sealed with a PTFE line cap, and the resultant orange reaction mixture was warmed to 50° C. After 1.5 h, the reaction mixture was allowed to cool to ambient temperature and diluted with aqueous HCl solution (1.0 M, 5 mL) and EtOAc (5 mL). The layers were separated and the aqueous layer extracted with additional EtOAc (2×5 mL). The combined organic layers were, dried over anhydrous magnesium sulfate, filtered, concentrated under reduced pressure and purified reverse phase HPLC in 2 separate injections (XBridge Prep Shield RP18 19×100 mm Mobile phase: 0.1% TFA in water/acetonitrile Flow rate: 40 ml/min Inj: 1000 uL Gradient: 12 min 25-70%). The fractions containing product were frozen and lyophilized to afford (Rac)-1-(4'-chloro-2-fluoro-3',5-dimethoxy-[1,1'-biphenyl]-4-yl)-2-oxo-N-(pyridazin-3-yl)-1,2,7,8-tetrahydro-1,6-naphthyridine-6(5H)-sulfonamide (24.0 mg, 0.042 mmol, 21.4% yield) as a off-white solid. $^1$H NMR (400 MHz, DMSO-$d_6$) δ ppm 7.67 (dd, J=9.54, 4.15 Hz, 1H) 7.57 (d, J=8.19 Hz, 1H) 7.29-7.44 (m, 4H) 7.23 (dt, J=8.16, 1.83 Hz, 1H) 6.39 (d, J=9.43 Hz, 1H) 4.01-4.17 (m, 2H) 3.95 (s, 3H) 3.81 (s, 3H) 3.21-3.29 (m, 2H) 2.40-2.46 (m, 1H) 2.07-2.23 (m, 1H). m/z (ESI) 572.1 (M+H)$^+$.

Separation Step: Racemic product of Example 2 was subjected to chiral SFC (Regis Whelk-O (s,s), 50% methanol) to give (Example 2-P) (peak 1) and (Example 2-M) (peak 2) as an off-white solids.

Example 3

A Mixture of (Rac)-N-(Isoxazol-3-Yl)-5-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide and (Rac)-N-(Isoxazol-3-Yl)-7-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide

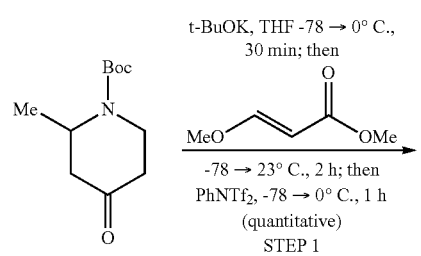

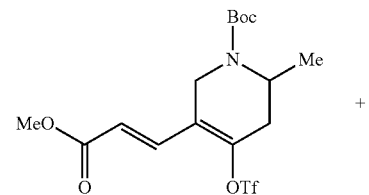

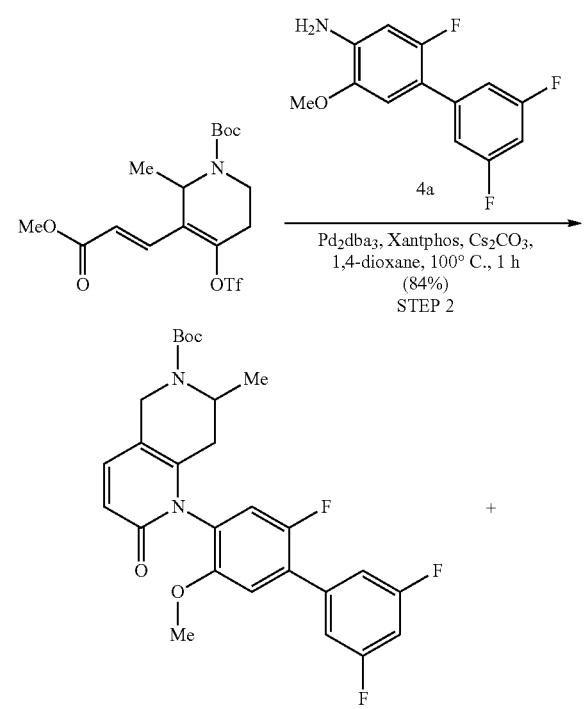

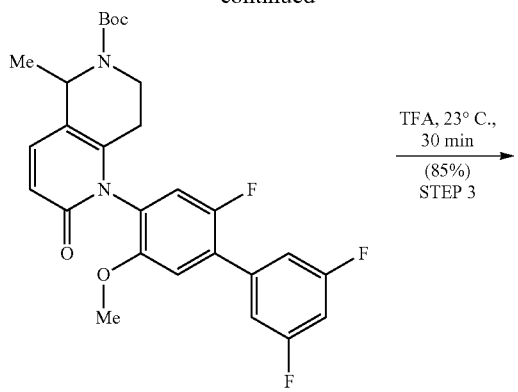

TFA, 23° C., 30 min
(85%)
STEP 3

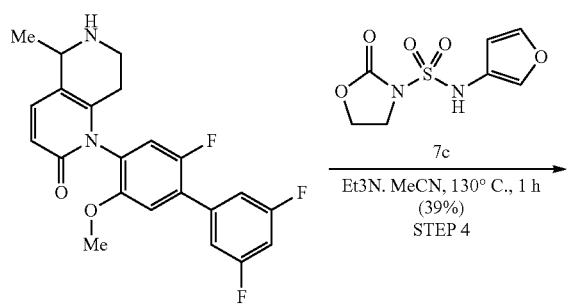

7c
Et3N, MeCN, 130° C., 1 h
(39%)
STEP 4

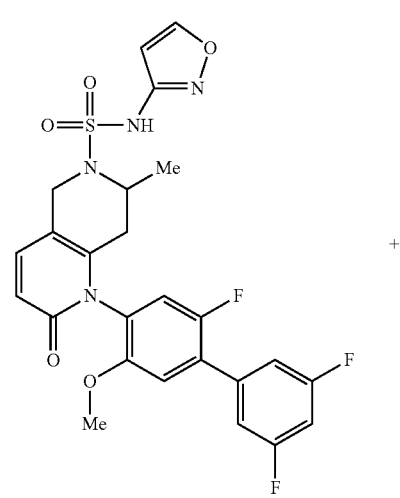

+

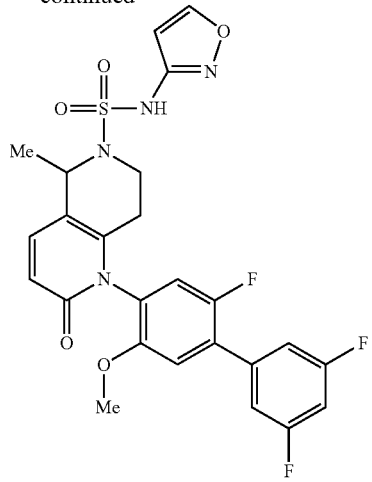

Step 1: (Rac)-(E)-Tert-Butyl 3-(3-Methoxy-3-Oxo-prop-1-EN-1-Yl)-6-Methyl-4-(((Trifluoromethyl) Sulfonyl)Oxy)-5,6-Dihydropyridine-1 (2H)-Carboxylate and (Rac)-(E)-Tert-Butyl 3-(3-Methoxy-3-Oxoprop-1-EN-1-Yl)-2-Methyl-4-(((Trifluoromethyl) Sulfonyl)Oxy)-5,6-Dihydropyridne-1 (2H)-Carboxylate A 250-mL round-bottom flask was charged with (Rac)-tert-butyl 3-methyl-4-oxopiperidine-1-carboxylate (5.00 g, 23.4 mmol) and purged with nitrogen. THF (47.0 ml) was introduced and the reaction mixture was cooled to −78° C. in a dry ice-acetone bath. A solution of potassium tert-butoxide (1.6 M in THF, 19.0 mL, 29.9 mmol) was added to the reaction mixture via syringe over 5 min. Following addition, the reaction mixture was allowed to warm to 0° C. in an ice-water bath. After 30 min, the reaction mixture was cooled to −78° C. Methyl 3-methoxyacrylate (5.29 ml, 49.2 mmol) was added dropwise to the reaction mixture via syringe over 5 min. Following addition, the reaction mixture was allowed to warm to ambient temperature. After 2 h, the resultant red reaction mixture was cooled was cooled to −78° C. N-phenyl bis-trifluoromethane sulfonamide (13.2 g, 37.0 mmol) was added to the vigorously stirred, cooled reaction mixture in one portion and the reaction mixture was subsequently allowed to warm to 0° C. in an ice-water bath. After 1 h, saturated aqueous sodium bicarbonate solution (100 mL) and EtOAc (100 mL) were added to the reaction mixture, and the layers were separated. The aqueous layer was extracted with EtOAc (3×50 mL) and the combined organic layers were dried over anhydrous sodium sulfate, filtered, and concentrated under reduced pressure. The residue was purified by flash column chromatography in two portions (100-g silica gel Biotage column, eluent: gradient, 0 to 30% EtOAc in heptane) to afford a mixture of (Rac)-(E)-tert-butyl 3-(3-methoxy-3-oxoprop-1-en-1-yl)-6-methyl-4-(((trifluoromethyl)sulfonyl)oxy)-5,6-dihydropyridine-1(2H)-carboxylate and (Rac)-(E)-tert-butyl 3-(3-methoxy-3-oxoprop-1-en-1-yl)-2-methyl-4-(((trifluoromethyl)sulfonyl)oxy)-5,6-dihydropyridine-1(2H)-carboxylate (11.75 g, 27.4 mmol, 117% yield) as a yellow solid.

Step 2: (Rac)-tert-Butyl 7-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Carboxylate and (Rac)-tert-Butyl 5-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Carboxylate A 20-mL vial was charged with a mixture of (Rac)-(E)-tert-butyl 3-(3-methoxy-3-oxoprop-1-en-1-yl)-6-methyl-4-(((trifluoromethyl)sulfonyl)oxy)-5,6-dihydropyridine-1(2H)-carboxylate and (Rac)-(E)-tert-butyl 3-(3-methoxy-3-oxoprop-1-en-1-yl)-2-methyl-4-(((trifluoromethyl)sulfonyl)oxy)-5,6-dihydropyridine-1 (2H)-carboxylate (716 mg, 1.668 mmol), 2,3',5'-trifluoro-5-methoxy-[1,1'-biphenyl]-4-amine (Preparation 4h, 352 mg, 1.39 mmol), (9,9-dimethyl-9H-xanthene-4,5-diyl)bis(diphenylphosphine) (101 mg, 0.174 mmol), cesium carbonate (1.36 g, 4.17 mmol), tris(dibenzylideneacetone)dipalladium(0) (63.9 mg, 0.07 mmol), and 1,4-dioxane (6.95 mL) then sparged with nitrogen for 10 min. The needle was then removed and the reaction was heated to 100° C. After 3 h, the reaction mixture was allowed to cool to ambient temperature and was diluted with EtOAc (15 mL) and filtered through a Celite® pad. The pad was rinsed with EtOAc (3×15 mL). The filtrate was concentrated under reduced pressure and purified by flash column chromatography (50-g silica gel Biotage column, eluent: gradient, 0 to 35% 3:1 EtOAc/EtOH in heptane with DCM as a 10% additive) to afford a mixture of (Rac)-tert-butyl 7-methyl-2-oxo-1-(2,3',5'-trifluoro-5-methoxy-[1,1'-biphenyl]-4-yl)-1,2,7,8-tetrahydro-1,6-naphthyridine-6(5H)-carboxylate and (Rac)-tert-butyl 5-methyl-2-oxo-1-(2,3',5'-trifluoro-5-methoxy-[1,1'-biphenyl]-4-yl)-1,2,7,8-tetrahydro-1,6-naphthyridine-6(5H)-carboxylate (587 mg, 1.17 mmol, 84.0%) as a brown solid. m/z (ESI) 501.2 (M+H)$^+$.

Step 3: (Rac)-7-Methyl-1-(2,3',5'-Trifluoro-5-Methoxy-[1,1'-Biphenyl]-4-YL)-5,6,7, 8-Tetrahydro-1,6-Naphthyridin-2(1H)-One and (Rac)-5-Methyl-1-(2,3',5'-Trifluoro-5-Methoxy-[1,1'-Biphenyl]-4-YL)-5,6,7,8-Tetrahydro-1,6-Naphthyridin-2(1H)-One A 20-mL vial was charged with a mixture of (Rac)-tert-butyl 7-methyl-2-oxo-1-(2,3',5'-trifluoro-5-methoxy-[1,1'-biphenyl]-4-yl)-1,2,7,8-tetrahydro-1,6-naphthyridine-6(5H)-carboxylate and (Rac)-tert-butyl 5-methyl-2-oxo-1-(2,3',5'-trifluoro-5-methoxy-[1,1'-biphenyl]-4-yl)-1,2,7,8-tetrahydro-1,6-naphthyridine-6(5H)-carboxylate (587 mg, 1.173 mmol) and trifluoroacetic acid (5.86 mL) at ambient temperature. After 30 min, the reaction mixture was concentrated under reduced pressure, dissolved in DCM (15 mL) and carefully poured into saturated aqueous sodium bicarbonate solution (15 mL). The layers were separated and the aqueous layer extracted with additional DCM (3×15 mL). The combined organic layers were dried over anhydrous magnesium sulfate, filtered, concentrated under reduced pressure to afford a mixture of (Rac)-7-methyl-1-(2,3',5'-trifluoro-5-methoxy-[1,1'-biphenyl]-4-yl)-5,6,7,8-tetrahydro-1,6-naphthyridin-2(1H)-one and (Rac)-5-methyl-1-(2,3',5'-trifluoro-5-methoxy-[1,1'-biphenyl]-4-yl)-5,6,7,8-tetrahydro-1,6-naphthyridin-2(1H)-one (400 mg, 1.00 mmol, 85.0%) as a tan amorphous solid, which was used without further purification.

Step 4: (Rac)-N-(Isoxazol-3-Yl)-7-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide and (Rac)-N-(Isoxazol-3-Yl)-5-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide A 20-mL vial was charged with a mixture of (Rac)-7-methyl-1-2,3',5'-trifluoro-5-methoxy-[1,1'-biphenyl]-4-yl)-5,6,7,8-tetrahydro-1,6-naphthyridin-2(1H)-one and (Rac)-5-methyl-1-(2,3',5'-trifluoro-5-methoxy-[1,1'-biphenyl]-4-yl)-5,6,7,8-tetrahydro-1,6-naphthyridin-2(1H)-one (400 mg, 1.00 mmol), N-(isoxazol-3-yl)-2-oxooxazolidine-3-sulfonamide (Preparation 7c, 349 mg, 1.50 mmol), acetonitrile (5.00 mL), and triethylamine (975 μL, 6.99 mmol). The vial was sealed with a PTFE lined cap and heated to 130° C. After 1 h, the resultant brown reaction mixture was cooled to ambient temperature and diluted to 3 mL total volume with DMSO and filtered through a 0.4 micron filter. The filtrate was purified by reverse phase HPLC in 3 separate injections (XBridge Prep Shield RP18 19×100 mm Mobile phase: 0.1% TFA in water/acetonitrile Flow rate: 40 ml/min Inj: 2000 uL Gradient: 12 min 25-70%). The fractions containing product were frozen and lyophilized to afford (Rac)-N-(isoxazol-3-yl)-7-methyl-2-oxo-1-(2,3',5'-trifluoro-5-methoxy-[1,1'-biphenyl]-4-yl)-1,2,7,8-tetrahydro-1,6-naphthyridine-6(5H)-sulfonamide and (Rac)-N-(isoxazol-3-yl)-5-methyl-2-oxo-1-(2,3',5'-trifluoro-5-methoxy-[1,1'-biphenyl]-4-yl)-1,2,7,8-tetrahydro-1,6-naphthyridine-6(5H)-sulfonamide (212 mg, 0.39 mmol, 38.8% yield) as an orange solid, which was a mixture of 8 isomers.

Separation Step: Examples 3a-P, 3a-M, 3b-P, 3b-M, 3c-P, 3c-M, 3d-P, and 3d-M; which are named:

Example 3a-P: (P)—(R)—N-(Isoxazol-3-Yl)-5-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide Example 3a-M: (M)-(R)—N-(Isoxazol-3-Yl)-5-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide Example 3b-P: (P)—(S)—N-(Isoxazol-3-Yl)-5-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide Example 3b-M: (M)-(S)—N-(Isoxazol-3-Yl)-5-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide Example 3c-P: (P)—(S)—N-(Isoxazol-3-Yl)-7-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide Example 3c-M: (M)-(S)—N-(Isoxazol-3-Yl)-7-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide Example 3d-P: (P)—(R)—N-(Isoxazol-3-Yl)-7-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide Example 3d-M: (M)-(R)—N-(Isoxazol-3-Yl)-7-Methyl-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide -continued Example 3a-M

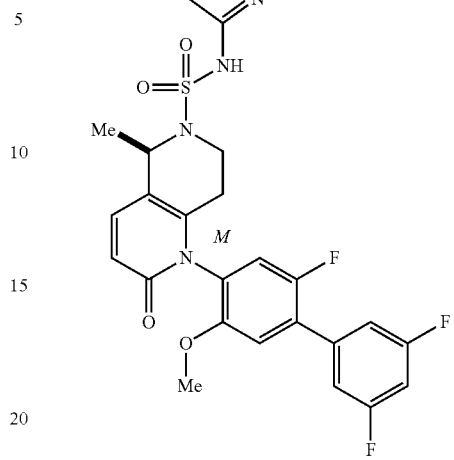

Example 3b-P

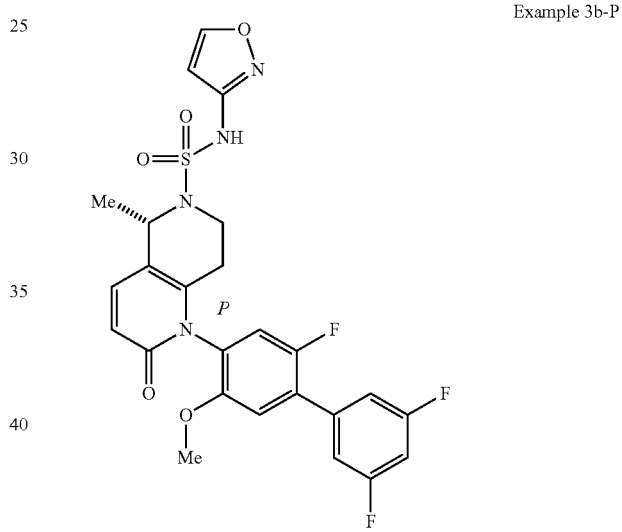

Example 3a-P

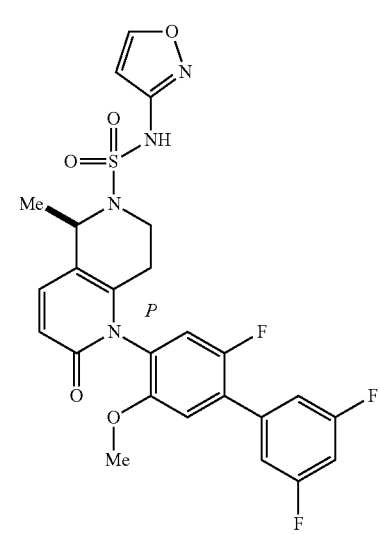

Example 3b-M

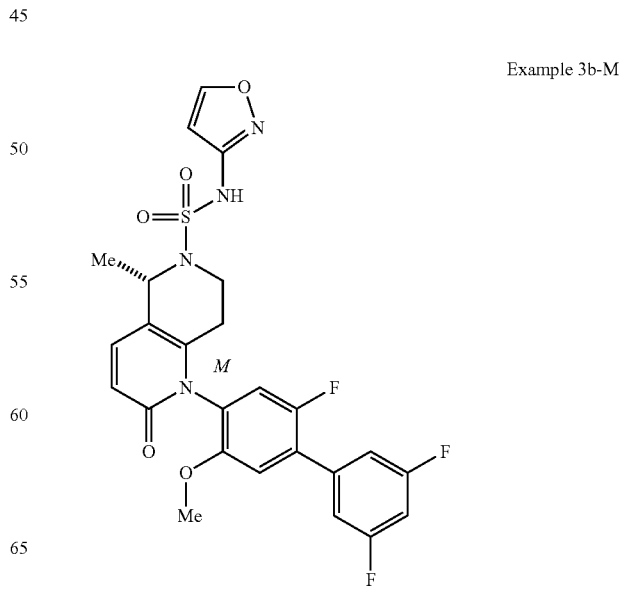

Example 3c-P

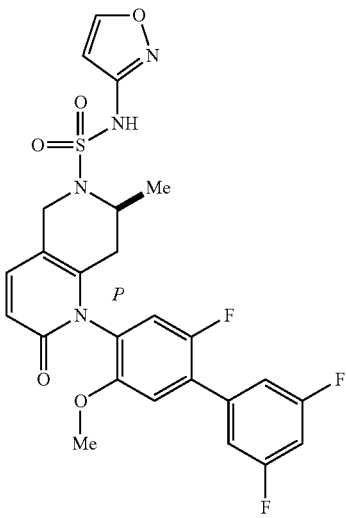

Example 3c-M

Example 3d-P

Example 3d-M

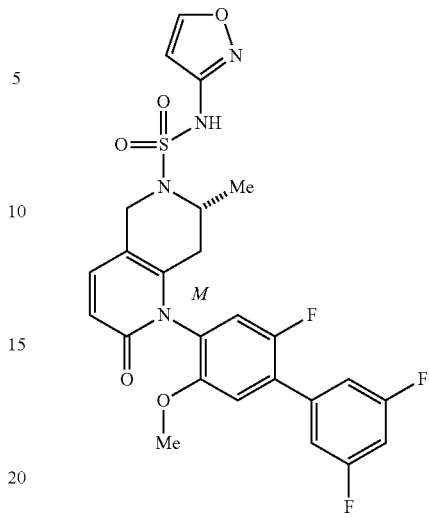

A mixture of Racemic product of Example 3 was subjected to chiral SFC (Regis Whelk-O (s,s), 5 to 55% methanol gradient) to give the following:
Peak 1: Example 3a-P;
Peak 2: Example 3a-M;
Peak 3: 1:1 mixture of Example 3a-P and Example 3d-P. (This fraction was further purified by chiral SFC (Chiralpak IC (s,s), 55% ethanol) to give the following as an off-white solids: Peak 1: Example 3a-P; Peak 2: Example 3d-P)
Peak 4: Example 3b-M;
Peak 5: Example 3c-P;
Peak 6: Example 3c-M;
Peak 7: Example 3d-M.

Example 3a-P $^1$H NMR (400 MHz, DMSO-$d_6$) δ=11.10 (br. s., 1H), 8.70 (d, J=1.8 Hz, 1H), 7.44 (dd, J=1.2, 6.5 Hz, 2H), 7.40-7.34 (m, 2H), 7.29 (dd, J=9.9, 15.7 Hz, 2H), 6.38-6.30 (m, 2H), 4.40 (d, J=16.6 Hz, 1H), 4.25-4.14 (m, 1H), 4.11 (d, J=16.6 Hz, 1H), 3.80 (s, 3H), 2.60 (dd, J=6.1, 17.5 Hz, 1H), 1.74 (d, J=17.5 Hz, 1H), 1.07 (d, J=6.8 Hz, 3H). m/z (ESI) 547.2 (M+H)$^+$.

Example 3a-M $^1$H NMR (400 MHz, DMSO-$d_6$) δ ppm 11.02 (s, 1H) 8.68 (s, 1H) 7.44 (d, J=7.77 Hz, 2H) 7.34-7.40 (m, 2H) 7.32 (d, J=9.54 Hz, 1H) 7.14 (d, J=10.37 Hz, 1H) 6.36 (d, J=1.76 Hz, 1H) 6.31 (d, J=9.54 Hz, 1H) 4.69-4.84 (m, 1H) 3.81 (s, 3H) 3.71 (dd, J=14.72, 6.84 Hz, 1H) 3.21-3.29 (m, 1H) 2.39-2.47 (m, 1H) 1.75-1.87 (m, 1H) 1.37 (d, J=6.63 Hz, 3H). m/z (ESI) 547.2 (M+H)$^+$.

Example 3b-P $^1$H NMR (600 MHz, DMSO) δ=11.17 (br. s., 1H), 8.74 (d, J=1.5 Hz, 1H), 7.47-7.42 (m, 3H), 7.40-7.35 (m, 2H), 7.33 (d, J=7.0 Hz, 1H), 6.39 (d, J=9.5 Hz, 1H), 6.29 (d, J=1.8 Hz, 1H), 4.80 (q, J=6.4 Hz, 1H), 3.77-3.62 (m, 4H), 3.27-3.14 (m, 1H), 2.17-2.09 (m, 2H), 1.36 (d, J=6.4 Hz, 3H). m/z (ESI) 547.1 (M+H)$^+$.

Example 3b-M $^1$H NMR (400 MHz, DMSO-$d_6$) δ ppm 11.01 (s, 1H) 8.68 (s, 1H) 7.30-7.48 (m, 5H) 7.14 (d, J=10.37 Hz, 1H) 6.36 (d, J=1.87 Hz, 1H) 6.31 (d, J=9.33 Hz, 1H) 4.76 (q, J=6.81 Hz, 1H) 3.81 (s, 3H) 3.71 (dd, J=14.93, 7.15 Hz, 1H) 2.40-2.46 (m, 1H) 1.81 (dd, J=17.88, 4.20 Hz, 1H) 1.37 (d, J=6.84 Hz, 3H). m/z (ESI) 547.2 (M+H)$^+$.

Example 3c-P $^1$H NMR (400 MHz, DMSO-$d_6$) δ ppm 11.10 (s, 1H) 8.70 (s, 1H) 7.42-7.49 (m, 2H) 7.34-7.41 (m, 2H) 7.31 (d, J=9.43 Hz, 1H) 7.27 (d, J=10.47 Hz, 1H) 6.31-6.39 (m, 2H) 4.40 (d, J=15.45 Hz, 1H) 4.19 (d, J=6.74

Hz, 1H) 4.11 (d, J=16.07 Hz, 1H) 3.80 (s, 3H) 2.54-2.65 (m, 1H) 1.74 (d, J=17.10 Hz, 1H) 1.07 (d, J=6.84 Hz, 3H). m/z (ESI) 547.2 (M+H)⁺.

Example 3c-M ¹H NMR (400 MHz, DMSO-d₆) δ ppm 11.14 (br. s., 1H) 8.74 (d, J=1.76 Hz, 1H) 7.27-7.49 (m, 6H) 6.40 (d, J=9.23 Hz, 1H) 6.30 (d, J=1.76 Hz, 1H) 4.43 (d, J=16.27 Hz, 1H) 4.13-4.22 (m, 1H) 4.09 (d, J=16.38 Hz, 1H) 2.29-2.45 (m, 1H) 2.02 (d, J=17.21 Hz, 1H) 1.08 (d, J=6.74 Hz, 3H). m/z (ESI) 547.2 (M+H)⁺.

Example 3d-P ¹H NMR (600 MHz, DMSO) δ=11.20 (br. s., 1H), 8.76 (d, J=1.8 Hz, 1H), 7.50-7.32 (m, 6H), 6.40 (d, J=9.5 Hz, 1H), 6.31 (d, J=1.8 Hz, 1H), 4.43 (d, J=15.9 Hz, 1H), 4.21-4.13 (m, 1H), 4.09 (d, J=15.9 Hz, 1H), 3.75 (s, 3H), 2.38 (dd, J=5.8, 17.4 Hz, 1H), 2.02 (d, J=17.1 Hz, 1H), 1.08 (d, J=7.0 Hz, 3H). m/z (ESI) 547.1 (M+H)⁺.

Example 3d-M ¹H NMR (400 MHz, DMSO-d₆) δ ppm 11.13 (s, 1H) 8.74 (d, J=1.76 Hz, 1H) 7.22-7.49 (m, 6H) 6.39 (d, J=9.43 Hz, 1H) 6.29 (d, J=1.76 Hz, 1H) 4.81 (q, J=6.57 Hz, 1H) 3.60-3.78 (m, 4H) 3.15-3.26 (m, 1H) 2.08-2.19 (m, 2H) 1.37 (d, J=6.74 Hz, 3H). m/z (ESI) 547.2 (M+H)⁺.

Example 4

(Rac)-; (P)-; and (M)-1-(3'-Chloro-2,5'-Difluoro-5-Methoxy-[1,1'-Biphenyl]-4-Yl)-N-(6-Methylpyrimidin-4-Yl)-2-Oxo-1,2,7,8-Tetrahydro-1,6-Naphthyridine-6(5H)-Sulfonamide

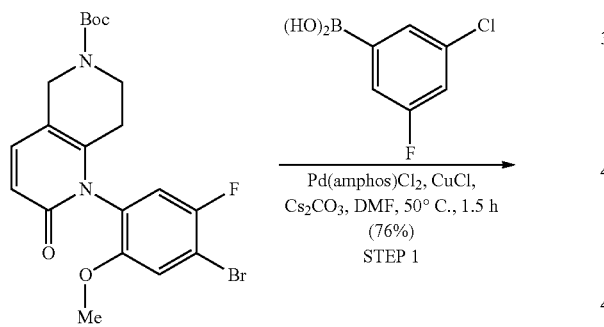

Step 1: (Rac)-tert-Butyl 1-(3'-Chloro-2,5'-Difluoro-5-Methoxy-[1, 1'-Biphenyl]-4-Yl)-2-Oxo-1,2,7,8-Tetrahydro-1,6-Naphthyridine-6(5H)-Carboxylate A 50-mL round-bottom flask was charged with (Rac)-tert-butyl 1-(4-bromo-5-fluoro-2-methoxyphenyl)-2-oxo-1,2,7,8-tetrahydro-1,6-naphthyridine-6(5H)-carboxylate (See Preparation 8a, step 1, 800 mg, 1.765 mmol), (3-chloro-5-fluorophenyl)boronic acid (Matrix Scientific, 923 mg, 5.29 mmol), cesium carbonate (2.30 g, 7.06 mmol), copper chloride (524 mg, 5.29 mmol), 1,1-bis[(di-t-butyl-p-methylaminophenyl]palladium(II) chloride (250 mg, 0.35 mmol), then purged with nitrogen. DMF (8.90 mL) was introduced and the resultant orange reaction mixture was warmed to 50° C. After 1.5 h, the reaction mixture was allowed to cool to ambient temperature and diluted with a 1:1 mixture of saturated aqueous solution of ethylenediaminetetraacetic acid and water (25 mL) and EtOAc (15 mL). The mixture was filtered through a pad of Celite® then rinsed with EtOAc (2×10 mL). The layers were separated and the aqueous layer was extracted with EtOAc (3×5 mL). The combined organic layers were washed with brine (25 mL), dried over anhydrous magnesium sulfate, filtered, and concentrated under reduced pressure and purified by flash column chromatography (25-g silica gel Biotage column, eluent: gradient, 0 to 50% 3:1 EtOAc/EtOH in heptane with DCM as a 10% additive) to afford (Rac)-tert-butyl 1-(3'-chloro-2,5'-difluoro-5-methoxy-[1,1'-biphenyl]-4-yl)-2-oxo-1,2,7,8-tetrahydro-1,6-naphthyridine-6(5H)-carboxylate (678 mg, 1.35 mmol, 76% yield) as a tan solid. ¹H NMR (400 MHz, DMSO-$d_6$) δ ppm 7.61-7.65 (m, 1H) 7.57 (dd, J=9.02, 1.55 Hz, 1H) 7.36-7.45 (m, 2H) 6.41 (d, J=9.43 Hz, 1H) 4.30 (s, 2H) 3.82 (s, 3H) 3.48-3.60 (m, 1H) 3.37-3.48 (m, 1H) 2.26-2.39 (m, 1H) 1.97-2.10 (m, 1H) 1.42 (s, 9H). m/z (ESI) 503.2 (M+H)$^+$.

Step 2: (Rac)-1-(3-Chloro-2,5'-Difluoro-5-Methoxy [1,1'-Biphenyl]-4-Yl)-5,6,7,8-Tetrahydro-1,6-Naphthyridin-2(1H)-One A 50-mL round-bottom flask was charged with (Rac)-tert-butyl 1-(3'-chloro-2,5'-difluoro-5-methoxy-[1,1'-biphenyl]-4-yl)-2-oxo-1,2,7,8-tetrahydro-1,6-naphthyridine-6(5H)-carboxylate (678 mg, 1.35 mmol) and trifluoroacetic acid (10.0 mL) then stirred for 30 min at ambient temperature. The reaction mixture was concentrated under reduced pressure, dissolved in DCM (25 mL) and carefully poured into saturated aqueous sodium bicarbonate solution (25 mL). The layers were separated and the aqueous layer extracted with additional DCM (3×25 mL). The combined organic layers were dried over anhydrous magnesium sulfate, filtered, concentrated under reduced pressure to afford (Rac)-1-(3'-chloro-2,5'-difluoro-5-methoxy-[1,1'-biphenyl]-4-yl)-5,6,7,8-tetrahydro-1,6-naphthyridin-2(1H)-one (500 mg, 1.24 mmol, 92% yield) as a brown foam which was used without further purification. $^1$H NMR (400 MHz, DMSO-$d_6$) δ ppm 7.63 (d, J=1.35 Hz, 1H) 7.53-7.60 (m, 2H) 7.31-7.40 (m, 2H) 7.26 (d, J=9.33 Hz, 1H) 6.34 (d, J=9.33 Hz, 1H) 3.55-3.73 (m, 2H) 3.33 (s, 3H) 2.83 (t, J=5.44 Hz, 2H) 2.09-2.25 (m, 1H) 1.85-1.99 (m, 1H). m/z (ESI) 403.2 (M+H)$^+$.

Step 3: (Rac)-1-(3'-Chloro-2,5'-Difluoro-5-Methoxy-[1,1'-Biphenyl]-4-Yl)-N-(6-Methylpyrimidin-4-Yl)-2-Oxo-1,2,7,8-Tetrahydro-1,6-Naphthyridine-6(5H)-Sulfonamide A 3-mL vial was charged with (Rac)-1-(3'-chloro-2,5'-difluoro-5-methoxy-[1,1'-biphenyl]-4-yl)-5,6,7,8-tetrahydro-1,6-naphthyridin-2(1H)-one (100 mg, 0.25 mmol), N-(4-methoxybenzyl)-N-(6-methylpyrimidin-4-yl)-1H-imidazole-1-sulfonamide (Preparation 7e, 134 mg, 0.37 mmol), acetonitrile (2 mL), and triethylamine (242 μL, 1.74 mmol). The vial was sealed with a PTFE lined cap and heated to 130° C. After 30 min, the resultant brown reaction mixture was cooled to ambient temperature and diluted to 3 mL total volume with DMSO and filtered through a 0.4 micron filter. The filtrate was purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-70%). The fractions containing product were frozen and lyophilized to afford (Rac)-1-(3'-chloro-2,5'-difluoro-5-methoxy-[1,1'-biphenyl]-4-yl)-N-(6-methylpyrimidin-4-yl)-2-oxo-1,2,7,8-tetrahydro-1,6-naphthyridine-6(5H)-sulfonamide (45.6 mg, 0.08 mmol, 32.0% yield) as an off-white solid. $^1$H NMR (400 MHz, DMSO-$d_6$) δ ppm 8.54 (s, 1H) 7.62 (d, J=1.24 Hz, 1H) 7.53-7.59 (m, 2H) 7.35-7.42 (m, 2H) 7.31 (d, J=10.37 Hz, 1H) 6.86 (s, 1H) 6.39 (d, J=9.43 Hz, 1H) 4.17-4.28 (m, 2H) 3.80 (s, 3H) 3.38 (br. s., 2H) 2.41 (d, J=18.04 Hz, 1H) 2.05-2.17 (m, 1H). m/z (ESI) 574.0 (M+H)$^+$.

Separation Step: Racemic product of Example 4 was subjected to chiral SFC separation ((s,s) Whelk-O column, 40% methanol) to afford Example 4-P (peak 1) and Example 4-M (peak 2) as off-white solids.

Example 5

(Rac)-; (P)-; and (M)-1-(3'-Chloro-2,5'-Difluoro-5-Methoxy-[1,1'-Biphenyl]-4-Yl)-2-Oxo-N-(1,2,4-Thiadiazol-5-Yl)-1,2,7,8-Tetrahydro-1,6-Naphthyridine-6(5H)-Sulfonamide

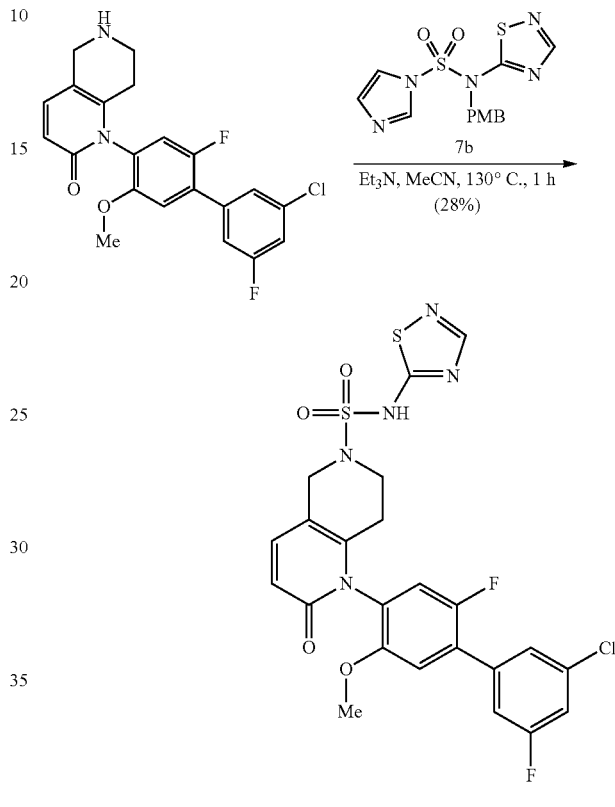

A 3-mL vial was charged with (Rac)-1-(3'-chloro-2,5'-difluoro-5-methoxy-[1,1'-biphenyl]-4-yl)-5,6,7,8-tetrahydro-1,6-naphthyridin-2(1H)-one (See Example 4, step 2, 100 mg, 0.25 mmol), N-(4-methoxybenzyl)-N-(1,2,4-thiadiazol-5-yl)-1H-imidazole-1-sulfonamide (Preparation 7b, 174 mg, 0.50 mmol), acetonitrile (2.0 mL), and triethylamine (0.24 mL, 1.74 mmol). The vial was sealed with a PTFE lined cap and heated to 130° C. After 30 min, the resultant brown reaction mixture was cooled to ambient temperature and diluted to 3 mL total volume with DMSO and filtered through a 0.4 micron filter. The filtrate was purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-70%). The fractions containing product were frozen and lyophilized to afford (Rac)-1-(3'-chloro-2, 5'-difluoro-5-methoxy-[1,1'-biphenyl]-4-yl)-2-oxo-N-(1,2, 4-thiadiazol-5-yl)-1,2,7,8-tetrahydro-1,6-naphthyridine-6 (5H)-sulfonamide (39.4 mg, 0.07 mmol, 28.0% yield) as an off-white solid. $^1$H NMR (400 MHz, DMSO-$d_6$) δ ppm 7.87 (s, 1H) 7.62 (d, J=1.35 Hz, 1H) 7.52-7.59 (m, 2H) 7.41 (d, J=10.47 Hz, 1H) 7.29-7.38 (m, 2H) 6.34 (d, J=9.43 Hz, 1H) 3.86-3.99 (m, 2H) 3.82 (s, 3H) 3.17 (d, J=4.25 Hz, 2H) 3.07-3.15 (m, 2H) 2.34-2.46 (m, 1H) 2.01-2.16 (m, 1H). m/z (ESI) 566.0 (M+H)$^+$.

Separation Step: Racemic product of Example 5 was subjected to chiral SFC separation ((S,S) AS-H column, 50% methanol) to afford (Example 5-P) (peak 1) and (Example 5-M) (peak 2) as off-white solids.

Example 6

(Rac-; (P)-; and (M)-1-(3'-Chloro-2,5'-Difluoro-5-Methoxy-[1,1'-Biphenyl]-4-Yl)-N-(2-Methylpyrimidin-4-Yl)-2-Oxo-1,2,7,8-Tetrahydro-1,6-Naphthyridine-6(5H)-Sulfonamide

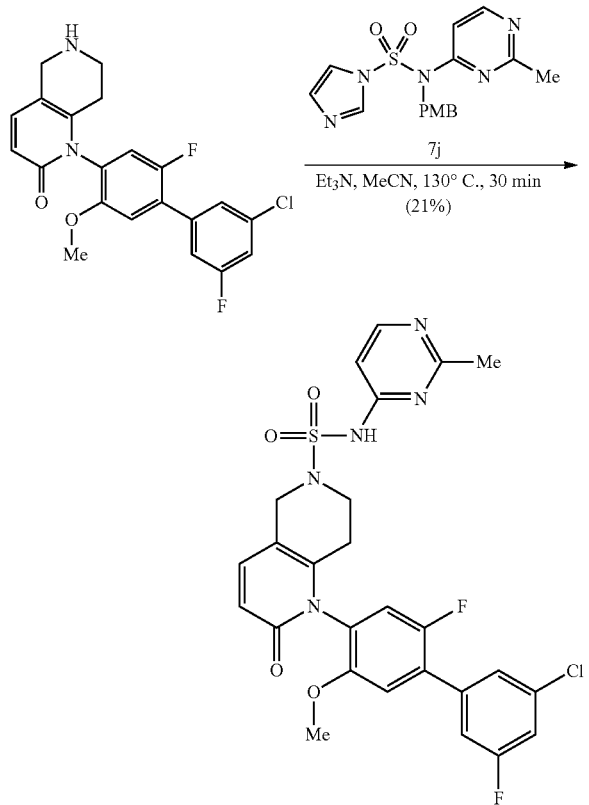

A 3-mL vial was charged with (Rac)-1-(3'-chloro-2,5'-difluoro-5-methoxy-[1,1'-biphenyl]-4-yl)-5,6,7,8-tetrahydro-1,6-naphthyridin-2(1H)-one (See Example 4, step 2, 100 mg, 0.248 mmol), N-(4-methoxybenzyl)-N-(2-methylpyrimidin-4-yl)-1H-imidazole-1-sulfonamide (Preparation 7j, 134 mg, 0.372 mmol), acetonitrile (1.24 mL), and triethylamine (242 µL, 1.74 mmol). The vial was sealed with a PTFE lined cap and heated to 130° C. After 30 min, the resultant brown reaction mixture was cooled to ambient temperature and diluted to 3 mL total volume with DMSO and filtered through a 0.4 micron filter. The filtrate was purified by reverse phase HPLC in 2 separate injections (Xbridge Prep Shield RP18 19×100 mm Mobile phase: 0.1% TFA in water/acetonitrile Flow rate: 40 ml/min Inj: 1500 uL Gradient: 12 min 25-70%). The fractions containing product were frozen and lyophilized to afford 1-(3'-chloro-2,5'-difluoro-5-methoxy-[1-biphenyl]-4-yl)-N-(2-methylpyrimidin-4-yl)-2-oxo-1,2,7,8-tetrahydro-1,6-naphthyridine-6(5H)-sulfonamide (30.3 mg, 0.05 mmol, 21.3% yield) as a tan solid. $^1$H NMR (400 MHz, DMSO-$d_6$) δ ppm 8.11 (br. s., 1H) 7.62 (d, J=1.35 Hz, 1H) 7.56 (dd, J=9.07, 1.61 Hz, 2H) 6.83 (br. s., 1H) 6.39 (d, J=9.33 Hz, 1H) 4.06-4.24 (m, 2H) 3.80 (s, 1H) 3.27-3.34 (m, 2H) 2.39-2.45 (m, 1H) 2.04-2.18 (m, 1H). m/z (ESI) 574.0 (M+H)$^+$.

Separation Step: Racemic product of Example 6 was subjected to chiral SFC separation ((S,S) AS-H column, 50% methanol) to afford Example 6-P (peak 1) and Example 6-M (peak 2) as off-white solids.

Example 7

(Rac)-; (P)-; and (M)-1-(3'-Chloro-5'-Fluoro-3-Methoxy-[1,1'-Biphenyl]-4-Yl)-N-(Isoxazol-3-Yl)-2-Oxo-1,2,7,8-Tetrahydro-1,6-Naphthyridine-6(5H)-Sulfonamide

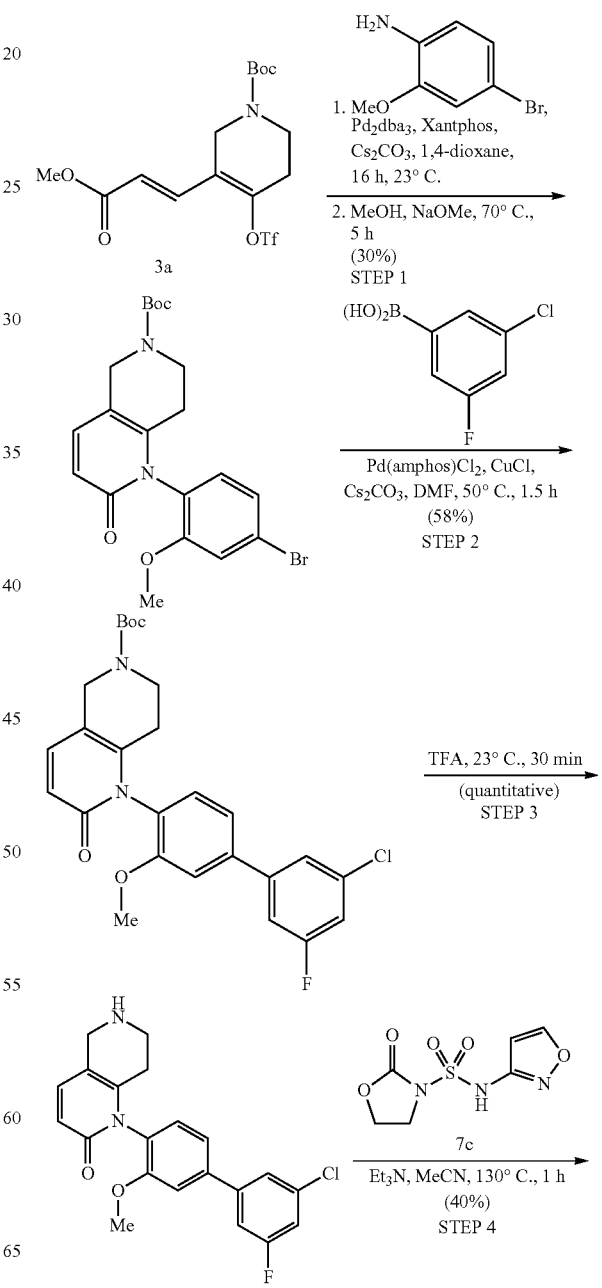

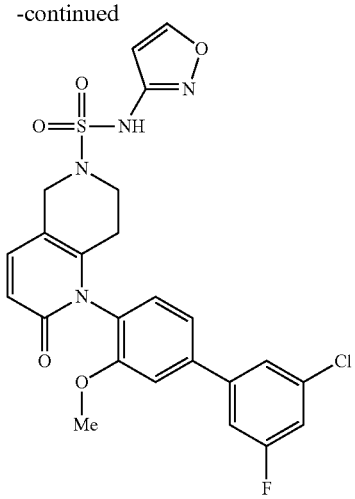

Step 1: (Rac)-tert-Butyl 1-(4-Bromo-2-Methoxyphenyl)-2-Oxo-1,2,7,8-Tetrahydro-1,6-Naphthyridine-6(5H)-Carboxylate A 100-mL round-bottom flask was charged with (E)-tert-butyl 3-(3-methoxy-3-oxoprop-1-en-1-yl)-4-(((trifluoromethyl)sulfonyl)oxy)-5,6-dihydropyridine-1(2H)-carboxylate (Preparation 3a, 3.00 g, 7.22 mmol), 2-amino-5-bromoanisole (Alfa Asear, 1.61 g, 7.94 mmol), xantphos (0.52 g, 0.90 mmol), cesium carbonate (7.06 g, 21.7 mmol), tris(dibenzylideneacetone)dipalladium(0) (0.33 g, 0.36 mmol), and 1,4-dioxane (36 mL) then sparged with nitrogen for 15 min. The reaction mixture stirred vigorously for 20 h at ambient temperature. The reaction mixture was subsequently vacuum filtered through a 1.0 cm plug of silica gel and the pad was rinsed with EtOAc (3×50 mL). The filtrate was concentrated under reduced pressure to give a brown foam that was used immediately without further purification.

The brown foam was diluted with MeOH (72 mL) and transferred to a 125-mL pressure vessel equipped with a stir bar. The reaction vessel was subsequently charged with sodium methoxide (25 wt. % in MeOH, 0.80 ml, 3.61 mmol) and sealed with a Teflon cap equipped with a pressure-relief valve. The reaction vessel was placed in a 70° C. oil bath and stirred vigorously. After 5 h, the reaction mixture was allowed to cool to ambient temperature, transferred to a 250-mL round-bottom flask with additional MeOH and concentrated under reduced pressure. The brown oil was redissolved in DCM (50 mL) and filtered through a pad of Celite® (3 cm) to facilitate loading the material onto a column. The Celite® pad was rinsed with DCM (3×50 mL). The brown filtrate was concentrated under reduced pressure and purified by flash column chromatography (100-g silica gel Biotage column, eluent: gradient, 5 to 70% 3:1 EtOAc/EtOH in heptane with DCM as a 10% additive) to afford (Rac)-tert-butyl 1-(4-bromo-2-methoxyphenyl)-2-oxo-1,2,7,8-tetrahydro-1,6-naphthyridine-6(5H)-carboxylate (933 mg, 2.143 mmol, 29.7% yield) as a tan foam. $^1$H NMR (400 MHz, DMSO-$d_6$) δ ppm 7.42-7.43 (m, 1H) 7.36 (d, J=9.32 Hz, 1H) 7.27 (dd, J=4.77 Hz, 1H) 7.17 (d, J=8.19 Hz, 1H) 6.38 (d, J=9.43 Hz, 1H) 4.27 (s, 2H) 3.76 (s, 3H) 3.36-3.55 (m, 2H) 2.12-2.28 (m, 1H) 1.94-2.03 (m, 1H) 1.35-1.47 (m, 9H). m/z (ESI) 437.2 (M+H)$^+$.

Step 2: (Rac)-tert-Butyl 1-(3'-Chloro-5'-Fluoro-3-Methoxy-[1,1'-Biphenyl]-4-Yl)-2-Oxo-1,2,7,8-Tetrahydro-1,6-Naphthyridine-6(5H)-Carboxylate A 50-mL round-bottom flask was charged with (Rac)-tert-butyl 1-(4-bromo-2-methoxyphenyl)-2-oxo-1,2,7,8-tetrahydro-1,6-naphthyridine-6(5H)-carboxylate (450 mg, 1.03 mmol), (3-chloro-5-fluorophenyl)boronic acid (541 mg, 3.10 mmol), cesium carbonate (1.35 g, 4.13 mmol), copper chloride (307 mg, 3.10 mmol), 1,1-bis[(di-t-butyl-p-methylaminophenyl]palladium(II) chloride (146 mg, 0.21 mmol), then purged with nitrogen. DMF (8.9 ml) was introduced and the vigorously stirred reaction mixture was warmed to 50° C. After 1.5 h, the reaction mixture was allowed to cool to ambient temperature and diluted with a 1:1 mixture of saturated aqueous solution of ethylenediaminetetraacetic acid and water (50 mL) and EtOAc (25 mL). The mixture was filtered through a pad of Celite® then rinsed with EtOAc (2×20 mL). The layers were separated and the aqueous layer was extracted with EtOAc (3×15 mL). The combined organic layers were washed with brine (50 mL), dried over anhydrous magnesium sulfate, filtered, and concentrated under reduced pressure and purified by flash column chromatography (50-g silica gel Biotage column, eluent: gradient, 0 to 50% 3:1 EtOAc/EtOH in heptane with DCM as a 10% additive) to afford (Rac)-tert-butyl 1-(3'-chloro-5'-fluoro-3-methoxy-[1,1'-biphenyl]-4-yl)-2-oxo-1,2,7,8-tetrahydro-1,6-naphthyridine-6(5H)-carboxylate (292 mg, 0.60 mmol, 58.2% yield) as a tan solid. m/z (ESI) 485.2 (M+H)$^+$.

Step 3: (Rac)-1-(3'-Chloro-5'-Fluoro-3-Methoxy-[1,1'-Biphenyl]-4-Yl)-5,6,7,8-Tetrahydro-1,6-Naphthyridin-2(1H)-One A 50-mL round-bottom flask was charged with (Rac)-tert-butyl 1-(3'-chloro-5'-fluoro-3-methoxy-[1,1'-biphenyl]-4-yl)-2-oxo-1,2,7,8-tetrahydro-1,6-naphthyridine-6(5H)-carboxylate (292 mg, 0.60 mmol) and trifluoroacetic acid (6.0 mL) then stirred for 30 min at ambient temperature. The reaction mixture was concentrated under reduced pressure, dissolved in DCM (25 mL) and carefully poured into saturated aqueous sodium bicarbonate solution (25 mL). The layers were separated and the aqueous layer extracted with additional DCM (3×25 mL). The combined organic layers were dried over anhydrous magnesium sulfate, filtered, concentrated under reduced pressure to afford (Rac)-1-(3'-chloro-5'-fluoro-3-methoxy-[1,1'-biphenyl]-4-yl)-5,6,7,8-tetrahydro-1,6-naphthyridin-2(1H)-one (241 mg, 0.63 mmol, 104% yield) as a tan solid which was used without further purification. $^1$H NMR (400 MHz, DMSO-$d_6$) δ ppm 7.77 (t, J=1.55 Hz, 1H) 7.67-7.73 (m, 1H) 7.41-7.55 (m, 3H) 7.25 (dd, J=13.58, 8.71 Hz, 2H) 6.34 (d, J=9.23 Hz, 1H) 3.87 (s, 3H) 3.58-3.74 (m, 2H) 2.86 (d, J=2.07 Hz, 2H) 2.04-2.21 (m, 1H) 1.85-2.01 (m, 1H). m/z (ESI) 385.2 (M+H)$^+$.

Step 4: (Rac)-1-(3'-Chloro-5'-Fluoro-3-Methoxy-[1,1'-Biphenyl]-4-Yl)-N-(Isoxazol-3-Yl)-2-Oxo-1,2,7,8-Tetrahydro-1,6-Naphthyridine-6(5H)-Sulfonamide A 5-mL vial was charged with (Rac)-1-(3'-chloro-5'-fluoro-3-methoxy-[1,1'-biphenyl]-4-yl)-5,6,7,8-tetrahydro-1,6-naphthyridin-2(1H)-one (120 mg, 0.312 mmol), N-(isoxazol-3-yl)-2-oxooxazolidine-3-sulfonamide (Preparation 7c, 109 mg, 0.468 mmol), acetonitrile (1.56 mL), and triethylamine (304 µL, 2.18 mmol). The vial was sealed with a PTFE lined cap and heated to 130° C. After 30 min, the resultant brown reaction mixture was cooled to ambient temperature and diluted to 3 mL total volume with DMSO and filtered through a 0.4 micron filter. The filtrate was purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-95%). The fractions containing product were frozen and lyophilized to afford (Rac)-1-(3'-chloro-5'-fluoro-3-methoxy-[1,1'-biphenyl]-4-yl)-N-(isoxazol-3-yl)-2-oxo-1,2,7,8-tetrahydro-1,6-naphthyridine-6(5H)-sulfonamide (66.6 mg, 0.13 mmol, 40.2% yield) as a white solid. $^1$H NMR (400 MHz, DMSO-$d_6$) δ ppm 8.47 (s, 1H) 7.77 (t, J=1.50 Hz, 1H) 7.66-7.73 (m, 1H) 7.40-7.53 (m, 3H) 7.33 (d, J=9.43 Hz, 1H) 7.25 (d, J=8.09 Hz, 1H) 6.35 (d, J=9.43 Hz, 1H) 6.31 (d, J=1.76 Hz, 1H) 4.02-4.10 (m, 2H) 3.85 (s, 3H) 3.19-3.27 (m, 2H) 2.23-2.33 (m, 1H) 1.99-2.08 (m, 1H). m/z (ESI) 531.0 (M+H)$^+$.

Separation Step: Racemic product of Example 7 was subjected to chiral SFC separation ((S,S) AS-H column, 40% methanol) to afford Example 7-P (peak 1) and Example 7-M (peak 2) as off-white solids.

Example 8

(Rac)-; (P)-; and (M)-1-(3'-Chloro-5'-Fluoro-3-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

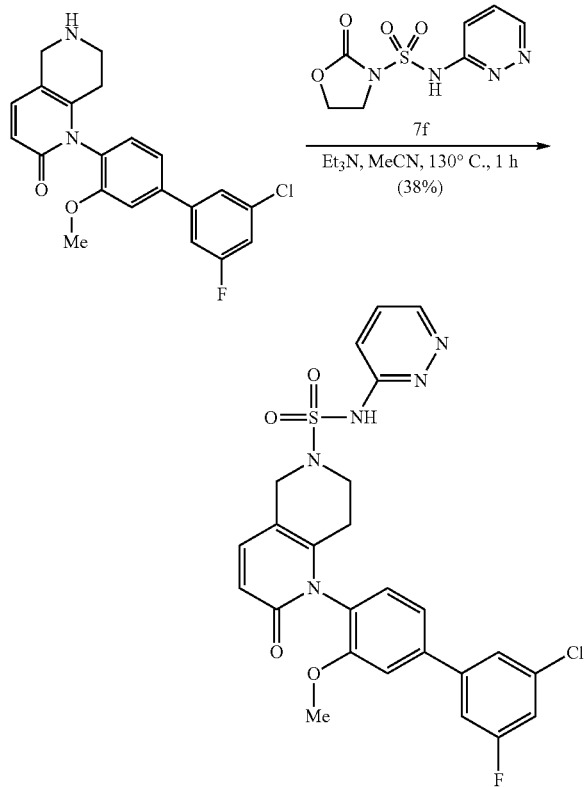

A 5-mL vial was charged with 1-(3'-chloro-5'-fluoro-3-methoxy-[1,1'-biphenyl]-4-yl)-5,6,7,8-tetrahydro-1,6-naphthyridin-2(1H)-one (See Example 7, step 3, 120 mg, 0.31 mmol), 2-oxo-N-(pyridazin-3-yl)oxazolidine-3-sulfonamide (Preparation 7f, 114 mg, 0.47 mmol), acetonitrile (1.56 mL), and triethylamine (304 μL, 2.18 mmol). The vial was sealed with a PTFE lined cap and heated to 130° C. After 80 min, the resultant brown reaction mixture was cooled to ambient temperature and cooled to ambient temperature and diluted to 3 mL total volume with DMSO and filtered through a 0.4 micron filter. The filtrate was purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-95%). The fractions containing product were frozen and lyophilized to afford (Rac)-1-(3'-chloro-5'-fluoro-3-methoxy-[1,1'-biphenyl]-4-yl)-2-oxo-N-(pyridazin-3-yl)-1,2,7,8-tetrahydro-1,6-naphthyridine-6(5H)-sulfonamide (64.1 mg, 0.118 mmol, 37.9% yield) as a white solid. $^1$H NMR (400 MHz, DMSO-$d_6$) δ ppm 8.31 (br. s., 1H) 7.77 (t, J=1.50 Hz, 1H) 7.70 (dt, J=9.69, 2.15 Hz, 1H) 7.60 (dd, J=9.59, 4.09 Hz, 1H) 7.47-7.54 (m, 2H) 7.44 (dd, J=8.14, 1.92 Hz, 1H) 7.37 (d, J=9.43 Hz, 1H) 7.27 (d, J=8.09 Hz, 1H) 6.37 (d, J=9.33 Hz, 1H) 4.00-4.15 (m, 2H) 3.86 (s, 3H) 3.22 (t, J=6.01 Hz, 2H) 2.28-2.39 (m, 1H) 2.06-2.16 (m, 1H). m/z (ESI) 542.2 (M+H)$^+$.

Separation Step: Racemic product of Example 8 was subjected to chiral SFC separation ((S,S) Whelk-O1 column, 55% methanol) to afford Example 8-P (peak 1) and Example 8-M (peak 2) as off-white solids.

Example 9

(Rac)-; (P)-; and (M)-1-(5'-Chloro-2-Fluoro-5-Methoxy-2'-Methyl-[1,1'-Biphenyl]-4-Yl)-N-(Isoxazol-3-Yl)-2-Oxo-1,2,7,8-Tetrahydro-1,6-Naphthyridine-6(5H)-Sulfonamide

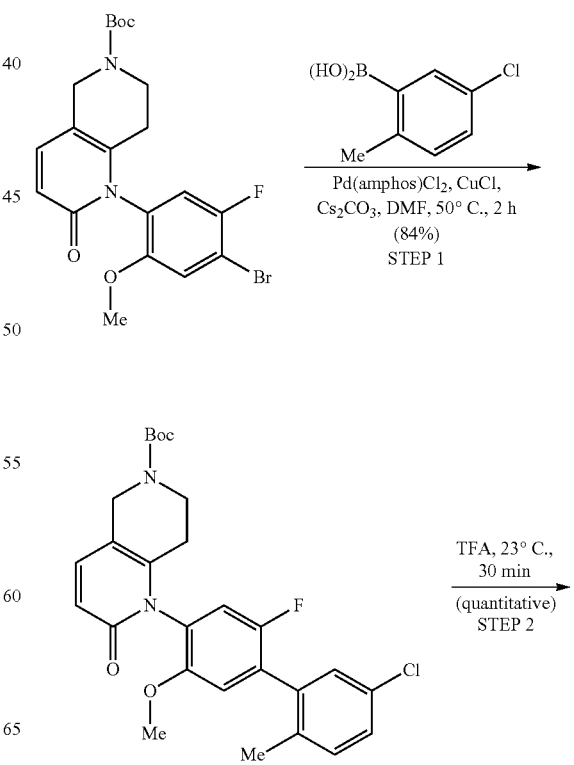

97

-continued

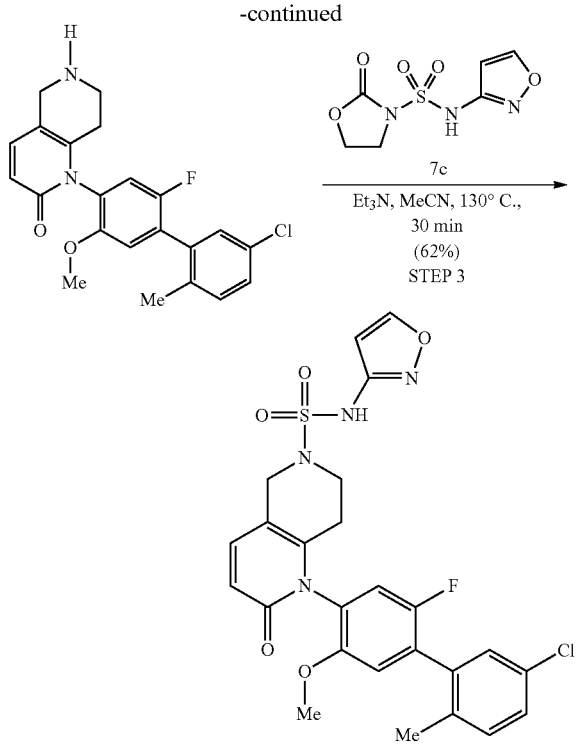

Step 1: (Rac)-tert-Butyl 1-(3'-Chloro-5'-Fluoro-3-Methoxy-[1,1'-Biphenyl]-4-Yl)-2-Oxo-1,2,7,8-Tetrahydro-1,6-Naphthyridine-6(5H)-Carboxylate A 25-mL round-bottom flask was charged with (Rac)-tert-butyl 1-(4-bromo-5-fluoro-2-methoxyphenyl)-2-oxo-1,2,7,8-tetrahydro-1,6-naphthyridine-6(5H)-carboxylate (See Preparation 8a, step 1, 300 mg, 0.66 mmol), (5-chloro-2-methylphenyl)boronic acid (Alfa Aesar, 338 mg, 1.99 mmol), cesium carbonate (863 mg, 2.65 mmol), copper chloride (197 mg, 1.99 mmol), 1,1-bis[(di-t-butyl-p-methylaminophenyl]palladium(II) chloride (94.0 mg, 0.20 mmol), then purged with nitrogen. DMF (3.3 ml) was introduced and the vigorously stirred reaction mixture was warmed to 50° C. After 2 h, the reaction mixture was allowed to cool to ambient temperature and diluted with a 1:1 mixture of saturated aqueous solution of ethylenediaminetetraacetic acid and water (20 mL) and EtOAc (10 mL). The mixture was filtered through a pad of Celite® then rinsed with EtOAc (2×10 mL). The layers were separated and the aqueous layer was extracted with EtOAc (3×10 mL). The combined organic layers were washed with brine (25 mL), dried over anhydrous magnesium sulfate, filtered, and concentrated under reduced pressure and purified by flash column chromatography (50-g silica gel Biotage column, eluent: gradient, 0 to 50% 3:1 EtOAc/EtOH in heptane with DCM as a 10% additive) to afford (Rac)-tert-butyl 1-(5'-chloro-2-fluoro-5-methoxy-2'-methyl-[1,1'-biphenyl]-4-yl)-2-oxo-1,2,7,8-tetrahydro-1,6-naphthyridine-6(5H)-carboxylate (278 mg, 0.56 mmol, 84% yield) as a tan solid. m/z (ESI) 500.2 (M+H)+.

98

Step 2: (Rac)-1-(5'-Chloro-2-Fluoro-5-Methoxy-2'-Methyl-[1,1'-Biphenyl]-4-Yl)-5,6,7,8-Tetrahydro-1,6-Naphthyridin-2(1H)-One A 25-mL round-bottom flask was charged with (Rac)-tert-butyl 1-(5'-chloro-2-fluoro-5-methoxy-2'-methyl-[1,1'-biphenyl]-4-yl)-2-oxo-1,2,7,8-tetrahydro-1,6-naphthyridine-6(5H)-carboxylate (227 mg, 0.46 mmol) and trifluoroacetic acid (2.3 mL) then stirred for 30 min at ambient temperature. The reaction mixture was concentrated under reduced pressure, dissolved in DCM (25 mL) and carefully poured into saturated aqueous sodium bicarbonate solution (25 mL). The layers were separated and the aqueous layer extracted with additional DCM (3×25 mL). The combined organic layers were dried over anhydrous magnesium sulfate, filtered, concentrated under reduced pressure to afford (Rac)-1-(5'-chloro-2-fluoro-5-methoxy-2'-methyl-[1,1'-biphenyl]-4-yl)-5,6,7,8-tetrahydro-1,6-naphthyridin-2(1H)-one (187 mg, 0.47 mmol, 103% yield) as a tan amorphous solid, which was used without further purification. $^1$H NMR (400 MHz, DMSO-$d_6$) δ ppm 7.37-7.46 (m, 3H) 7.29 (dd, J=9.43, 6.74 Hz, 2H) 7.16 (d, J=6.63 Hz, 1H) 6.37 (d, J=9.33 Hz, 1H) 3.77 (s, 3H) 3.63-3.74 (m, 2H) 2.89 (t, J=5.34 Hz, 2H) 2.16-2.25 (m, 1H) 1.94-2.11 (m, 1H). m/z (ESI) 399.2 (M+H)+.

Step 3: (Rac)-1-(5'-Chloro-2-Fluoro-5-Methoxy-2'-Methyl-[1,1'-Biphenyl]-4-Yl)-N-(Isoxazol-3-Yl)-2-Oxo-1,2,7,8-Tetrahydro-1,6-Naphthyridine-6(5H)-Sulfonamide A 5-mL vial was charged with (Rac)-1-(5'-chloro-2-fluoro-5-methoxy-2'-methyl-[1,1'-biphenyl]-4-yl)-5,6,7,8-tetrahydro-1,6-naphthyridin-2(1H)-one (95 mg, 0.24 mmol), N-(isoxazol-3-yl)-2-oxooxazolidine-3-sulfonamide (Preparation 7c, 83 mg, 0.36 mmol), acetonitrile (1.20 mL), and triethylamine (232 µL, 1.67 mmol). The vial was sealed with a PTFE lined cap and heated to 130° C. After 30 min, the resultant brown reaction mixture was cooled to ambient temperature and diluted to 3 mL total volume with DMSO and filtered through a 0.4 micron filter. The filtrate was purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-85%). The fractions containing product were frozen and lyophilized to afford (Rac)-1-(5'-chloro-2-fluoro-5-methoxy-2'-methyl-[1,1'-biphenyl]-4-yl)-N-(isoxazol-3-yl)-2-oxo-1,2,7,8-tetrahydro-1,6-naphthyridine-6(5H)-sulfonamide (80 mg, 0.147 mmol, 61.6% yield) as an off-white solid. $^1$H NMR (400 MHz, DMSO-$d_6$) δ ppm 8.75 (d, J=1.76 Hz, 1H) 7.37-7.47 (m, 3H) 7.34 (d, J=9.43 Hz, 1H) 7.28 (d, J=9.43 Hz, 1H) 7.16 (d, J=6.53 Hz, 1H) 6.34-6.42 (m, 2H) 4.17-4.33 (m, 2H) 3.74 (s, 3H) 3.42 (d, J=5.91 Hz, 2H) 2.37-2.47 (m, 1H) 2.03-2.14 (m, 1H). m/z (ESI) 545.0 (M+H)+.

Separation Step: Racemic product of Example 9 was subjected to chiral SFC separation ((S,S) Whelk-O column, 35% methanol) to afford Example 9-P (peak 1) and Example 9-M (peak 2) as off-white solids.

Example 10

(Rac); (P)-; and (M)-N-(5-Fluoropyrimidin-2-Yl)-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide

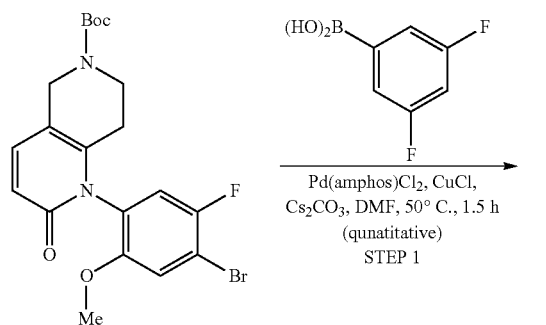

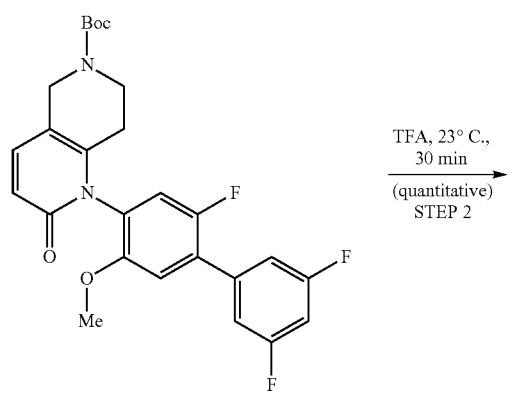

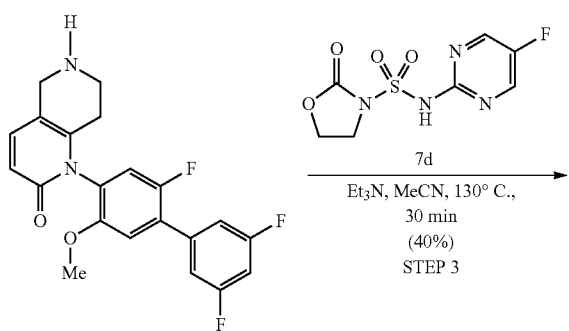

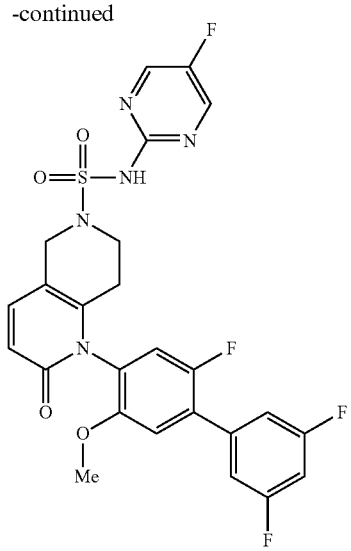

Step 1: (Rac)-tert-Butyl 2-Oxo-1-(2,3',5'-Trifluoro-5-Methoxy-[1,1'-Biphenyl]-4-Yl)-1,2,7,8-Tetrahydro-1,6-Naphthyridne-6(5H)-Carboxylate A 50-mL round-bottom flask was charged with (Rac)-tert-butyl 1-(4-bromo-5-fluoro-2-methoxyphenyl)-2-oxo-1,2,7,8-tetrahydro-1,6-naphthyridine-6(5H)-carboxylate (See Preparation 8a, step 1, 806 mg, 1.78 mmol), (3,5-difluorophenyl)boronic acid (Combi-Blocks, 844 mg, 5.35 mmol), cesium carbonate (2.32 g, 7.13 mmol), copper chloride (529 mg, 5.35 mmol), 1,1-bis[(di-t-butyl-p-methylaminophenyl] palladium(II) chloride (252 mg, 0.36 mmol), then purged with nitrogen. DMF (8.90 mL) was introduced, the vial was sealed with a PTFE line cap, and the resultant orange reaction mixture was warmed to 50° C. After 1.5 h, the reaction mixture was allowed to cool to ambient temperature and diluted with a 1:1 mixture of saturated aqueous solution of ethylenediaminetetraacetic acid and water (25 mL) and EtOAc (15 mL). The mixture was filtered through a pad of Celite® then rinsed with EtOAc (2×10 mL). The layers were separated and the aqueous layer was extracted with EtOAc (3×5 mL). The combined organic layers were washed with brine (25 mL), dried over anhydrous magnesium sulfate, filtered, and concentrated under reduced pressure and purified by flash column chromatography (25-g silica gel Biotage column, eluent: gradient, 0 to 50% 3:1 EtOAc/EtOH in heptane with DCM as a 10% additive) to afford (Rac)-tert-butyl 2-oxo-1-(2,3',5'-trifluoro-5-methoxy-[1,1'-biphenyl]-4-yl)-1,2,7,8-tetrahydro-1,6-naphthyridine-6(5H)-carboxylate (1.08 g, 2.22 mmol, 124% yield) as a tan solid. m/z (ESI) 487.0 (M+H)$^+$.

Step 2: (Rac)-1-(2,3',5'-Trifluoro-5-Methoxy-[1,1'-Biphenyl]-4-Yl)-5,6,7,8-Tetrahydro-1,6-Naphthyridin-2(1H)-One A 50-mL round-bottom flask was charged with (Rac)-tert-butyl 1-(3'-chloro-5'-fluoro-3-methoxy-[1,1'-biphenyl]-4-yl)-2-oxo-1,2,7,8-tetrahydro-1,6-naphthyridine-6(5H)-carboxylate (844 mg, 1.74 mmol) and trifluoroacetic acid (8.7 mL) then stirred for 30 min at ambient temperature. The reaction mixture was concentrated under reduced pressure, dissolved in DCM (25 mL) and carefully poured into saturated aqueous sodium bicarbonate solution (25 mL). The layers were separated and the aqueous layer extracted with additional DCM (3×25 mL). The combined organic layers were dried over anhydrous magnesium sulfate, filtered, concentrated under reduced pressure to afford (Rac)-1-(2,3', 5'-trifluoro-5-methoxy-[1,1'-biphenyl]-4-yl)-5,6,7,8-tetrahydro-1,6-naphthyridin-2(1H)-one (699 mg, 1.81 mmol, 104% yield) as a yellow-tan amorphous solid, which was used without further purification. m/z (ESI) 387.2 (M+H)+.

Step 3: (Rac)-N-(5-Fluoropyrimidin-2-Yl)-2-Oxo-1-(2,3,5'-Trifluoro-5-Methoxy-[1,1'-Biphenyl]-4-Yl)-1,2,7,8-Tetrahydro-1,6-Naphthyridine-6(5H)-Sulfonamide A 5-mL vial was charged with (Rac)-1-(2,3',5'-trifluoro-5-methoxy-[1,1'-biphenyl]-4-yl)-5,6,7,8-tetrahydro-1,6-naphthyridin-2(1H)-one (127 mg, 0.329 mmol), N-(5-fluoropyrimidin-2-yl)-2-oxooxazolidine-3-sulfonamide (Preparation 7d, 189 mg, 0.721 mmol), acetonitrile (1.80 mL), and triethylamine (352 µL, 2.53 mmol). The vial was sealed with a PTFE lined cap and heated to 130° C. After 30 min, the resultant brown reaction mixture was cooled to ambient temperature and diluted to 3 mL total volume with DMSO and filtered through a 0.4 micron filter. The filtrate was purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-85%). The fractions containing product were frozen and lyophilized to afford (Rac)-N-(5-fluoropyrimidin-2-yl)-2-oxo-1-(2,3',5'-trifluoro-5-methoxy-[1,1'-biphenyl]-4-yl)-1,2,7,8-tetrahydro-1,6-naphthyridine-6(5H)-sulfonamide (80 mg, 0.142 mmol, 39.5% yield) as an off-white solid. $^1$H NMR (400 MHz, DMSO-$d_6$) δ=11.41 (s, 1H), 8.65 (s, 2H), 7.48-7.29 (m, 6H), 6.39 (d, J=9.4 Hz, 1H), 4.41-4.27 (m, 2H), 3.77 (s, 3H), 3.51 (t, J=5.8 Hz, 2H), 2.45-2.33 (m, 1H), 2.16-2.05 (m, 1H). m/z (ESI) 562.0 (M+H)+.

Separation Step: Racemic product of Example 10 was subjected to chiral SFC separation ((S,S) AS-H column, 45% methanol) to afford Example 10-P (peak 1) and Example 10-M (peak 2) as off-white solids.

Example 11

(Rac)-; (P)-; and (M)-1-(3'-Chloro-2,5'-Difluoro-5-Methoxy-[1,1'-Biphenyl]-4-Yl)-2-Oxo-N-(Pyridin-2-Yl)-1,2,7,8-Tetrahydro-1,6-Naphthyridine-6(5H)-Sulfonamide

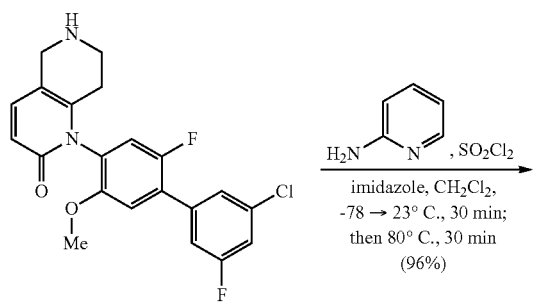

H$_2$N—⟨pyridine⟩, SO$_2$Cl$_2$
imidazole, CH$_2$Cl$_2$,
-78 → 23° C., 30 min;
then 80° C., 30 min
(96%)

-continued

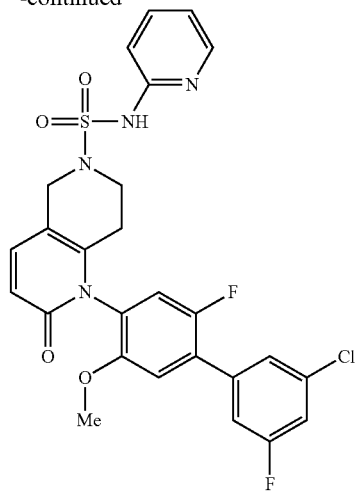

A 5-mL vial was charged with imidazole (85 mg, 1.24 mmol) and 2-aminopyridine (Sigma Aldrich, 37.4 mg, 0.40 mmol) then purged with nitrogen. CH$_2$Cl$_2$ (1.24 mL) was introduced and the reaction mixture was cooled to −78° C. in a dry ice-acetone bath. Sulfuryl chloride (32.2 µL, 0.40 mmol) was added dropwide via syringe to the reaction mixture. Following addition, the cold bath was removed and the resultant mixture was allowed to warm to ambient temperature. After 30 minutes, (Rac)-1-(3'-chloro-2,5'-difluoro-5-methoxy-[1,1'-biphenyl]-4-yl)-5,6,7,8-tetrahydro-1,6-naphthyridin-2(1H)-one (See Example 4, step 2, 100 mg, 0.25 mmol) was introduced in a single portion followed by CH$_2$Cl$_2$ (1.0 mL). The vial was sealed with a PTFE lined cap and the reaction mixture was warmed to 80° C. After 30 min, the reaction mixture was cooled to ambient the resultant brown temperature mixture was cooled to ambient temperature and diluted with an aqueous solution of citric acid (1.0 M, 5 mL), brine (5 mL), and EtOAc (15 mL). The layers were separated and the aqueous layer was extracted with EtOAc (3×5 mL). The combined organic layers were dried over anhydrous magnesium sulfate, filtered, and concentrated under reduced pressure and purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-70%). The fractions containing product were frozen and lyophilized to afford (Rac)-1-(3'-chloro-2,5'-difluoro-5-methoxy-[1,1'-biphenyl]-4-yl)-2-oxo-N-(pyridin-2-yl)-1,2,7,8-tetrahydro-1,6-naphthyridine-6(5H)-sulfonamide (133 mg, 0.24 mmol, 96% yield) as an off-white solid. $^1$H NMR (400 MHz, DMSO-$d_6$) δ ppm 8.11 (br. s., 1H) 7.81-7.86 (m, 1H) 7.62-7.72 (m, 4H) 7.37-7.48 (m, 4H) 6.47 (d, J=9.38 Hz, 1H) 4.28 (br. s., 2H) 3.88 (s, 3H) 3.43 (br. s., 2H) 2.42-2.52 (m, 1H) 2.14-2.23 (m, 1H). m/z (ESI) 559.0 (M+H)+.

Separation Step: Racemic product of Example 11 was subjected to chiral SFC separation ((S,S) Whelk-O column, 40% methanol) to afford Example 11-P (peak 1) and Example 11-M (peak 2) as off-white solids.

Example 12

(Rac)-; (P)-; and (M)-1-(3'-Chloro-2,5'-Difluoro-5-Methoxy-[1,1'-Biphenyl]-4-Yl)-N-(5-Fluoropyridin-2-Yl)-2-Oxo-1,2,7,8-Tetrahydro-1,6-Naphthyridine-6(5H)-Sulfonamide

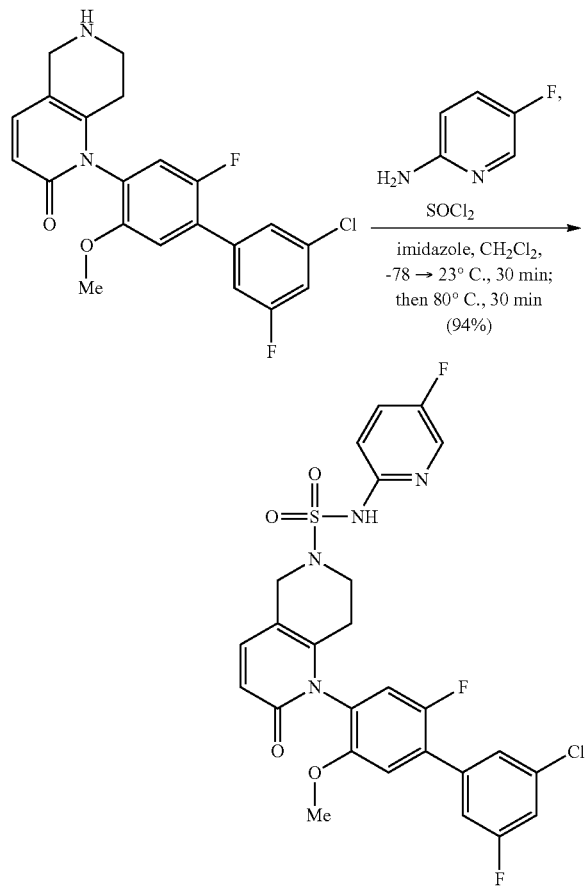

A 5-mL vial was charged with imidazole (85 mg, 1.24 mmol) and 5-fluoropyridin-2-amine (Acros Organics, 44.5 mg, 0.40 mmol) then purged with nitrogen. CH$_2$Cl$_2$ (1.24 mL) was introduced and the reaction mixture was cooled to −78° C. in a dry ice-acetone bath. Sulfuryl chloride (32.2 μL, 0.40 mmol) was added dropwise via syringe to the reaction mixture. Following addition, the cold bath was removed and the resultant mixture was allowed to warm to ambient temperature. After 30 minutes, (Rac)-1-(3'-chloro-2,5'-difluoro-5-methoxy-[1,1'-biphenyl]-4-yl)-5,6,7,8-tetrahydro-1,6-naphthyridin-2(1H)-one (See Example 4, step 2, 100 mg, 0.25 mmol) was introduced in a single portion followed by CH$_2$Cl$_2$ (1.0 mL). The vial was sealed with a PTFE lined cap and the reaction mixture was warmed to 80° C. After 30 min, the reaction mixture was cooled to ambient the resultant brown temperature mixture was cooled to ambient temperature and diluted with an aqueous solution of citric acid (1.0 M, 5 mL), brine (5 mL), and EtOAc (15 mL). The layers were separated and the aqueous layer was extracted with EtOAc (3×5 mL). The combined organic layers were dried over anhydrous magnesium sulfate, filtered, and concentrated under reduced pressure and purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-80%). The fractions containing product were frozen and lyophilized to afford (Rac)-1-(3'-chloro-2,5'-difluoro-5-methoxy-[1,1'-biphenyl]-4-yl)-N-(5-fluoropyridin-2-yl)-2-oxo-1,2,7,8-tetrahydro-1,6-naphthyridine-6(5H)-sulfonamide (134 mg, 0.23 mmol, 94% yield) as a tan solid. 6 ppm 10.81 (br. s., 1H) 8.29 (d, J=3.01 Hz, 1H) 7.79 (td, J=8.35 Hz, 1H) 7.63-7.72 (m, 3H) 7.38-7.50 (m, 3H) 7.17 (dd, J=9.07, 3.73 Hz, 1H) 6.46 (d, J=9.38 Hz, 1H) 4.22-4.49 (m, 2H) 3.87 (s, 3H) 3.46-3.56 (m, 2H) 2.41-2.53 (m, 1H) 2.11-2.21 (m, 1H). m/z (ESI) 575.0 (M+H)$^+$.

Separation Step: Racemic product of Example 12 was subjected to chiral SFC separation ((S,S) Whelk-O column, 45% methanol) to afford Example 12-P (peak 1) and Example 12-M (peak 2) as off-white solids.

Example 13

(Rac)-; (P)-; and (M)-1-(3'-Chloro-2,5'-Difluoro-5-Methoxy-[1,1'-Biphenyl]-4-Yl)-N-(6-Fluoropyridin-2-Yl)-2-Oxo-1,2,7,8-Tetrahydro-1,6-Naphthyridine-6(5H)-Sulfonamide

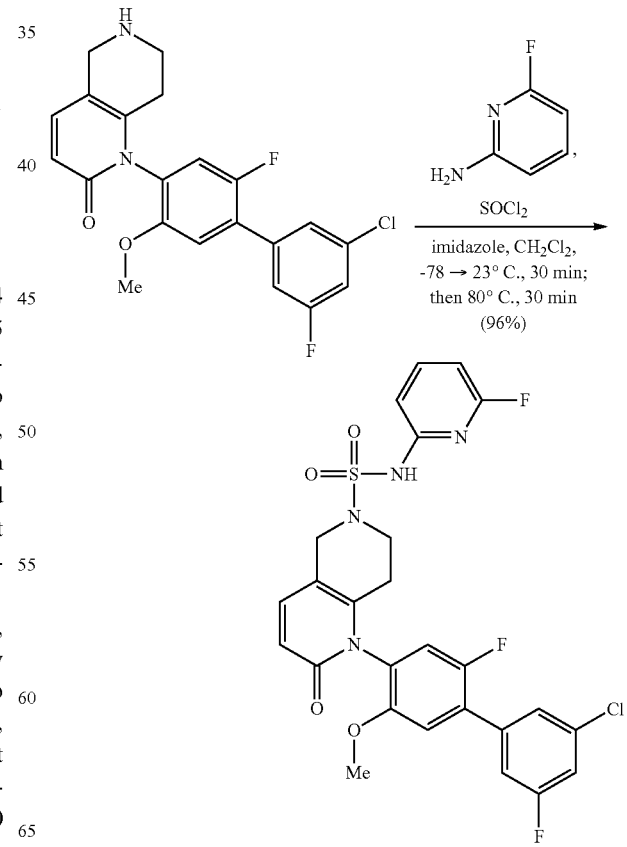

A 5-mL vial was charged with imidazole (85 mg, 1.24 mmol) and 6-fluoropyridin-2-amine (Matrix Scientific, 44.5 mg, 0.40 mmol) then purged with nitrogen. CH$_2$Cl$_2$ (1.24 mL) was introduced and the reaction mixture was cooled to −78° C. in a dry ice-acetone bath. Sulfuryl chloride (32.2 μL, 0.40 mmol) was added dropwise via syringe to the reaction mixture. Following addition, the cold bath was removed and the resultant mixture was allowed to warm to ambient temperature. After 30 minutes, (Rac)-1-(3'-chloro-2,5'-difluoro-5-methoxy-[1,1'-biphenyl]-4-yl)-5,6,7,8-tetrahydro-1,6-naphthyridin-2(1H)-one (See Example 4, step 2, 100 mg, 0.25 mmol) was introduced in a single portion followed by CH$_2$Cl$_2$ (1.0 mL). The vial was sealed with a PTFE lined cap and the reaction mixture was warmed to 80° C. After 30 min, the reaction mixture was cooled to ambient the resultant brown temperature mixture was cooled to ambient temperature and diluted with an aqueous solution of citric acid (1.0 M, 5 mL), brine (5 mL), and EtOAc (15 mL). The layers were separated and the aqueous layer was extracted with EtOAc (3×5 mL). The combined organic layers were dried over anhydrous magnesium sulfate, filtered, and concentrated under reduced pressure and purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-80%). The fractions containing product were frozen and lyophilized to afford (Rac)-1-(3'-chloro-2,5'-difluoro-5-methoxy-[1,1'-biphenyl]-4-yl)-N-(6-fluoropyridin-2-yl)-2-oxo-1,2,7,8-tetrahydro-1,6-naphthyridine-6(5H)-sulfonamide (137 mg, 0.24 mmol, 96% yield) as a tan solid. $^1$H NMR (400 MHz, DMSO-d$_6$) δ ppm 10.97 (s, 1H) 7.88 (q, J=8.12 Hz, 1H) 7.52-7.64 (m, 3H) 7.32-7.41 (m, 2H) 7.28 (d, J=10.37 Hz, 1H) 6.92 (dd, J=7.98, 1.87 Hz, 1H) 6.75 (dd, J=7.93, 2.23 Hz, 1H) 6.37 (d, J=9.43 Hz, 1H) 4.23-4.39 (m, 2H) 3.77 (s, 3H) 3.42-3.53 (m, 2H) 2.37-2.47 (m, 1H) 2.04-2.17 (m, 1H). m/z (ESI) 575.0 (M+H)$^+$.

Separation Step: Racemic product of Example 13 was subjected to chiral SFC separation ((S,S) Whelk-O column, 40% methanol) to afford Example 13-P (peak 1) and Example 13-M (peak 2) as off-white solids.

Example 14

(Rac)-; (P)-; and (M)-N-(6-Fluoropyridin-2-Yl)-2-Oxo-1-(2',3',5'-Trifluoro-5-Methoxy-[1,1'-Biphenyl]-4-Yl)-1,2,7,8-Tetrahydro-1,6-Naphthyridine-6(5H)-Sulfonamide

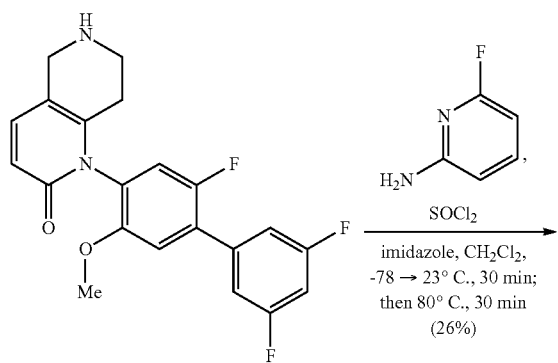

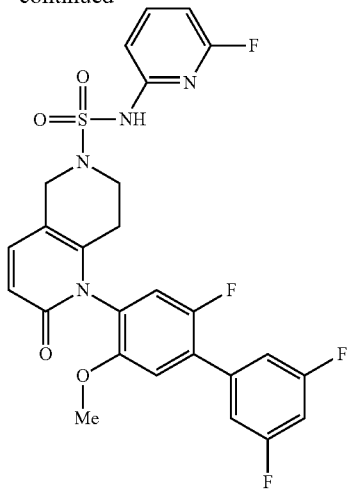

A 5-mL vial was charged with imidazole (110 mg, 1.62 mmol) and 6-fluoropyridin-2-amine (Matrix Scientific, 58.0 mg, 0.52 mmol) then purged with nitrogen. CH$_2$Cl$_2$ (1.62 mL) was introduced and the reaction mixture was cooled to −78° C. in a dry ice-acetone bath. Sulfuryl chloride (42.0 μL, 0.52 mmol) was added dropwise via syringe to the reaction mixture. Following addition, the cold bath was removed and the resultant mixture was allowed to warm to ambient temperature. After 30 minutes, (Rac)-1-(2,3',5'-trifluoro-5-methoxy-[1,1'-biphenyl]-4-yl)-5,6,7,8-tetrahydro-1,6-naphthyridin-2(1H)-one (See Example 10, step 2, 125 mg, 0.32 mmol) was introduced in a single portion followed by CH$_2$Cl$_2$ (1.0 mL). The vial was sealed with a PTFE lined cap and the reaction mixture was warmed to 80° C. After 30 min, the reaction mixture was cooled to ambient the resultant brown temperature mixture was cooled to ambient temperature and diluted with an aqueous solution of citric acid (1.0 M, 5 mL), brine (5 mL), and EtOAc (15 mL). The layers were separated and the aqueous layer was extracted with EtOAc (3×5 mL). The combined organic layers were dried over anhydrous magnesium sulfate, filtered, and concentrated under reduced pressure and purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-70%). The fractions containing product were frozen and lyophilized to afford (Rac)-N-(6-fluoropyridin-2-yl)-2-oxo-1-(2',3',5'-trifluoro-5-methoxy-[1,1'-biphenyl]-4-yl)-1,2,7,8-tetrahydro-1,6-naphthyridine-6(5H)-sulfonamide (47.2 mg, 0.08 mmol, 26.0% yield) as a white solid. $^1$H NMR (400 MHz, DMSO-d$_6$) δ ppm 10.96 (s, 1H) 7.88 (q, J=7.98 Hz, 1H) 7.26-7.47 (m, 6H) 6.92 (dd, J=7.83, 1.92 Hz, 1H) 6.75 (dd, J=7.98, 2.18 Hz, 1H) 6.37 (d, J=9.54 Hz, 1H) 4.25-4.36 (m, 2H) 3.77 (s, 2H) 2.35-2.48 (m, 1H) 2.05-2.14 (m, 1H). m/z (ESI) 559.0 (M+H)$^+$.

Separation Step: Racemic product of Example 14 was subjected to chiral SFC separation ((S,S) Whelk-O column, 35% methanol) to afford Example 14-P (peak 1) and Example 14-M (peak 2) as off-white solids.

Example 15

(Rac)-; (P)-; and (M)-1-(2-Fluoro-3',5-Dimethoxy-4'-Chloro-[1,1'-Biphenyl]-4-YL)-N-(Isoxazol-3-YL)-2-Oxo-1, 2,7,8-Tetrahydro-1,6-Naphthyridine-6 (5H)-Sulfonamide

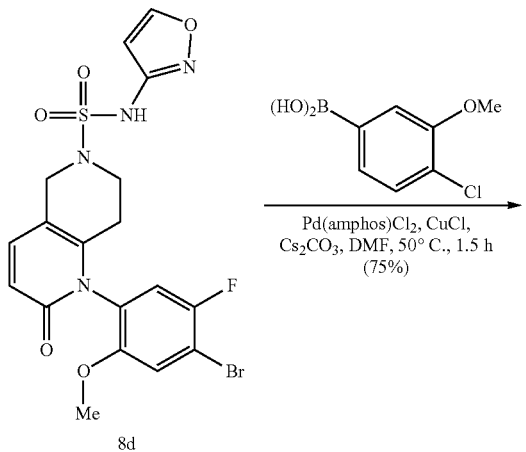

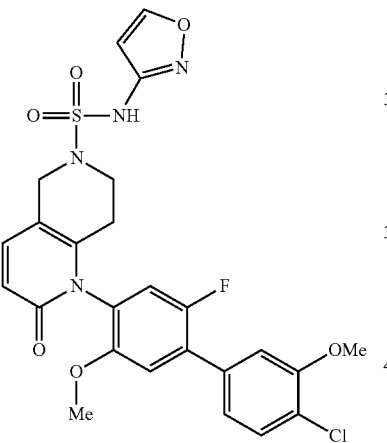

A 5-mL vial was charged with (Rac)-1-(4-bromo-5-fluoro-2-methoxyphenyl)-N-(isoxazol-3-yl)-2-oxo-1,2,7,8-tetrahydro-1,6-naphthyridine-6(5H)-sulfonamide (Preparation 8d, 100 mg, 0.20 mmol), 3-methoxy-4-methylphenylboronic acid (Acros Organics, 100 mg, 0.60 mmol), cesium carbonate (261 mg 0.80 mmol), copper chloride (59.5 mg, 0.60 mmol), 1,1-bis[(di-t-butyl-p-methylaminophenyl]palladium(II) chloride (28.4 mg, 0.04 mmol), then purged with nitrogen. DMF (1.0 mL) was introduced, the vial was sealed with a PTFE line cap, and the resultant orange reaction mixture was warmed to 50° C. After 1.5 h, the reaction mixture was allowed to cool to ambient temperature and diluted with a 1:1 mixture of saturated aqueous solution of ethylenediaminetetraacetic acid and water (5 mL) and EtOAc (5 mL). The mixture was filtered through a pad of Celite® then rinsed with EtOAc (2×10 mL). The layers were separated and the aqueous layer was extracted with EtOAc (3×5 mL). The combined organic layers were washed with brine (25 mL), dried over anhydrous magnesium sulfate, filtered, and concentrated under reduced pressure and purified by flash column chromatography (50-g silica gel Biotage column, eluent: gradient, 0 to 50% 3:1 EtOAc/EtOH in heptane with DCM as a 10% additive) to afford (Rac)-1-(2-fluoro-3',5-dimethoxy-4'-methyl-[1,1'-biphenyl]-4-yl)-N-(isoxazol-3-yl)-2-oxo-1,2,7, 8-tetrahydro-1,6-naphthyridine-6(5H)-sulfonamide (81.0 mg, 0.15 mmol, 74.8% yield) as a tan solid. $^1$H NMR (400 MHz, DMSO-$d_6$) δ ppm 11.16 (s, 1H) 8.74 (d, J=1.76 Hz, 1H) 7.22-7.36 (m, 4H) 7.09-7.18 (m, 2H) 6.35-6.42 (m, 2H) 4.23 (br. s., 2H) 3.87 (s, 3H) 3.78 (s, 3H) 3.36-3.48 (m, 2H) 2.43 (br. s., 1H) 2.22 (s, 3H) 2.05-2.14 (m, 1H). m/z (ESI) 541.2 (M+H)$^+$.

Separation Step: Racemic product of Example 15 was subjected to chiral SFC separation ((S,S) Whelk-O column, 40% methanol) to afford Example 15-P (peak 1) and Example 15-M (peak 2) as off-white solids.

Example 16

(Rac)-; (P)-; and (M)-1-(2-Fluoro-5-Methoxy-3'-(Trifluoromethyl)-[1,1'-Biphenyl]-4-Yl)-N-(Isoxazol-3-Yl)-2-Oxo-1,2,7,8-Tetrahydro-1,6-Naphthyridine-6(5H)-Sulfonamide

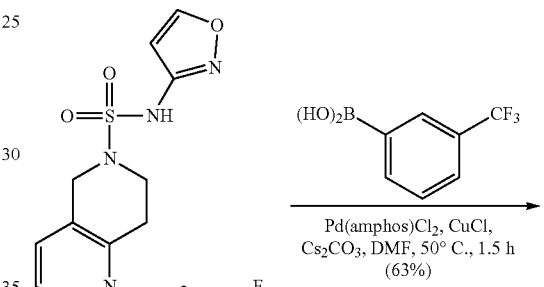

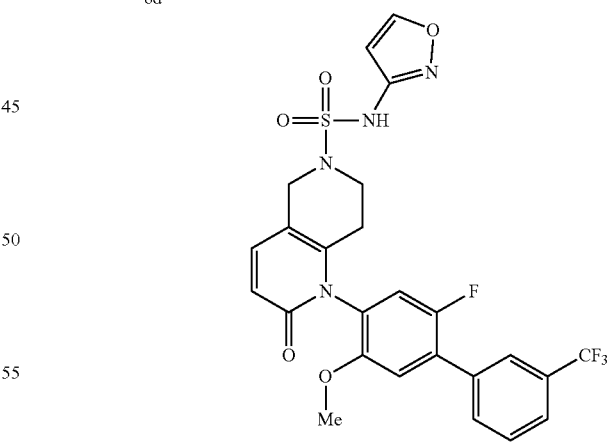

This compound was prepared analogous to the procedure of Example 15 from (Rac)-1-(4-bromo-5-fluoro-2-methoxyphenyl)-N-(isoxazol-3-yl)-2-oxo-1,2,7,8-tetrahydro-1,6-naphthyridine-6(5H)-sulfonamide (Preparation 8d) and 3-(trifluoromethyl)benzeneboronic acid (purchased from Synthonix) as the boronic acid. $^1$H NMR (400 MHz, DMSO-$d_6$) δ ppm 11.17 (s, 1H) 8.74 (s, 1H) 7.97 (s, J=5.59 Hz, 2H) 7.76-7.88 (m, 2H) 7.26-7.45 (m, 3H) 6.36-6.42 (m, 2H) 4.23 (d, J=3.21 Hz, 2H) 3.81 (s, 3H) 3.36-3.50 (m, 2H) 2.38-2.49 (m, 1H) 2.05-2.16 (m, 1H). m/z (ESI) 565.2 (M+H)+.

Separation Step: Racemic product of Example 16 was subjected to chiral SFC separation ((S,S) Whelk-O column, 35% methanol) to afford Example 16-P (peak 1) and Example 16-m (peak 2) as off-white solids.

Example 17

(Rac)-; (P)-; and (M)-N-(1,2,4-Oxadiazol-3-Yl)-2-Oxo-1-(2,3',5'-Trifluoro-5-Methoxy-[1,1'-Biphenyl]-4-Yl)-1,2,7,8-Tetrahydro-1,6-Naphthyridine-6(5H)-Sulfonamide

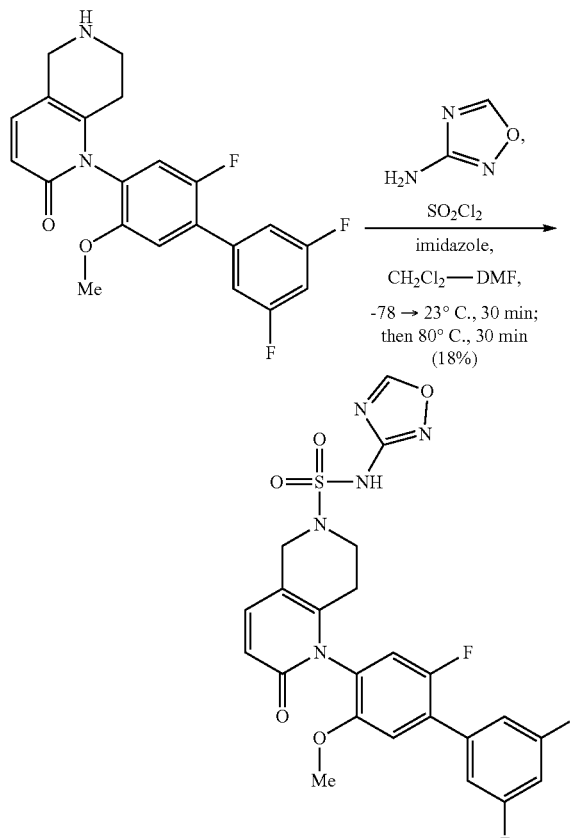

A 5-mL vial was charged with imidazole (88.0 mg, 1.29 mmol) and 1,2,4-oxadiazol-3-amine (Enamine, 35.2 mg, 0.41 mmol) then purged with nitrogen. $CH_2Cl_2$ (971 µL) and DMF (324 µL) were introduced and the reaction mixture was cooled to −78° C. in a dry ice-acetone bath. Sulfuryl chloride (55.9 µL, 0.41 mmol) was added dropwise via syringe to the reaction mixture. Following addition, the cold bath was removed and the resultant mixture was allowed to warm to ambient temperature. After 30 minutes, (Rac)-1-(2,3',5'-trifluoro-5-methoxy-[1,1'-biphenyl]-4-yl)-5,6,7,8-tetrahydro-1,6-naphthyridin-2(1H)-one (See Example 10, step 2, 100 mg, 0.26 mmol) was introduced. The vial was sealed with a PTFE lined cap and the reaction mixture was warmed to 80° C. After 30 min, the reaction mixture was cooled to ambient temperature and diluted with an aqueous solution of citric acid (1.0 M, 5 mL), brine (5 mL) and EtOAc (10 mL). The layers were separated and the aqueous layer was extracted with EtOAc (3×10 mL). The combined organic layers were dried over anhydrous magnesium sulfate, filtered, and concentrated under reduced pressure and The combined organic layers were dried over anhydrous magnesium sulfate, filtered, and concentrated under reduced pressure and purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-80%). The fractions containing product were frozen and lyophilized to afford (Rac)-N-(1,2,4-oxadiazol-3-yl)-2-oxo-1-(2,3',5'-trifluoro-5-methoxy-[1,1'-biphenyl]-4-yl)-1,2,7,8-tetrahydro-1,6-naphthyridine-6(5H)-sulfonamide (25.2 mg, 0.05 mmol, 18.3% yield) as a tan solid. $^1H$ NMR (400 MHz, DMSO-$d_6$) δ=11.78 (br. s., 1H), 9.41 (s, 1H), 7.47-7.32 (m, 7H), 6.39 (d, J=9.4 Hz, 1H), 4.37-4.26 (m, 2H), 3.80 (s, 3H), 3.48 (d, J=7.7 Hz, 2H), 2.48-2.41 (m, 1H), 2.13 (d, J=17.8 Hz, 1H). m/z (ESI) 532.0 (M+H)+.

Separation Step: Racemic product of Example 17 was subjected to chiral SFC separation ((S,S) Whelk-O column, 35% methanol) to afford Example 17-P (peak 1) and Example 17-M (peak 2) as off-white solids.

Example 18

(Rac)-; (P)-; and (M)-1-(3'-Chloro-2,5'-Difluoro-5-Methoxy-[1,1'-Biphenyl]-4-Yl)-N-(Isoxazol-3-Yl)-2-Oxo-1,2,7,8-Tetrahydro-1,6-Naphthyridine-6(5H)-Sulfonamide

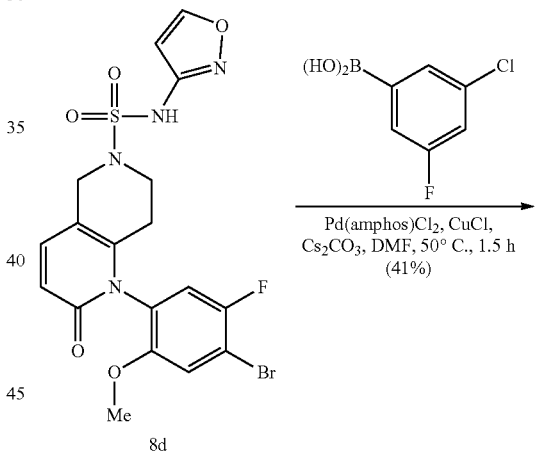

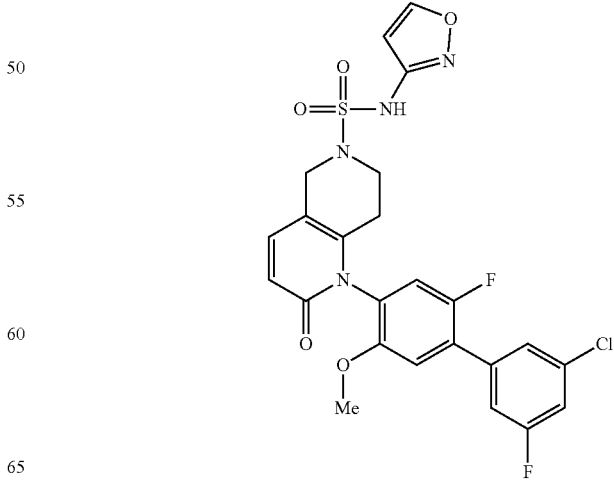

This compound was prepared analogous to the procedure of Example 15 from (Rac)-1-(4-bromo-5-fluoro-2-methoxyphenyl)-N-(isoxazol-3-yl)-2-oxo-1,2,7,8-tetrahydro-1,6-naphthyridine-6(5H)-sulfonamide (Preparation 8d) and 3-borono-5-fluorochlorobenzene (purchased from Accela ChemBio Inc.) as the boronic acid. $^1$H NMR (400 MHz, DMSO-$d_6$) δ ppm 11.16 (s, 1H) 8.74 (s, 1H) 7.54-7.64 (m, 3H) 7.31-7.40 (m, 3H) 6.36-6.41 (m, 2H) 4.18-4.29 (m, 2H) 3.81 (s, 3H) 3.37-3.47 (m, 2H) 2.38-2.48 (m, 1H) 2.03-2.13 (m, 1H). m/z (ESI) 549.2 (M+H)$^+$.

Separation Step: Racemic product of Example 18 was subjected to chiral SFC separation ((S,S) Whelk-O column, 40% methanol) to afford Example 18-P (peak 1) and Example 18-M (peak 2) as off-white solids.

Example 19

(Rac)-; (P)-; and (M)-1-(3'-(Difluoromethoxy)-2-Fluoro-5-Methoxy-[1,1'-Biphenyl]-4-Yl)-N-(Isoxazol-3-Yl)-2-Oxo-1,2,7,8-Tetrahydro-1,6-Naphthyridine-6(5H)-Sulfonamide

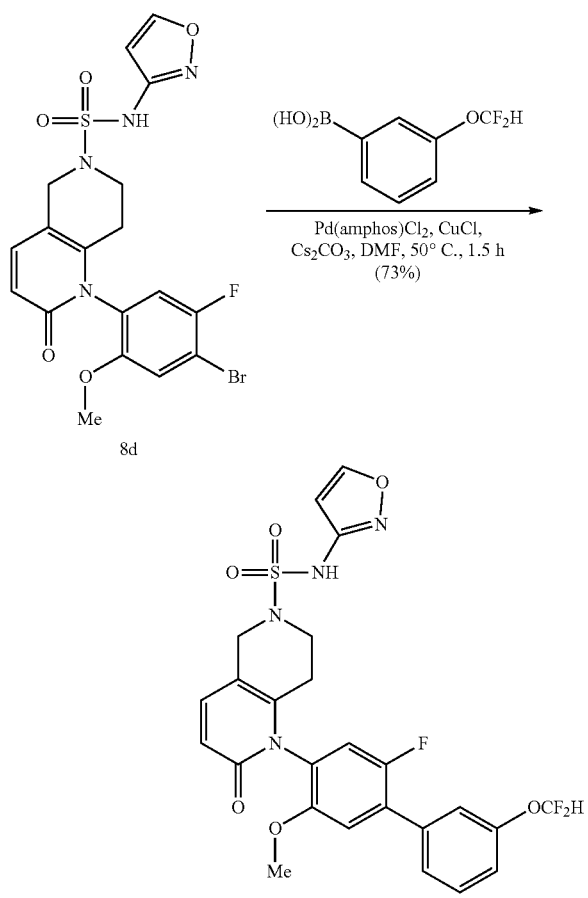

This compound was prepared analogous to the procedure of Example 15 from 1-(4-bromo-5-fluoro-2-methoxyphenyl)-N-(isoxazol-3-yl)-2-oxo-1,2,7,8-tetrahydro-1,6-naphthyridine-6(5H)-sulfonamide (Preparation 8d) and 3-(difluoromethoxy)phenylboronic acid (purchased from Focus Synthesis) as the boronic acid. $^1$H NMR (400 MHz, DMSO-$d_6$) δ=11.16 (s, 1H), 8.74 (d, J=1.8 Hz, 1H), 7.66-7.51 (m, 2H), 7.46 (s, 1H), 7.40-7.23 (m, 4H), 6.43-6.34 (m, 2H), 4.31-4.17 (m, 2H), 3.80 (s, 3H), 3.48-3.37 (m, 2H), 2.15-2.03 (m, 1H), 1.34-1.25 (m, 1H). m/z (ESI) 563.2 (M+H)$^+$.

Separation Step: Racemic product of Example 19 was subjected to chiral SFC separation ((S,S) Whelk-O column, 35% methanol) to afford Example 19-P (peak 1) and Example 19-M (peak 2) as off-white solids.

Example 20

(Rac)-; (P)-; and (M)-N-(Isoxazol-3-Yl)-2-Oxo-1-(2,3',4'-Trifluoro-5-Methoxy-[1,1'-Biphenyl]-4-Yl)-1,2,7,8-Tetrahydro-1,6-Naphthyridine-6(5H)-Sulfonamide

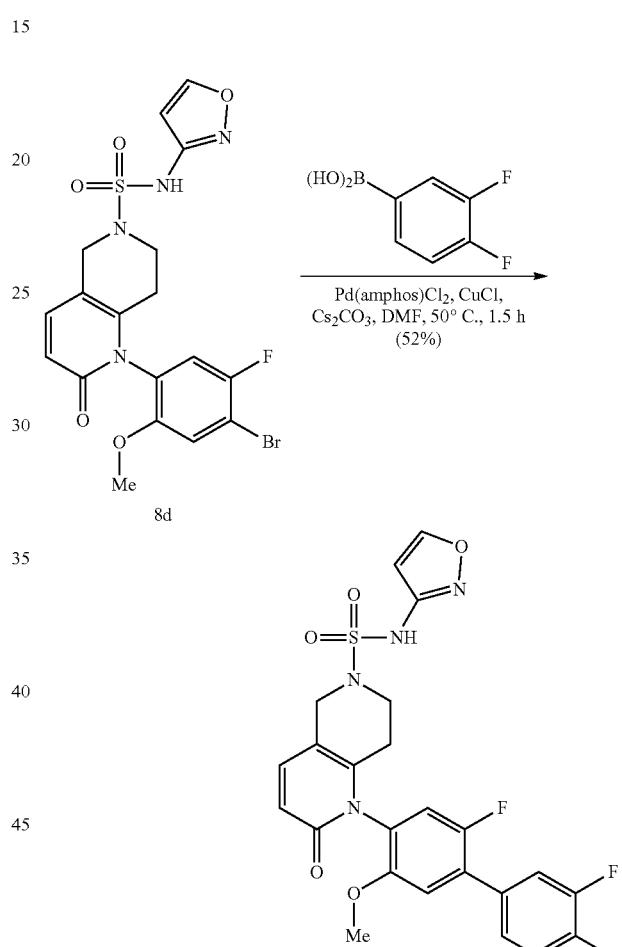

This compound was prepared analogous to the procedure of Example 15 from 1-(4-bromo-5-fluoro-2-methoxyphenyl)-N-(isoxazol-3-yl)-2-oxo-1,2,7,8-tetrahydro-1,6-naphthyridine-6(5H)-sulfonamide (Preparation 8d) and (3,4-difluorophenyl)boronic acid (purchased from Sigma-Aldrich Chemical Company, Inc.) as the boronic acid. $^1$H NMR (400 MHz, DMSO-$d_6$) δ ppm 11.17 (s, 1H) 8.71-8.75 (m, 2H) 8.19 (d, J=2.38 Hz, 1H) 7.26-7.38 (m, 3H) 6.36-6.42 (m, 2H) 4.18-4.28 (m, 2H) 4.00 (s, 3H) 3.75 (s, 3H) 3.39-3.46 (m, 2H) 2.38-2.48 (m, 1H) 2.05-2.14 (m, 1H). m/z (ESI) 533.0 (M+H)$^+$.

Separation Step: Racemic product of Example 20 was subjected to chiral SFC separation ((S,S) Whelk-O column, 40% methanol) to afford Example 20-P (peak 1) and Example 20-M (peak 2) as off-white solids.

Example 21

(Rac)-; (P)-; and (M)-1-(2,3'-Difluoro-5-Methoxy-4'-Methyl-[1,1'-Biphenyl]-4-Yl)-N-(Isoxazol-3-Yl)-2-Oxo-1,2,7,8-Tetrahydro-1,6-Naphthyridine-6(5H)-Sulfonamide

Example 22

(Rac)-; (P)-; and (M)-1-(2,4'-Difluoro-5-Methoxy-3'-Methyl-[1,1'-Biphenyl]-4-Yl)-N-(Isoxazol-3-Yl)-2-Oxo-1,2,7,8-Tetrahydro-1,6-Naphthyridine-6(5H)-Sulfonamide

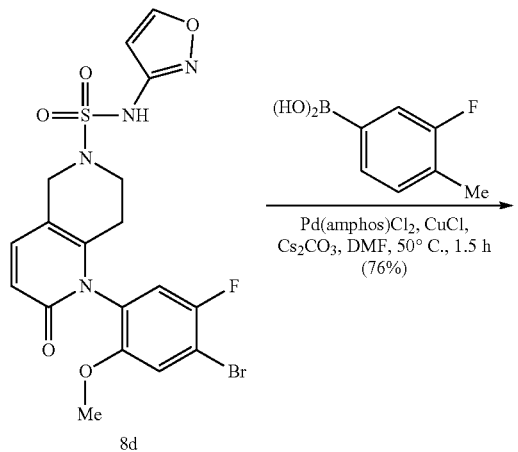

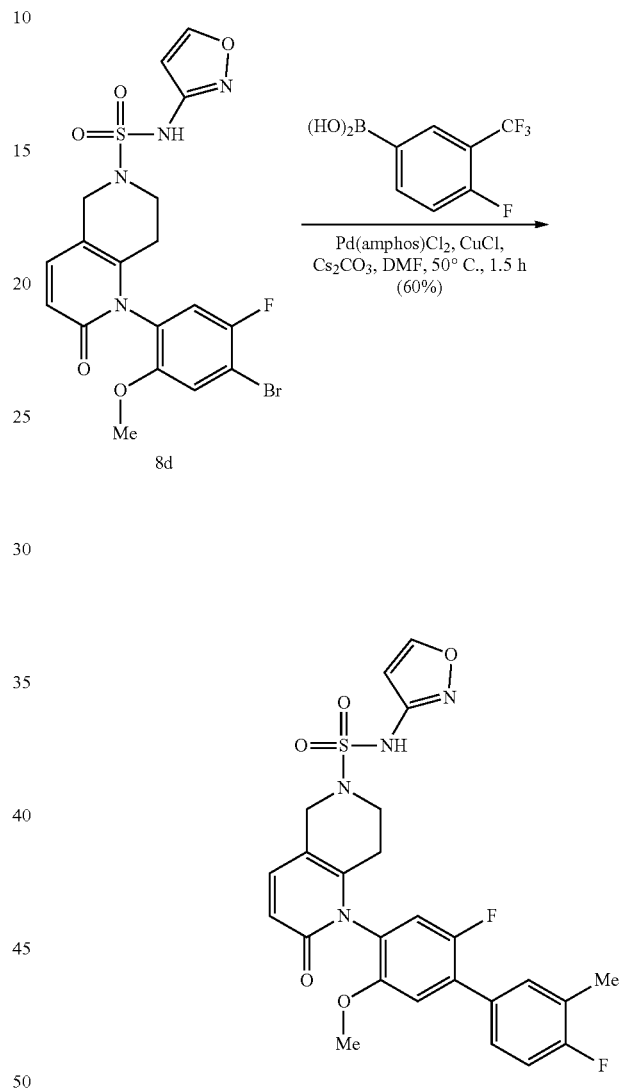

This compound was prepared analogous to the procedure of Example 15 from 1-(4-bromo-5-fluoro-2-methoxyphenyl)-N-(isoxazol-3-yl)-2-oxo-1,2,7,8-tetrahydro-1,6-naphthyridine-6(5H)-sulfonamide (Preparation 8d) and 3-fluoro-4-methyl-phenylboronic acid (purchased from Alfa Aesar, a Johnson Matthey Company) as the boronic acid. $^1$H NMR (400 MHz, DMSO-$d_6$) δ ppm 11.16 (s, 1H) 8.74 (d, J=1.76 Hz, 1H) 7.39-7.54 (m, 3H) 7.25-7.37 (m, 3H) 6.35-6.41 (m, 2H) 4.22 (br. s., 2H) 3.79 (s, 3H) 3.35-3.46 (m, 2H) 2.55-2.62 (m, 1H) 2.42 (s, 1H) 2.30-2.35 (m, 3H). m/z (ESI) 529.2 (M+H)$^+$.

Separation Step: Racemic product of Example 21 was subjected to chiral SFC separation ((S,S) Whelk-O column, 40% methanol) to afford Example 21-P (peak 1) and Example 21-M (peak 2) as off-white solids.

This compound was prepared analogous to the procedure of Example 15 from 1-(4-bromo-5-fluoro-2-methoxyphenyl)-N-(isoxazol-3-yl)-2-oxo-1,2,7,8-tetrahydro-1,6-naphthyridine-6(5H)-sulfonamide (Preparation 8d) and 4-fluoro-3-methyl-phenylboronic acid (purchased from Acros Organics) as the boronic acid. $^1$H NMR (400 MHz, DMSO-$d_6$) δ ppm 11.15 (s, 1H) 8.73 (d, J=2.03 Hz, 1H) 7.47-7.60 (m, 2H) 7.24-7.34 (m, 4H) 6.34-6.39 (m, 2H) 4.09-4.35 (m, 2H) 3.73-3.79 (m, 3H) 3.34-3.47 (m, 2H) 2.37-2.47 (m, 1H) 2.32 (d, J=1.66 Hz, 3H) 2.03-2.13 (m, 1H). m/z (ESI) 529.2 (M+H)$^+$.

Separation Step: Racemic product of Example 22 was subjected to chiral SFC separation ((S,S) Whelk-O column, 40% methanol) to afford Example 22-P (peak 1) and Example 22-M (peak 2) as off-white solids.

Example 23

(Rac)-1-(5-Fluoro-2-Methoxy-4-(2-Methoxy-5-(Trifluoromethyl)Pyridin-3-Yl)Phenyl)-N-(Isoxazol-3-Yl)-2-Oxo-1,2,7,8-Tetrahydro-1,6-Naphthyridine-6(5H)-Sulfonamide

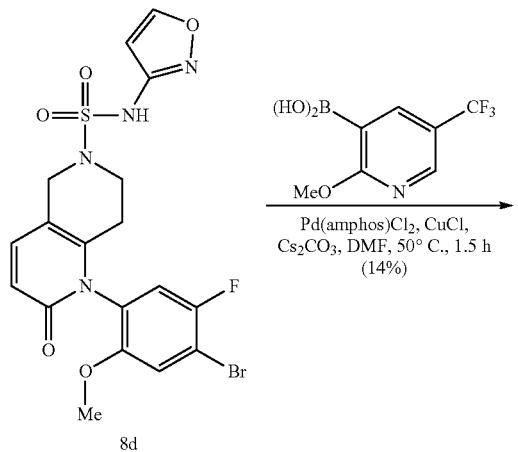

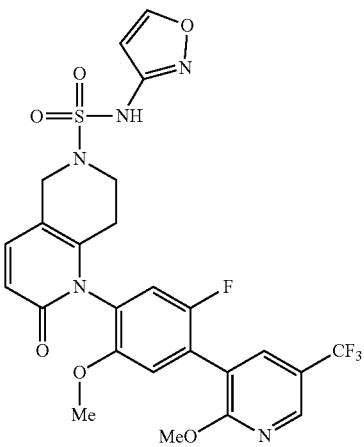

This compound was prepared analogous to the procedure of Example 15 from 1-(4-bromo-5-fluoro-2-methoxyphenyl)-N-(isoxazol-3-yl)-2-oxo-1,2,7,8-tetrahydro-1,6-naphthyridine-6(5H)-sulfonamide (Preparation 8d) and 2-methoxy-5-trifluoromethylpyridine-3-boronic acid (purchased from Combi-Blocks Inc.) as the boronic acid. $^1$H NMR (400 MHz, DMSO-$d_6$) δ ppm 11.16 (s, 1H) 8.74 (d, J=1.76 Hz, 1H) 7.75-7.86 (m, 1H) 7.48-7.67 (m, 2H) 7.27-7.38 (m, 3H) 6.35-6.41 (m, 2H) 4.17-4.28 (m, 2H) 3.79 (s, 3H) 3.37-3.49 (m, 2H) 2.38-2.47 (m, 1H) 2.03-2.14 (m, 1H). m/z (ESI) 596.2 (M+H)$^+$.

Example 24

(Rac)-; (P)-; and (M)-1-(4'-Chloro-2-Fluoro-5-Methoxy-3'-Methyl-[1,1'-Biphenyl]-4-Yl)-N-(Isoxazol-3-Yl)-2-Oxo-1,2,7,8-Tetrahydro-1,6-Naphthyridine-6(5H)-Sulfonamide

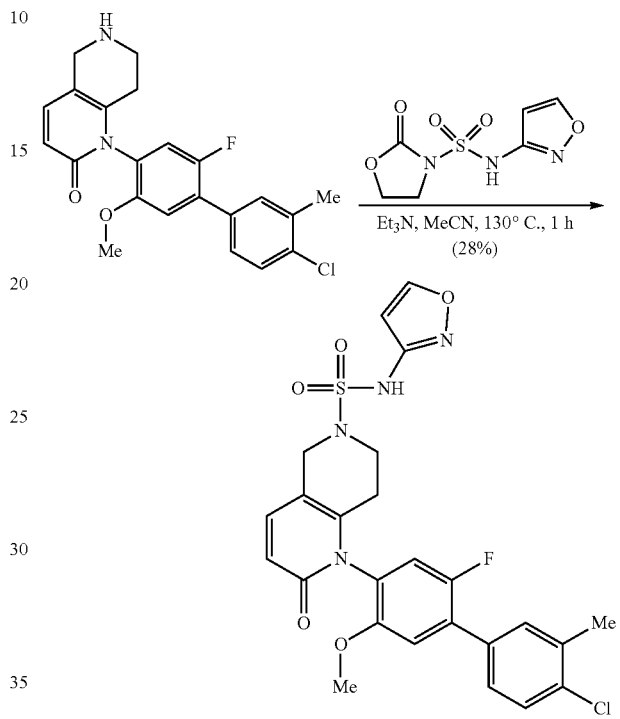

A 5-mL vial was charged with (Rac)-1-(4'-chloro-2-fluoro-5-methoxy-3'-methyl-[1,1'-biphenyl]-4-yl)-5,6,7,8-tetrahydro-1,6-naphthyridin-2(1H)-one (See Example 1, step 2, 200 mg, 0.501 mmol), N-(isoxazol-3-yl)-2-oxooxazolidine-3-sulfonamide (Preparation 7c, 175 mg, 0.752 mmol), acetonitrile (2.50 mL), and triethylamine (489 μL, 3.51 mmol). The vial was sealed with a PTFE lined cap and heated to 130° C. After 30 min, the resultant brown reaction mixture was cooled to ambient temperature and cooled to ambient temperature and diluted to 6 mL total volume with DMSO and filtered through a 0.4 micron filter. The filtrate was purified by reverse phase HPLC in 3 separate injections (XBridge Prep Shield RP18 19×100 mm Mobile phase: 0.1% TFA in water/acetonitrile Flow rate: 40 ml/min Inj: 2000 uL Gradient: 12 min 25-95%). The fractions containing product were frozen and lyophilized to afford (Rac)-1-(4'-chloro-2-fluoro-5-methoxy-3'-methyl-[1,1'-biphenyl]-4-yl)-N-(isoxazol-3-yl)-2-oxo-1,2,7,8-tetrahydro-1,6-naphthyridine-6(5H)-sulfonamide (76 mg, 0.14 mmol, 27.8% yield) as a off-white solid. $^1$H NMR (400 MHz, DMSO-$d_6$) δ ppm 8.75 (d, J=1.76 Hz, 1H) 7.37-7.47 (m, 3H) 7.34 (d, J=9.43 Hz, 1H) 7.28 (d, J=9.43 Hz, 1H) 7.16 (d, J=6.53 Hz, 1H) 6.34-6.42 (m, 2H) 4.17-4.33 (m, 2H) 3.74 (s, 3H) 3.42 (d, J=5.91 Hz, 2H) 2.37-2.47 (m, 1H) 2.03-2.14 (m, 1H). m/z (ESI) 545.0 (M+H)$^+$.

Separation Step: Racemic product of Example 24 was subjected to chiral SFC separation ((S,S) Whelk-O column, 40% methanol) to afford Example 24-P (peak 1) and Example 24-M (peak 2) as off-white solids.

Example 25

(Rac)-; (P)-; and (M)-N-(Isoxazol-3-Yl)-2-Oxo-1-(2,3',5'-Trifluoro-5-Methoxy-[1,1'-Biphenyl]-4-Yl)-1,2,7,8-Tetrahydro-1,6-Naphthyridne-6(5H)-Sulfonamide

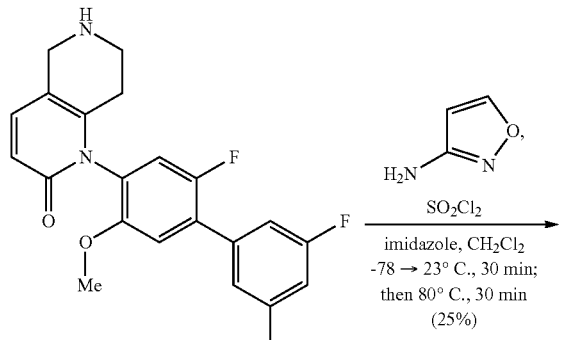

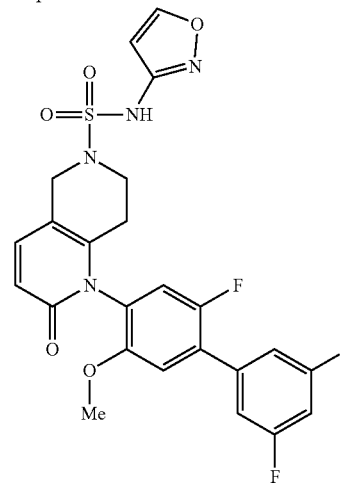

A 5-mL vial was charged with imidazole (88.0 mg, 1.29 mmol) and 3-aminoisoxazole (30.6 μL, 0.41 mmol) then purged with nitrogen. CH₂Cl₂ (1 mL) was introduced and the reaction mixture was cooled to −78° C. in a dry ice-acetone bath. Sulfuryl chloride (55.9 μL, 0.41 mmol) was added dropwise via syringe to the reaction mixture. Following addition, the cold bath was removed and the resultant mixture was allowed to warm to ambient temperature. After 30 minutes, (Rac)-1-(2,3',5'-trifluoro-5-methoxy-[1,1'-biphenyl]-4-yl)-5,6,7,8-tetrahydro-1,6-naphthyridin-2(1H)-one (See Example 10, step 2, 100 mg, 0.26 mmol) was introduced. The vial was sealed with a PTFE lined cap and the reaction mixture was warmed to 80° C. After 30 min, the reaction mixture was cooled to ambient temperature and diluted with an aqueous solution of citric acid (1.0 M, 5 mL), brine (5 mL) and EtOAc (10 mL). The layers were separated and the aqueous layer was extracted with EtOAc (3×10 mL). The combined organic layers were dried over anhydrous magnesium sulfate, filtered, and concentrated under reduced pressure and The combined organic layers were dried over anhydrous magnesium sulfate, filtered, and concentrated under reduced pressure and purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-70%). The fractions containing product were frozen and lyophilized to afford (Rac)-N-(isoxazol-3-yl)-2-oxo-1-(2,3',5'-trifluoro-5-methoxy-[1,1'-biphenyl]-4-yl)-1,2,7,8-tetrahydro-1,6-naphthyridine-6(5H)-sulfonamide (35 mg, 0.07 mmol, 25.4% yield) as a tan solid. ¹H NMR (400 MHz, DMSO-d₆) δ=11.78 (br. s., 1H), 9.41 (s, 1H), 7.47-7.32 (m, 7H), 6.39 (d, J=9.4 Hz, 1H), 4.37-4.26 (m, 2H), 3.80 (s, 3H), 3.48 (d, J=7.7 Hz, 2H), 2.48-2.41 (m, 1H), 2.13 (d, J=17.8 Hz, 1H). m/z (ESI) 531.0 (M+H)⁺.

Separation Step: Racemic product of Example 25 was subjected to chiral SFC separation ((S,S) CHIRALPAK® AS-H column, 38% methanol) to afford Example 25-P (peak 1) and Example 25-M (peak 2) as off-white solids.

Example 26

(Rac)-; (P)-; and (M)-N-(Isoxazol-3-Yl)-1-(2-Methoxy-4-(Trifluoromethyl)Phenyl)-2-Oxo-1,2,7,8-Tetrahydro-1,6-Naphthyridine-6(5H)-Sulfonamide

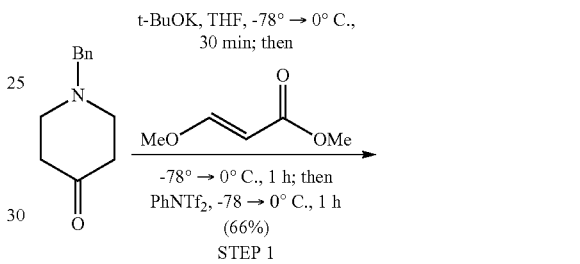

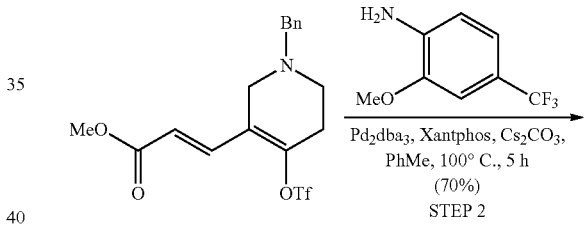

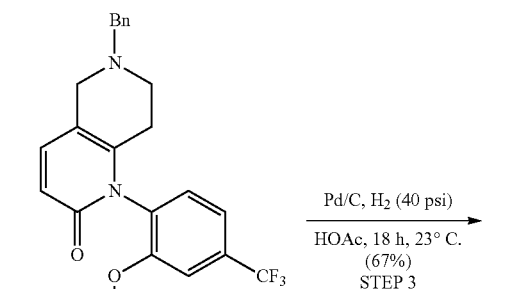

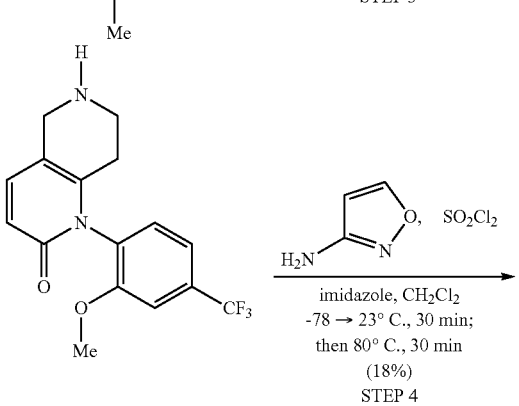

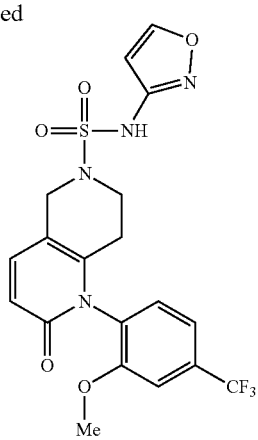

Step 1: (E)-Methyl 3-(1-Benzyl-4-(((Trifluoromethyl)Sulfonyl)Oxy)-1,2,5,6-Tetrahydropyridin-3-Yl)Acrylate A 250-mL round-bottom flask was charged with 1-benzyl-4-piperidone (Sigma Aldrich, 2.68 ml, 15.0 mmol) and purged with nitrogen. THF (75 ml) was introduced, and the resultant solution cooled to −78° C. in a dry ice-acetone bath. A solution of potassium tert-butoxide (1.0 M in THF, 18.0 mL, 18.0 mmol) was added to the reaction mixture via syringe over 5 min. Following addition, the reaction mixture was allowed to warm to 0° C. in an ice-water bath. After 30 min, the reaction mixture was cooled to −78° C. Methyl 3-methoxyacrylate (22.8 mL, 212 mmol) was added dropwise to the reaction mixture via syringe over 5 min. Following addition, the reaction mixture was allowed to warm to ambient temperature. After 1 h, the reaction mixture was cooled was cooled to −78° C. N-phenyl bis-trifluoromethane sulfonimide (6.43 g, 159 mmol) was added to the vigorously stirred, cooled reaction mixture in one portion and the reaction mixture was subsequently allowed to warm to 0° C. in an ice-water bath. After 1 h, saturated aqueous sodium bicarbonate solution (50 mL) and EtOAc (50 mL) were added to the reaction mixture, and the layers were separated. The aqueous layer was extracted with EtOAc (3×50 mL) and the combined organic layers were dried over anhydrous sodium sulfate, filtered, and concentrated under reduced pressure. The residue was purified by flash column chromatography (100-g silica gel Biotage column, eluent: gradient, 0 to 30% EtOAc in heptane) to afford (E)-methyl 3-(1-benzyl-4-(((trifluoromethyl)sulfonyl)oxy)-1,2,5,6-tetrahydropyridin-3-yl)acrylate (4.04 g, 9.97 mmol, 66.4% yield) as an orange oil. $^1$H NMR (400 MHz, DMSO-$d_6$) δ ppm 7.27-7.47 (m, 7H) 7.18-7.25 (m, 1H) 6.11 (d, J=16.02 Hz, 1H) 3.68-3.76 (m, 4H) 3.43 (br. s., 2H) 2.67-2.78 (m, 2H) 2.57-2.65 (m, 2H). m/z (ESI) 406.2 (M+H)$^+$.

Step 2: (Rac)-6-Benzyl-1-(2-Methoxy-4-(Trifluoromethyl)Phenyl)-5,6,7,8-Tetrahydro-1,6-Naphthyridin-2(1H)-One A 20-mL vial was charged with (E)-methyl 3-(1-benzyl-4-(((trifluoromethyl)sulfonyl)oxy)-1,2,5,6-tetrahydropyridin-3-yl)acrylate (500 mg, 1.23 mmol), (9,9-dimethyl-9H-xanthene-4,5-diyl)bis(diphenylphosphine) (89 mg, 0.15 mmol), 2-methoxy-4-trifluoromethyl-aniline (Matrix Scientific, 354 mg, 1.85 mmol), tris(dibenzylideneacetone)dipalladium(0)-chloroform adduct (63.8 mg, 0.06 mmol), cesium carbonate (1.21 g, 3.70 mmol), and PhMe (6.17 mL) then sparged with nitrogen for 10 min. The needle was removed and the reaction was heated to 100° C. After 5 h, the reaction mixture was allowed to cool to ambient temperature and was diluted with EtOAc (15 mL) and filtered through a Celite® pad. The pad was rinsed with EtOAc (3×15 mL). The filtrate was concentrated under reduced pressure and purified by flash column chromatography (50-g silica gel Biotage column, eluent: gradient, 30 to 100% 3:1 EtOAc/EtOH in heptane) to afford (Rac)-6-benzyl-1-(2-methoxy-4-(trifluoromethyl)phenyl)-5,6,7,8-tetrahydro-1,6-naphthyridin-2(1H)-one (359 mg, 0.87 mmol, 70.2% yield) as a brown solid. $^1$H NMR (400 MHz, DMSO-$d_6$) δ=7.54-7.40 (m, 3H), 7.37-7.23 (m, 6H), 6.32 (d, J=9.4 Hz, 1H), 3.85 (s, 3H), 3.62 (s, 2H), 3.32 (s, 2H), 2.63-2.53 (m, 2H), 2.22 (td, J=5.6, 17.3 Hz, 1H), 2.05-1.95 (m, 1H). m/z (ESI) 415.2 (M+H)$^+$.

Step 3: (Rac)-1-(2-Methoxy-4-(Trifluoromethyl)Phenyl)-5,6,7,8-Tetrahydro-1,6-Naphthyridin-2(1H)-One A 20-mL vial was charged with (Rac)-6-benzyl-1-(2-methoxy-4-(trifluoromethyl)phenyl)-5,6,7,8-tetrahydro-1,6-naphthyridin-2(1H)-one (359 mg, 0.87 mmol), palladium on activated carbon wet (10 wt. % (dry basis), 461 mg, 4.33 mmol), and acetic acid (8.66 mL). The vial was placed in a pressure vessel and purged with 40 psi $H_2$ gas (×5) before the reaction mixture stirred vigorously at ambient temperature under a 40 psi $H_2$ atmosphere. After 18 h, the reaction vessel was vented and the black reaction mixture was filtered through a pad of Celite® and rinsed with EtOAc (3×10 mL). The filtrate was concentrated under reduced pressure. The residue was dissolved in DCM (30 mL) and washed with a saturated solution of sodium bicarbonate (15 mL). The aqueous layer was extracted with DCM (15 mL) and the combined organic layers were washed with brine (30 mL). The organic layer was dried over anhydrous magnesium sulfate, filtered, and concentrated under reduced pressure to afford (Rac)-1-(2-methoxy-4-(trifluoromethyl)phenyl)-5,6,7,8-tetrahydro-1,6-naphthyridin-2(1H)-one (187 mg, 0.58 mmol, 66.6% yield) as a tan foam. $^1$H NMR (400 MHz, DMSO-$d_6$) δ ppm 7.51 (s, 1H) 7.24-7.47 (m, 3H) 6.33 (d, J=9.23 Hz, 1H) 3.84 (s, 3H) 3.61 (s, 2H) 2.72-2.86 (m, 2H) 1.97-2.10 (m, 1H) 1.78-1.91 (m, 1H). m/z (ESI) 325.2 (M+H)$^+$.

Step 4: (Rac)-N-(Isoxazol-3-Yl)-1-(2-Methoxy-4-(Trifluoromethyl)Phenyl)-2-Oxo-1,2,7,8-Tetrahydro-1,6-Naphthyridine-6(5H)-Sulfonamide A 5-mL vial was charged with imidazole (105 mg, 1.54 mmol) and 3-aminoisoxazole (36.5 μL, 0.49 mmol) then purged with nitrogen. $CH_2Cl_2$ (1.0 mL) was introduced and the reaction mixture was cooled to −78° C. in a dry ice-acetone bath. Sulfuryl chloride (40.1 μL, 0.49 mmol) was added dropwise via syringe to the reaction mixture. Following addition, the cold bath was removed and the resultant mixture was allowed to warm to ambient temperature. After 30 minutes, (Rac)-1-(2-methoxy-4-(trifluoromethyl)phenyl)-5,6,7,8-tetrahydro-1,6-naphthyridin-2(1H)-one (100 mg, 0.31 mmol) was introduced. The vial was sealed with a PTFE lined cap and the reaction mixture was warmed to 80° C. After 30 min, the reaction mixture was cooled to ambient temperature and diluted with an aqueous solution of citric acid (1.0 M, 5 mL), brine (5 mL), and EtOAc (10 mL). The layers were separated and the aqueous layer was extracted with EtOAc (3×10 mL). The combined organic layers were dried over anhydrous magnesium sulfate, filtered, and concentrated under reduced pressure and The combined organic layers were dried over anhydrous magnesium sulfate, filtered, and concentrated under reduced pressure and purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-70%). The fractions containing product were frozen and lyophilized to afford (Rac)-N-(isoxazol-3-yl)-1-(2-methoxy-4-(trifluoromethyl)phenyl)-2-oxo-1,2,7,8-tetrahydro-1,6-naphthyridine-6(5H)-sulfonamide (32.0 mg, 0.07 mmol, 22.1% yield). (25.2 mg, 0.05 mmol, 18.3% yield) as a tan solid. $^1$H NMR (400 MHz, ACETONITRILE-$d_3$) δ=8.59 (br. s., 1H), 8.40 (d, J=1.8 Hz, 1H), 7.47-7.41 (m, 2H), 7.40-7.34 (m, 1H), 7.25 (d, J=9.5 Hz, 1H), 6.44-6.37 (m, 2H), 4.29 (s, 2H), 3.84 (s, 3H), 3.57-3.36 (m, 2H), 2.30 (d, J=6.6 Hz, 1H), 2.17-2.07 (m, 1H). m/z (ESI) 469.0 (M+H)$^+$.

Separation Step: Racemic product of Example 26 was subjected to chiral SFC separation ((S,S) Whelk-O column, 35% methanol) to afford Example 26-P (peak 1) and Example 26-M (peak 2) as off-white solids.

Example 27

(Rac)-N-(Isoxazol-3-Yl)-1-(2-Methoxyphenyl)-2-Oxo-1,2,7,8-Tetrahydro-1,6-Naphthyridine-6(5H)-Sulfonamide

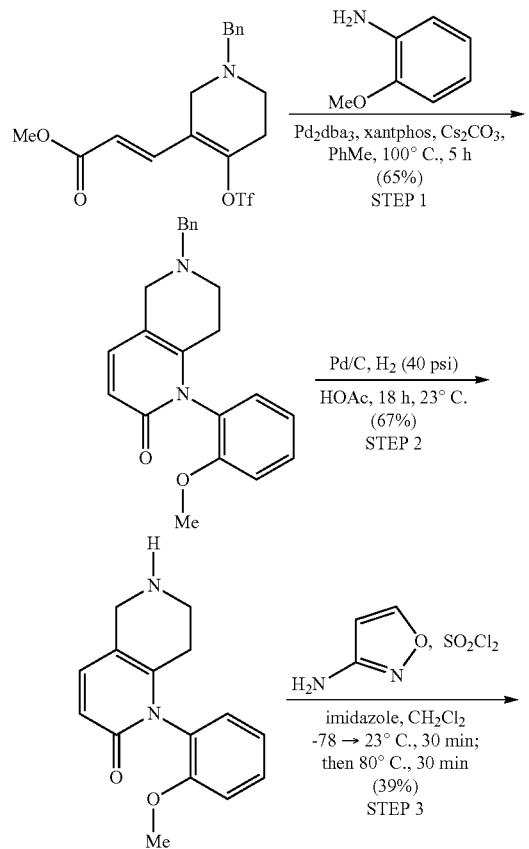

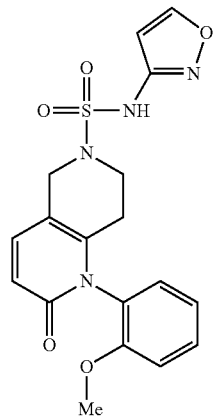

Step 1: (Rac)-6-Benzyl-1-(2-Methoxyphenyl)-5,6,7,8-Tetrahydro-1,6-Naphthyridin-2(1H)-One A 20-mL vial was charged with (E)-methyl 3-(1-benzyl-4-(((trifluoromethyl)sulfonyl)oxy)-1,2,5,6-tetrahydropyridin-3-yl)acrylate (See Example 26, step 1, 526 mg, 1.30 mmol), (9,9-dimethyl-9H-xanthene-4,5-diyl)bis(diphenylphosphine) (94 mg, 0.16 mmol), 2-methoxyaniline (Sigma Aldrich, 219 µL, 1.95 mmol), tris(dibenzylideneacetone)dipalladium(0)-chloroform adduct (67.2 mg, 0.07 mmol), cesium carbonate (1.27 g, 3.89 mmol), and PhMe (6.5 mL) then sparged with nitrogen for 10 min. The needle was removed and the reaction was heated to 100° C. After 5 h, the reaction mixture was allowed to cool to ambient temperature and was diluted with EtOAc (15 mL) and filtered through a Celite® pad. The pad was rinsed with EtOAc (3×15 mL). The filtrate was concentrated under reduced pressure and purified by flash column chromatography (50-g silica gel Biotage column, eluent: gradient, 30 to 100% 3:1 EtOAc/EtOH in heptane) to afford (Rac)-6-benzyl-1-(2-methoxyphenyl)-5,6,7,8-tetrahydro-1,6-naphthyridin-2(1H)-one (290 mg, 0.837 mmol, 64.5% yield) as a brown solid. $^1$H NMR (400 MHz, DMSO-$d_6$) δ ppm 7.44 (t, J=7.93 Hz, 1H) 7.15-7.37 (m, 8H) 6.98-7.11 (m, 1H) 6.29 (d, J=9.33 Hz, 1H) 3.75 (s, 3H) 3.61 (s, 2H) 3.31 (br. s., 2H) 2.53-2.60 (m, 2H) 2.15-2.24 (m, 1H) 1.95-2.05 (m, 2H). m/z (ESI) 347.2 (M+H)$^+$.

Step 2: (Rac)-1-(2-Methoxyphenyl)-5,6,7,8-Tetrahydro-1,6-Naphthyridin-2(1H)-One

A 20-mL vial was charged with (Rac)-6-benzyl-1-(2-methoxyphenyl)-5,6,7,8-tetrahydro-1,6-naphthyridin-2(1H)-one (189 mg, 0.55 mmol), palladium on activated carbon wet (10 wt. % (dry basis), 290 mg, 2.73 mmol), and acetic acid (5.5 mL). The vial was placed in a pressure vessel and purged with 40 psi H$_2$ gas (×5) before the reaction mixture stirred vigorously at ambient temperature under a 40 psi H$_2$ atmosphere. After 18 h, the reaction vessel was vented and the black reaction mixture was filtered through a pad of Celite® and rinsed with EtOAc (3×10 mL). The filtrate was concentrated under reduced pressure. The residue was dissolved in DCM (30 mL) and washed with a saturated solution of sodium bicarbonate (15 mL). The aqueous layer was extracted with DCM (15 mL) and the combined organic layers were washed with brine (30 mL). The organic layer was dried over anhydrous magnesium sulfate, filtered, and concentrated under reduced pressure to afford (Rac)-1-(2-methoxyphenyl)-5,6,7,8-tetrahydro-1,6-naphthyridin-2(1H)-one (80.2 mg, 0.313 mmol, 57.4% yield) as a tan solid. $^1$H NMR (400 MHz, DMSO-$d_6$) δ ppm 7.44 (ddd, J=8.34, 7.20, 1.97 Hz, 1H) 7.23 (d, J=9.33 Hz, 1H) 7.20 (dd, J=8.34, 1.09 Hz, 1H) 7.03-7.12 (m, 2H) 6.31 (d, J=9.23 Hz, 1H) 3.73 (s, 3H) 3.64 (d, J=1.76 Hz, 2H) 2.77-2.87 (m, 2H) 1.98-2.11 (m, 1H) 1.81-1.92 (m, 1H). m/z (ESI) 257.2 (M+H)$^+$.

Step 3: (Rac)-N-(Isoxazol-3-Yl)-1-(2-Methoxyphenyl)-2-Oxo-1,2,7,8-Tetrahydro-1,6-Naphthyridine-6(5H)-Sulfonamide A 5-mL vial was charged with imidazole (96.0 mg, 1.41 mmol) and 3-aminoisoxazole (33.2 µL, 0.45 mmol) then purged with nitrogen. CH$_2$Cl$_2$ (1 mL) was introduced and the reaction mixture was cooled to −78° C. in a dry ice-acetone bath. Sulfuryl chloride (36.5 µL, 0.45 mmol) was added dropwise via syringe to the reaction mixture. Following addition, the cold bath was removed and the resultant mixture was allowed to warm to ambient temperature. After 30 minutes, (Rac)-1-(2-methoxyphenyl)-5,6,7,8-tetrahydro-1,6-naphthyridin-2(1H)-one (72.0 mg, 0.28 mmol) was introduced. The vial was sealed with a PTFE lined cap and the reaction mixture was warmed to 80° C. After 30 min, the reaction mixture was cooled to ambient temperature and diluted with an aqueous solution of citric acid (1.0 M, 5 mL), brine (5 mL), and EtOAc (10 mL). The layers were separated and the aqueous layer was extracted with EtOAc (3×10 mL). The combined organic layers were dried over anhydrous magnesium sulfate, filtered, and concentrated under reduced pressure and The combined organic layers were dried over anhydrous magnesium sulfate, filtered, and concentrated under reduced pressure and purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-80%). The fractions containing product were frozen and lyophilized to afford (Rac)-N-(isoxazol-3-yl)-1-(2-methoxyphenyl)-2-oxo-1,2,7,8-tetrahydro-1,6-naphthyridine-6(5H)-sulfonamide (44 mg, 0.11 mmol, 38.9% yield) as an off-white solid. $^1$H NMR (400 MHz, ACETONITRILE-$d_3$) δ ppm 8.82 (br. s., 1H) 8.37 (d, J=1.76 Hz, 1H) 7.43-7.51 (m, 1H) 7.29 (d, J=9.43 Hz, 1H) 7.04-7.17 (m, 3H) 6.49 (d, J=9.43 Hz, 1H) 6.35 (d, J=1.87 Hz, 1H) 4.28 (s, 2H) 3.73 (s, 3H) 3.34-3.51 (m, 2H) 2.32 (dt, J=17.75, 6.10 Hz, 1H) 2.08-2.18 (m, 1H). m/z (ESI) 401.2 (M+H)$^+$.

Example 28

(Rac)-; (P)-; and (M)-2-Oxo-N-(Pyrimidin-2-Yl)-1-(2,3',4'-Trifluoro-5-Methoxy-[1,1'-Biphenyl]-4-Yl)-1,2,7,8-Tetrahydro-1,6-Naphthyridine-6(5H)-Sulfonamide

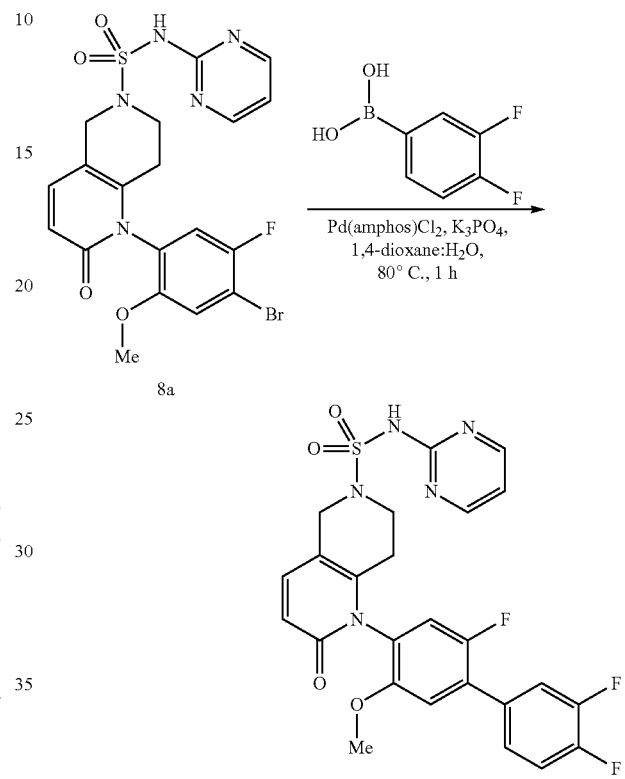

A vial was charged with (Rac)-1-(4-bromo-5-fluoro-2-methoxyphenyl)-2-oxo-N-(pyrimidin-2-yl)-1,2,7,8-tetrahydro-1,6-naphthyridine-6(5H)-sulfonamide (Preparation 8a, 100 mg, 0.196 mmol), (3,4-difluorophenyl)boronic acid (Matrix Scientific, 61.9 mg, 0.392 mmol), 1,1-bis[(di-t-butyl-p-methylaminophenyl]palladium(II) chloride (13.87 mg, 0.020 mmol), and potassium phosphate (125 mg, 0.588 mmol). The vial was flushed with Ar (g), then 1,4-dioxane (784 µL) and water (196 µL) were added. The vial was sealed and heated to 80° C. for 1 h in a Biotage Initiator microwave reactor. The organic layer was separated, and the aq. layer was diluted with 1N aq. HCl and extracted with EtOAc (2×) and 10% MeOH/EtOAc. The combined organic extracts were concentrated. The residue was purified by chromatography on silica gel (25-g SNAP Ultra column with 0-80% of a 3:1 EtOAc/EtOH mixture in heptane with 10% DCM) to give (Rac)-2-oxo-N-(pyrimidin-2-yl)-1-(2,3',4'-trifluoro-5-methoxy-[1,1'-biphenyl]-4-yl)-1,2,7,8-tetrahydro-1,6-naphthyridine-6(5H)-sulfonamide as a yellow solid. $^1$H NMR (400 MHz, DMSO-$d_6$) δ ppm 11.26 (br. s., 1H) 8.52 (d, J=4.77 Hz, 2H) 7.74-7.82 (m, 1H) 7.45-7.64 (m, 2H) 7.39 (d, J=9.43 Hz, 1H) 7.31 (d, J=7.05 Hz, 1H) 7.21 (d, J=10.37 Hz, 1H) 7.08 (t, J=4.82 Hz, 1H) 6.37 (d, J=9.43 Hz, 1H) 4.26-4.41 (m, 2H) 3.75 (s, 2H) 3.41-3.56 (m, 3H) 2.31-2.41 (m, 1H) 2.04-2.14 (m, 1H). m/z (ESI) 544.2 (M+H)$^+$.

Separation Step: (Racemic product of Example 28 was subjected to chiral SFC separation ((S,S) Whelk-O column, 40% methanol) to afford Example 28-P (peak 1) and Example 28-m (peak 2) as off-white solids.

Example 29

(Rac)-; (P)-; and (M)-1-(2,4'-Difluoro-5-Methoxy-3'-Methyl-[1,1'-Biphenyl]-4-Yl)-2-Oxo-N-(Pyrimidin-2-Yl)-1,2,7,8-Tetrahydro-1,6-Naphthyridine-6(5H)-Sulfonamide

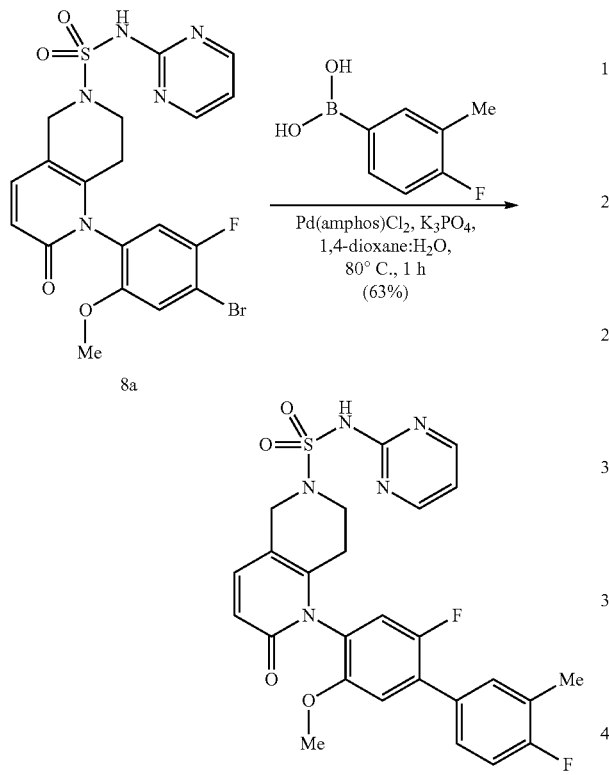

A vial was charged with (Rac)-1-(4-bromo-5-fluoro-2-methoxyphenyl)-2-oxo-N-(pyrimidin-2-yl)-1,2,7,8-tetrahydro-1,6-naphthyridine-6(5H)-sulfonamide (Preparation 8a, 100 mg, 0.196 mmol), (4-fluoro-3-methylphenyl)boronic acid (Acros Organics, 60.3 mg, 0.39 mmol), 1,1-bis[(di-t-butyl-p-methylaminophenyl]palladium(II) chloride (13.87 mg, 0.020 mmol), and potassium phosphate (125 mg, 0.588 mmol). The vial was flushed with Ar (g), then 1,4-dioxane (784 µL) and water (196 µL) were added. The vial was sealed and heated to 80° C. for 1 h in a Biotage Initiator microwave reactor. The organic layer was separated, and the aq. layer was diluted with 1N aq. HCl and extracted with EtOAc (2×) and 10% MeOH/EtOAc. The combined organic extracts were concentrated. The residue was purified by chromatography on silica gel (25-g SNAP Ultra column with 20-80% of a 3:1 EtOAc/EtOH mixture in heptane with 10% DCM) to give (Rac)-1-(2,4'-difluoro-5-methoxy-3'-methyl-[1,1'-biphenyl]-4-yl)-2-oxo-N-(pyrimidin-2-yl)-1,2,7,8-tetrahydro-1,6-naphthyridine-6(5H)-sulfonamide (66.1 mg, 0.12 mmol, 62.5% yield) as a light-yellow solid. $^1$H NMR (400 MHz, DMSO-$d_6$) δ ppm 11.26 (br. s., 1H) 8.52 (d, J=4.87 Hz, 2H) 7.57 (d, J=7.46 Hz, 1H) 7.44-7.53 (m, 1H) 7.38 (d, J=9.54 Hz, 1H) 7.25-7.31 (m, 1H) 7.24 (d, J=6.78 Hz, 1H) 7.16 (d, J=10.37 Hz, 1H) 7.08 (t, J=4.86 Hz, 1H) 6.37 (d, J=9.43 Hz, 1H) 4.26-4.40 (m, 2H) 3.74 (s, 2H) 3.40-3.56 (m, 3H) 2.32 (d, J=1.76 Hz, 4H) 2.05-2.16 (m, 1H). m/z (ESI) 540.2 (M+H)$^+$.

Separation Step: Racemic product of Example 29 was subjected to chiral SFC separation ((S,S) Whelk-O column, 40% methanol) to afford Example 29-P (peak 1) and Example 29-m (peak 2) as off-white solids.

Example 30

(Rac)-; (P)-; and (M)-1-(4'-Chloro-2-Fluoro-5-Methoxy-3'-Methyl-[1,1'-Biphenyl]-4-Yl)-2-Oxo-N-(Pyrimidin-2-Yl)-1,2,7,8-Tetrahydro-1,6-Naphthyridine-6(5H)-Sulfonamide

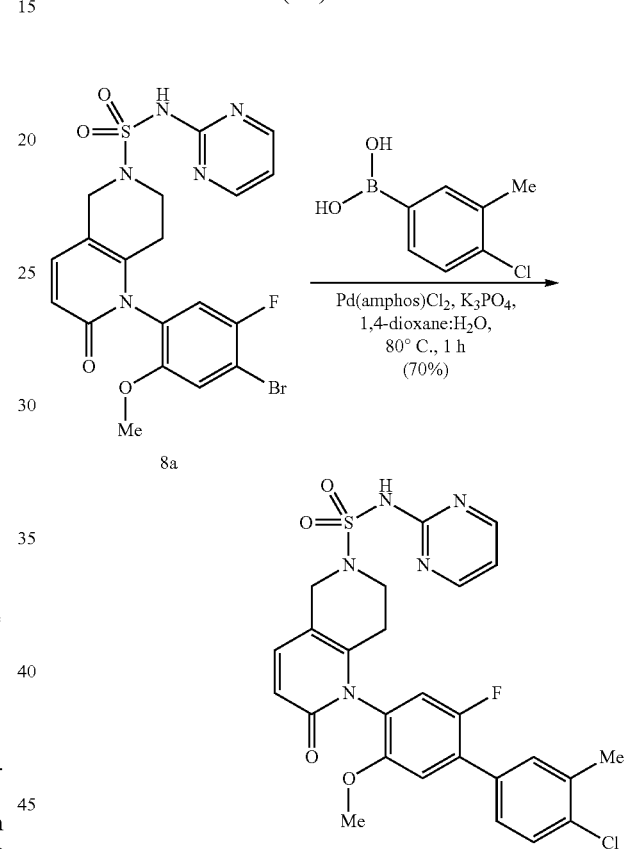

A vial was charged with (Rac)-1-(4-bromo-5-fluoro-2-methoxyphenyl)-2-oxo-N-(pyrimidin-2-yl)-1,2,7,8-tetrahydro-1,6-naphthyridine-6(5H)-sulfonamide (Preparation 8a, 99.2 mg, 0.194 mmol), (4-chloro-3-methylphenyl)boronic acid (Combi-Blocks, 66.2 mg, 0.389 mmol), 1,1-bis[(di-t-butyl-p-methylaminophenyl]palladium(II) chloride (13.76 mg, 0.019 mmol), and potassium phosphate (124 mg, 0.583 mmol). The vial was flushed with Ar (g), then 1,4-dioxane (778 µL) and water (194 µL) were added. The vial was sealed and heated to 80° C. for 1 h in a Biotage Initiator microwave reactor. The organic layer was separated, and the aq. layer was diluted with 1N aq. HCl and extracted with EtOAc (2×) and 10% MeOH/EtOAc. The combined organic extracts were concentrated. The residue was purified by chromatography on silica gel (25-g SNAP Ultra column with 0-80% of a 3:1 EtOAc/EtOH mixture in heptane with 10% DCM) to give (Rac)-1-(4'-chloro-2-fluoro-5-methoxy-3'-methyl-[1,1'-biphenyl]-4-yl)-2-oxo-N-(pyrimidin-2-yl)-1,2,7,8-tetrahydro-1,6-naphthyridine-6(5H)-sulfonamide (75.8 mg, 0.136 mmol, 70.1% yield) as a yellow solid. ¹H NMR (400 MHz, DMSO-d) δ ppm 8.52 (d, J=4.77 Hz, 2H) 7.64 (s, 1H) 7.56 (d, J=7.88 Hz, 1H) 7.49 (d, J=8.29 Hz, 1H) 7.39 (d, J=9.43 Hz, 1H) 7.26 (d, J=6.73 Hz, 1H) 7.18 (d, J=10.37 Hz, 1H) 7.08 (t, J=4.74 Hz, 1H) 6.37 (d, J=9.43 Hz, 1H) 4.26-4.41 (m, 2H) 4.03 (q, J=7.08 Hz, 1H) 3.74 (s, 3H) 3.40-3.57 (m, 2H) 2.42 (s, 4H) 2.03-2.14 (m, 1H). m/z (ESI) 556.2 (M+H)⁺.

Separation Step: Racemic product of Example 30 was subjected to chiral SFC ((S,S) Whelk-O, 45% methanol) to give Example 30-P (peak 1) and Example 30-M (peak 2) as off-white solids.

Example 31

(Rac)-; (P)-; and (M)-1-(3'-Chloro-2,5'-Difluoro-5-Methoxy-[1,1'-Biphenyl]-4-Yl)-2-Oxo-N-(Pyrimidin-2-Yl)-1,2,7,8-Tetrahydro-1,6-Naphthyridine-6(5H)-Sulfonamide

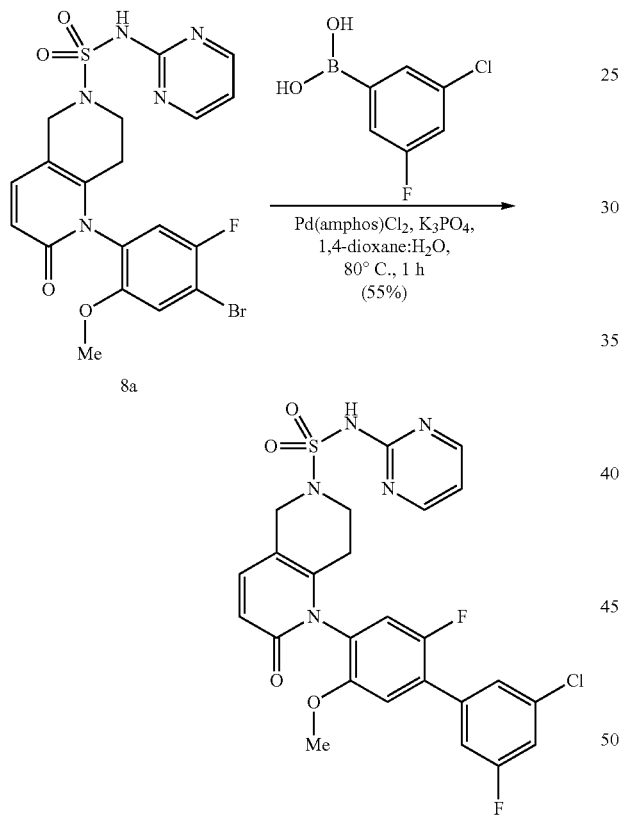

A vial was charged with (Rac)-1-(4-bromo-5-fluoro-2-methoxyphenyl)-2-oxo-N-(pyrimidin-2-yl)-1,2,7,8-tetrahydro-1,6-naphthyridine-6(5H)-sulfonamide (Preparation 8a, 92.3 mg, 0.181 mmol), (3-chloro-5-fluorophenyl)boronic acid (Accela, 63.1 mg, 0.362 mmol), 1,1-bis[(di-t-butyl-p-methylaminophenyl]palladium(II) chloride (12.81 mg, 0.018 mmol), and potassium phosphate (115 mg, 0.543 mmol). The vial was flushed with Ar (g), then 1,4-dioxane (723 μL) and water (181 μL) were added. The vial was sealed and heated to 80° C. for 1 h in a Biotage Initiator microwave reactor. LCMS showed 2:1 product to overcoupling. LCMS showed fairly clean conversion. The organic layer was separated, and the aq. layer was diluted with 1N aq. HCl and extracted with EtOAc (2×) and 10% MeOH/EtOAc. The combined organic extracts were concentrated. The residue was purified by chromatography on silica gel (25-g SNAP Ultra column with 0-80% of a 3:1 EtOAc/EtOH mixture in heptane with 10% DCM). A mixed fraction was discarded, and the remaining fractions containing product were combined and concentrated to give (Rac)-1-(3'-chloro-2,5'-difluoro-5-methoxy-[1,1'-biphenyl]-4-yl)-2-oxo-N-(pyrimidin-2-yl)-1,2,7,8-tetrahydro-1,6-naphthyridine-6(5H)-sulfonamide (55.2 mg, 0.01 mmol, 54.5% yield) as a yellow solid. ¹H NMR (400 MHz, DMSO-d₆) δ ppm 11.28 (br. s., 1H) 8.53 (d, J=4.87 Hz, 2H) 7.49-7.64 (m, 3H) 7.33-7.49 (m, 3H) 7.20-7.29 (m, 1H) 7.09 (t, J=4.82 Hz, 1H) 6.39 (d, J=9.33 Hz, 1H) 4.27-4.43 (m, 2H) 3.72-3.82 (m, 2H) 3.57 (s, 1H) 3.42-3.55 (m, 3H) 2.32-2.42 (m, 1H) 2.05-2.16 (m, 1H). m/z (ESI) 560.0 (M+H)⁺.

Separation Step: Racemic product of Example 31 was subjected to chiral SFC ((S,S) Whelk-O, 45% methanol) to give Example 31-P (peak 1) and Example 31-M (peak 2) as off-white solids.

Example 32

(Rac)-; (P)-; and (M)-2-Oxo-N-(Pyridazin-3-Yl)-1-(2,3',4'-Trifluoro-5-Methoxy-[1,1'-Biphenyl]-4-Yl)-1,2,7,8-Tetrahydro-1,6-Naphthyridine-6(5H)-Sulfonamide

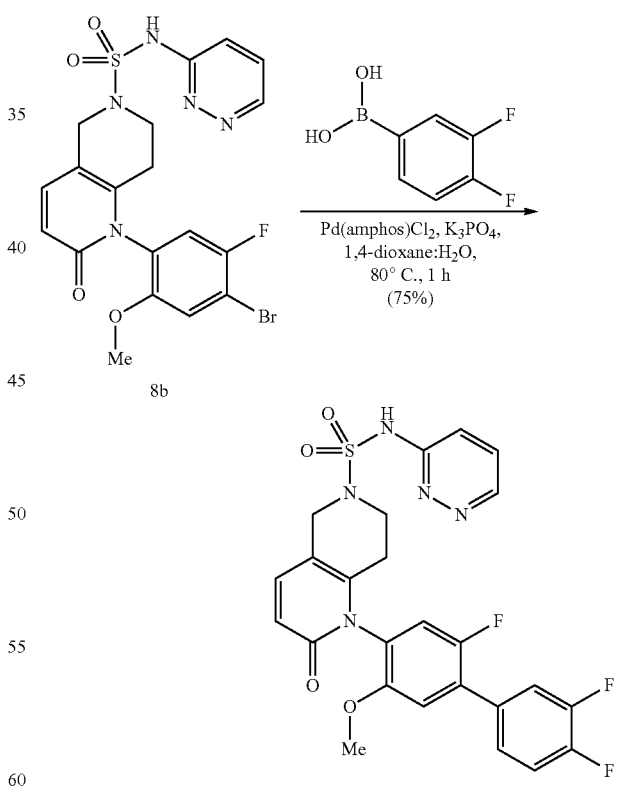

A vial was charged with (Rac)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b, 81.7 mg, 0.16 mmol), (3,4-difluorophenyl)boronic acid (Matrix Scientific, 50.6 mg, 0.32 mmol), 1,1-bis[(di-t-butyl-p-methylaminophenyl]palladium(II) chloride (11.34 mg, 0.016 mmol), and potassium phosphate (102 mg, 0.480 mmol). The vial was flushed with Ar (g), then 1,4-dioxane (640 µL) and water (160 µL) were added. The vial was sealed and heated to 80° C. for 1.5 h in a Biotage Initiator microwave reactor. The organic layer was separated, and the aq. layer was diluted with 1N aq. HCl and extracted with EtOAc (2×) and 10% MeOH/EtOAc. The combined organic extracts were concentrated. The residue was purified by chromatography on silica gel (25-g SNAP Ultra column with 20-70% of a 3:1 EtOAc/EtOH mixture in heptane with 10% DCM) to give (Rac)-2-oxo-N-(pyridazin-3-yl)-1-(2,3',4'-trifluoro-5-methoxy-[1,1'-biphenyl]-4-yl)-1,2,7,8-tetrahydro-1,6-naphthyridine-6(5H)-sulfonamide (64.8 mg, 0.12 mmol, 74.5% yield) as a yellow solid. $^1$H NMR (400 MHz, DMSO-$d_6$) δ ppm 14.21 (br. s., 1H), 8.29 (br. s., 1H), 7.73-7.94 (m, 2H), 7.51-7.70 (m, 3H), 7.32-7.46 (m, 3H), 6.37 (d, J=9.33 Hz, 1H), 3.99-4.15 (m, 2H), 3.81 (s, 3H), 3.30-3.25 (m, 2H), 2.40-2.48 (m, 1H), 2.05-2.19 (m, 1H). m/z (ESI) 544.2 (M+H)$^+$.

Separation Step: Racemic product of Example 32 was subjected to chiral SFC ((S,S) Shelk-O, 40% methanol) to give Example 32-P (peak 1) and Example 32M (peak 2) as off-white solids.

Example 33

(Rac)-1-(4'-Chloro-2-Fluoro-5-Methoxy-3'-Methyl-[1,1'-Biphenyl]-4-Yl)-2-Oxo-N-(Pyridazin-3-Yl)-1,2,7,8-Tetrahydro-1,6-Naphthyridine-6(5H)-Sulfonamide

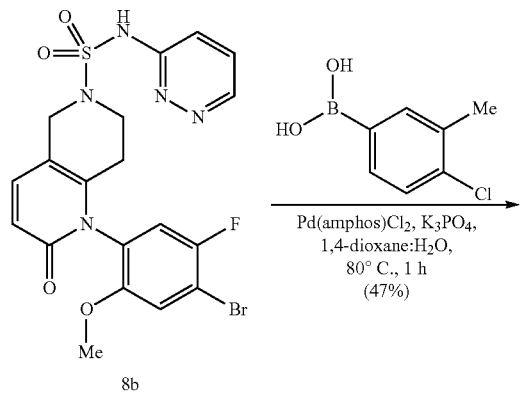

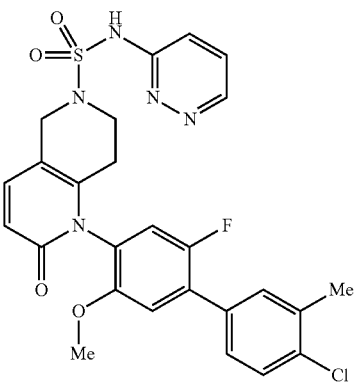

A vial was charged with (Rac)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b, 86.2 mg, 0.169 mmol), (4-chloro-3-methylphenyl)boronic acid (Combi-Blocks, 57.6 mg, 0.34 mmol), 1,1-bis [(di-t-butyl-p-methylaminophenyl]palladium(II) chloride (11.96 mg, 0.017 mmol), and potassium phosphate (108 mg, 0.507 mmol). The vial was flushed with Ar (g), then 1,4-dioxane (676 µL) and water (169 µL) were added. The vial was sealed and heated to 80° C. for 1 h in a Biotage Initiator microwave reactor. The vial was heated for an additional 30 min. The organic layer was separated, and the aq. layer was diluted with 1N aq. HCl and extracted with EtOAc (2×) and 10% MeOH/EtOAc. The combined organic extracts were concentrated. The residue was purified by chromatography on silica gel (25-g SNAP Ultra column with 20-70% of a 3:1 EtOAc/EtOH mixture in heptane with 10% DCM) to give (Rac)-1-(4'-chloro-2-fluoro-5-methoxy-3'-methyl-[1,1'-biphenyl]-4-yl)-2-oxo-N-(pyridazin-3-yl)-1,2,7,8-tetrahydro-1,6-naphthyridine-6(5H)-sulfonamide (44.3 mg, 0.080 mmol, 47.2% yield) as an off-white solid. $^1$H NMR (400 MHz, DMSO-$d_6$) δ ppm 14.22 (br. s., 1H), 8.27 (br. s., 1H), 7.86 (br. s., 1H), 7.61-7.71 (m, 2H), 7.44-7.59 (m, 2H), 7.27-7.41 (m, 3H), 6.39 (d, J=9.30 Hz, 1H), 3.97-4.15 (m, 2H), 3.80 (s, 3H), 3.25 (br. s., 2H), 2.43 (m, 4H), 2.06-2.20 (m, 1H). m/z (ESI) 556.2 (M+H)$^+$.

Separation Step: Racemic product of Example 33 was subjected to chiral SFC (Regis Whelk-O (s,s), 40% methanol) to give Example 33-P (peak 1) and Example 33-M (peak 2) as off-white solids.

Example 34

(Rac)-; (P)-; and (M)-1-(4-(Cyclopentylethynyl)-5-Fluoro-2-Methoxyphenyl)-N-(Isoxazol-3-Yl)-2-Oxo-1,2,7,8-Tetrahydro-1,6-Naphthyridine-6(5H)-Sulfonamide

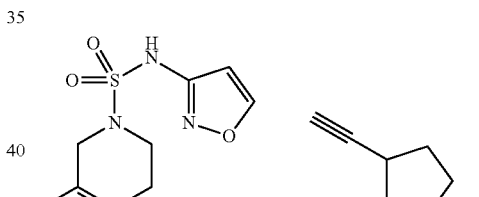

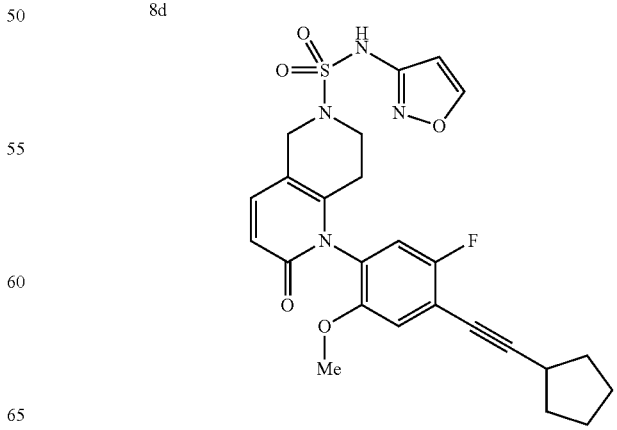

A vial was charged with (Rac)-1-(4-bromo-5-fluoro-2-methoxyphenyl)-N-(isoxazol-3-yl)-2-oxo-1,2,7,8-tetrahydro-1,6-naphthyridine-6(5H)-sulfonamide (See Example 15, step 1, 65.1 mg, 0.13 mmol), copper(I) iodide (3.72 mg, 0.02 mmol), and Pd(PPh$_3$)$_4$(15.1 mg, 0.01 mmol). The vial was flushed with Ar (g), then DMF (652 μL), diisopropylamine (186 μL, 1.30 mmol), and ethynylcyclopentane (61.4 mg, 0.652 mmol) were added in sequence. The vial was sealed and heated to 60° C. for 3 h. The mixture was diluted with 2N aq. HCl and extracted with EtOAc (4×). The combined organic extracts were concentrated. The residue was purified by chromatography on silica gel (20-70% of a 3:1 EtOAc/EtOH mixture in heptane with 10% DCM) to give (Rac)-1-(4-(cyclopentylethynyl)-5-fluoro-2-methoxyphenyl)-N-(isoxazol-3-yl)-2-oxo-1,2,7,8-tetrahydro-1,6-naphthyridine-6(5H)-sulfonamide (49.3 mg, 0.01 mmol, 73.8% yield) as a light-yellow solid. $^1$H NMR (400 MHz, DMSO-d$_6$) δ ppm 11.14 (s, 1H), 8.73 (s, 1H), 7.32 (d, J=9.43 Hz, 1H), 7.22 (d, J=9.46 Hz, 1H), 7.20 (d, J=2.03 Hz, 1H), 6.38 (d, J=2.03 Hz, 1H), 6.34 (d, J=9.46 Hz, 1H), 4.20 (d, J=3.32 Hz, 2H), 3.71 (s, 3H), 3.34-3.46 (m, 2H), 2.95 (t, J=7.41 Hz, 1H), 2.28-2.43 (m, 1H), 1.96-2.08 (m, 3H), 1.56-1.79 (m, 5H). m/z (ESI) 513.2 (M+H)$^+$.

Separation Step: Racemic product of Example 34 was subjected to chiral SFC (Chiralpak AS-H, 40% methanol) to give Example 34-P (peak 1) and Example 34-M (peak 2) as off-white solids.

Example 35

(Rac)-1-(4'-Chloro-3'-Cyano-2-Fluoro-5-Methoxy-[1,1'-Biphenyl]-4-Yl)-N-(Isoxazol-3-Yl)-2-Oxo-1,2,7,8-Tetrahydro-1,6-Naphthyridine-6(5H)-Sulfonamide

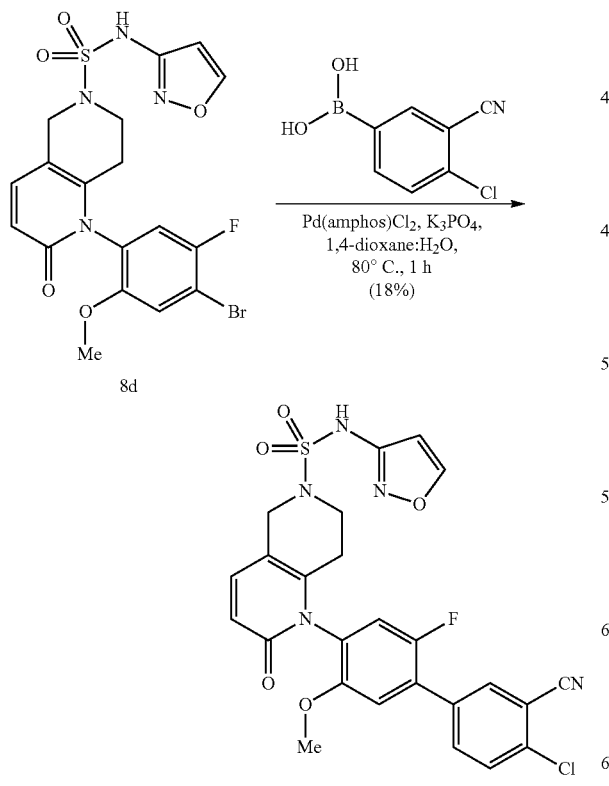

A vial was charged with (Rac)-1-(4-bromo-5-fluoro-2-methoxyphenyl)-N-(isoxazol-3-yl)-2-oxo-1,2,7,8-tetrahydro-1,6-naphthyridine-6(5H)-sulfonamide (See Example 15, step 1, 64.2 mg, 0.129 mmol), (4-chloro-3-cyanophenyl)boronic acid (Aururm Pharmatech, 46.6 mg, 0.26 mmol), 1,1-bis[(di-t-butyl-p-methylaminophenyl]palladium(II) chloride (9.10 mg, 0.013 mmol), and potassium phosphate (82 mg, 0.386 mmol). The vial was flushed with Ar (g), then 1,4-dioxane (514 μL) and water (129 μL) were added. The vial was sealed and heated to 80° C. for 1 h in a Biotage Initiator microwave reactor. LCMS showed a mix of product, over-coupling, and something else. The organic layer was separated, and the aq. layer was diluted with 2N aq. HCl and extracted with EtOAc (2×) and 10% MeOH/EtOAc. The combined organic extracts were concentrated. The residue was concentrated from MeOH, then taken up in MeOH and filtered. The filtrate was concentrated. The residue was purified by chromatography on silica gel (25-g SNAP Ultra column with 20-70% of a 3:1 EtOAc/EtOH mixture in heptane with 10% DCM) to give 30 mg of a solid. The material was dissolved in MeOH and purified by reverse-phase HPLC (25-70% CH$_3$CN/H$_2$O with 0.1% TFA). Fractions containing the desired product were combined with saturated aq. sodium bicarbonate solution and extracted with DCM (3×). The combined organic extracts were dried over sodium sulfate, filtered, and concentrated to give (Rac)-1-(4'-chloro-3'-cyano-2-fluoro-5-methoxy-[1,1'-biphenyl]-4-yl)-N-(isoxazol-3-yl)-2-oxo-1,2,7,8-tetrahydro-1,6-naphthyridine-6(5H)-sulfonamide (13 mg, 0.02 mmol, 18.2% yield) as an off-white solid. $^1$H NMR (400 MHz, DMSO-d$_6$) δ ppm 11.17 (s, 1H), 8.75 (s, 1H), 8.33 (d, J=1.97 Hz, 1H), 8.03 (dt, J=8.60, 1.97 Hz, 1H), 7.91 (d, J=8.50 Hz, 1H), 7.42 (d, J=7.05 Hz, 1H), 7.36 (s, 1H), 7.33 (s, 1H), 6.39 (s, 1H), 6.38 (d, J=10.40 Hz, 2H), 4.18-4.29 (m, 2H), 3.81 (s, 3H), 3.41 (m, J=5.60 Hz, 2H), 2.44 (dt, J=17.18, 5.71 Hz, 1H), 2.04-2.17 (m, 1H). m/z (ESI) 556.2 (M+H)$^+$ Example 36

(Rac)-1-(6-(3-Chloro-5-Fluorophenyl)-5-Fluoro-2-Methoxypyridin-3-Yl)-N-(Isoxazol-3-Yl)-2-Oxo-1,2,7,8-Tetrahydro-1,6-Naphthyridine-6(5H)-Sulfonamide

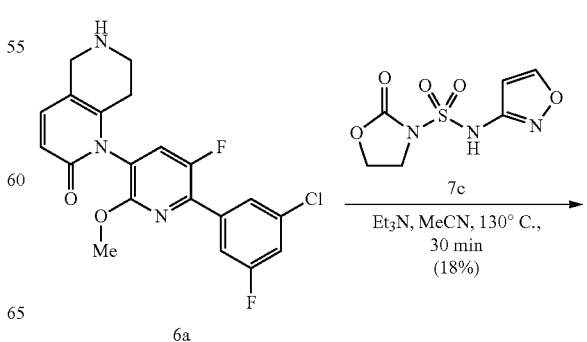

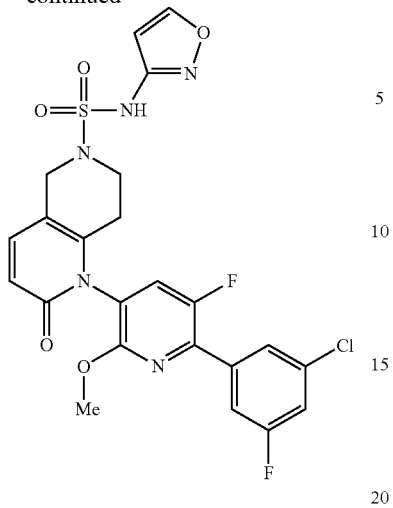

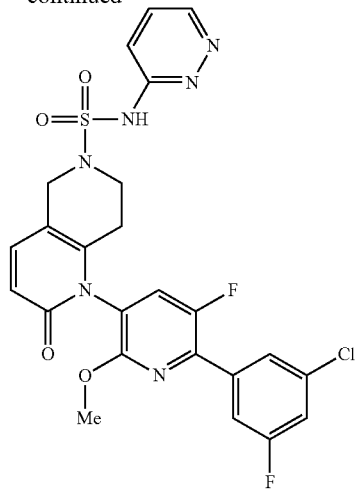

A vial was charged with (Rac)-1-(6-(3-chloro-5-fluorophenyl)-5-fluoro-2-methoxypyridin-3-yl)-5,6,7,8-tetrahydro-1,6-naphthyridin-2(1H)-one (Preparation 6a, 126 mg, 0.26 mmol), N-(isoxazol-3-yl)-2-oxooxazolidine-3-sulfonamide (Preparation 7c, 174 mg, 0.75 mmol), acetontrile (1.25 mL), and triethylamine (347 µL, 2.49 mmol). The vial was sealed and heated to 130° C. for 30 min in a Biotage Initiator microwave reactor. The mixture was concentrated in vacuo. The residue was taken up in 1N aq. HCl and DCM. The layers were separated, and the aq. layer was extracted with DCM (2×). The combined organic extracts were dried over sodium sulfate, filtered, and concentrated. The residue was purified by chromatography on silica gel (25-g SNAP Ultra column, 20-70% of 3:1 EtOAc/EtOH in heptane with 10% DCM) to give (Rac)-1-(6-(3-chloro-5-fluorophenyl)-5-fluoro-2-methoxypyridin-3-yl)-N-(isoxazol-3-yl)-2-oxo-1,2,7,8-tetrahydro-1,6-naphthyridine-6(5H)-sulfonamide (24.5 mg, 0.05 mmol, 17.9% yield) as a white solid. $^1$H NMR (400 MHz, DMSO-$d_6$) δ ppm 11.18 (s, 1H), 8.71-8.79 (m, 1H), 8.04 (d, J=10.47 Hz, 1H), 7.91 (s, 1H), 7.84 (d, J=9.63 Hz, 1H), 7.65 (d, J=7.95 Hz, 1H), 7.38 (d, J=9.64 Hz, 1H), 6.38-6.43 (m, 2H), 4.24 (br. s., 2H), 3.98-4.13 (m, 2H), 3.93 (s, 3H), 3.41-3.50 (m, 1H), 2.14 (d, J=17.52 Hz, 1H). m/z (ESI) 550.0 (M+H)$^+$.

A vial was charged with (Rac)-1-(6-(3-chloro-5-fluorophenyl)-5-fluoro-2-methoxypyridin-3-yl)-5,6,7,8-tetrahydro-1,6-naphthyridin-2(1H)-one (Preparation 6a, 127 mg, 0.252 mmol), 2-oxo-N-(pyridazin-3-yl)oxazolidine-3-sulfonamide (Preparation 7f, 123 mg, 0.50 mmol), acetontrile (1.26 mL), and triethylamine (210 µL, 1.51 mmol). The vial was sealed and heated to 130° C. for 1 h in a Biotage Initiator microwave reactor. The mixture was concentrated in vacuo. The residue was taken up in 1N aq. HCl and DCM. The layers were separated, and the aq. layer was extracted with DCM (2×). The combined organic extracts were dried over sodium sulfate, filtered, and concentrated. The residue was purified by chromatography on silica gel (25-g SNAP Ultra column, 20-70% of 3:1 EtOAc/EtOH in heptane with 10% DCM) to give (Rac)-1-(6-(3-chloro-5-fluorophenyl)-5-fluoro-2-methoxypyridin-3-yl)-2-oxo-N-(pyridazin-3-yl)-1,2,7,8-tetrahydro-1,6-naphthyridine-6(5H)-sulfonamide (12.5 mg, 0.02 mmol, 8.86% yield) as a tan foam. $^1$H NMR (400 MHz, DMSO-$d_6$) δ ppm 13.93-14.46 (m, 1H) 8.28 (d, J=10.57 Hz, 1H) 8.12 (d, J=10.47 Hz, 1H) 7.91 (s, 1H) 7.83 (d, J=9.95 Hz, 1H) 7.58-7.73 (m, 2H) 7.37-7.54 (m, 2H) 6.42 (d, J=9.54 Hz, 1H) 3.98-4.16 (m, 4H) 3.94 (s, 3H) 3.16-3.26 (m, 1H) 2.18 (d, J=17.52 Hz, 1H). m/z (ESI) 561.0 (M+H)$^+$.

Example 37

(Rac)-1-(6-(3-Chloro-5-Fluorophenyl)-5-Fluoro-2-Methoxypyridin-3-Yl)-2-Oxo-N-(Pyridazin-3-Yl)-1,2,7,8-Tetrahydro-1,6-Naphthyridine-6(5H)-Sulfonamide Example 38

(Rac)-1-(3'-Chloro-2,5'-Difluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

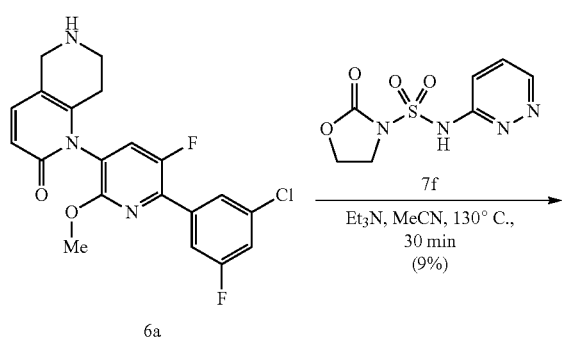

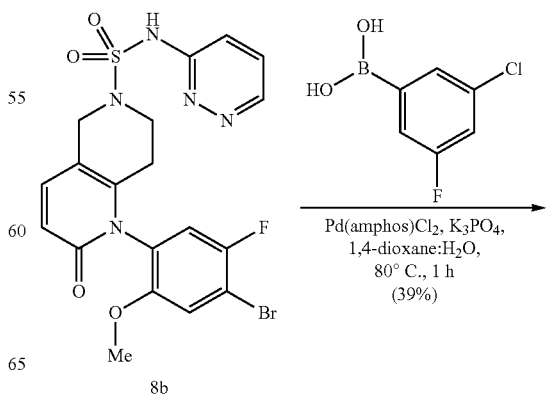

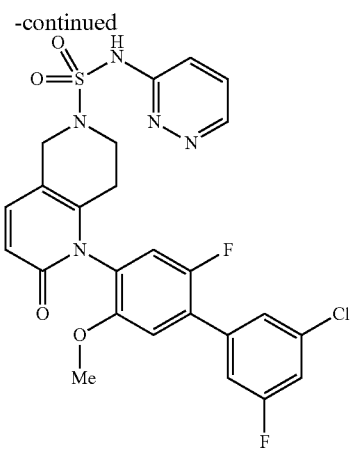

A vial was charged with (Rac)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b, 61.8 mg, 0.12 mmol), (3-chloro-5-fluorophenyl)boronic acid (Accela, 42.2 mg, 0.242 mmol), 1,1-bis[(di-t-butyl-p-methylaminophenyl]palladium(II) chloride (8.57 mg, 0.01 mmol), and potassium phosphate (77 mg, 0.36 mmol). The vial was flushed with Ar (g), then 1,4-dioxane (484 μL) and water (121 μL) were added. The vial was sealed and heated to 60° C. for 3 h, then 80° C. for 2 h. After being cooled, the layers were separated, and the aq. layer was diluted with 1N aq. HCl and extracted with EtOAc (2×) and 10% MeOH/EtOAc. The combined organic extracts were concentrated. The residue was purified by chromatography on silica gel (25-g SNAP Ultra column with 20-70% of a 3:1 EtOAc/EtOH mixture in heptane with 10% DCM) to give (Rac)-1-(3'-chloro-2,5'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide (26.7 mg, 0.05 mmol, 39.4% yield) as a light-yellow solid. $^1$H NMR (400 MHz, DMSO-$d_6$) δ ppm 14.22 (br. s., 1H), 8.26 (br. s., 1H), 7.86 (br. s., 1H), 7.52-7.70 (m, 4H), 7.34-7.44 (m, 3H), 6.39 (d, J=9.43 Hz, 1H), 4.03-4.15 (m, 2H), 3.82 (s, 3H), 3.25 (br. s., 2H), 2.41-2.49 (m, 1H), 2.14 (d, J=16.07 Hz, 1H). m/z (ESI) 560.0 (M+H)$^+$.

Separation Step: (P)-1-(3'-Chloro-2,5'-Difluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide (Example 38-P) and (M)-1-(3'-Chloro-2,5'-Difluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide (Example 38-M).

Racemic product of Example 38 was subjected to chiral SFC (Whelk O1, 50% methanol) to give Example 38-P (peak 1) and Example 38-M (peak 2) as off-white solids.

Example 39

(Rac)-1-(4'-Chloro-2-Fluoro-5-Methoxy-3'-Methyl-[1,1'-Biphenyl]-4-Yl)-2-Oxo-N-(Thiazol-2-Yl)-1,2,7,8-Tetrahydro-1,6-Naphthyridine-6(5H)-Sulfonamide

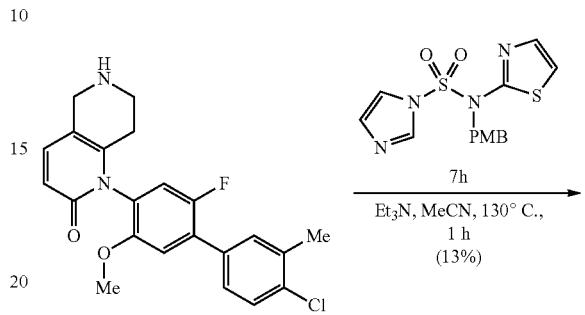

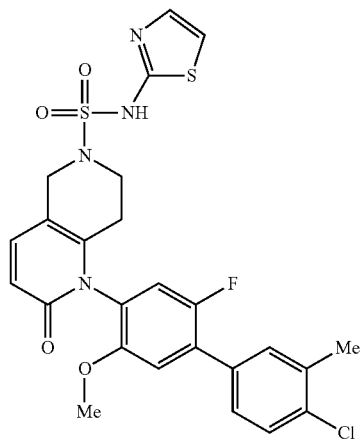

A 5-mL vial was charged with N-(4-methoxybenzyl)-N-(thiazol-2-yl)-1H-imidazole-1-sulfonamide (Preparation 7h, 260 mg, 0.75 mmol), (Rac)-1-(4'-chloro-2-fluoro-5-methoxy-3'-methyl-[1,1'-biphenyl]-4-yl)-5,6,7,8-tetrahydro-1,6-naphthyridin-2(1H)-one (From Example 1, step 2, 100 mg, 0.25 mmol), acetonitrile (1.25 ml), and triethylamine (245 μL, 1.76 mmol). The vial was sealed with a PTFE lined cap and irradiated at 130° C. for one hour. After 1 h, the resultant brown reaction mixture was cooled to ambient temperature and diluted to 3 mL total volume with DMSO and filtered through a 0.45 micron filter. The filtrate was purified by reverse phase HPLC (XBridge Prep Shield RP18 19×100 mm Mobile phase: 0.1% NH$_4$OH in water/acetonitrile Flow rate: 40 ml/min Inj: 2500 uL Gradient: 10 min 10-60%). The fractions containing product were frozen and lyophilized to afford (Rac)-1-(4'-chloro-2-fluoro-5-methoxy-3'-methyl-[1,1'-biphenyl]-4-yl)-2-oxo-N-(thiazol-2-yl)-1,2,7,8-tetrahydro-1,6-naphthyridine-6(5H)-sulfonamide (18.3 mg, 0.03 mmol, 13.0% yield) as an off-white solid. $^1$H NMR (400 MHz, DMSO-$d_6$) δ=6.68 (s, 1H), 6.60 (d, J=8.3 Hz, 1H), 6.53 (d, J=8.4 Hz, 1H), 6.41 (d, J=9.6 Hz, 1H), 6.37 (d, J=10.2 Hz, 1H), 6.32 (d, J=7.0 Hz, 1H), 6.24 (d, J=4.6 Hz, 1H), 5.83 (d, J=4.6 Hz, 1H), 5.42 (d, J=9.2 Hz, 1H), 3.10-3.01 (m, 4H), 2.84 (s, 3H), 2.32-2.22 (m, 4H). m/z (ESI) 561.0 (M+H)$^+$.

Example 40

(Rac)-1-(4'-Chloro-2-Fluoro-5-Methoxy-3'-Methyl-[1,1'-Biphenyl]-4-Yl)-N-(6-Methylpyrimidin-4-Yl)-2-Oxo-1,2,7,8-Tetrahydro-1,6-Naphthyridine-6(5H)-Sulfonamide

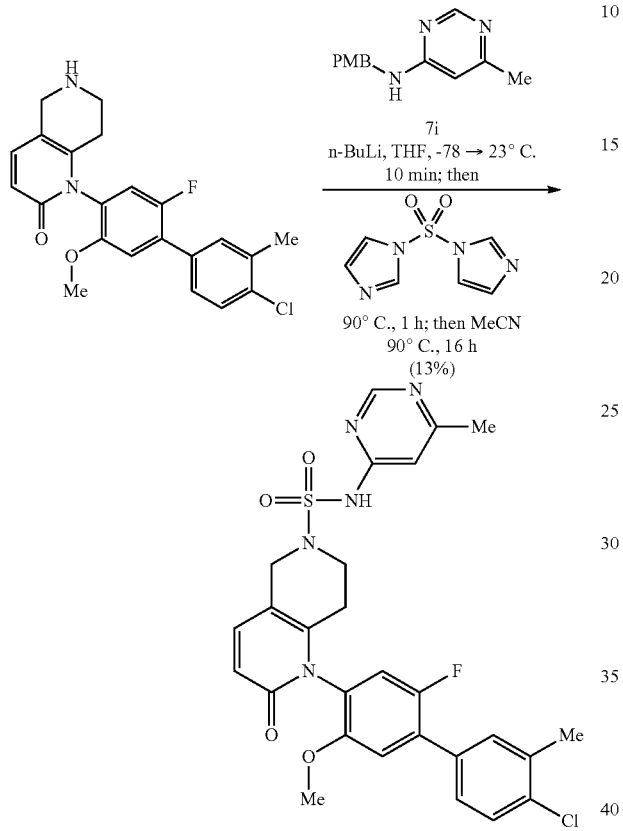

A 5-mL vial was charged with 6-methylpyrimidin-4-amine (Preparation 7i, 60 mg, 0.55 mmol) then purged with nitrogen. THF (2.0 mL) was introduced and the reaction mixture was cooled to −78° C. in a dry ice-acetone bath. A solution of n-butyllithium (2.7 M in heptane, 0.19 mL, 0.50 mmol) was added dropwise via syringe to the stirred cooled reaction mixture. Following addition, the cold bath was removed and the resultant mixture was allowed to warm to ambient temperature. After 10 min, 1,1'-sulfonyldiimidazole (99.0 mg, 0.50 mmol) was added to the stirred reaction mixture in a single portion. The vial was sealed with a PTFE lined cap and the reaction mixture was warmed to 90° C. After 1 h, the reaction mixture was allowed to cool to ambient temperature before (Rac)-1-(4'-chloro-2-fluoro-5-methoxy-3'-methyl-[1,1'-biphenyl]-4-yl)-5,6,7,8-tetrahydro-1,6-naphthyridin-2(1H)-one (See Example 1, step 2, 100 mg, 0.25 mmol) and acetonitrile (1.25 ml) were introduced. The resultant stirred reaction mixture was resealed and warmed to 90° C. After 16 h, the reaction mixture was allowed to cool to ambient temperature and diluted with an aqueous solution of HCl (1.0 M, 25 mL) and EtOAc (25 mL). The layers were separated and the organic layer was dried over anhydrous magnesium sulfate, filtered, and concentrated under reduced pressure and purified by flash column chromatography (25-g silica gel Biotage column, eluent: gradient, 10 to 100% 3:1 EtOAc/EtOH in heptane with DCM as a 10% additive) to afford (Rac)-1-(4'-chloro-2-fluoro-5-methoxy-3'-methyl-[1,1'-biphenyl]-4-yl)-N-(6-methylpyrimidin-4-yl)-2-oxo-1,2,7,8-tetrahydro-1,6-naphthyridine-6(5H)-sulfonamide (18.0 mg, 0.03 mmol, 12.6% yield) as an off-white solid. $^1$H NMR (400 MHz, DMSO-$d_6$) δ=8.47 (br. s., 1H), 7.64 (s, 1H), 7.59-7.18 (m, 2H), 7.41-7.21 (m, 4H), 6.82 (s, 1H), 6.38 (d, J=9.5 Hz, 1H), 4.11 (br. s., 2H), 3.77 (s, 3H), 3.35 (br. s., 2H), 2.42 (s, 3H), 2.39-2.30 (m, 4H), 2.18-2.04 (m, 1H). m/z (ESI) 570.0 (M+H)$^+$.

Example 41

(P)-1-(2,3'-Difluoro-5-Methoxy-5'-(Trifluoromethyl)-[1,1'-Biphenyl]-4-Yl)-2-Oxo-N-(Pyridazin-3-Yl)-1,2,7,8-Tetrahydro-1,6-Naphthyridine-6(5H)-Sulfonamide

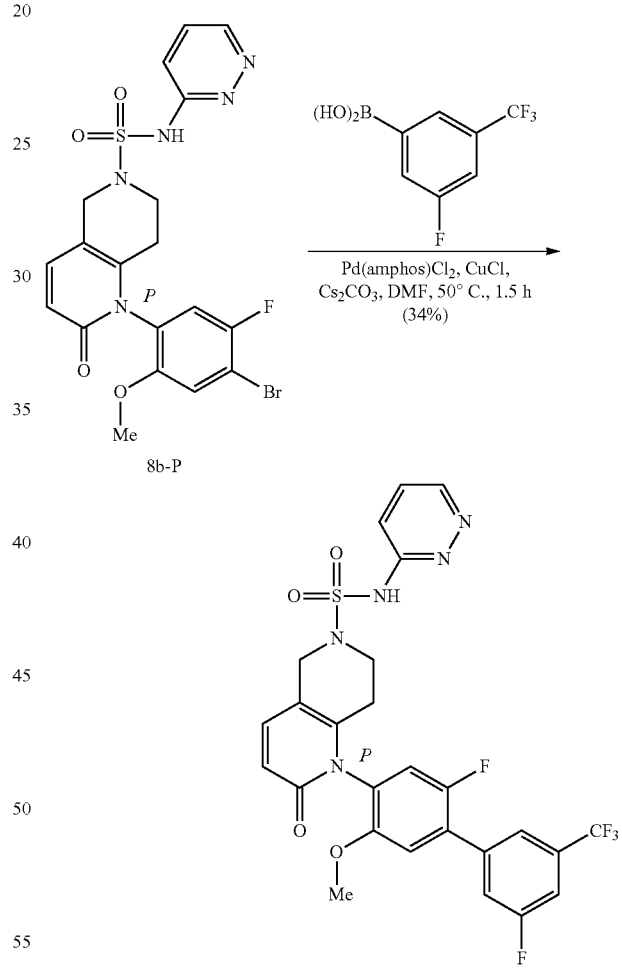

A 5-mL vial was charged with (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P, 150 mg, 0.29 mmol), (3-fluoro-5-(trifluoromethyl)phenyl)boronic acid (Combi Blocks, 183 mg, 0.88 mmol), cesium carbonate (383 mg 1.18 mmol), copper chloride (87.0 mg, 0.88 mmol), 1,1-bis[(di-t-butyl-p-methylaminophenyl]palladium(II) chloride (62.4 mg, 0.09 mmol), then purged with nitrogen. DMF (3.0 mL) was introduced, the vial was sealed with a PTFE line cap, and the resultant orange reaction mixture was warmed to 50° C. After 1.5 h, the reaction mixture was allowed to cool to ambient temperature and diluted with an aqueous HCl solution (1.0 M, 10 mL) and EtOAc (5 mL). The mixture was filtered through a pad of Celite® then rinsed with EtOAc (2×10 mL). The layers were separated and the aqueous layer was extracted with EtOAc (2×5 mL). The combined organic layers were dried over anhydrous magnesium sulfate, filtered, concentrated under reduced pressure and purified by reverse phase HPLC in 2 separate injections (XBridge Prep Shield RP18 19×100 mm Mobile phase: 0.1% formic acid in water/acetonitrile Flow rate: 40 ml/min Inj: 3000 uL Gradient: 12 min 25-70%). The fractions containing product were frozen and lyophilized to afford (P)-1-(2,3'-difluoro-5-methoxy-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide (60.0 mg, 0.10 mmol, 34.4% yield) as an off-white solid. $^1$H NMR (400 MHz, DMSO-$d_6$) δ ppm 2.14 (d, J=17.21 Hz, 1H) 2.44 (d, J=11.30 Hz, 1H) 3.24 (br. s., 2H) 3.79-3.87 (m, 3H) 4.07 (br. s., 2H) 6.39 (d, J=9.23 Hz, 1H) 7.36-7.47 (m, 3H) 7.67 (dd, J=9.48, 4.09 Hz, 1H) 7.79-7.96 (m, 4H) 8.26 (br. s., 1H) 14.23 (br. s., 1H). m/z (ESI) 594.0 (M+H)$^+$.

Example 42

(P)-1-(3'-CYCLOPROPYL-2-Fluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

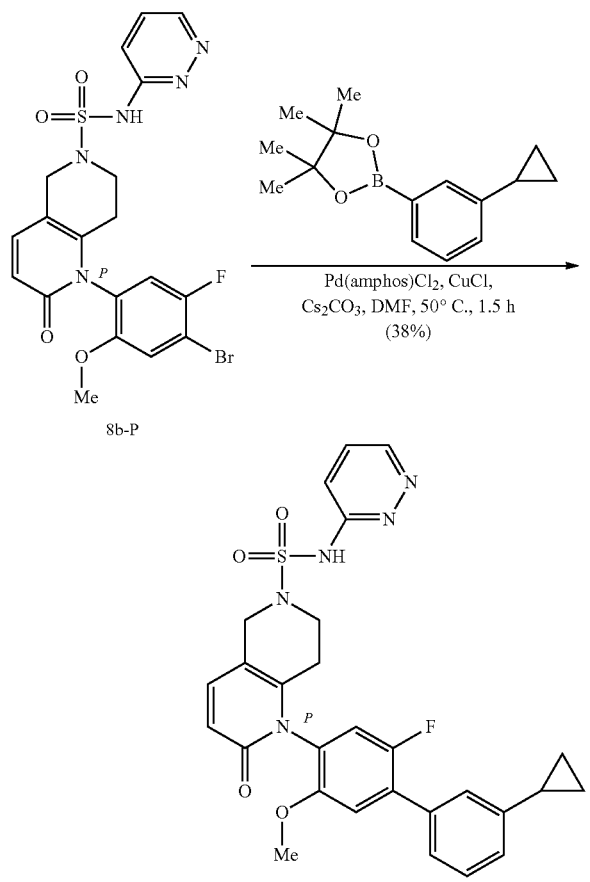

This compound was prepared analogously to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 2-(3-cyclopropylphenyl)-4,4,5,5-tetramethyl-1,3,2-dioxaborolane (purchased from Small Molecules Inc.) as the boronic ester. $^1$H NMR (400 MHz, DMSO-$d_6$) δ ppm 0.66-0.83 (m, 2H) 0.92-1.06 (m, 2H) 1.93-2.08 (m, 1H) 2.08-2.23 (m, 1H) 2.39-2.49 (m, 1H) 3.25 (br. s., 2H) 3.80 (s, 3H) 3.98-4.16 (m, 2H) 6.39 (d, J=9.33 Hz, 1H) 7.09-7.18 (m, 1H) 7.26 (d, J=7.05 Hz, 1H) 7.30-7.34 (m, 2H) 7.35-7.43 (m, 3H) 7.66 (dd, J=9.59, 4.09 Hz, 1H). m/z (ESI) 548.2 (M+H)$^+$.

Example 43

(P)-1-(2'-Chloro-2-Fluoro-5-Methoxy-5'-Methyl-[1,1'-Biphenyl]-4-Yl)-2-Oxo-N-(Pyridazin-3-Yl)-1,2,7,8-Tetrahydro-1,6-Naphthyridine-6(5H)-Sulfonamide

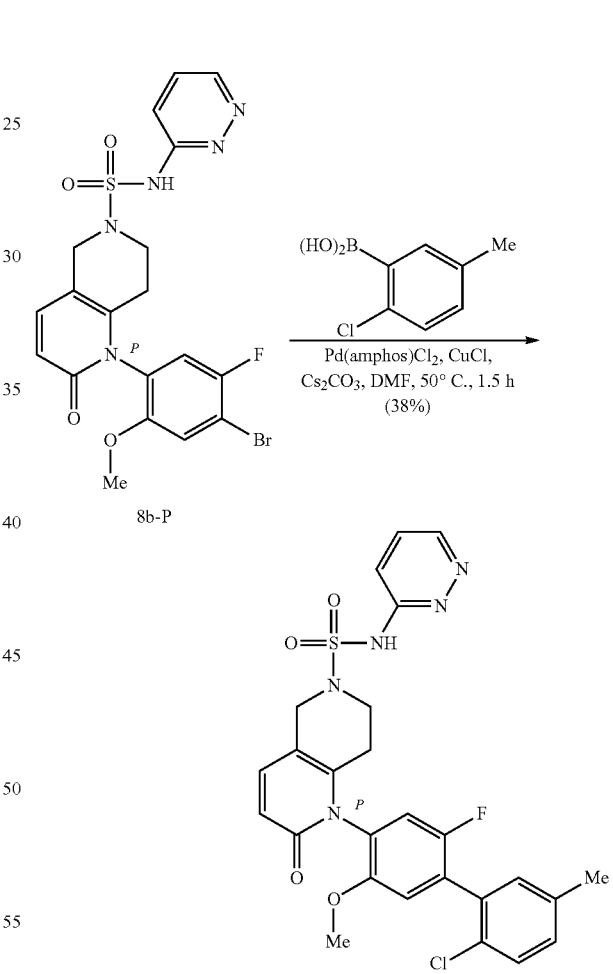

This compound was prepared analogously to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (2-chloro-5-methylphenyl)boronic acid (purchased from Combi Blocks) as the boronic acid. $^1$H NMR (400 MHz, DMSO-$d_6$) δ ppm 2.08-2.20 (m, 1H) 2.37 (s, 3H) 2.40-2.48 (m, 1H) 3.26 (br. s., 2H) 3.70-3.79 (m, 3H) 3.99-4.17 (m, 2H) 6.39 (d, J=9.33 Hz, 1H) 7.18 (d, J=6.53 Hz, 1H)

7.29-7.35 (m, 3H) 7.38 (d, J=9.43 Hz, 1H) 7.50 (d, J=8.09 Hz, 1H) 7.66 (dd, J=9.59, 4.09 Hz, 1H). m/z (ESI) 556.2 (M+H)+.

Example 44

(P)-1-(3'-Chloro-2-Fluoro-5-Methoxy-4'-Methyl-[1,1'-Biphenyl]-4-Yl)-2-Oxo-N-(Pyridazin-3-Yl)-1,2,7,8-Tetrahydro-1,6-Naphthyridine-6(5H)-Sulfonamide

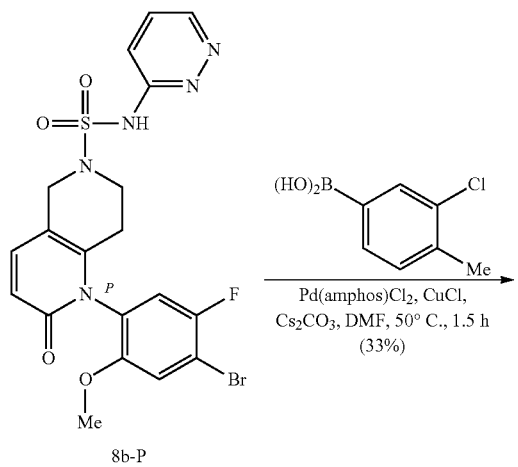

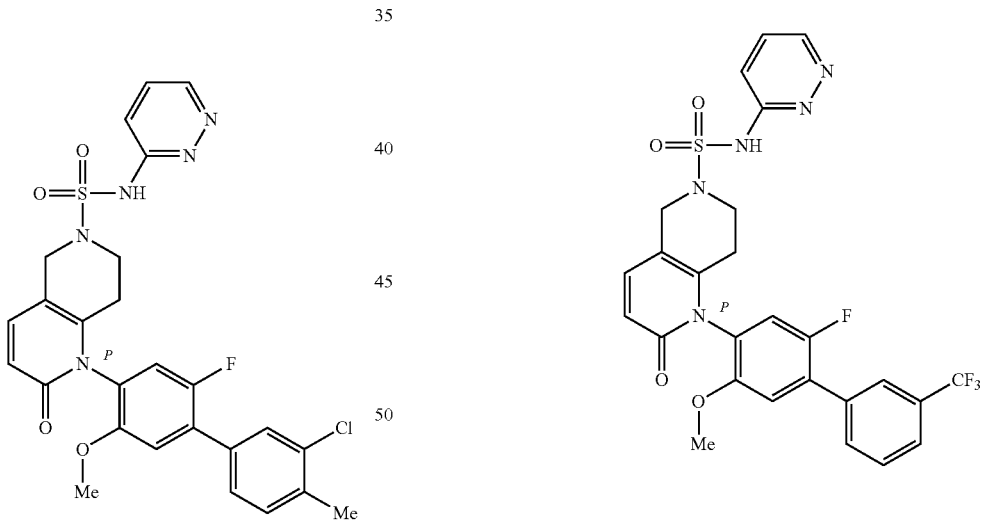

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-chloro-4-methylphenyl)boronic acid (purchased from Sigma Aldrich) as the boronic acid. $^1$H NMR (400 MHz, DMSO-$d_6$) δ ppm 14.22 (d, J=9.54 Hz, 1H) 8.29 (br. s., 1H) 7.84 (br. s., 1H) 7.71 (s, 1H) 7.67 (dd, J=9.59, 4.09 Hz, 1H) 7.48-7.58 (m, 2H) 7.28-7.41 (m, 3H) 6.39 (d, J=9.33 Hz, 1H) 3.93-4.20 (m, 2H) 3.81 (s, 3H) 3.25 (br. s., 2H) 2.38-2.49 (m, 4H) 2.08-2.20 (m, 1H). m/z (ESI) 556.2 (M+H)+.

Example 45

(P)-1-(2-Fluoro-5-Methoxy-3'-(Trifluoromethyl)-[1,1'-Biphenyl]-4-Yl)-2-Oxo-N-(Pyridazin-3-Yl)-1,2,7,8-Tetrahydro-1,6-Naphthyridine-6(5H)-Sulfonamide

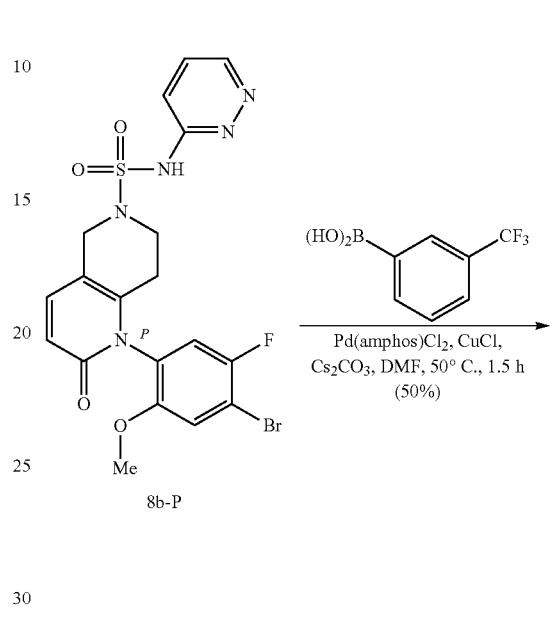

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-(trifluoromethyl)phenyl)boronic acid (purchased from Chem-Implex) as the boronic acid. $^1$H NMR (400 MHz, DMSO-$d_6$) δ ppm 14.22 (br. s., 1H) 8.27 (br. s., 1H) 7.97 (s, 2H) 7.73-7.92 (m, 3H) 7.67 (dd, J=9.64, 4.15 Hz, 1H) 7.34-7.48 (m, 3H) 6.39 (d, J=9.43 Hz, 1H) 4.07 (m, J=8.50 Hz, 2H) 3.82 (s, 3H) 3.18-3.30 (m, 2H) 2.41-2.49 (m, 1H) 2.06-2.24 (m, 1H). m/z (ESI) 576.2 (M+H)+.

Example 46

(P)-2-Oxo-N-(Pyridazin-3-Yl)-1-(2,3',4',5'-Tetra-fluoro-5-Methoxy-[1,1'-Biphenyl]-4-Yl)-1,2,7,8-Tetrahydro-1,6-Naphthyridine-6(5H)-Sulfonamide

Example 47

(P)-1-(4'-Chloro-2,3'-Difluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

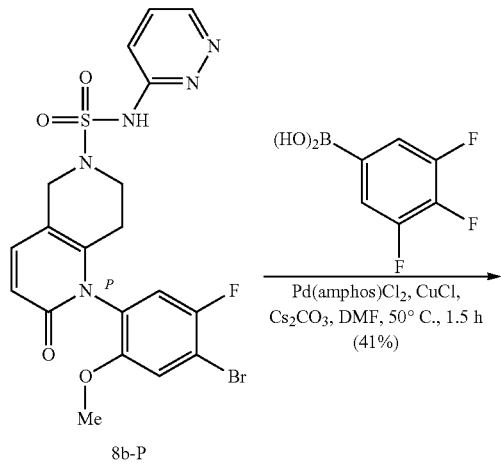

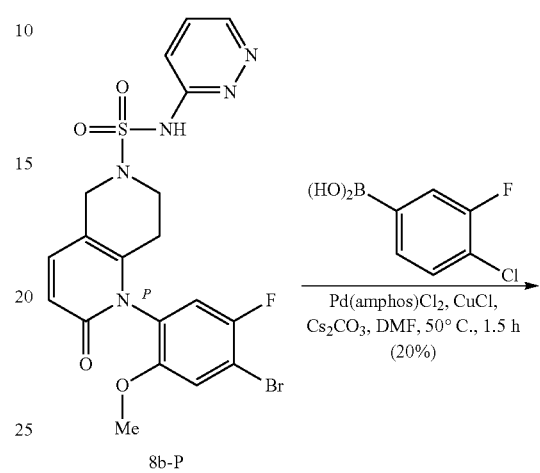

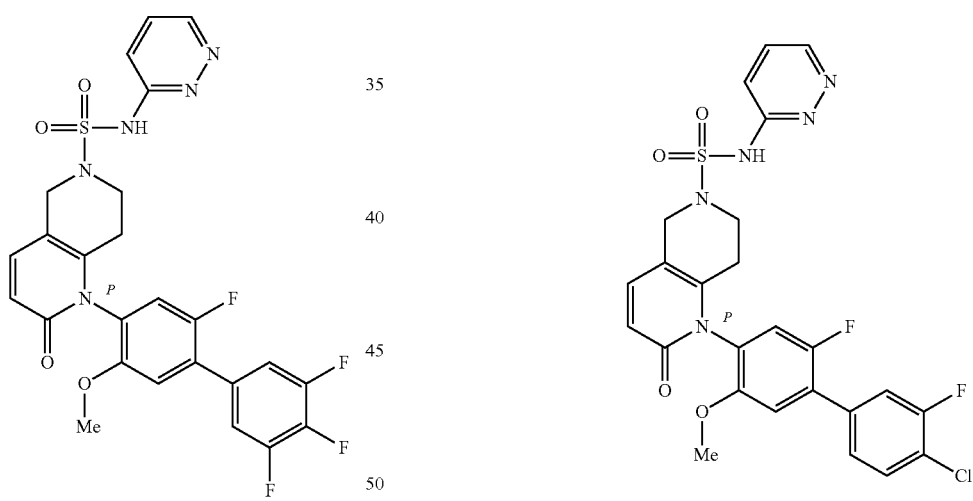

This compound was prepared analogous to the procedure of Example 41 from (P)-1-(4-bromo-5-fluoro-2-methoxy-phenyl)-2-oxo-N-(pyridazin-3-yl)-1,2,7,8-tetrahydro-1,6-naphthyridine-6(5H)-sulfonamide (Preparation 8b-P) and (3,4,5-trifluorophenyl)boronic acid (purchased from Matrix Scientific) as the boronic acid. $^1$H NMR (400 MHz, DMSO-$d_6$) δ ppm 13.93-14.42 (m, 1H) 8.30 (br. s., 1H) 7.83 (br. s., 1H) 7.60-7.79 (m, 3H) 7.30-7.48 (m, 3H) 6.39 (d, J=9.33 Hz, 1H) 3.94-4.24 (m, 2H) 3.82 (s, 3H) 3.17-3.31 (m, 2H) 2.36-2.49 (m, 1H) 2.04-2.24 (m, 1H). m/z (ESI) 562.1 (M+H)$^+$.

This compound was prepared analogous to the procedure of Example 41 from (P)-1-(4-bromo-5-fluoro-2-methoxy-phenyl)-2-oxo-N-(pyridazin-3-yl)-1,2,7,8-tetrahydro-1,6-naphthyridine-6(5H)-sulfonamide (Preparation 8b-P) and (4-chloro-3-fluorophenyl)boronic acid (purchased from *Aurum*) as the boronic acid. $^1$H NMR (400 MHz, DMSO-$d_6$) δ ppm 14.23 (br. s., 1H) 8.27 (br. s., 1H) 7.73-7.90 (m, 3H) 7.66 (dd, J=9.59, 4.09 Hz, 1H) 7.55 (d, J=8.29 Hz, 1H) 7.33-7.43 (m, 3H) 6.39 (d, J=9.43 Hz, 1H) 3.95-4.20 (m, 2H) 3.81 (s, 3H) 3.17-3.30 (m, 2H) 2.38-2.49 (m, 1H) 2.14 (d, J=17.21 Hz, 1H). m/z (ESI) 560.0 (M+H)$^+$.

Example 48

(P)-1-(3'-Chloro-2,4'-Difluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

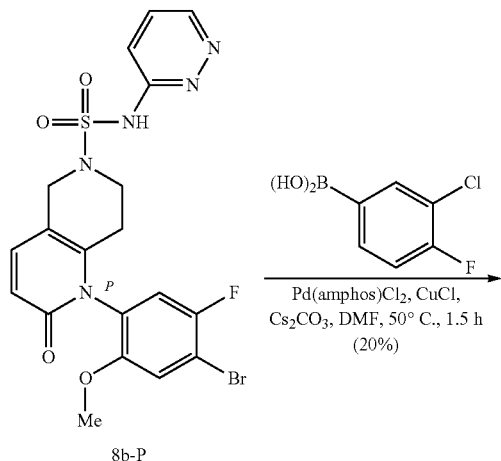

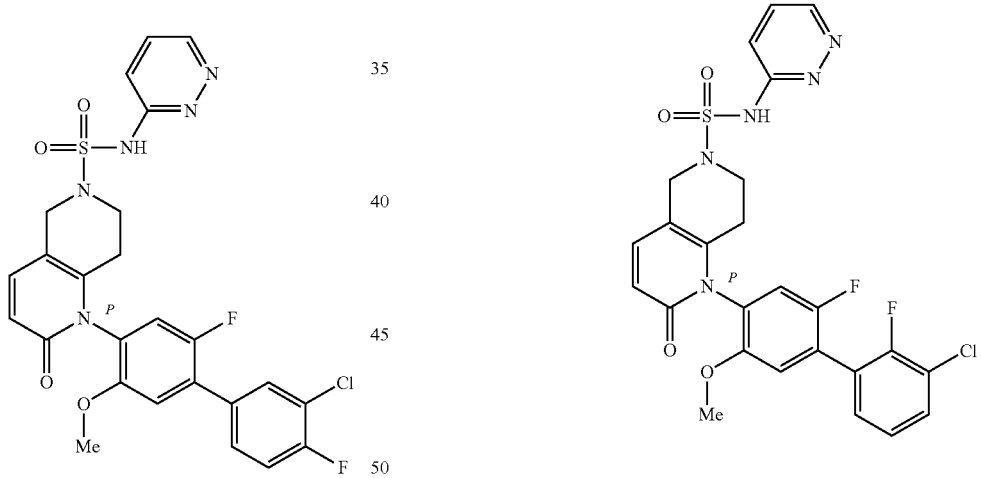

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-chloro-4-fluorophenyl)boronic acid (purchased from Sigma Aldrich) as the boronic acid. $^1$H NMR (400 MHz, DMSO-$d_6$) δ ppm 14.23 (br. s., 1H) 8.28 (br. s., 1H) 7.81-7.95 (m, 2H) 7.64-7.72 (m, 2H) 7.55-7.63 (m, 1H) 7.33-7.40 (m, 3H) 6.39 (d, J=9.43 Hz, 1H) 4.07 (d, J=8.71 Hz, 2H) 3.81 (s, 3H) 3.25 (br. s., 2H) 2.39-2.49 (m, 1H) 2.06-2.22 (m, 1H). m/z (ESI) 560.2 (M+H)$^+$.

Example 49

(P)-1-(3'-Chloro-2,2'-Difluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

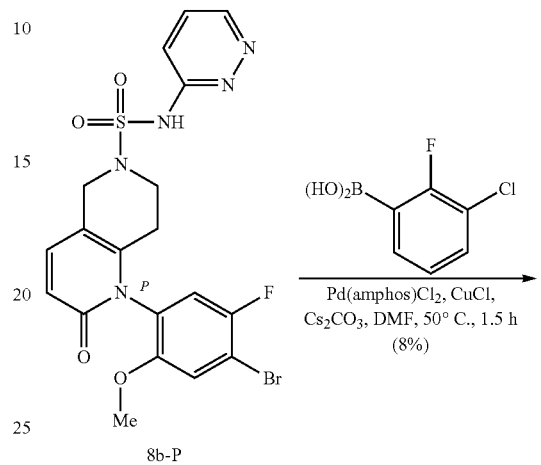

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-chloro-2-fluorophenyl)boronic acid (purchased from Sigma Aldrich) as the boronic acid. $^1$H NMR (400 MHz, DMSO-$d_6$) δ ppm 14.22 (s, 1H) 8.29 (br. s., 1H) 7.83 (br. s., 1H) 7.74 (td, J=7.57, 1.66 Hz, 1H) 7.65 (dd, J=9.28, 4.20 Hz, 1H) 7.54-7.61 (m, 1H) 7.37-7.45 (m, 3H) 7.32 (d, J=6.53 Hz, 1H) 6.39 (d, J=9.33 Hz, 1H) 3.97-4.17 (m, 2H) 3.70-3.85 (m, 3H) 3.27 (d, J=13.58 Hz, 2H) 2.40-2.48 (m, 1H) 2.09-2.22 (m, 1H). m/z (ESI) 560.2 (M+H)$^+$.

Example 50

(P)-1-(4-(5-Chloro-6-Methoxypyridin-3-Yl)-5-Fluoro-2-Methoxyphenyl)-2-Oxo-N-(Pyridazin-3-Yl)-1,2,7,8-Tetrahydro-1,6-Naphthyridine-6(5H)-Sulfonamide

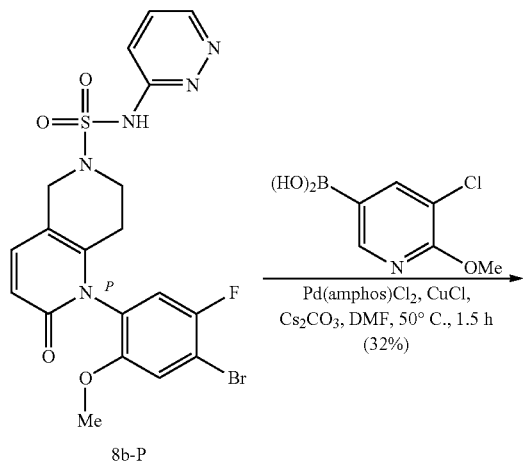

Example 51

(P)-1-(2-Chloro-3',4'-Difluoro-5-Methoxy-[1,1'-Biphenyl]-4-Yl)-N-(Isoxazol-3-Yl)-2-Oxo-1,2,7,8-Tetrahydro-1,6-Naphthyridine-6(5H)-Sulfonamide

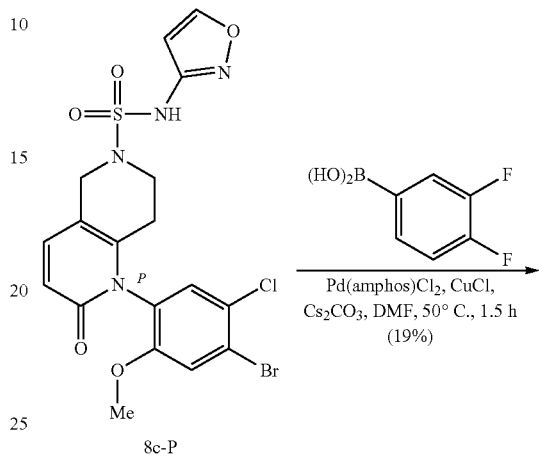

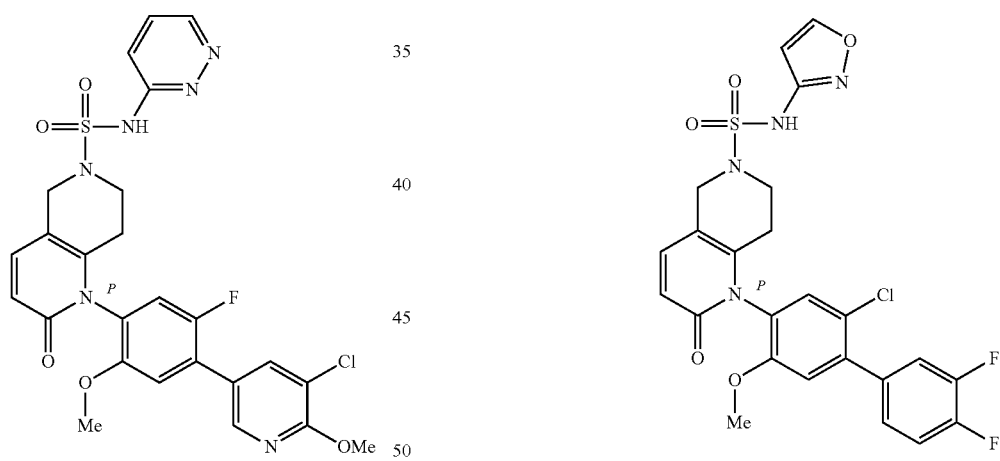

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 3-chloro-2-methoxypyridine-5-boronic acid (purchased from Combi-Blocks Inc.) as the boronic acid. $^1$H NMR (400 MHz, DMSO-$d_6$) δ ppm 14.23 (br. s., 1H) 8.28 (br. s., 1H) 7.81-7.95 (m, 2H) 7.64-7.72 (m, 2H) 7.55-7.63 (m, 1H) 7.33-7.40 (m, 3H) 6.39 (d, J=9.43 Hz, 1H) 4.07 (d, J=8.71 Hz, 2H) 3.81 (s, 3H) 3.25 (br. s., 2H) 2.39-2.49 (m, 1H) 2.06-2.22 (m, 1H). m/z (ESI) 573.2 (M+H)$^+$.

This compound was prepared analogous to the procedure of Example 41 from (P)-1-(4-bromo-5-chloro-2-methoxyphenyl)-N-(isoxazol-3-yl)-2-oxo-1,2,7,8-tetrahydro-1,6-naphthyridine-6(5H)-sulfonamide (Preparation 8c-P) and (3,4-difluorophenyl)boronic acid (purchased from Sigma Aldrich) as the boronic acid. $^1$H NMR (400 MHz, DMSO-$d_6$) δ=11.18 (s, 1H), 8.74 (d, J=1.8 Hz, 1H), 7.72-7.54 (m, 2H), 7.46 (s, 1H), 7.41 (ddd, J=1.8, 4.3, 8.2 Hz, 1H), 7.34 (d, J=9.5 Hz, 1H), 7.27 (s, 1H), 6.42-6.34 (m, 2H), 4.32-4.14 (m, 2H), 3.78 (s, 3H), 3.50-3.37 (m, 2H), 2.48-2.37 (m, 1H), 2.15-2.01 (m, 1H). m/z (ESI) 549.0 (M+H)$^+$.

Example 52

(P)-1-(2,4'-Dichloro-3',5-Dimethoxy-[1,1'-Biphenyl]-4-Yl)-N-(Isoxazol-3-Yl)-2-Oxo-1,2,7,8-Tetrahydro-1,6-Naphthyridine-6(5H)-Sulfonamide

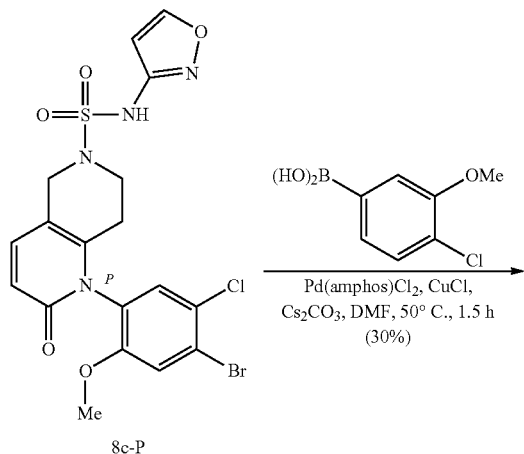

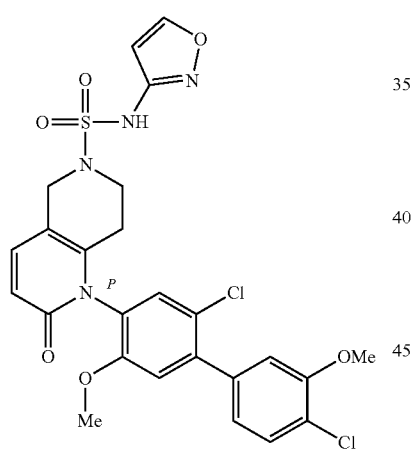

This compound was prepared analogous to the procedure of Example 41 from (P)-1-(4-bromo-5-chloro-2-methoxyphenyl)-N-(isoxazol-3-yl)-2-oxo-1,2,7,8-tetrahydro-1,6-naphthyridine-6(5H)-sulfonamide (Preparation 8c-P) and (4-chloro-3-methoxyphenyl)boronic acid (purchased from Acros Organics) as the boronic acid. $^1$H NMR (400 MHz, DMSO-d$_6$) δ=11.18 (s, 1H), 8.74 (d, J=1.8 Hz, 1H), 7.56 (d, J=8.1 Hz, 1H), 7.44 (s, 1H), 7.34 (d, J=9.4 Hz, 1H), 7.29-7.24 (m, 2H), 7.11 (dd, J=1.9, 8.1 Hz, 1H), 6.42-6.34 (m, 2H), 4.31-4.15 (m, 2H), 3.94 (s, 3H), 3.78 (s, 3H), 3.48-3.36 (m, 2H), 2.49-2.38 (m, 1H), 2.16-2.00 (m, 1H). m/z (ESI) 578.0 (M+H)$^+$.

Example 53

(P)-1-(2,3'-Dichloro-5'-Fluoro-5-Methoxy-[1,1'-Biphenyl]-4-Yl)-N-(Isoxazol-3-Yl)-2-Oxo-1,2,7,8-Tetrahydro-1,6-Naphthyridine-6(5H)-Sulfonamide

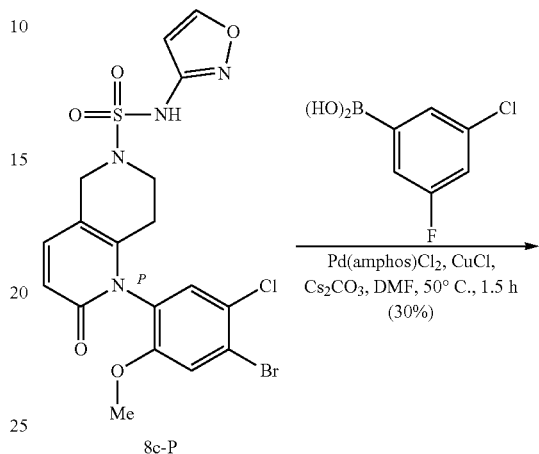

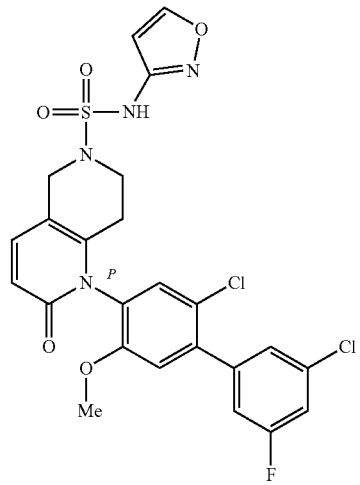

This compound was prepared analogous to the procedure of Example 41 from (P)-1-(4-bromo-5-chloro-2-methoxyphenyl)-N-(isoxazol-3-yl)-2-oxo-1,2,7,8-tetrahydro-1,6-naphthyridine-6(5H)-sulfonamide (Preparation 8c-P) and (3-chloro-5-fluorophenyl)boronic acid (purchased from Sigma Aldrich) as the boronic acid. $^1$H NMR (400 MHz, DMSO-d$_6$) δ=11.18 (s, 1H), 8.75 (d, J=1.9 Hz, 1H), 7.58 (td, J=2.2, 8.8 Hz, 1H), 7.49 (t, J=1.5 Hz, 1H), 7.47 (s, 1H), 7.46-7.41 (m, 1H), 7.34 (d, J=9.4 Hz, 1H), 7.31 (s, 1H), 6.43-6.28 (m, 2H), 4.32-4.14 (m, 2H), 3.78 (s, 3H), 3.50-3.35 (m, 2H), 2.48-2.35 (m, 1H), 2.14-1.99 (m, 1H). m/z (ESI) 567.0 (M+H)$^+$.

Example 54

(P)-1-(2-Chloro-5-Methoxy-3'-(Trifluoromethyl)-[1,1'-Biphenyl]-4-Yl)-N-(Isoxazol-3-Yl)-2-Oxo-1,2,7,8-Tetrahydro-1,6-Naphthyridine-6(5H)-Sulfonamide

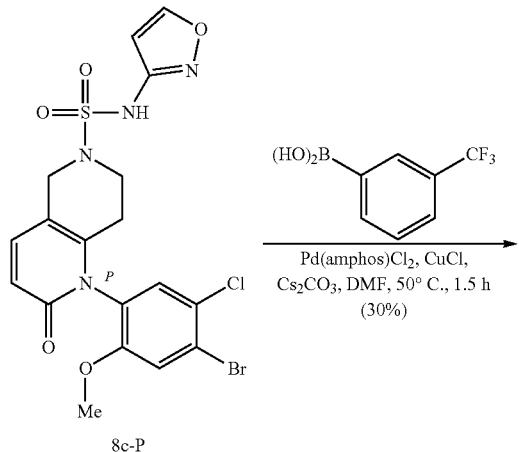

This compound was prepared analogous to the procedure of Example 41 from (P)-1-(4-bromo-5-chloro-2-methoxyphenyl)-N-(isoxazol-3-yl)-2-oxo-1,2,7,8-tetrahydro-1,6-naphthyridine-6(5H)-sulfonamide (Preparation 8c-P) and (3-(trifluoromethyl)phenyl)boronic acid (purchased from Acros) as the boronic acid. $^1$H NMR (400 MHz, DMSO-$d_6$) δ=11.18 (s, 1H), 8.75 (d, J=1.8 Hz, 1H), 7.90-7.72 (m, 4H), 7.48 (s, 1H), 7.37-7.28 (m, 2H), 6.42-6.35 (m, 2H), 4.32-4.15 (m, 2H), 3.79 (s, 3H), 3.49-3.35 (m, 2H), 2.48-2.37 (m, 1H), 2.16-2.01 (m, 1H). m/z (ESI) 581.0 (M+H)$^+$.

Example 55

(Rac)-; (P)-; and (M)-1-(3'-Chloro-4-Methoxy-4'-Methyl-[1,1'-Biphenyl]-3-Yl)-2-Oxo-N-(Pyridazin-3-Yl)-1,2,7,8-Tetrahydro-1,6-Naphthyridine-6(5H)-Sulfonamide

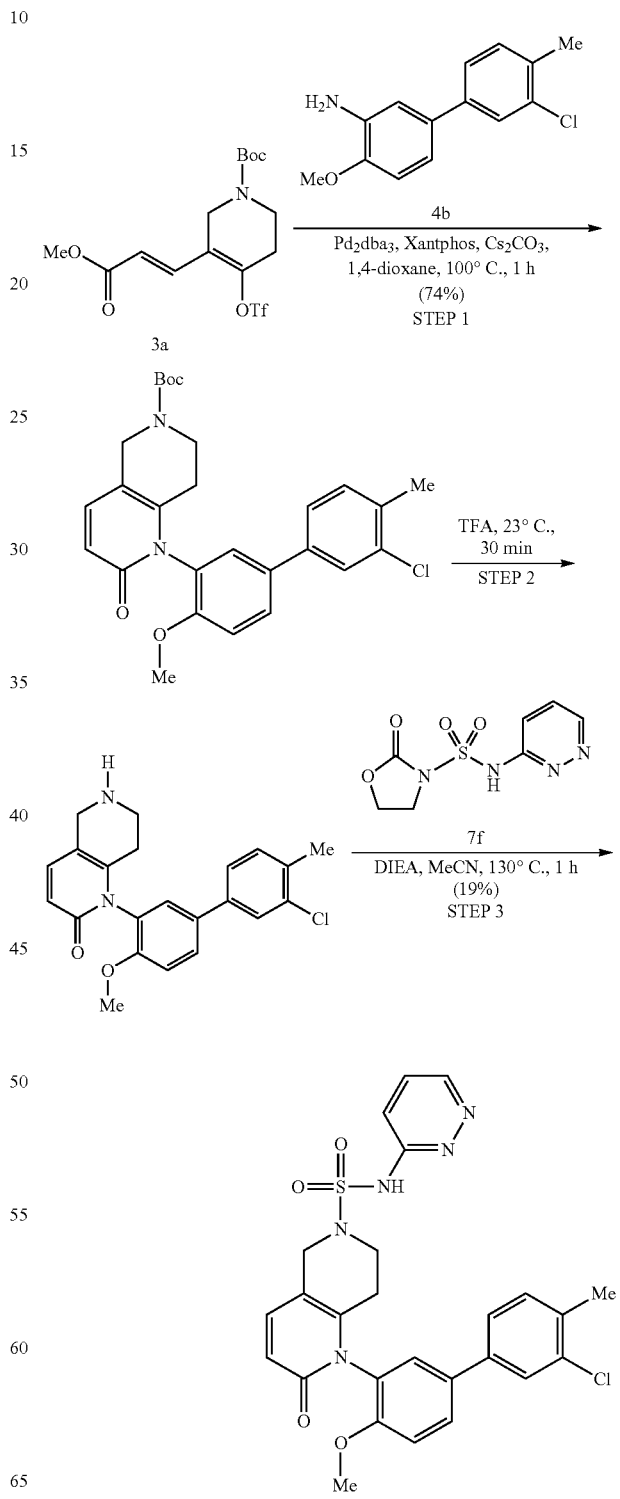

Step 1: (Rac)-tert-Butyl 1-(3'-Chloro-4-Methoxy-4'-Methyl-[1,1'-Biphenyl]-3-Yl)-2-Oxo-1,2,7,8-Tetrahydro-1,6-Naphthyridine-6(5H)-Carboxylate A 40-mL vial was charged with (E)-tert-butyl 3-(3-methoxy-3-oxoprop-1-en-1-yl)-4-(((trifluoromethyl)sulfonyl)oxy)-5,6-dihydropyridine-1(2H)-carboxylate (Preparation 3a, 1.00 g, 2.41 mmol). (9,9-dimethyl-9H-xanthene-4,5-diyl)bis(diphenylphosphine) (174 mg, 0.30 mmol), 3'-chloro-4-methoxy-4'-methyl-[1,1'-biphenyl]-3-amine (Preparation 4b, 716 mg, 2.89 mmol) and cesium carbonate (2.35 g, 7.22 mmol), 1,4-dioxane (12.0 mL) then sparged with nitrogen for 10 min. The needle was then removed and the reaction was heated to 100° C. After 1 h, the reaction mixture was allowed to cool to ambient temperature, diluted with EtOAc (15 mL), and filtered through a pad of Celite®. The pad was rinsed with EtOAc (3×15 mL) and the filtrate was concentrated under reduced pressure. The residue was purified by flash column chromatography (100-g Biotage column, eluent: gradient, 0 to 35% (3:1) EtOAc/EtOH in heptane with 10% DCM as an additive) to afford (Rac)-tert-butyl 1-(3'-chloro-4-methoxy-4'-methyl-[1,1'-biphenyl]-3-yl)-2-oxo-1,2,7,8-tetrahydro-1,6-naphthyridine-6(5H)-carboxylate (848 mg, 1.76 mmol, 73.2% yield) as a tan solid. $^1$H NMR (400 MHz, DMSO-$d_6$) δ=7.81 (dd, J=2.4, 8.7 Hz, 1H), 7.77 (d, J=2.0 Hz, 1H), 7.64-7.55 (m, 2H), 7.39 (dd, J=9.0, 12.6 Hz, 2H), 7.28 (d, J=8.8 Hz, 1H), 6.39 (d, J=9.3 Hz, 1H), 4.38-4.23 (m, 2H), 3.78 (s, 3H), 3.59-3.48 (m, 1H), 3.46-3.37 (m, 1H), 2.42-2.28 (m, 4H), 2.11-1.92 (m, 1H). m/z (ESI) 481.2 (M+H)+.

Step 2: (Rac)-1-(3'-Chloro-4-Methoxy-4'-Methyl-[1,1'-Biphenyl]-3-Yl)-5,6,7,8-Tetrahydro-1,6-Naphthyridin-2(1H)-One A 40 mL vial was charged with (Rac)-tert-butyl 1-(3'-chloro-4-methoxy-4'-methyl-[1,1'-biphenyl]-3-yl)-2-oxo-1,2,7,8-tetrahydro-1,6-naphthyridine-6(5H)-carboxylate (848 mg, 1.76 mmol) and trifluroacetic acid (8.80 mL) then stirred at ambient temperature. After 30 min, the reaction mixture was concentrated under reduced pressure, dissolved in DCM (50 mL) and carefully poured into saturated aqueous sodium bicarbonate solution (50 mL). The layers were separated and the aqueous layer extracted with additional DCM (4×25 mL). The combined organic layers were dried over anhydrous magnesium sulfate, filtered, concentrated under reduced pressure to afford (Rac)-1-(3'-chloro-4-methoxy-4'-methyl-[1,1'-biphenyl]-3-yl)-5,6,7,8-tetrahydro-1,6-naphthyridin-2(1H)-one (763 mg, 2.00 mmol, 114% yield) as a tan foam which was used without further purification. $^1$H NMR (400 MHz, DMSO-$d_6$) δ=7.80 (dd, J=2.4, 8.7 Hz, 1H), 7.75 (d, J=1.9 Hz, 1H), 7.58 (dd, J=1.9, 7.9 Hz, 1H), 7.52 (d, J=2.4 Hz, 1H), 7.41 (d, J=8.4 Hz, 1H), 7.26 (dd, J=9.1, 11.1 Hz, 2H), 6.32 (d, J=9.3 Hz, 1H), 4.11 (d, J=4.5 Hz, 2H), 3.78 (s, 3H), 3.70-3.52 (m, 2H), 2.87-2.72 (m, 2H), 2.35 (s, 3H), 2.18 (td, J=5.2, 17.5 Hz, 1H), 1.88 (td, J=5.2, 17.0 Hz, 1H). m/z (ESI) 381.2 (M+H)+.

Step 3: (Rac)-1-(3'-Chloro-4-Methoxy-4'-Methyl-[1,1'-Biphenyl]-3-Yl)-2-Oxo-N-(Pyridazin-3-Yl)-1,2,7,8-Tetrahydro-1,6-Naphthyridine-6(5H)-Sulfonamide A 5-mL vial was charged with (Rac)-1-(3'-chloro-4-methoxy-4'-methyl-[1,1'-biphenyl]-3-yl)-5,6,7,8-tetrahydro-1,6-naphthyridin-2(1H)-one (200 mg, 0.53 mmol), 2-oxo-N-(pyridazin-3-yl)oxazolidine-3-sulfonamide (Preparation 7f, 256 mg, 1.05 mmol), N,N-diisopropylethylamine (639 μL, 3.68 mmol), and MeCN (1.05 mL). The vial was sealed with a PTFE lined cap and heated to 130° C. After 1 h, the resultant brown reaction mixture was cooled to ambient temperature and diluted to 3 mL total volume with DMSO and filtered through a 0.4 micron filter. The filtrate was purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-70%). The fractions containing product were frozen and lyophilized to afford (Rac)-1-(3'-chloro-4-methoxy-4'-methyl-[1,1'-biphenyl]-3-yl)-2-oxo-N-(pyridazin-3-yl)-1,2,7,8-tetrahydro-1,6-naphthyridine-6(5H)-sulfonamide (54.1 mg, 0.10 mmol, 19.2% yield) as an off-white solid. $^1$H NMR (400 MHz, DMSO-$d_6$) δ=11.41 (s, 1H), 8.65 (s, 2H), 7.48-7.29 (m, 6H), 6.39 (d, J=9.4 Hz, 1H), 4.41-4.27 (m, 2H), 3.77 (s, 3H), 3.51 (t, J=5.8 Hz, 2H), 2.45-2.33 (m, 1H), 2.16-2.05 (m, 1H). m/z (ESI) 538.2 (M+H)+.

Separation Step: Racemic product of Example 55 was subjected to chiral SFC (Regis Whelk-O (s,s), 50% methanol) to give Example 55-P (peak 1) and Example 55-M (peak 2) as off-white solids.

Example 56

(Rac)-; (P)-; and (M)-1-(4'-Chloro-4-Methoxy-3'-Methyl-[1,1'-Biphenyl]-3-Yl)-2-Oxo-N-(Pyridazin-3-Yl)-1,2,7,8-Tetrahydro-1,6-Naphthyridine-6(5H)-Sulfonamide

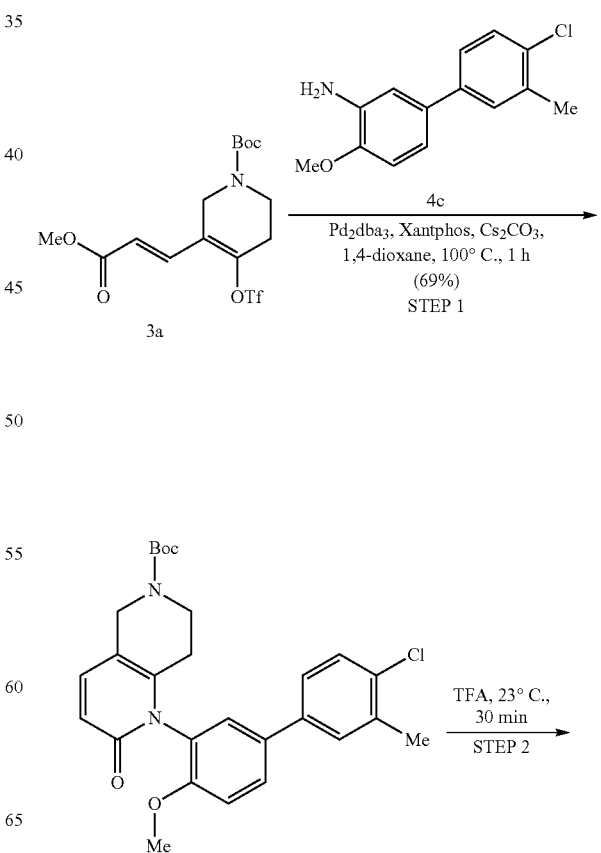

155

-continued

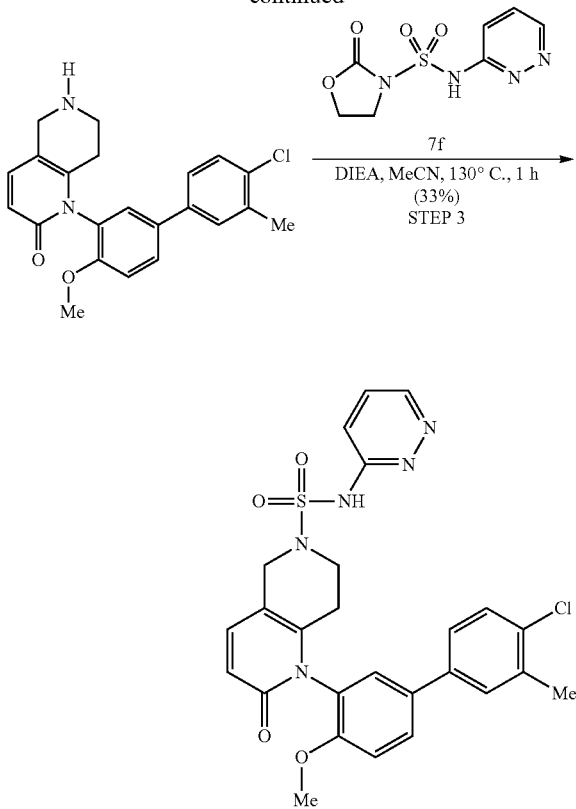

Step 1: (Rac)-tert-Butyl 1-(4'-Chloro-4-Methoxy-3'-Methyl-[1,1'-Biphenyl]-3-Yl)-2-Oxo-1,2,7,8-Tetrahydro-1,6-Naphthyridine-6(5H)-Carboxylate A 40-mL vial was charged with (E)-tert-butyl 3-(3-methoxy-3-oxoprop-1-en-1-yl)-4-(((trifluoromethyl)sulfonyl)oxy)-5,6-dihydropyridine-1(2H)-carboxylate (Preparation 3a, 1.00 g, 2.41 mmol) (9,9-dimethyl-9H-xanthene-4,5-diyl)bis(diphenylphosphine) (174 mg, 0.30 mmol), 4'-chloro-4-methoxy-3'-methyl-[1,1'-biphenyl]-3-amine (Preparation 4c, 716 mg, 2.89 mmol) and cesium carbonate (2.35 g, 7.22 mmol), 1,4-dioxane (12.0 mL) then sparged with nitrogen for 10 min. The needle was then removed and the reaction was heated to 100° C. After 1 h, the reaction mixture was allowed to cool to ambient temperature, diluted with EtOAc (15 mL), and filtered through a pad of Celite®. The pad was rinsed with EtOAc (3×15 mL) and the filtrate was concentrated under reduced pressure. The residue was purified by flash column chromatography (100-g Biotage column, eluent: gradient, 0 to 35% (3:1) EtOAc/EtOH in heptane with 10% DCM as an additive) to afford (Rac)-tert-butyl 1-(4'-chloro-4-methoxy-3'-methyl-[1,1'-biphenyl]-3-yl)-2-oxo-1,2,7,8-tetrahydro-1,6-naphthyridine-6(5H)-carboxylate (799 mg, 1.661 mmol, 69.0% yield) as a tan solid. $^1$H NMR (400 MHz, DMSO-$d_6$) δ=7.80 (dd, J=2.4, 8.7 Hz, 1H), 7.72 (d, J=2.1 Hz, 1H), 7.59-7.52 (m, 2H), 7.45 (d, J=8.4 Hz, 1H), 7.38 (d, J=9.4 Hz, 1H), 7.29 (d, J=8.7 Hz, 1H), 6.40 (d, J=9.4 Hz, 1H), 4.39-4.18 (m, 2H), 3.84-3.69 (m, 3H), 3.61-3.48 (m, 1H), 3.45-3.35 (m, 1H), 2.41-2.25 (m, 4H), 2.09-1.93 (m, 1H), 1.51-1.25 (m, 9H). m/z (ESI) 481.2 (M+H)+.

156

Step 2: (Rac)-1-(4'-Chloro-4-Methoxy-3'-Methyl-[1,1'-Biphenyl]-3-Yl)-5,6,7,8-Tetrahydro-1,6-Naphthyridin-2(1H)-One A 40 mL vial was charged with (Rac)-tert-butyl 1-(4'-chloro-4-methoxy-3'-methyl-[1,1'-biphenyl]-3-yl)-2-oxo-1,2,7,8-tetrahydro-1,6-naphthyridine-6(5H)-carboxylate (799 mg, 1.66 mmol) and trifluroacetic acid (8.31 mL) then stirred at ambient temperature. After 30 min, the reaction mixture was concentrated under reduced pressure, dissolved in DCM (50 mL) and carefully poured into saturated aqueous sodium bicarbonate solution (50 mL). The layers were separated and the aqueous layer extracted with additional DCM (4×25 mL). The combined organic layers were dried over anhydrous magnesium sulfate, filtered, concentrated under reduced pressure to afford (Rac)-1-(4'-chloro-4-methoxy-3'-methyl-[1,1'-biphenyl]-3-yl)-5,6,7,8-tetrahydro-1,6-naphthyridin-2(1H)-one (687 mg, 1.804 mmol, 109% yield) as a tan foam which was used without further purification. $^1$H NMR (400 MHz, DMSO-$d_6$) δ=7.80 (dd, J=2.4, 8.7 Hz, 1H), 7.71 (d, J=2.1 Hz, 1H), 7.57-7.51 (m, 1H), 7.50 (d, J=2.4 Hz, 1H), 7.48-7.43 (m, 1H), 7.29 (dd, J=4.8, 9.0 Hz, 2H), 6.36 (d, J=9.3 Hz, 1H), 3.83-3.63 (m, 5H), 2.90 (t, J=5.8 Hz, 2H), 2.39 (s, 3H), 2.31-2.17 (m, 1H), 1.97 (td, J=5.6, 17.4 Hz, 1H). m/z (ESI) 381.2 (M+H)+.

Step 3: (Rac)-1-(4'-Chloro-4-Methoxy-3'-Methyl-[1,1'-Biphenyl]-3-Yl)-2-Oxo-N-(Pyridazin-3-Yl)-1,2,7,8-Tetrahydro-1,6-Naphthyridine-6(5H)-Sulfonamide A 5-mL vial was charged with (Rac)-1-(4'-chloro-4-methoxy-3'-methyl-[1,1'-biphenyl]-3-yl)-5,6,7,8-tetrahydro-1,6-naphthyridin-2(1H)-one (200 mg, 0.53 mmol), 2-oxo-N-(pyridazin-3-yl)oxazolidine-3-sulfonamide (Preparation 7f, 256 mg, 1.05 mmol), N,N-diisopropylethylamine (639 μL, 3.68 mmol), and MeCN (1.05 mL). The vial was sealed with a PTFE lined cap and heated to 130° C. After 1 h, the resultant brown reaction mixture was cooled to ambient temperature and diluted to 3 mL total volume with DMSO and filtered through a 0.4 micron filter. The filtrate was purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-70%). The fractions containing product were frozen and lyophilized to afford (Rac)-1-(4'-chloro-4-methoxy-3'-methyl-[1,1'-biphenyl]-3-yl)-2-oxo-N-(pyridazin-3-yl)-1,2,7,8-tetrahydro-1,6-naphthyridine-6(5H)-sulfonamide (91.8 mg, 0.17 mmol, 32.5% yield) as an off-white solid. $^1$H NMR (400 MHz, DMSO-$d_6$) δ ppm 8.30 (br. s., 1H) 7.80 (dd, J=8.66, 2.44 Hz, 2H) 7.72 (d, J=2.07 Hz, 1H) 7.64 (dd, J=9.59, 4.09 Hz, 1H) 7.52-7.58 (m, 2H) 7.45 (d, J=8.29 Hz, 1H) 7.38 (d, J=9.43 Hz, 1H) 7.29 (d, J=8.81 Hz, 1H) 6.38 (d, J=9.33 Hz, 1H) 3.96-4.16 (m, 2H) 3.78 (s, 3H) 3.22 (br. s., 2H) 2.32-2.48 (m, 4H) 2.03-2.19 (m, 1H). m/z (ESI) 538.2 (M+H)+.

Separation Step: Racemic product of Example 56 was subjected to chiral SFC (Regis Whelk-O (s,s), 50% methanol) to give Example 56-P (peak 1) and Example 56-M (peak 2) as off-white solids.

Example 57

(Rac)-; (P)-; and (M)-1-(3'-Chloro-4-Methoxy-2'-Methyl-[1,1'-Biphenyl]-3-Yl)-2-Oxo-N-(Pyridazin-3-Yl)-1,2,7,8-Tetrahydro-1,6-Naphthyridine-6(5H)-Sulfonamide

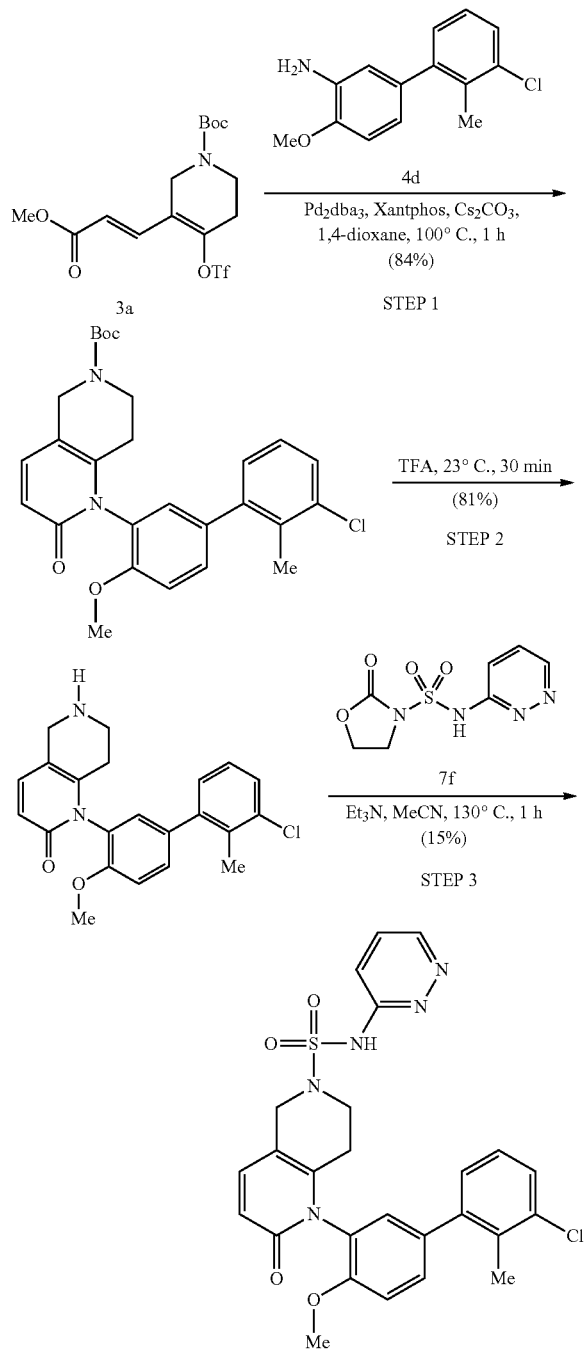

Step 1: (Rac)-tert-Butyl 1-(3'-Chloro-4-Methoxy-2'-Methyl-[1,1'-Biphenyl]-3-Yl)-2-Oxo-1,2,7,8-Tetrahydro-1,6-Naphthyridine-6(5H)-Carboxylate A 40-mL vial was charged with (E)-tert-butyl 3-(3-methoxy-3-oxoprop-1-en-1-yl)-4-(((trifluoromethyl)sulfonyl)oxy)-5,6-dihydropyridine-1(2H)-carboxylate (Preparation 3a, 379 mg, 0.91 mmol). (9,9-dimethyl-9H-xanthene-4,5-diyl)bis(diphenylphosphine) (66.0 mg, 0.11 mmol), 3'-chloro-4-methoxy-2'-methyl-[1,1'-biphenyl]-3-amine (Preparation 4d, 226 mg, 0.91 mmol) and cesium carbonate (892 mg, 2.74 mmol), 1,4-dioxane (4.56 mL) then sparged with nitrogen for 10 min. The needle was then removed and the reaction was heated to 100° C. After 1 h, the reaction mixture was allowed to cool to ambient temperature, diluted with EtOAc (15 mL), and filtered through a pad of Celite®. The pad was rinsed with EtOAc (3×15 mL) and the filtrate was concentrated under reduced pressure. The residue was purified by flash column chromatography (100-g Biotage column, eluent: gradient, 0 to 35% (3:1) EtOAc/EtOH in heptane with 10% DCM as an additive) to afford (Rac)-tert-butyl 1-(3'-chloro-4-methoxy-2'-methyl-[1,1'-biphenyl]-3-yl)-2-oxo-1,2,7,8-tetrahydro-1,6-naphthyridine-6(5H)-carboxylate (369 mg, 0.77 mmol, 84% yield) as a tan solid. $^1$H NMR (400 MHz, DMSO-$d_6$) δ=7.49-7.41 (m, 2H), 7.36 (d, J=9.4 Hz, 1H), 7.32-7.19 (m, 4H), 6.39 (d, J=9.4 Hz, 1H), 4.36-4.22 (m, 2H), 3.88-3.70 (m, 3H), 3.61-3.47 (m, 1H), 3.43 (br. s., 1H), 2.39-2.20 (m, 4H), 2.05 (td, J=5.2, 17.4 Hz, 1H), 1.53-1.30 (m, 9H). m/z (ESI) 481.2 (M+H)+.

Step 2: (Rac)-1-(3'-Chloro-4-Methoxy-2'-Methyl-[1,1'-Biphenyl]-3-Yl)-5,6,7,8-Tetrahydro-1,6-Naphthyridin-2(1H)-One A 40 mL vial was charged with (Rac)-tert-butyl 1-(3'-chloro-4-methoxy-2'-methyl-[1,1'-biphenyl]-3-yl)-2-oxo-1,2,7,8-tetrahydro-1,6-naphthyridine-6(5H)-carboxylate (369 mg, 0.77 mmol) and trifluroacetic acid (3.84 mL) then stirred at ambient temperature. After 30 min, the reaction mixture was concentrated under reduced pressure, dissolved in DCM (50 mL) and carefully poured into saturated aqueous sodium bicarbonate solution (50 mL). The layers were separated and the aqueous layer extracted with additional DCM (4×25 mL). The combined organic layers were dried over anhydrous magnesium sulfate, filtered, concentrated under reduced pressure to afford (Rac)-1-(3'-chloro-4-methoxy-2'-methyl-[1,1'-biphenyl]-3-yl)-5,6,7,8-tetrahydro-1,6-naphthyridin-2(1H)-one (238 mg, 0.63 mmol, 81% yield) as a tan foam which was used without further purification. $^1$H NMR (400 MHz, DMSO-$d_6$) δ=7.48-7.39 (m, 2H), 7.32-7.20 (m, 4H), 7.13 (d, J=2.2 Hz, 1H), 6.31 (d, J=9.3 Hz, 1H), 3.84-3.74 (m, 3H), 3.69-3.53 (m, 2H), 2.89-2.75 (m, 2H), 2.29 (s, 3H), 2.22-2.03 (m, 1H), 2.01-1.81 (m, 1H). m/z (ESI) 381.2 (M+H)+.

Step 3: (Rac)-1-(3'-Chloro-4-Methoxy-2'-Methyl-[1,1'-Biphenyl]-3-Yl)-2-Oxo-N-(Pyridazin-3-Yl)-1,2,7,8-Tetrahydro-1,6-Naphthyridine-6(5H)-Sulfonamide A 5-mL vial was charged with (Rac)-1-(3'-chloro-4-methoxy-2'-methyl-[1,1'-biphenyl]-3-yl)-5,6,7,8-tetrahydro-1,6-naphthyridin-2(1H)-one (115 mg, 0.30 mmol), 2-oxo-N-(pyridazin-3-yl)oxazolidine-3-sulfonamide (Preparation 7f, 147 mg, 0.60 mmol), N,N-diisopropylethylamine (368 μL, 2.11 mmol), and MeCN (0.60 μL). The vial was sealed with a PTFE lined cap and heated to 130° C. After 1 h, the resultant brown reaction mixture was cooled to ambient temperature and diluted to 3 mL total volume with DMSO and filtered through a 0.4 micron filter. The filtrate was purified by reverse phase HPLC in 2 separate injections (XBridge Prep Shield RP18 19×100 mm Mobile phase: 0.1% TFA in water/acetonitrile Flow rate: 40 ml/min Inj: 1500 uL Gradient: 12 min 25-70%). The fractions containing product were frozen and lyophilized to afford (Rac)-1-(3'-chloro-4-methoxy-2'-methyl-[1,1'-biphenyl]-3-yl)-2-oxo-N-(pyridazin-3-yl)-1,2,7,8-tetrahydro-1,6-naphthyridine-6(5H)-sulfonamide (25 mg, 0.05 mmol, 15.4% yield) as an off-white solid. $^1$H NMR (400 MHz, DMSO-$d_6$) δ ppm 14.18 (br. s., 1H) 8.11-8.31 (m, 1H) 7.86 (br. s., 1H) 7.64 (dd, J=9.43, 4.15 Hz, 1H) 7.40-7.47 (m, 2H) 7.35 (d, J=9.43 Hz, 1H) 7.16-7.31 (m, 4H) 6.35 (d, J=9.33 Hz, 1H) 4.05 (br. s., 2H) 3.74-3.81 (m, 3H) 3.23 (br. s., 2H) 2.34-2.46 (m, 1H) 2.28 (s, 3H) 2.14 (d, J=18.14 Hz, 1H). m/z (ESI) 538.2 (M+H)$^+$.

Separation Step: Racemic product of Example 57 was subjected to chiral SFC (Regis Whelk-O (s,s), 50% methanol) to give Example 57-P (peak 1) and Example 57-M (peak 2) as off-white solids.

Example 58

(Rac-; (P)-; and (M)-1-(2-Fluoro-3',5-Dimethoxy-4'-Methyl-[1,1'-Biphenyl]-4-Yl)-N-(Isoxazol-3-Yl)-2-Oxo-1,2,7,8-Tetrahydro-1,6-Naphthyridine-6(5H)-Sulfonamide

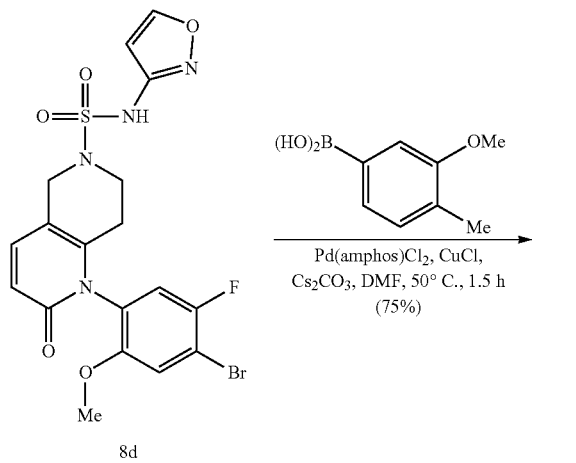

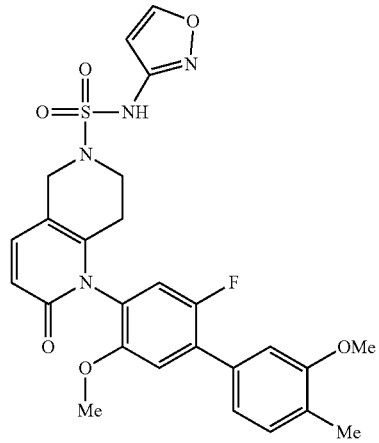

This compound was prepared analogous to the procedure of Example 15 from (Rac)-1-(4-bromo-5-fluoro-2-methoxyphenyl)-N-(isoxazol-3-yl)-2-oxo-1,2,7,8-tetrahydro-1,6-naphthyridine-6(5H)-sulfonamide (Preparation 8d) and 3-methoxy-4-methylphenyl boronic acid (purchased from Alfa Aesar) as the boronic acid. $^1$H NMR (400 MHz, DMSO-$d_6$) δ ppm 11.16 (s, 1H) 8.74 (d, J=1.76 Hz, 1H) 7.22-7.36 (m, 4H) 7.09-7.18 (m, 2H) 6.35-6.42 (m, 2H) 4.23 (br. s., 2H) 3.87 (s, 3H) 3.78 (s, 3H) 3.36-3.48 (m, 2H) 2.43 (br. s., 1H) 2.22 (s, 3H) 2.05-2.14 (m, 1H). m/z (ESI) 541.2 (M+H)$^+$.

Separation Step: Racemic product of Example 58 was subjected to chiral SFC separation ((s,s) Whelk-O column, 50% methanol) to afford Example 58-P (peak 1) and Example 58-M (peak 2) as off-white solids.

Example 59

(P)-1-(5'-Chloro-2-Fluoro-2',5-Dimethoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

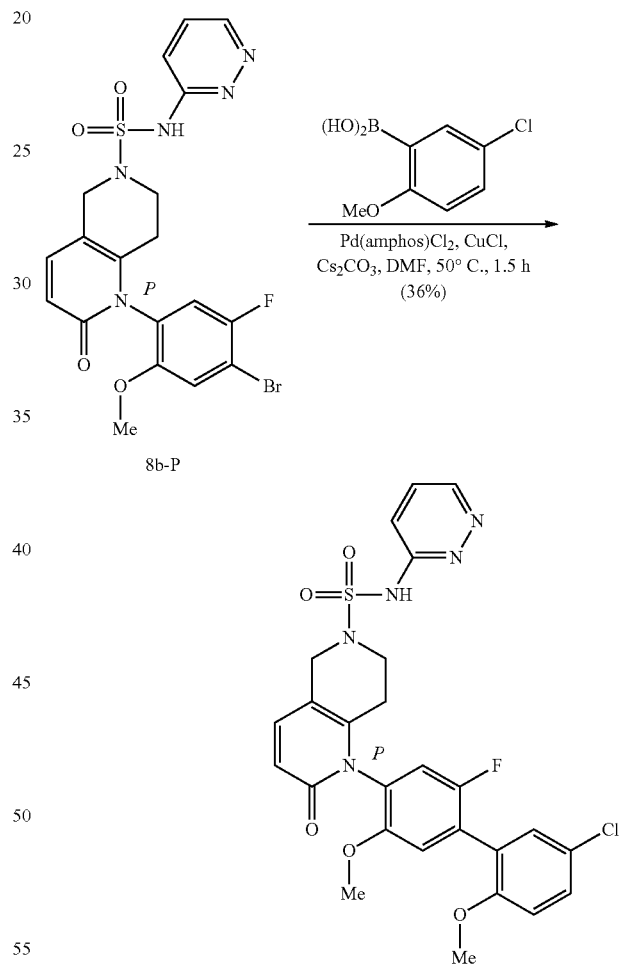

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 5-chloro-2-methoxyphenylboronic acid (purchased from Combi-Blocks Inc.) as the boronic acid. $^1$H NMR (400 MHz, DMSO-$d_6$) δ ppm 14.24 (br. s., 1H) 8.26 (br. s., 1H) 7.88 (d, J=7.77 Hz, 1H) 7.67 (dd, J=9.64, 4.25 Hz, 1H) 7.50 (dd, J=8.81, 2.70 Hz, 1H) 7.34-7.42 (m, 2H) 7.27 (d, J=9.54 Hz, 1H) 7.16-7.23 (m, 2H) 6.39 (d, J=9.33 Hz, 1H) 4.06 (d, J=9.85 Hz, 2H) 3.81 (s, 3H) 3.75 (s, 3H) 3.24 (br. s., 2H) 2.38-2.48 (m, 1H) 2.15 (d, J=16.90 Hz, 1H). m/z (ESI) 572.0 (M+H)+.

Example 60

(P)-1-(4-(5-Chloro-2-Methoxypyridin-3-Yl)-5-Fluoro-2-Methoxyphenyl)-2-Oxo-N-(Pyridazin-3-Yl)-1,2,7,8-Tetrahydro-1,6-Naphthyridine-6(5H)-Sulfonamide

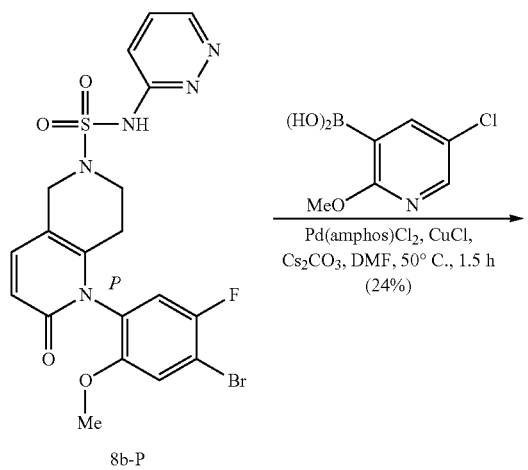

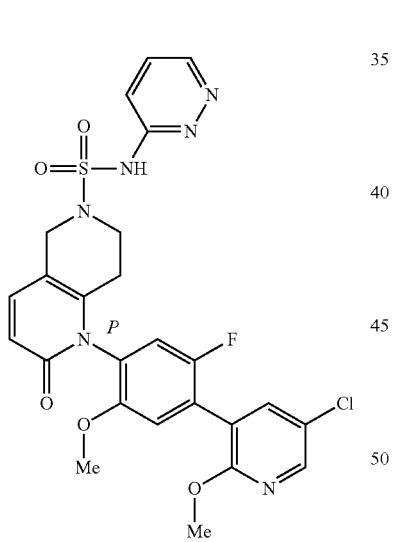

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (5-chloro-2-methoxypyridin-3-yl)boronic acid (purchased from Acros Organics) as the boronic acid. $^1$H NMR (400 MHz, DMSO-$d_6$) δ ppm 14.23 (br. s., 1H) 8.46 (t, J=2.02 Hz, 1H) 8.25 (dd, J=2.13, 1.09 Hz, 2H) 7.88 (d, J=9.02 Hz, 1H) 7.67 (dd, J=9.54, 4.25 Hz, 1H) 7.30-7.44 (m, 3H) 6.39 (d, J=9.12 Hz, 1H) 3.97-4.12 (m, 5H) 3.82 (s, 3H) 3.23 (br. s., 2H) 2.45 (d, J=16.79 Hz, 1H) 2.14 (d, J=16.79 Hz, 1H). m/z (ESI) 573.0 (M+H)+.

Example 61

(P)-1-(4'-Chloro-2-Fluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

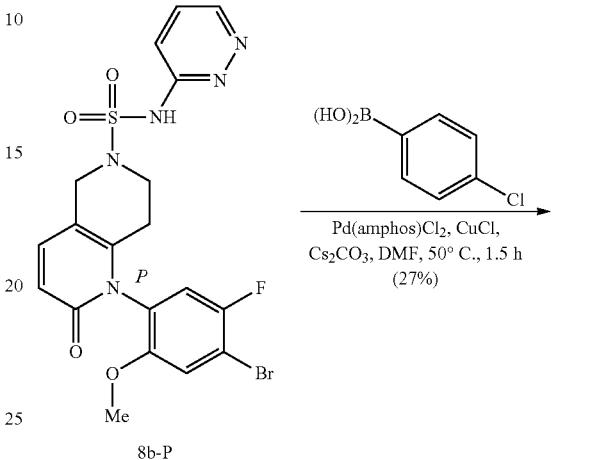

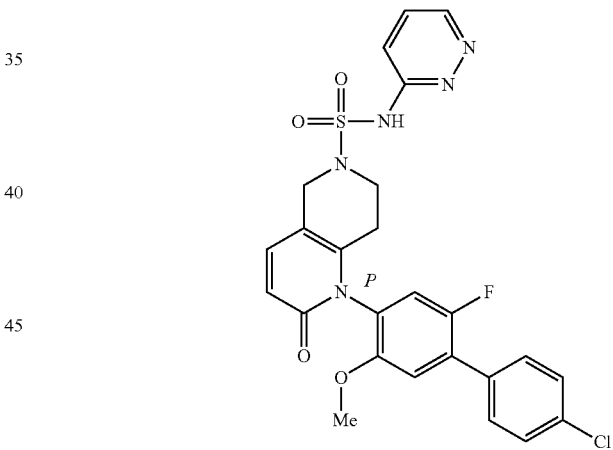

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (4-chlorophenyl)boronic acid (purchased from Sigma-Aldrich Chemical Company, Inc.) as the boronic acid. $^1$H NMR (400 MHz, DMSO-$d_6$) δ ppm 14.23 (br. s., 1H) 8.25 (br. s., 1H) 7.88 (d, J=10.05 Hz, 1H) 7.64-7.73 (m, 3H) 7.57-7.63 (m, 2H) 7.34-7.42 (m, 2H) 7.31 (d, J=7.05 Hz, 1H) 6.39 (d, J=9.54 Hz, 1H) 3.96-4.15 (m, 2H) 3.80 (s, 3H) 3.23 (br. s., 2H) 2.43 (br. s., 1H) 2.07-2.23 (m, 1H). m/z (ESI) 542.0 (M+H)+.

Example 62

(P)-1-(3'-Chloro-2-Fluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

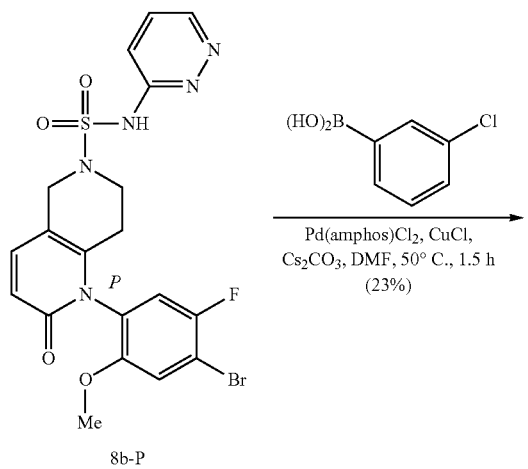

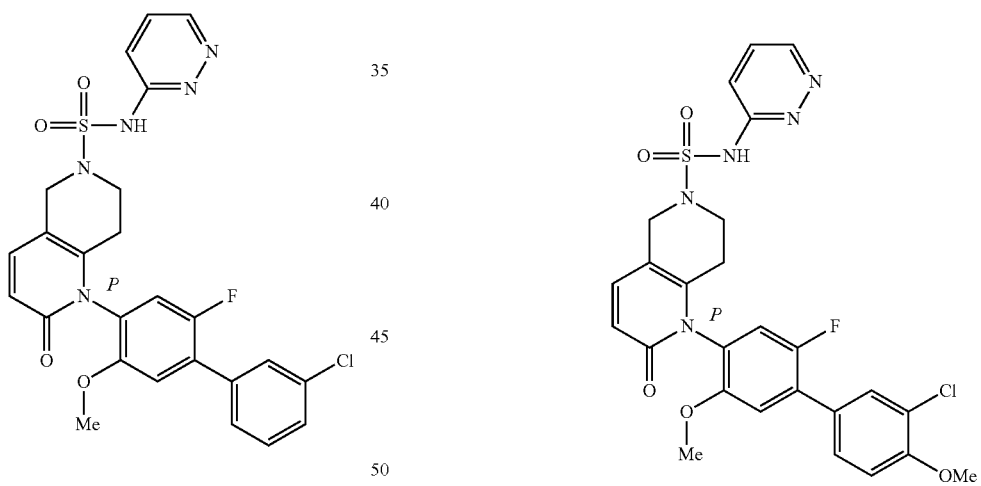

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-chlorophenyl)boronic acid (purchased from Sigma-Aldrich Chemical Company, Inc.) as the boronic acid. $^1$H NMR (400 MHz, DMSO-d$_6$) δ ppm 14.23 (br. s., 1H) 8.25 (br. s., 1H) 7.88 (d, J=8.29 Hz, 1H) 7.73 (s, 1H) 7.61-7.71 (m, 2H) 7.51-7.60 (m, 2H) 7.31-7.43 (m, 3H) 6.39 (d, J=9.33 Hz, 1H) 3.96-4.16 (m, 2H) 3.82 (s, 3H) 3.23 (br. s., 2H) 2.39-2.48 (m, 1H) 2.15 (d, J=18.24 Hz, 1H). m/z (ESI) 542.0 (M+H)$^+$.

Example 63

(P)-1-(3'-Chloro-2-Fluoro-4',5-Dimethoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

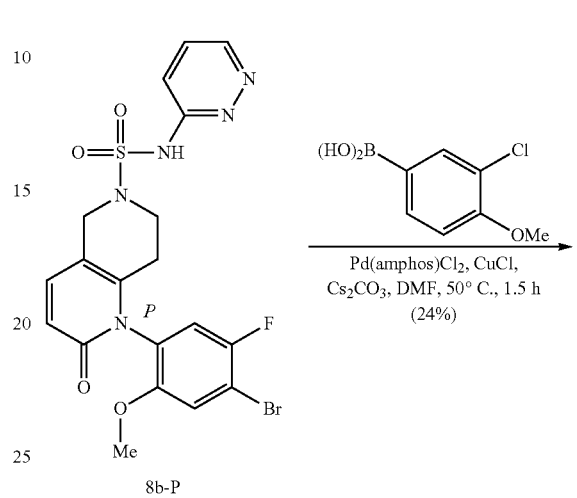

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-chloro-4-methoxyphenyl)boronic acid (purchased from Alfa Aesar) as the boronic acid. $^1$H NMR (400 MHz, DMSO-d$_6$) δ ppm 14.23 (br. s., 1H) 8.26 (br. s., 1H) 7.87 (br. s., 1H) 7.74 (dd, J=2.18, 1.14 Hz, 1H) 7.59-7.70 (m, 2H) 7.26-7.42 (m, 4H) 6.38 (d, J=9.43 Hz, 1H) 3.98-4.14 (m, 2H) 3.92-3.97 (m, 3H) 3.81 (s, 3H) 3.23 (br. s., 2H) 2.40-2.48 (m, 1H) 2.14 (d, J=17.00 Hz, 1H). m/z (ESI) 572.0 (M+H)$^+$.

Example 64

(P)-1-(5-Fluoro-2-Methoxy-4-(2-Methoxy-5-(Trifluoromethyl)Pyridin-3-Yl)Phenyl)-2-Oxo-N-(Pyridazin-3-Yl)-1,2,7,8-Tetrahydro-1,6-Naphthyridine-6(5H)-Sulfonamide

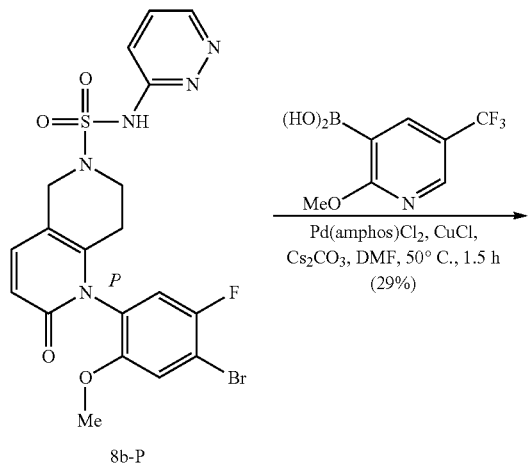

Example 65

(P)-1-(3'-Chloro-2-Fluoro-2',5-Dimethoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

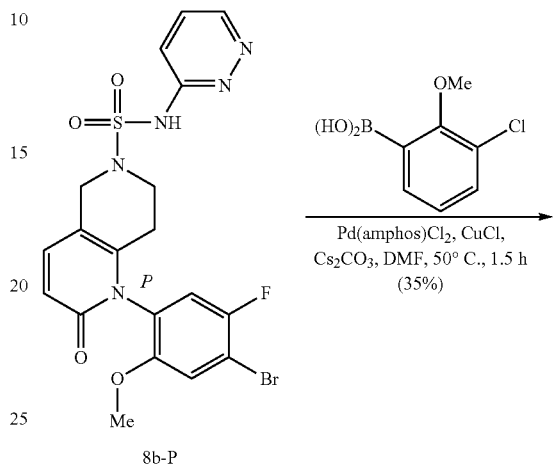

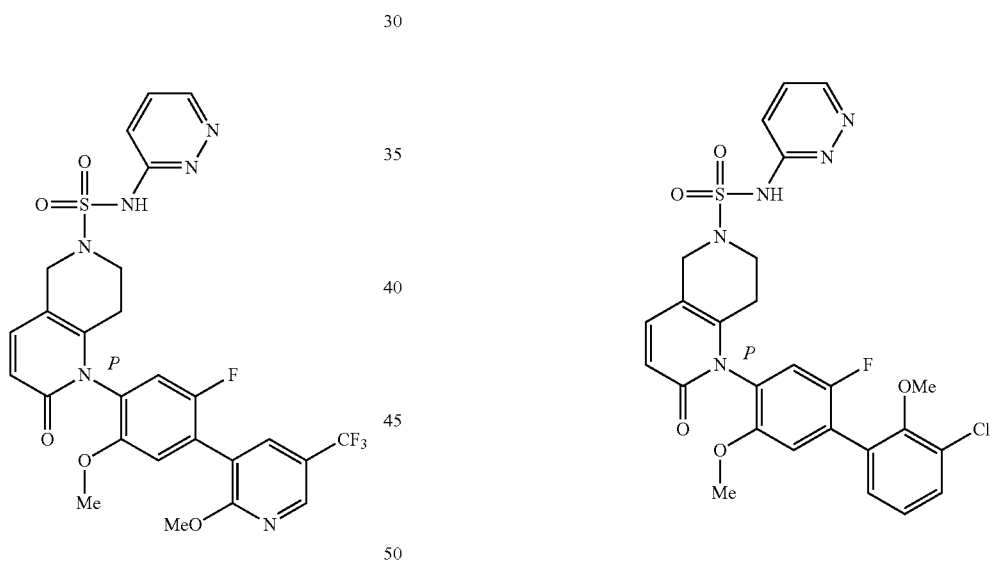

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (2-methoxy-5-(trifluoromethyl)pyridin-3-yl)boronic acid (purchased from Combi Blocks, Inc.) as the boronic acid. $^1$H NMR (400 MHz, DMSO-$d_6$) δ ppm 14.24 (br. s., 1H) 8.72 (dd, J=2.38, 1.04 Hz, 1H) 8.25 (br. s., 1H) 8.19 (d, J=2.38 Hz, 1H) 7.87 (br. s., 1H) 7.68 (dd, J=9.12, 4.35 Hz, 1H) 7.31-7.45 (m, 3H) 6.40 (d, J=9.33 Hz, 1H) 3.93-4.18 (m, 6H) 3.77 (s, 3H) 3.24 (br. s., 2H) 2.37-2.48 (m, 1H) 2.15 (d, J=18.45 Hz, 1H). m/z (ESI) 607.2 (M+H)$^+$.

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-chloro-2-methoxyphenyl)boronic acid (purchased from Acros Organics) as the boronic acid. $^1$H NMR (400 MHz, DMSO-$d_6$) δ ppm 14.24 (br. s., 1H) 8.72 (dd, J=2.38, 1.04 Hz, 1H) 8.25 (br. s., 1H) 8.19 (d, J=2.38 Hz, 1H) 7.87 (br. s., 1H) 7.68 (dd, J=9.12, 4.35 Hz, 1H) 7.31-7.45 (m, 3H) 6.40 (d, J=9.33 Hz, 1H) 3.93-4.18 (m, 6H) 3.77 (s, 3H) 3.24 (br. s., 2H) 2.37-2.48 (m, 1H) 2.15 (d, J=18.45 Hz, 1H). m/z (ESI) 572.0 (M+H)$^+$.

Example 66

(P)-1-(2-Fluoro-5-Methoxy-3'-(Trifluoromethoxy)-[1,1'-Biphenyl]-4-Yl)-2-Oxo-N-(Pyridazin-3-Yl)-1,2,7,8-Tetrahydro-1,6-Naphthyridine-6(5H)-Sulfonamide

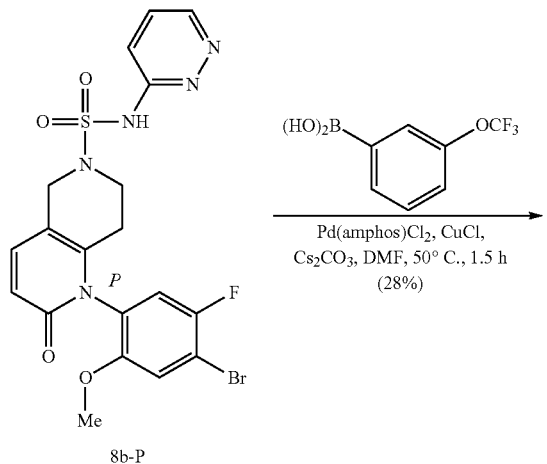

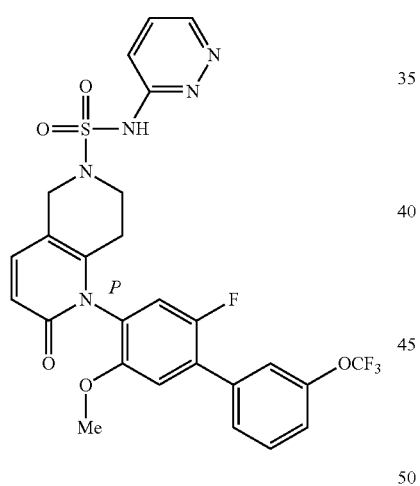

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-(trifluoromethoxy)phenyl)boronic acid (purchased from Sigma-Aldrich Chemical Company, Inc.) as the boronic acid. $^1$H NMR (400 MHz, DMSO-d$_6$) δ ppm 2.14 (d, J=17.31 Hz, 1H) 2.39-2.46 (m, 1H) 3.23 (br. s., 2H) 3.81 (s, 3H) 4.05 (d, J=9.38 Hz, 2H) 6.38 (d, J=9.54 Hz, 1H) 7.30-7.43 (m, 3H) 7.48 (d, J=8.81 Hz, 1H) 7.62-7.74 (m, 4H) 7.86 (br. s., 1H) 8.25 (br. s., 1H) 14.22 (br. s., 1H). m/z (ESI) 592.2 (M+H)$^+$.

Example 67

(P)-1-(2-Fluoro-5-Methoxy-4'-(Trifluoromethyl)-[1,1'-Biphenyl]-4-Yl)-2-Oxo-N-(Pyridazin-3-Yl)-1,2,7,8-Tetrahydro-1,6-Naphthyridine-6(5H)-Sulfonamide

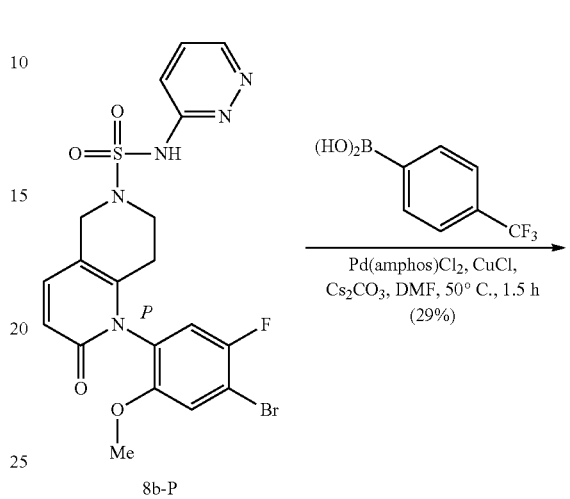

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (4-(trifluoromethyl)phenyl)boronic acid (purchased from Sigma-Aldrich Chemical Company, Inc.) as the boronic acid. $^1$H NMR (400 MHz, DMSO-d$_6$) δ ppm 2.15 (d, J=17.05 Hz, 1H) 2.44 (br. s., 1H) 3.24 (br. s., 2H) 3.81 (s, 3H) 4.08 (br. s., 2H) 6.38 (d, J=9.38 Hz, 1H) 7.32-7.46 (m, 3H) 7.66 (dd, J=9.56, 4.12 Hz, 1H) 7.89 (s, 5H) 8.25 (br. s., 1H) 14.22 (br. s., 1H). m/z (ESI) 576.2 (M+H)$^+$.

Example 68

(P)-1-(2-Fluoro-5-Methoxy-3'-(2,2,2-Trifluoroethoxy)-[1,1'-Biphenyl]-4-Yl)-2-Oxo-N-(Pyridazin-3-Yl)-1,2,7,8-Tetrahydro-1,6-Naphthyridine-6(5H)-Sulfonamide

Example 69

(P)-1-(3'-Chloro-2-Fluoro-5-Methoxy-5'-Methyl-[1,1'-Biphenyl]-4-Yl)-2-Oxo-N-(Pyridazin-3-Yl)-1,2,7,8-Tetrahydro-1,6-Naphthyridine-6(5H)-Sulfonamide

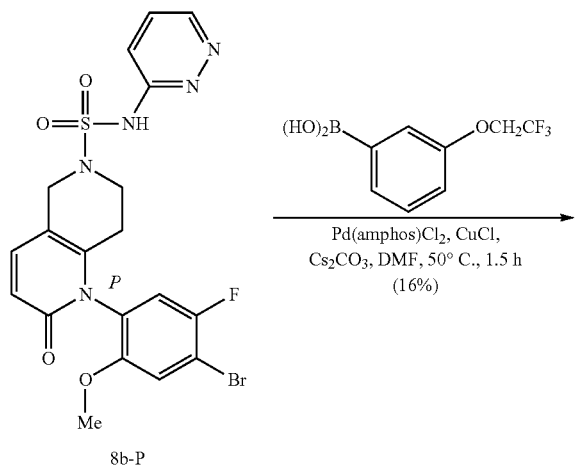

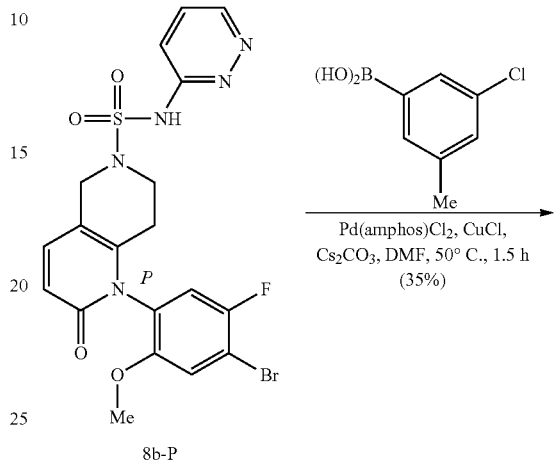

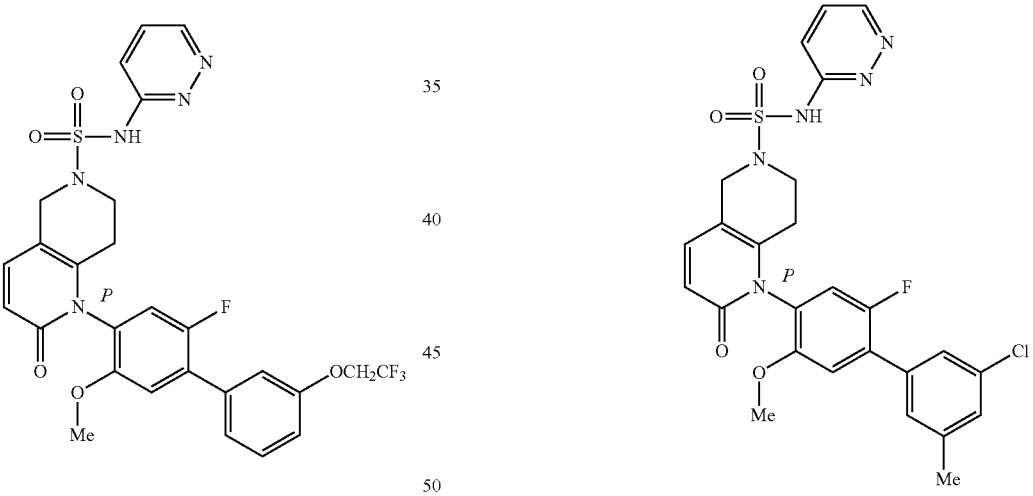

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-(2,2,2-trifluoroethoxy)phenyl)boronic acid (purchased from Alfa Aesar) as the boronic acid. $^1$H NMR (400 MHz, DMSO-d$_6$) δ ppm 2.08 (br. s., 1H) 2.41 (s, 1H) 3.19 (br. s., 2H) 3.77 (s, 3H) 4.03 (br. s., 2H) 4.82 (q, J=8.93 Hz, 2H) 6.34 (d, J=8.66 Hz, 1H) 7.12 (d, J=8.40 Hz, 1H) 7.24-7.36 (m, 4H) 7.45 (t, J=8.19 Hz, 1H) 7.64 (d, J=3.52 Hz, 1H) 7.86 (s, 1H) 8.21 (br. s., 1H) 14.18 (br. s., 1H). m/z (ESI) 606.1 (M+H)$^+$.

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 3-chloro-5-methylphenylboronic acid (purchased from Combi-Blocks, Inc.) as the boronic acid. $^1$H NMR (400 MHz, DMSO-d$_6$) δ ppm 14.23 (br. s., 1H) 8.25 (br. s., 1H) 7.87 (br. s., 1H) 7.67 (dd, J=9.64, 3.94 Hz, 1H) 7.25-7.58 (m, 6H) 6.39 (d, J=9.33 Hz, 1H) 3.94-4.16 (m, 2H) 3.81 (s, 3H) 3.23 (br. s., 2H) 2.37-2.47 (m, 4H) 2.07-2.21 (m, 1H). m/z (ESI) 556.2 (M+H)$^+$.

Example 70

(P)-1-(3'-Chloro-2-Fluoro-5,5'-Dimethoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

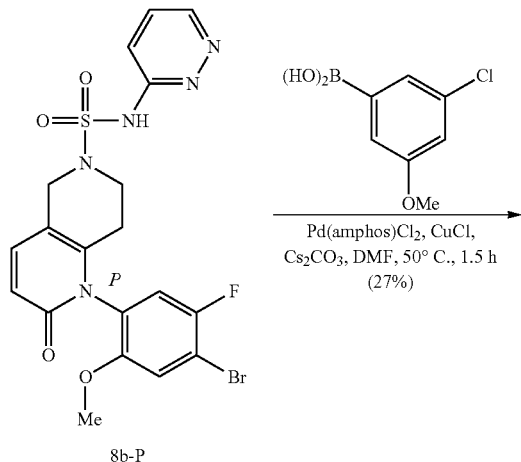

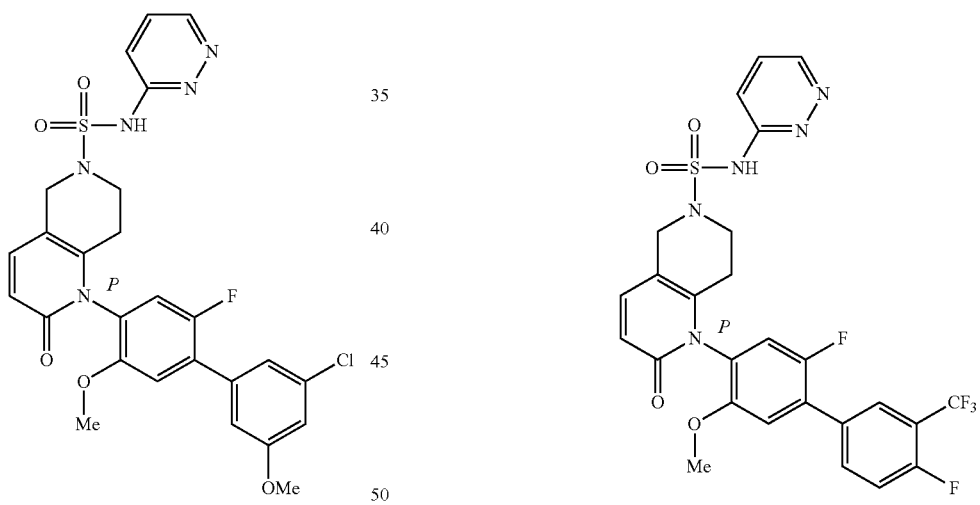

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 3-chloro-5-methoxybenzeneboronic acid (purchased from Combi-Blocks Inc.) as the boronic acid. $^1$H NMR (400 MHz, DMSO-$d_6$) δ ppm 14.23 (br. s., 1H) 8.26 (br. s., 1H) 7.96-8.10 (m, 2H) 7.88 (d, J=7.98 Hz, 1H) 7.61-7.78 (m, 2H) 7.30-7.46 (m, 3H) 6.39 (d, J=9.54 Hz, 1H) 3.95-4.17 (m, 2H) 3.82 (s, 3H) 3.36 (s, 3H) 3.23 (br. s., 2H) 2.39-2.48 (m, 1H) 2.06-2.24 (m, 1H). m/z (ESI) 572.2 (M+H)$^+$.

Example 71

(P)-1-(2,4'-Difluoro-5-Methoxy-3'-(Trifluoromethyl)-[1,1'-Biphenyl]-4-Yl)-2-Oxo-N-(Pyridazin-3-Yl)-1,2,7,8-Tetrahydro-1,6-Naphthyridine-6(5H)-Sulfonamide

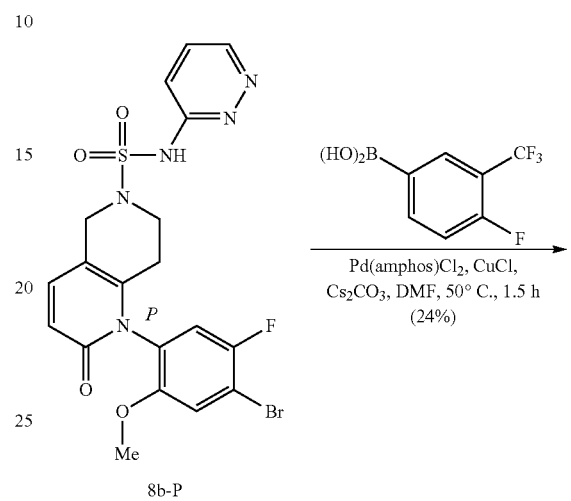

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (4-fluoro-3-(trifluoromethyl)phenyl)boronic acid (purchased from Matrix Scientific) as the boronic acid. $^1$H NMR (400 MHz, DMSO-$d_6$) δ ppm 14.23 (br. s., 1H) 8.26 (br. s., 1H) 7.87 (br. s., 1H) 7.67 (dd, J=9.59, 4.20 Hz, 1H) 7.25-7.44 (m, 4H) 7.11-7.21 (m, 2H) 6.39 (d, J=9.64 Hz, 1H) 4.07 (br. s., 2H) 3.86 (s, 3H) 3.81 (s, 3H) 3.24 (br. s., 2H) 2.36-2.47 (m, 1H) 2.04-2.24 (m, 1H). m/z (ESI) 594.2 (M+H)$^+$.

Example 72

(P)-1-(3'-(Difluoromethyl)-2-Fluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

Example 73

(P)-1-(2,4'-Difluoro-5-Methoxy-3'-Methyl-[1,1'-Biphenyl]-4-Yl)-2-Oxo-N-(Pyridazin-3-Yl)-1,2,7,8-Tetrahydro-1,6-Naphthyridine-6(5H)-Sulfonamide

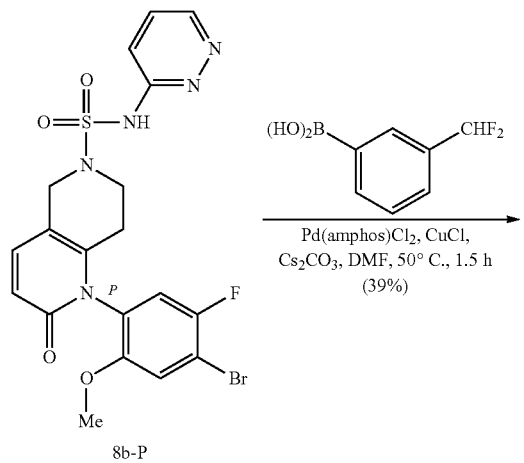

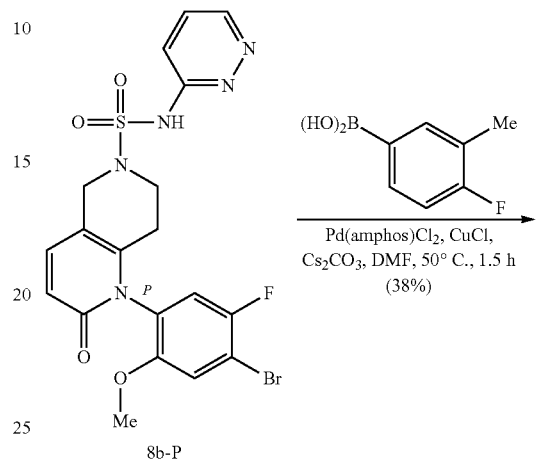

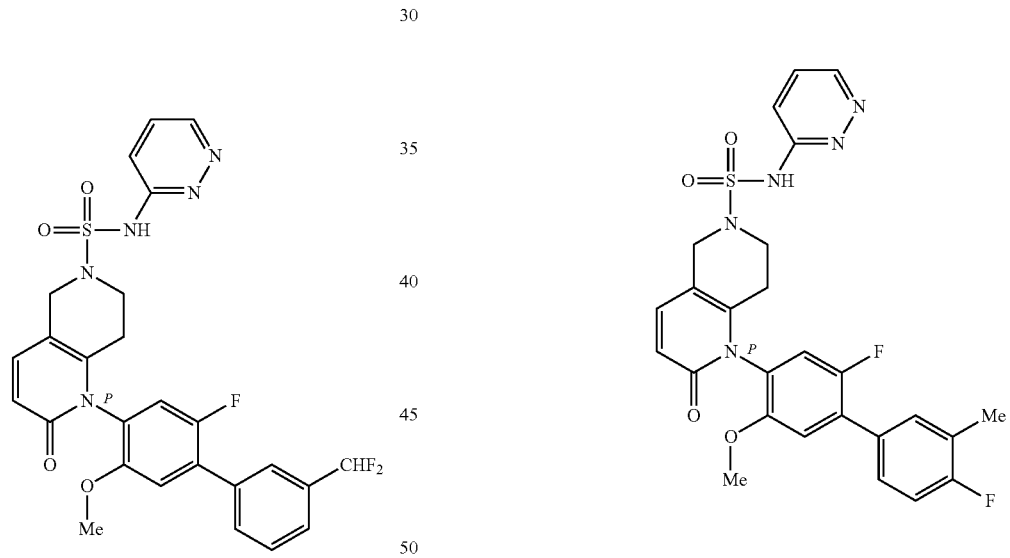

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-(difluoromethyl)phenyl)boronic acid (purchased from Ark Pharm) as the boronic acid. $^1$H NMR (400 MHz, DMSO-$d_6$) δ ppm 14.23 (br. s., 1H) 8.26 (br. s., 1H) 7.83 (s, 3H) 7.62-7.76 (m, 3H) 7.31-7.45 (m, 3H) 7.00 (s, 1H) 6.96-7.29 (m, 1H) 6.39 (d, J=9.43 Hz, 1H) 4.08 (br. s., 2H) 3.82 (s, 3H) 3.25 (br. s., 2H) 2.40-2.49 (m, 1H) 2.09-2.22 (m, 1H). m/z (ESI) 558.2 (M+H)$^+$.

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 4-fluoro-3-methylbenzeneboronic acid (purchased from Sigma-Aldrich Chemical Company, Inc.) as the boronic acid. $^1$H NMR (400 MHz, DMSO-$d_6$) δ ppm 2.09-2.22 (m, 1H) 2.33 (d, J=1.55 Hz, 3H) 2.39-2.49 (m, 1H) 3.25 (br. s., 2H) 3.80 (s, 3H) 4.07 (d, J=9.43 Hz, 2H) 6.38 (d, J=9.43 Hz, 1H) 7.21-7.42 (m, 4H) 7.46-7.54 (m, 1H) 7.59 (d, J=7.46 Hz, 1H) 7.67 (dd, J=9.59, 4.09 Hz, 1H) 7.87 (br. s., 1H) 8.26 (br. s., 1H) 14.23 (br. s., 1H). m/z (ESI) 540.2 (M+H)$^+$.

Example 74

(P)-1-(2-Fluoro-2',5-Dimethoxy-5'-(Trifluoromethyl)-[1,1'-Biphenyl]-4-Yl)-2-Oxo-N-(Pyridazin-3-Yl)-1,2,7,8-Tetrahydro-1,6-Naphthyridine-6(5H)-Sulfonamide

Example 75

(P)-1-(2-Fluoro-5-Methoxy-3'-Methyl-5'-(Trifluoromethyl)-[1,1'-Biphenyl]-4-Yl)-2-Oxo-N-(Pyridazin-3-Yl)-1,2,7,8-Tetrahydro-1,6-Naphthyridine-6(5H)-Sulfonamide

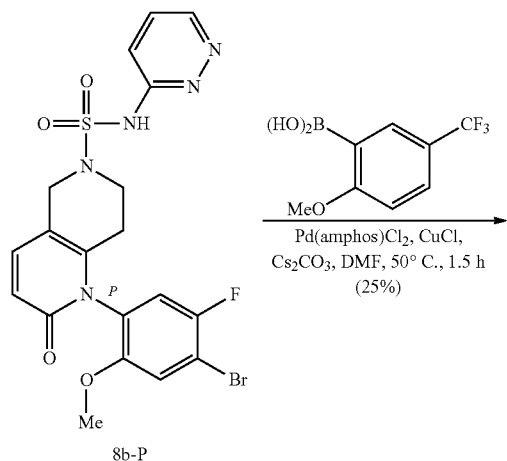

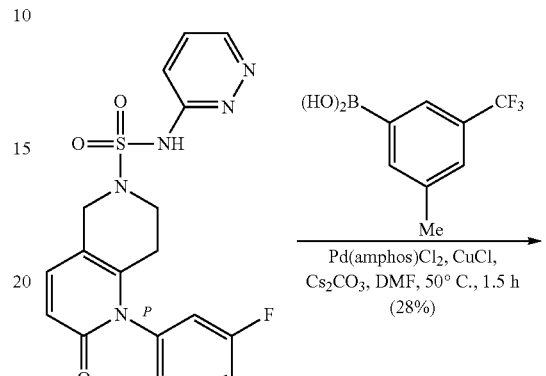

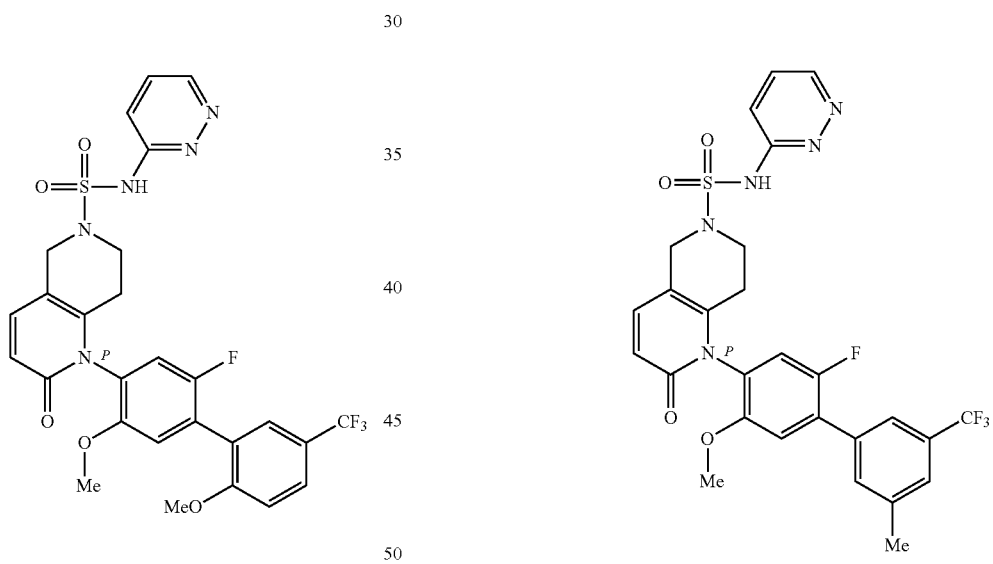

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 2-methoxy-5-trifluoromethylphenylboronic acid (purchased from Combi-Blocks Inc.) as the boronic acid. $^1$H NMR (400 MHz, DMSO-$d_6$) δ ppm 2.07-2.22 (m, 1H) 2.39-2.47 (m, 1H) 3.24 (br. s., 2H) 3.75 (s, 3H) 3.90 (s, 3H) 4.06 (d, J=10.99 Hz, 2H) 6.39 (d, J=8.60 Hz, 1H) 7.23 (d, J=6.43 Hz, 1H) 7.29 (d, J=9.23 Hz, 1H) 7.34-7.42 (m, 2H) 7.62-7.72 (m, 2H) 7.78-7.93 (m, 2H) 8.26 (br. s., 1H) 14.24 (br. s., 1H). m/z (ESI) 606.2 (M+H)$^+$.

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-methyl-5-(trifluoromethyl)phenyl)boronic acid (purchased from Matrix Scientific) as the boronic acid. $^1$H NMR (400 MHz, DMSO-$d_6$) δ ppm 14.23 (br. s., 1H) 8.26 (br. s., 1H) 7.87 (br. s., 1H) 7.77 (d, J=14.20 Hz, 2H) 7.63-7.71 (m, 2H) 7.29-7.44 (m, 3H) 6.39 (d, J=9.43 Hz, 1H) 3.97-4.16 (m, 2H) 3.82 (s, 3H) 3.24 (br. s., 2H) 2.40-2.48 (m, 1H) 2.15 (dt, J=17.10, 6.10 Hz, 1H). m/z (ESI) 590.2 (M+H)$^+$.

Example 76

(P)-1-(2-Fluoro-3',5-Dimethoxy-5'-(Trifluoromethoxy)-[1,1'-Biphenyl]-4-Yl)-2-Oxo-N-(Pyridazin-3-Yl)-1,2,7,8-Tetrahydro-1,6-Naphthyridine-6(5H)-Sulfonamide

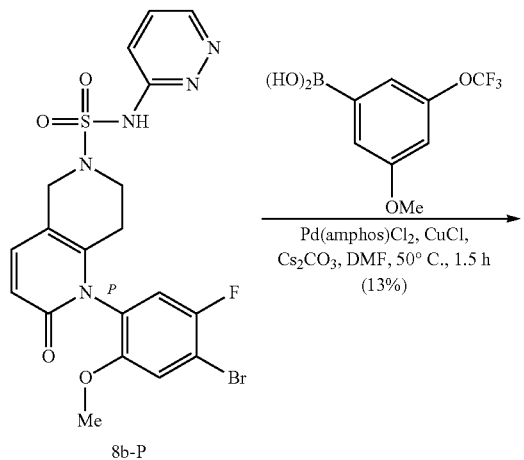

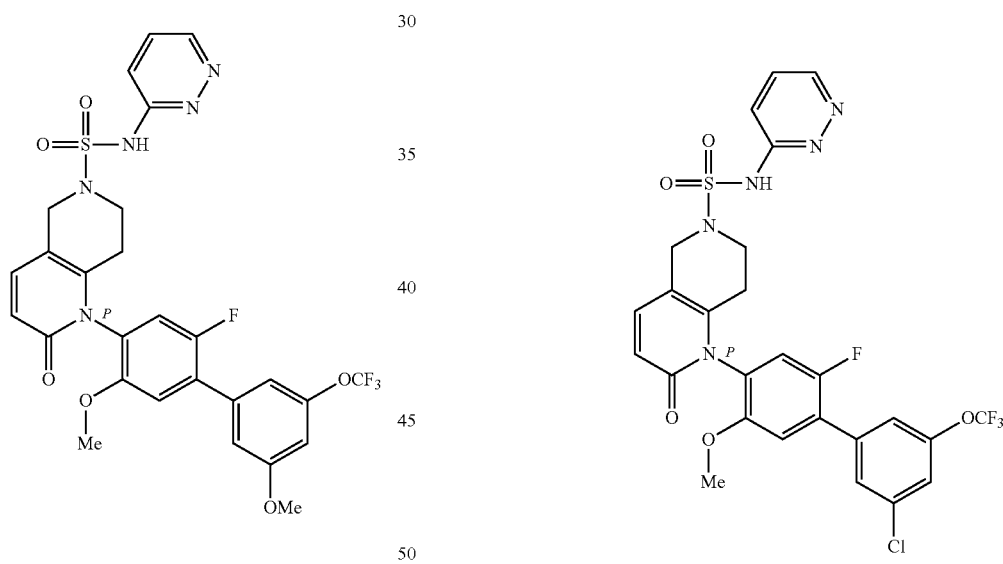

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-methoxy-5-(trifluoromethoxy)phenyl)boronic acid (purchased from Matrix Scientific) as the boronic acid. $^1$H NMR (400 MHz, DMSO-$d_6$) δ ppm 14.23 (br. s., 1H) 8.26 (br. s., 1H) 7.87 (br. s., 1H) 7.67 (dd, J=9.64, 4.04 Hz, 1H) 7.31-7.43 (m, 3H) 7.25 (d, J=1.14 Hz, 1H) 7.20 (s, 1H) 7.06 (d, J=0.93 Hz, 1H) 6.39 (d, J=9.43 Hz, 1H) 4.07 (br. s., 2H) 3.89 (s, 3H) 3.82 (s, 3H) 3.24 (br. s., 2H) 2.45 (d, J=17.21 Hz, 1H) 2.15 (d, J=17.21 Hz, 1H). m/z (ESI) 622.0 (M+H)$^+$.

Example 77

(P)-1-(3'-Chloro-2-Fluoro-2-Fluoro-5-Methoxy-5'-(Trifluoromethoxy)-[1,1'-Biphenyl]-4-Yl)-2-Oxo-N-(Pyridazin-3-Yl)-1,2,7,8-Tetrahydro-1,6-Naphthyridine-6(5H)-Sulfonamide

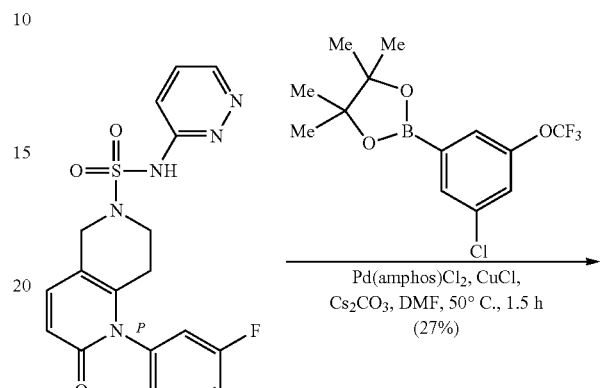

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 3-chloro-5-(trifluoromethoxy)phenylboronic acid, pinacol ester (purchased from Combi-Blocks Inc.) as the boronic ester. $^1$H NMR (400 MHz, DMSO-$d_6$) δ ppm 14.23 (br. s., 1H) 8.25 (br. s., 1H) 7.80-7.95 (m, 2H) 7.57-7.73 (m, 3H) 7.33-7.48 (m, 3H) 6.39 (d, J=9.54 Hz, 1H) 3.97-4.16 (m, 2H) 3.83 (s, 3H) 3.23 (br. s., 2H) 2.37-2.48 (m, 1H) 2.06-2.21 (m, 1H). m/z (ESI) 626.2 (M+H)$^+$.

Example 78

(P)-1-(2-Fluoro-5-Methoxy-3'-Methyl-5'-(Trifluoromethoxy)-[1,1'-Biphenyl]-4-Yl)-2-Oxo-N-(Pyridazin-3-Yl)-1,2,7,8-Tetrahydro-1,6-Naphthyridine-6(5H)-Sulfonamide

Example 79

(P)-2-Oxo-N-(Pyridazin-3-Yl)-1-(2,3',4'-Trifluoro-5,5'-Dimethoxy-[1,1'-Biphenyl]-4-Yl)-1,2,7,8-Tetrahydro-1,6-Naphthyridne-6(5H)-Sulfonamide

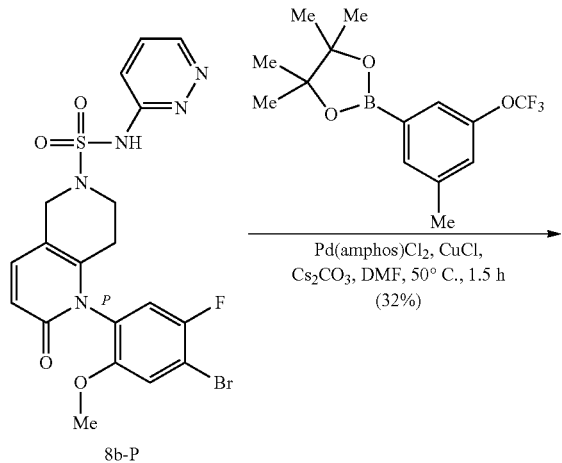

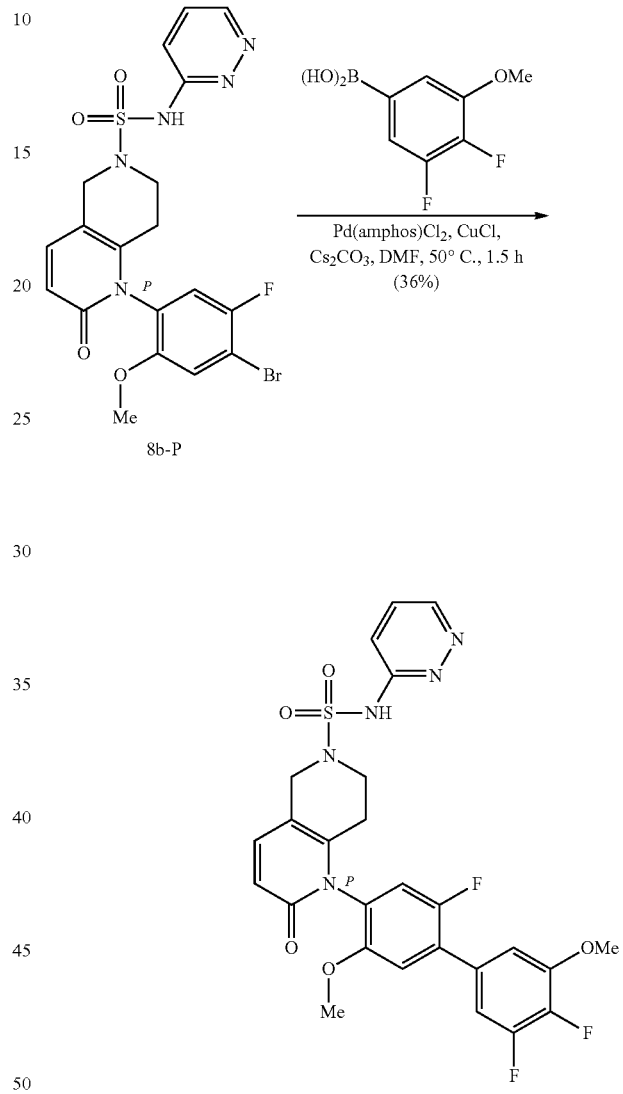

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 4,4,5,5-tetramethyl-2-(3-methyl-5-(trifluoromethoxy)phenyl)-1,3,2-dioxaborolane (purchased from Combi-Blocks Inc.) as the boronic ester. $^1$H NMR (400 MHz, DMSO-$d_6$) δ ppm 14.23 (br. s., 1H) 8.26 (br. s., 1H) 7.88 (d, J=9.43 Hz, 1H) 7.67 (dd, J=9.64, 4.25 Hz, 1H) 7.53 (s, 1H) 7.26-7.47 (m, 6H) 6.39 (d, J=9.23 Hz, 1H) 3.95-4.19 (m, 2H) 3.81 (s, 3H) 3.23 (br. s., 2H) 2.38-2.48 (m, 4H) 2.15 (d, J=17.73 Hz, 1H). m/z (ESI) 606.2 (M+H)$^+$.

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3,4-difluoro-5-methoxyphenyl)boronic acid (purchased from Combi-Blocks Inc.) as the boronic acid. $^1$H NMR (400 MHz, DMSO-$d_6$) δ ppm 14.21 (br. s., 1H) 8.25 (br. s., 1H) 7.86 (br. s., 1H) 7.66 (dd, J=9.59, 4.04 Hz, 1H) 7.22-7.44 (m, 3H) 6.91-7.19 (m, 1H) 6.38 (d, J=9.38 Hz, 1H) 4.00-4.15 (m, 2H) 3.96 (s, 3H) 3.81 (s, 3H) 3.23 (br. s., 2H) 2.37-2.48 (m, 1H) 2.14 (d, J=16.95 Hz, 1H). m/z (ESI) 574.0 (M+H)$^+$.

Example 80

(P)-1-(5-Fluoro-2-Methoxy-4-(6-Methoxy-5-(Trifluoromethyl)Pyridin-3-Yl)Phenyl)-2-Oxo-N-(Pyridazin-3-Yl)-1,2,7,8-Tetrahydro-1,6-Naphthyridine-6(5H)-Sulfonamide

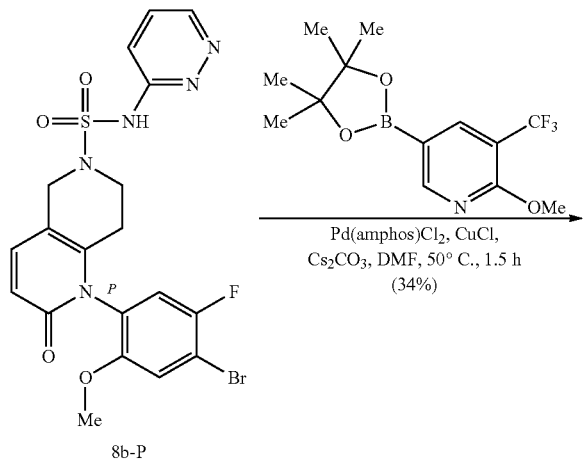

Example 81

(P)-1-(2,4'-Difluoro-5-Methoxy-3'-(Trifluoromethoxy)-[1,1'-Biphenyl]-4-Yl)-2-Oxo-N-(Pyridazin-3-Yl)-1,2,7,8-Tetrahydro-1,6-Naphthyridine-6(5H)-Sulfonamide

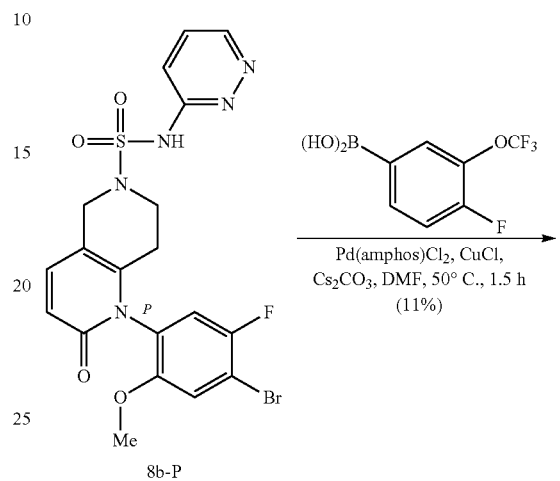

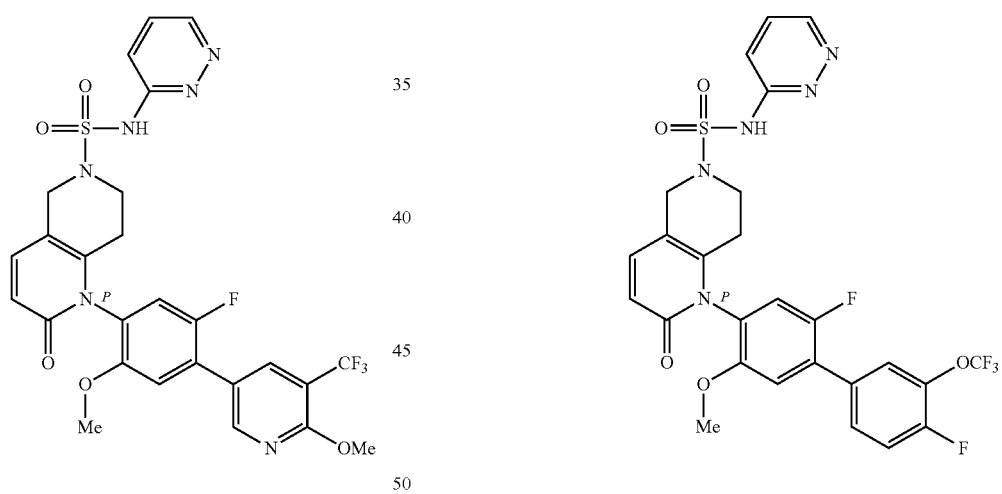

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 2-methoxy-5-(4,4,5,5-tetramethyl-1,3,2-dioxaborolan-2-yl)-3-(trifluoromethyl)pyridine (purchased from Combi-Blocks Inc.) as the boronic ester. $^1$H NMR (400 MHz, DMSO-$d_6$) δ ppm 14.21 (br. s., 1H) 8.75 (s, 1H) 8.34 (s, 1H) 8.25 (br. s., 1H) 7.87 (br. s., 1H) 7.66 (dd, J=9.56, 4.07 Hz, 1H) 7.32-7.51 (m, 3H) 6.38 (d, J=9.38 Hz, 1H) 3.96-4.20 (m, 5H) 3.81 (s, 3H) 3.25 (d, J=12.28 Hz, 2H) 2.38-2.48 (m, 1H) 2.14 (d, J=17.10 Hz, 1H). m/z (ESI) 607.0 (M+H)$^+$.

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (4-fluoro-3-(trifluoromethoxy)phenyl)boronic acid (purchased from Chemplex Chemicals, Inc.) as the boronic acid. $^1$H NMR (400 MHz, DMSO-$d_6$) δ ppm 2.09-2.23 (m, 1H) 2.38-2.48 (m, 1H) 3.17-3.30 (m, 2H) 3.92 (s, 3H) 3.97-4.16 (m, 2H) 6.38 (d, J=9.43 Hz, 1H) 7.31-7.42 (m, 4H) 7.50 (d, J=10.94 Hz, 2H) 7.66 (dd, J=9.59, 4.15 Hz, 1H) 7.85 (br. s., 1H) 8.27 (br. s., 1H) 14.20 (br. s., 1H). m/z (ESI) 610.0 (M+H)$^+$.

183
Example 82

(P)-1-(2-Fluoro-4',5-Dimethoxy-3'-(Trifluoromethyl)-[1,1'-Biphenyl]-4-Yl)-2-Oxo-N-(Pyridazin-3-Yl)-1,2,7,8-Tetrahydro-1,6-Naphthyridine-6(5H)-Sulfonamide

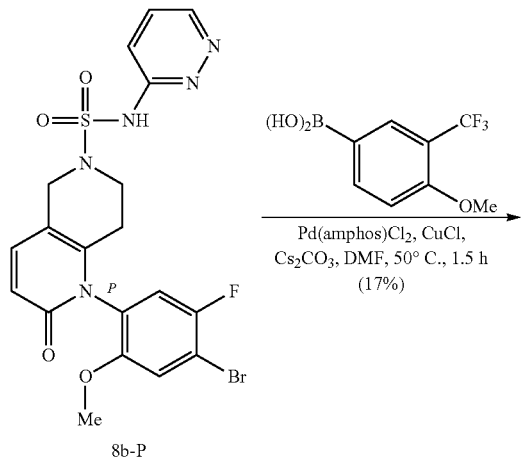

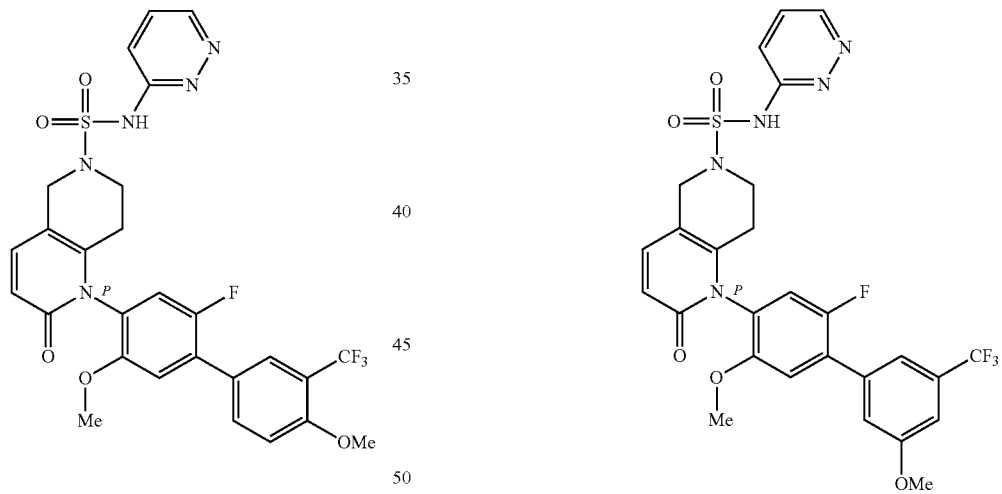

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (4-methoxy-3-(trifluoromethyl)phenyl)boronic acid (purchased from Combi-Blocks Inc.) as the boronic acid. $^1$H NMR (400 MHz, DMSO-$d_6$) δ ppm 2.09-2.22 (m, 1H) 2.40-2.49 (m, 1H) 3.19-3.30 (m, 2H) 3.97 (s, 3H) 4.00-4.17 (m, 2H) 6.38 (d, J=9.38 Hz, 1H) 7.28-7.40 (m, 3H) 7.43 (d, J=8.81 Hz, 1H) 7.66 (dd, J=9.59, 4.09 Hz, 1H) 7.84 (s, 2H) 7.93 (d, J=8.81 Hz, 1H) 8.30 (br. s., 1H). m/z (ESI) 606.2 (M+H)$^+$.

184
Example 83

(P)-1-(2-Fluoro-3',5-Dimethoxy-5'-(Trifluoromethyl)-[1,1'-Biphenyl]-4-Yl)-2-Oxo-N-(Pyridazin-3-Yl)-1,2,7,8-Tetrahydro-1,6-Naphthyridine-6(5H)-Sulfonamide

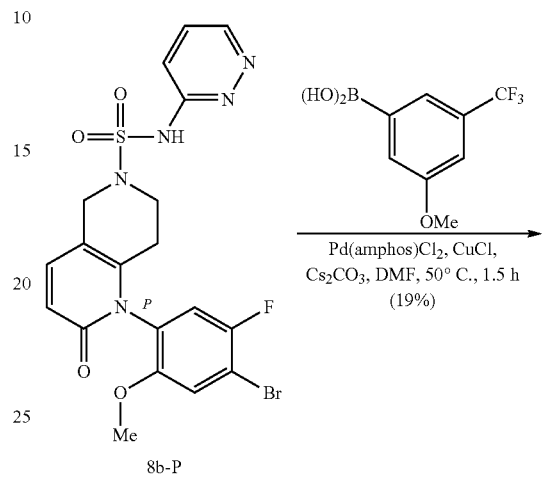

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and (3-methoxy-5-(trifluoromethyl)phenyl)boronic acid (purchased from Acros Organics) as the boronic acid. $^1$H NMR (400 MHz, DMSO-$d_6$) δ ppm 2.03-2.20 (m, 1H) 2.29-2.42 (m, 1H) 3.19 (br. s., 2H) 3.76 (s, 3H) 4.02 (d, J=7.62 Hz, 2H) 6.34 (d, J=9.38 Hz, 1H) 7.25-7.40 (m, 3H) 7.55-7.69 (m, 2H) 7.69-7.76 (m, 1H) 7.82 (d, J=7.26 Hz, 2H) 8.21 (br. s., 1H) 14.17 (br. s., 1H). m/z (ESI) 606.2 (M+H)$^+$.

Example 84

(P)-1-(3'-(Difluoromethyl)-2,5'-Difluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

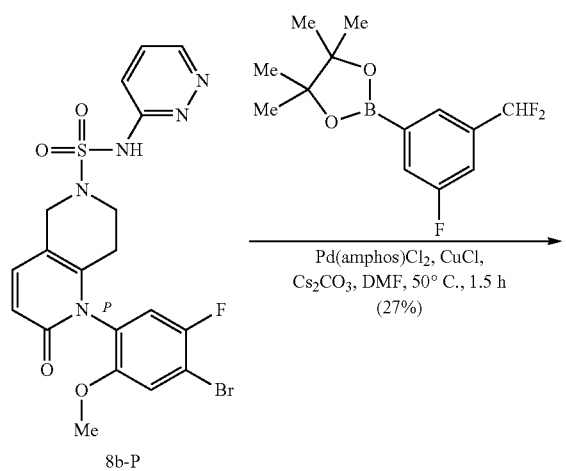

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 2-(3-(difluoromethyl)-5-fluorophenyl)-4,4,5,5-tetramethyl-1,3,2-dioxaborolane (purchased from Chemshuttle Inc.) as the boronic ester. $^1$H NMR (400 MHz, DMSO-d$_6$) δ ppm 14.21 (br. s., 1H) 8.26 (br. s., 1H) 7.86 (br. s., 1H) 7.63-7.81 (m, 3H) 7.55 (d, J=8.71 Hz, 1H) 7.34-7.45 (m, 3H) 7.28 (s, 1H) 7.14 (s, 1H) 7.00 (s, J=6.65 Hz, 1H) 6.39 (d, J=9.38 Hz, 1H) 3.94-4.20 (m, 2H) 3.74-3.89 (m, 3H) 3.25 (br. s., 2H) 2.43 (br. s., 1H) 2.14 (d, J=17.26 Hz, 1H). m/z (ESI) 576.1 (M+H)+.

Example 85

(P)-1-(3'-(Difluoromethyl)-2,4'-Difluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

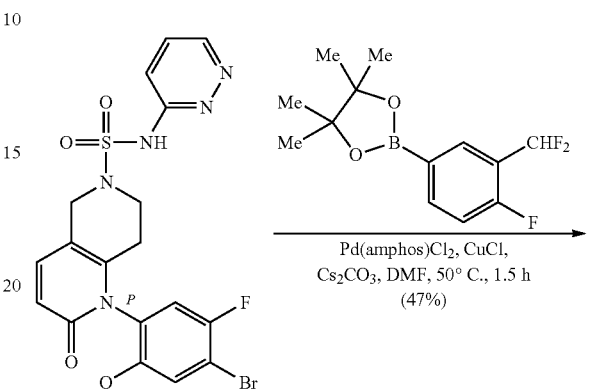

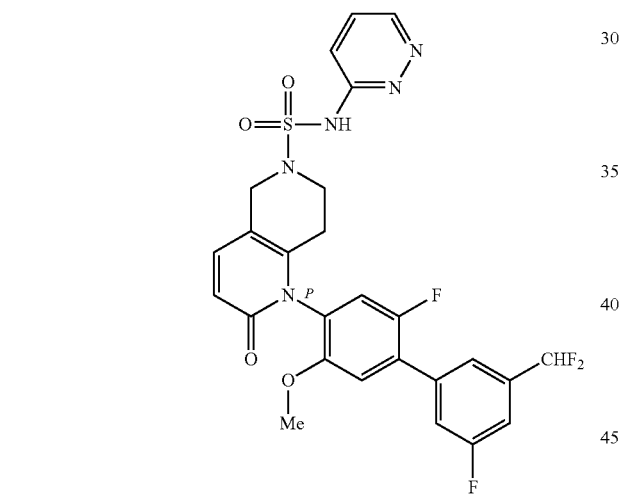

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 2-(3-(difluoromethyl)-4-fluorophenyl)-4,4,5,5-tetramethyl-1,3,2-dioxaborolane, which was prepared below, as the boronic ester. $^1$H NMR (400 MHz, DMSO-d$_6$) δ ppm 14.21 (br. s., 1H) 8.27 (br. s., 1H) 7.89 (d, J=6.01 Hz, 3H) 7.66 (dd, J=9.59, 4.09 Hz, 1H) 7.56 (t, J=9.64 Hz, 1H) 7.11-7.46 (m, 4H) 6.38 (d, J=9.38 Hz, 1H) 3.96-4.16 (m, 2H) 3.81 (s, 3H) 3.25 (br. s., 2H) 2.36-2.49 (m, 1H) 2.03-2.23 (m, 1H). m/z (ESI) 576.2 (M+H)$^+$.

Preparation of 2-(3-(difluoromethyl)-4-fluorophenyl)-4,4,5,5-tetramethyl-1,3,2-dioxaborolane

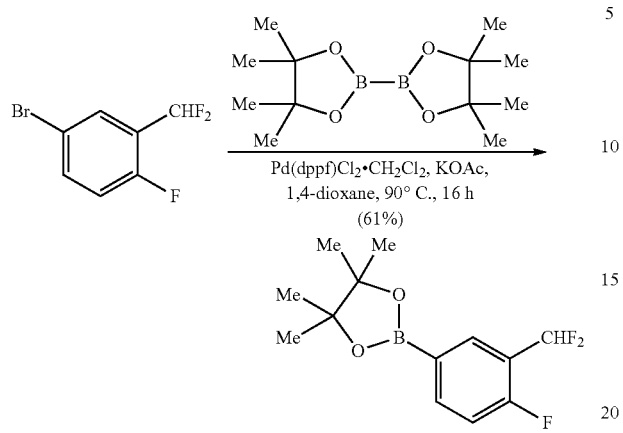

A 500-mL round-bottom flask was charged with 4-bromo-2-(difluoromethyl)-1-fluorobenzene (Combi-Blocks Inc., 10.0 g, 44.4 mmol), bis(pinacolato)diboron (13.5 g, 53.3 mmol), potassium acetate (13.1 g, 133 mmol), 1,1'-bis(diphenylphosphino)ferrocene palladium(II)dichloride dichloromethane adduct (3.63 g, 4.44 mmol), and 1,4-dioxane (150 ml). The reaction mixture was sparged with nitrogen for 15 min then warmed to 90° C. After 16 h, the reaction mixture was allowed to cool to ambient temperature, filtered through a pad of Celite® (3 cm), and the Celite® pad was rinsed with EtOAc (250 mL). The filtrate was concentrated under reduced pressure and purified by flash column chromatography (120-g silica gel Redi-Sep column, eluent: gradient, 0 to 10% EtOAc in hexane) to afford 2-(3-(difluoromethyl)-4-fluorophenyl)-4,4,5,5-tetramethyl-1,3,2-dioxaborolane (7.35 g, 27.0 mmol, 60.8% yield) as yellow oil. $^1$H NMR (400 MHz, DMSO-d$_6$) δ 8.02-7.78 (m, 2H), 7.44-7.02 (m, 2H), 1.30 (s, 12H).

Example 86

(P)-1-(3'-(Difluoromethyl)-2,4',5'-Trifluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

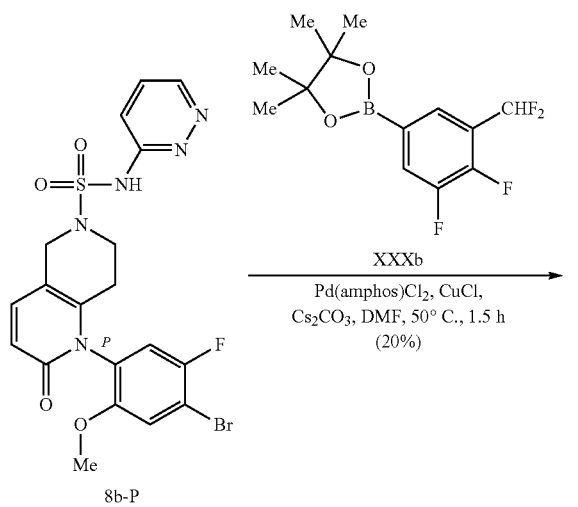

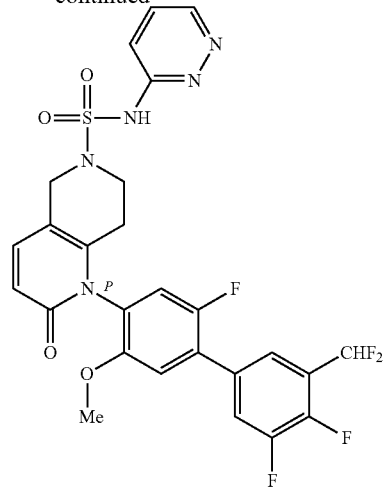

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 2-(3-(difluoromethyl)-4,5-difluorophenyl)-4,4,5,5-tetramethyl-1,3,2-dioxaborolane, prepared below, as the boronic ester. $^1$H NMR (400 MHz, DMSO-d$_6$) δ ppm 14.21 (br. s., 1H) 8.26 (br. s., 1H) 7.99-8.11 (m, 1H) 7.86 (br. s., 1H) 7.62-7.78 (m, 2H) 7.16-7.54 (m, 4H) 6.38 (d, J=9.38 Hz, 1H) 4.07 (d, J=7.26 Hz, 2H) 3.81 (s, 3H) 3.24 (br. s., 2H) 2.44 (d, J=17.26 Hz, 1H) 2.05-2.21 (m, 1H). m/z (ESI) 594.2 (M+H)$^+$.

Preparation of 2-(3-(difluoromethyl)-4,5-difluorophenyl)-4,4,5,5-tetramethyl-1,3,2-dioxaborolane

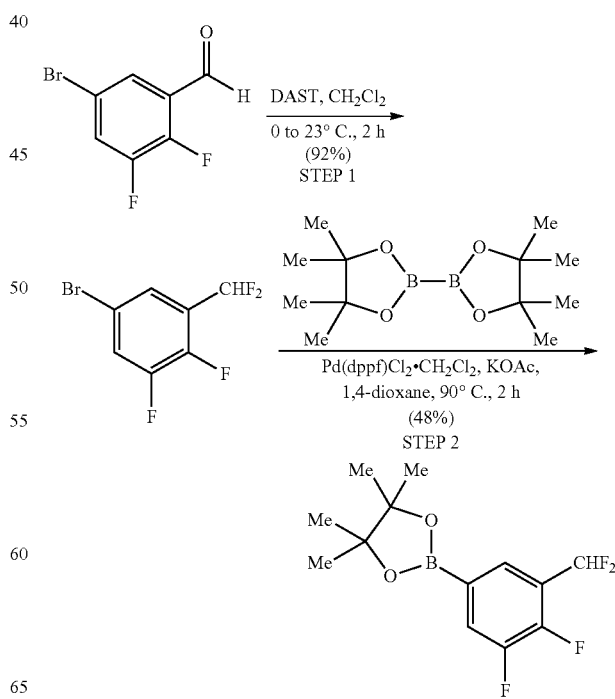

Step-1: 5-Bromo-1-(Difluoromethyl)-2,3-Difluorobenzene

A 250-mL round-bottom flask was charged with 5-bromo-2,3-difluorobenzaldehyde (Biogene Organics, Inc., 10.0 g, 45.2 mmol) and DCM (100 ml) then cooled to −78° C. Diethylaminosulfur trifluoride (23.9 mL, 181 mmol) was added dropwise to the reaction mixture via syringe, which was subsequently allowed to warm to ambient temperature. After 2 h, saturated aqueous sodium bicarbonate was introduced (100 mL) and the layers were separated. The aqueous layer was extracted with DCM (2×100 mL). The combined organic layers were washed with brine (50 mL), dried over sodium sulfate, filtered, concentrated under reduced pressure to afford 5-bromo-1-(difluoromethyl)-2,3-difluorobenzene (10.1 g, 41.6 mmol, 92% yield) as yellow oil, which was used without further purification. $^1$H NMR (400 MHz, Chloroform-d) δ 7.52-7.46 (m, 2H), 6.86 (t, J=54.4 Hz, 1H).

Step-2: 2-(3-(Difluoromethyl)-4,5-Difluorophenyl)-4,4,5,5-Tetramethyl-1,3,2-DIOXABOROLANE A 500-mL round-bottom flask was charged with 5-bromo-1-(difluoromethyl)-2,3-difluorobenzene (10.1 g, 41.6 mmol), bis(pinacolato)diboron (12.7 g, 49.9 mmol), potassium acetate (12.2 g, 125 mmol), 1,1'-bis(diphenylphosphino)ferrocene palladium(II)dichloride dichloromethane adduct (3.39 g, 4.16 mmol), and 1,4-dioxane (150 ml). The reaction mixture was sparged with nitrogen for 15 min then warmed to 90° C. After 2 h, the reaction mixture was allowed to cool to ambient temperature, filtered through a pad of Celite® (3 cm), and the Celite® pad was rinsed with EtOAc (500 mL). The filtrate was concentrated under reduced pressure and purified by flash column chromatography (120-g silica gel Redi-Sep column, eluent: gradient, 0 to 10% EtOAc in hexane) to afford 2-(3-(difluoromethyl)-4,5-difluorophenyl)-4,4,5,5-tetramethyl-1,3,2-dioxaborolane (5.80 g, 20.0 mmol, 48.1% yield) as yellow oil. $^1$H NMR (400 MHz, DMSO-d$_6$) δ 7.83-7.57 (m, 2H), 7.29 (t, J=53.8 Hz, 1H), 1.31 (s, 12H).

Example 87

(P)-1-(4'-(Difluoromethyl)-2,3'-Difluoro-5-Methoxy-[1,1'-Biphenyl]-4-Yl)-2-Oxo-N-(Pyridazin-3-Yl)-1,2,7,8-Tetrahydro-1,6-Naphthyridine-6(5H)-Sulfonamide

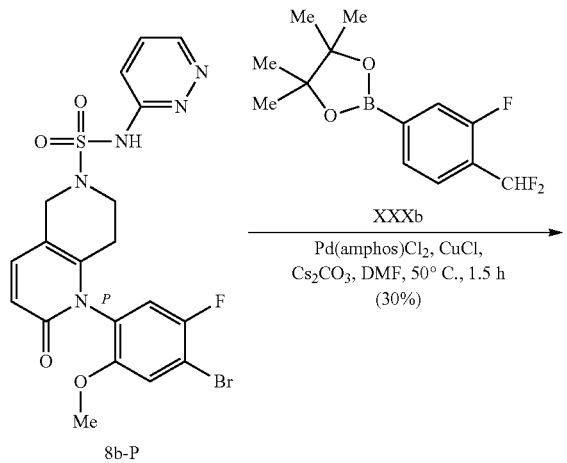

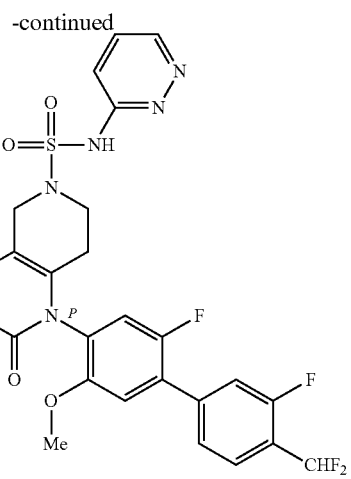

This compound was prepared analogous to the procedure of Example 41 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P) and 2-(4-(difluoromethyl)-3-fluorophenyl)-4,4,5,5-tetramethyl-1,3,2-dioxaborolane, prepared below, as the boronic ester. $^1$H NMR (400 MHz, DMSO-d$_6$) δ ppm 14.20 (br. s., 1H) 8.28 (br. s., 1H) 7.62-7.97 (m, 5H) 7.12-7.49 (m, 4H) 6.39 (d, J=9.43 Hz, 1H) 3.97-4.19 (m, 2H) 3.81 (s, 3H) 3.25 (br. s., 2H) 2.37-2.48 (m, 1H) 2.03-2.24 (m, 1H). m/z (ESI) 576.2 (M+H)$^+$.

Preparation of 2-(4-(difluoromethyl)-3-fluorophenyl)-4,4,5,5-tetramethyl-1,3,2-dioxaborolane

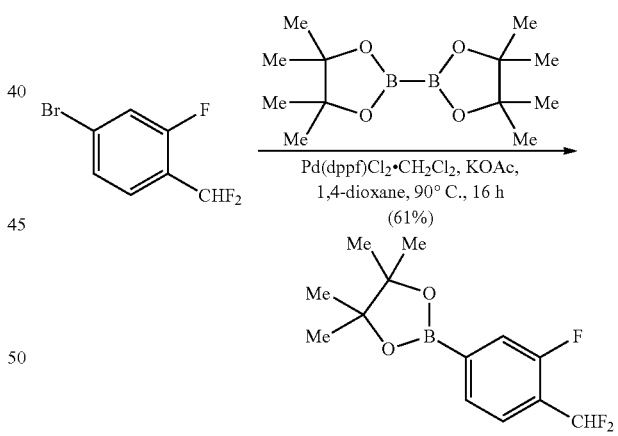

A 500-mL round-bottom flask was charged with 4-bromo-1-(difluoromethyl)-2-fluorobenzene (Combi-Blocks Inc., 10.0 g, 44.4 mmol), bis(pinacolato)diboron (13.5 g, 53.3 mmol), potassium acetate (13.09 g, 133 mmol), 1,1'-bis(diphenylphosphino)ferrocene palladium(II)dichloride dichloromethane adduct (3.63 g, 4.44 mmol), and 1,4-dioxane (150 ml). The reaction mixture was sparged with nitrogen for 15 min then warmed to 90° C. After 16 h, the reaction mixture was allowed to cool to ambient temperature, filtered through a pad of Celite® (3 cm), and the Celite® pad was rinsed with EtOAc (250 mL). The filtrate was concentrated under reduced pressure and purified by flash column chromatography (120-g silica gel Redi-Sep column, eluent:

gradient, 0 to 10% EtOAc in hexane) to afford 2-(4-(difluoromethyl)-3-fluorophenyl)-4,4,5,5-tetramethyl-1,3,2-dioxaborolane (7.35 g, 27.0 mmol, 60.8% yield) as yellow oil. $^1$H NMR (400 MHz, DMSO-d$_6$) δ 7.68-7.61 (m, 2H), 7.48 (dd, J=10.5, 1.2 Hz, 1H), 7.24 (t, J=54.2 Hz, 1H), 1.31 (s, 12H).

Example 88

(P)-2-Oxo-N-(Pyrimidin-4-Yl)-1-(2,3',5'-Trifluoro-5-Methoxy-[1,1'-Biphenyl]-4-Yl)-1,2,7,8-Tetrahydro-1,6-Naphthyridine-6(5H)-Sulfonamide

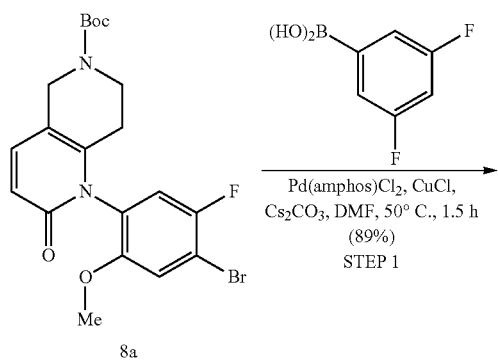

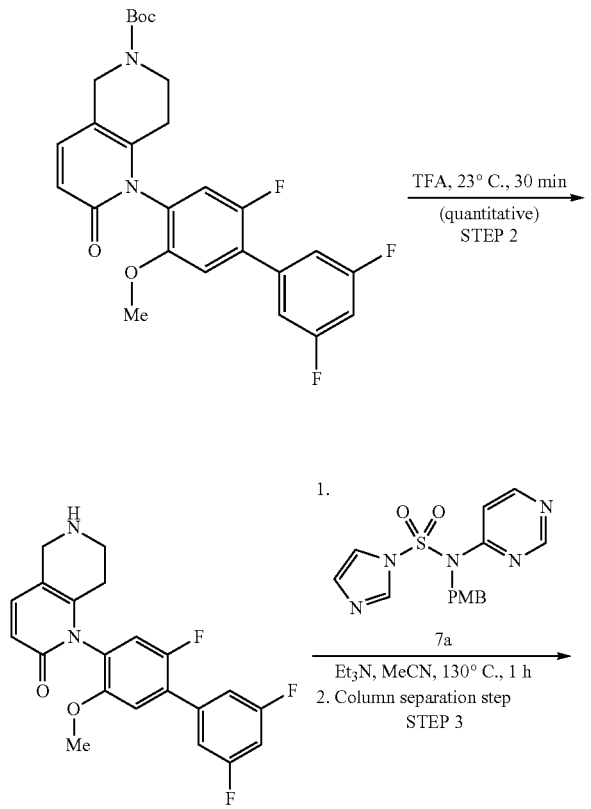

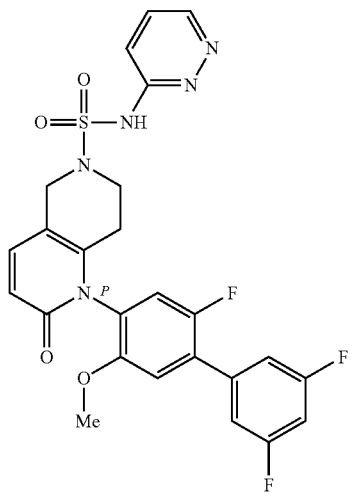

This compound was prepared analogous to the procedure of Example 1 from (Rac)-tert-butyl 1-(4-bromo-5-fluoro-2-methoxyphenyl)-2-oxo-1,2,7,8-tetrahydro-1,6-naphthyridine-6(5H)-carboxylate (See Preparation 8a, step 1). $^1$H NMR (400 MHz, DMSO-d$_6$) δ ppm 8.62 (s, 1H) 8.34 (br. s., 1H) 7.23-7.59 (m, 7H) 6.98 (d, J=4.98 Hz, 1H) 6.39 (d, J=9.43 Hz, 1H) 4.12-4.35 (m, 2H) 3.79 (s, 3H) 3.39 (br. s., 2H) 2.35-2.48 (m, 1H) 2.04-2.20 (m, 1H). m/z (ESI) 544.2 (M+H)$^+$.

Example 89

(P)-N-(Isoxazol-3-YL)-2-Oxo-1-(3'-Chloro-2-Fluoro-5,5'-Dimethoxy-[1,1'Biphenyl]-4-YL)1,5,7,8-Tetrahydro-1,6-Naphthyridine-6(2H)-Sulfonamide

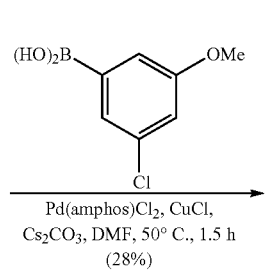

193

-continued

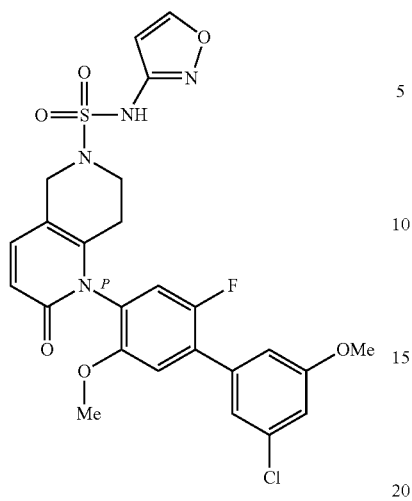

This compound was prepared analogous to the procedure of Example 15 from (P)-1-(4-bromo-5-fluoro-2-methoxyphenyl)-N-(isoxazol-3-yl)-2-oxo-1,2,7,8-tetrahydro-1,6-naphthyriding-6(5H)-sulfonamide (Preparation 8d-P) and (3-chloro-5-methoxyphenyl)boronic acid (purchased from Alfa Asar) as the boronic acid. $^1$H NMR (400 MHz, DMSO-$d_6$) δ ppm 11.17 (s, 1H) 7.11-7.39 (m, 7H) 6.31-6.42 (m, 2H) 4.12-4.33 (m, 2H) 3.86 (s, 3H) 3.79 (s, 3H) 3.36-3.49 (m, 2H). m/z (ESI) 561.0 (M+H)$^+$.

Example 90

(P)-1-(2-Fluoro-3',5,5'-Trimethoxy-[1,1'-Biphenyl]-4-Yl)-N-(Isoxazol-3-Yl)-2-Oxo-1,2,7,8-Tetrahydro-1,6-Naphthyridine-6(5H)-Sulfonamide

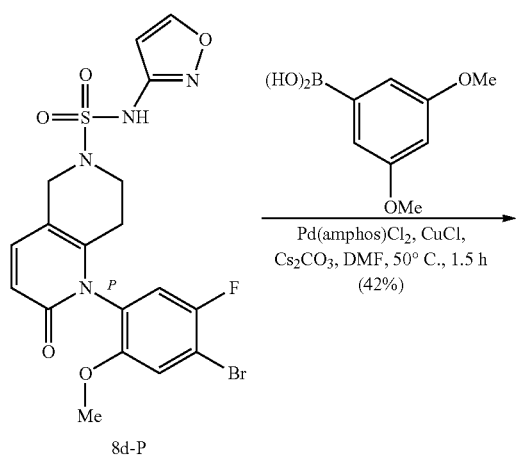

8d-P

194

-continued

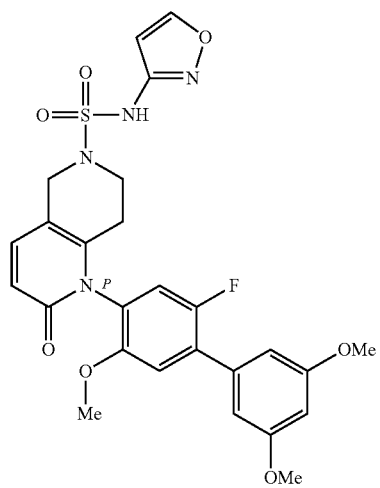

This compound was prepared analogous to the procedure of Example 15 from (P)-1-(4-bromo-5-fluoro-2-methoxyphenyl)-N-(isoxazol-3-yl)-2-oxo-1,2,7,8-tetrahydro-1,6-naphthyriding-6(5H)-sulfonamide (Preparation 8d-P) and (3,5-dimethoxyphenyl)boronic acid (purchased from Sigma-Aldrich Chemical Company, Inc.) as the boronic acid. $^1$H NMR (400 MHz, DMSO-$d_6$) δ ppm 8.64-8.81 (m, 1H) 7.21-7.37 (m, 3H) 6.76 (d, J=1.45 Hz, 2H) 6.58-6.64 (m, 1H) 6.34-6.41 (m, 2H) 4.15-4.31 (m, 2H) 3.75-3.87 (m, 9H) 3.36-3.49 (m, 2H) 2.40-2.48 (m, 1H) 2.01-2.16 (m, 1H). m/z (ESI) 557.0 (M+H)+.

Example 91

(Rac)-; (P)-; and (M)-1-(2-Chloro-5-Methoxy-3'-(Trifluoromethyl)-[1,1'-Biphenyl]-4-Yl)-2-Oxo-N-(Pyridazin-3-Yl)-1,2,7,8-Tetrahydro-1,6-Naphthyridine-6(5H)-Sulfonamide

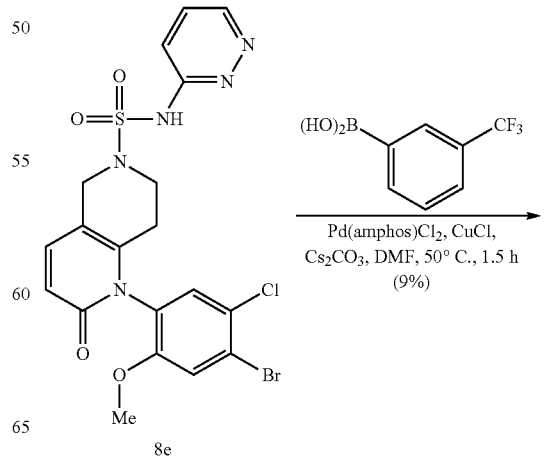

8e

-continued

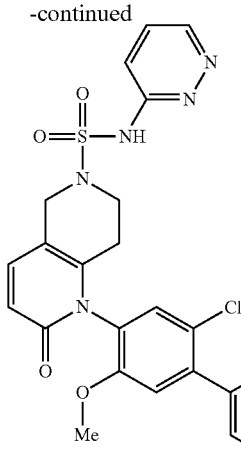

A 4-mL vial was charged with (Rac)-1-(4-bromo-5-chloro-2-methoxyphenyl)-2-oxo-N-(pyridazin-3-yl)-1,2,7,8-tetrahydro-1,6-naphthyridine-6(5H)-sulfonamide (Preparation 8e, 250 mg, 0.475 mmol), (3-(trifluoromethyl)phenyl)boronic acid (Chem-Implex, 270 mg, 1.424 mmol), cesium carbonate (618 mg, 1.90 mmol), copper chloride (141 mg, 1.42 mmol), and 1,1-bis[(di-t-butyl-p-methylaminophenyl] palladium(II) chloride (101 mg, 0.14 mmol), then purged with nitrogen. DMF (4.7 mL) was introduced, the vial was sealed with a PTFE line cap, and the resultant orange reaction mixture was warmed to 50° C. After 1.5 h, the reaction mixture was allowed to cool to ambient temperature and diluted with aqueous HCl solution (1.0 M, 5 mL) and EtOAc (5 mL). The layers were separated and the aqueous layer extracted with additional EtOAc (2×5 mL). The combined organic layers were, dried over anhydrous magnesium sulfate, filtered, concentrated under reduced pressure and purified reverse phase HPLC in 2 separate injections (XBridge Prep Shield RP18 19×100 mm Mobile phase: 0.1% formic acid in water/acetonitrile Flow rate: 40 ml/min Inj: 1000 uL Gradient: 12 min 25-70%). The fractions containing product were frozen and lyophilized to afford (Rac)-1-(2-chloro-5-methoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide (25 mg, 0.04 mmol, 8.90% yield) as an off-white solid. $^1$H NMR (400 MHz, DMSO-$d_6$) δ ppm 14.24 (br. s., 1H) 8.25 (br. s., 1H) 7.82-7.93 (m, 4H) 7.75-7.80 (m, 1H) 7.68 (dd, J=9.48, 4.09 Hz, 1H) 7.56 (s, 1H) 7.39 (d, J=9.74 Hz, 1H) 7.32 (s, 1H) 6.40 (d, J=9.33 Hz, 1H) 3.95-4.22 (m, 2H) 3.81 (s, 3H) 3.25 (br. s., 2H) 2.44 (d, J=10.57 Hz, 1H) 2.19 (br. s., 1H). m/z (ESI) 592.0 (M+H)$^+$.

Separation Step: Racemic product of Example 91-Rac was subjected to chiral SFC (Regis Whelk-O (s,s), 45% methanol) to give (Example 91-P) (peak 1) and (Example 91-M) (peak 2) as an off-white solids.

Example 92

(Rac)-; (P)-; and (M)-1-(2-Chloro-4'-Fluoro-5-Methoxy-3'-Methyl-[1,1'-Biphenyl]-4-Yl)-2-Oxo-N-(Pyridazin-3-Yl)-1,2,7,8-Tetrahydro-1,6-Naphthyridine-6(5H)-Sulfonamide

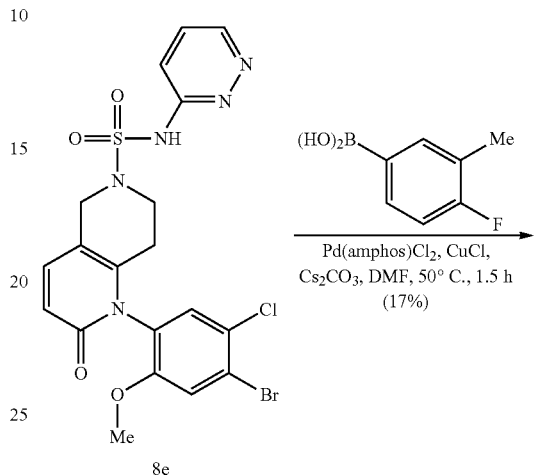

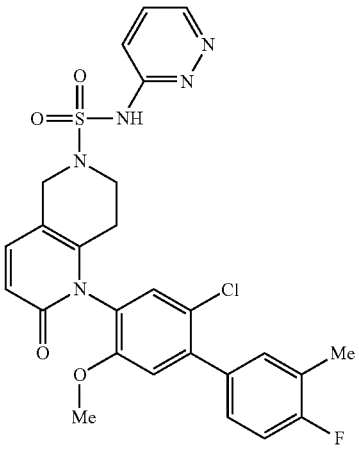 [SMILES: COc1cc(-c2ccc(F)c(C)c2)c(C)cc1-n1c2c(ccc1=O)CN(S(=O)(=O)Nc1cccnn1)CC2]

This compound was prepared analogous to the procedure of Example 91 from (Rac)-1-(4-bromo-5-chloro-2-methoxyphenyl)-2-oxo-N-(pyridazin-3-yl)-1,2,7,8-tetrahydro-1,6-naphthyridine-6(5H)-sulfonamide (Preparation 8e) and (4-fluoro-3-methylphenyl)boronic acid (purchased from Acros Organics) as the boronic acid. $^1$H NMR (400 MHz, DMSO-$d_6$) δ ppm 14.24 (br. s., 1H) 8.25 (br. s., 1H) 7.87 (br. s., 1H) 7.67 (dd, J=9.48, 4.51 Hz, 1H) 7.44-7.53 (m, 2H) 7.35-7.42 (m, 2H) 7.29 (d, J=9.64 Hz, 1H) 7.21 (s, 1H) 6.39 (d, J=9.54 Hz, 1H) 3.94-4.19 (m, 2H) 3.70-3.86 (m, 3H) 3.24 (br. s., 2H) 2.44 (d, J=17.73 Hz, 1H) 2.32 (d, J=1.45 Hz, 3H) 2.08-2.23 (m, 1H). m/z (ESI) 556.2 (M+H)$^+$.

Separation Step: Racemic product of Example 92 was subjected to chiral SFC (Regis Whelk-O (s,s), 45% methanol) to give (Example 92-P) (peak 1) and (Example 92-M) (peak 2) as an off-white solids.

Example 93

(Rac)-; (P)-; and (M)-1-(4'-Fluoro-5-Methoxy-2,3'-Dimethyl-[1,1'-Biphenyl]-4-Yl)-2-Oxo-N-(Pyridazin-3-Yl)-1,2,7,8-Tetrahydro-1,6-Naphthyridine-6(5H)-Sulfonamide

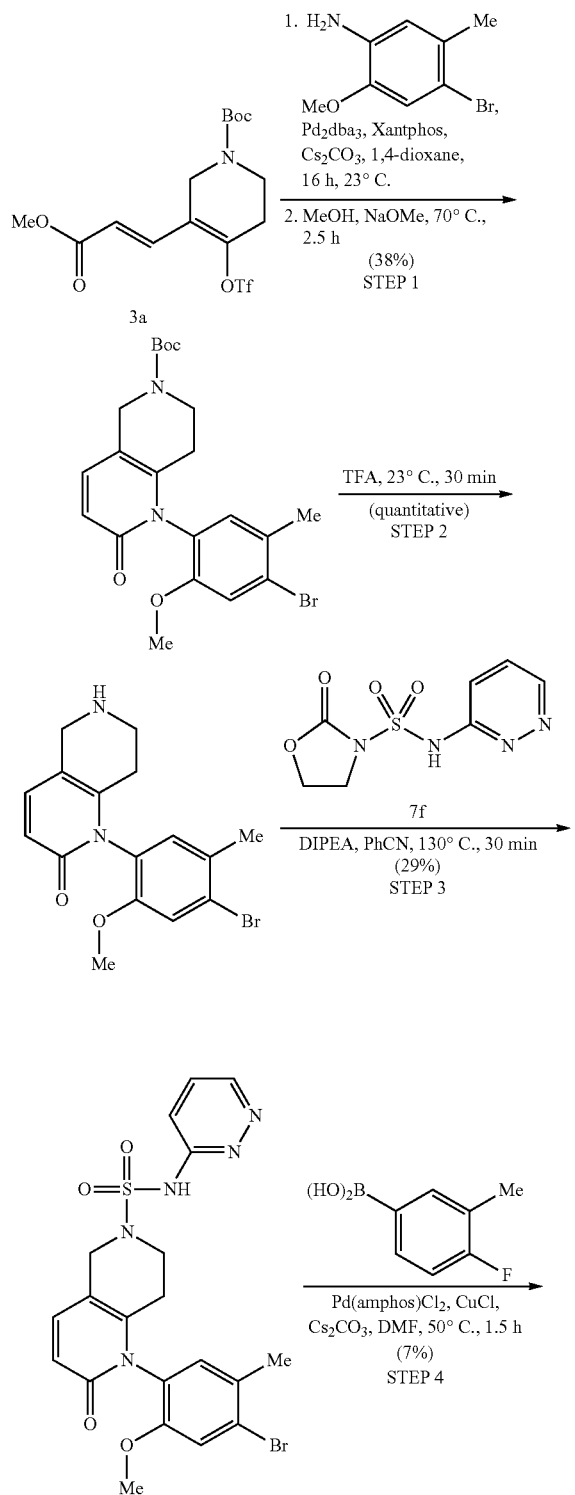

Step 1: (Rac)-tert-Butyl 1-(4-Bromo-2-Methoxy-5-Methylphenyl)-2-Oxo-1,2,7,8-Tetrahydro-1,6-Naphthyridine-6(5H)-Carboxylate A 250-mL round-bottom flask was charged with (E)-tert-butyl 3-(3-methoxy-3-oxoprop-1-en-1-yl)-4-(((trifluoromethyl)sulfonyl)oxy)-5,6-dihydropyridine-1(2H)-carboxylate (Preparation 3a, 4.56 g, 11.0 mmol), xantphos (0.79 g, 1.37 mmol), cesium carbonate (10.7 g, 32.9 mmol), 4-bromo-2-methoxy-5-methylaniline (Acros Organics, 2.37 g, 11.0 mmol), tris(dibenzylideneacetone)dipalladium (0) (0.50 g, 0.55 mmol) and 1,4-dioxane (55 mL) then sparged with nitrogen for 15 min. The reaction mixture stirred vigorously for 16 h at ambient temperature. The reaction mixture was subsequently vacuum filtered through a 1.0 cm plug of silica gel and the pad was rinsed with EtOAc (3×50 mL). The filtrate was concentrated under reduced pressure to give a brown foam that was used immediately without further purification.

The brown foam was diluted with MeOH (110 mL) and transferred to a 350-mL pressure vessel equipped with a stir bar. The reaction vessel was subsequently charged with sodium methoxide (25 wt. % in MeOH, 1.25 ml, 5.48 mmol) and sealed with a Teflon cap equipped with a pressure-relief valve. The reaction vessel was placed in a 70° C. oil bath and stirred vigorously. After 2.5 h, the reaction mixture was allowed to cool to ambient temperature, transferred to a 250-mL round-bottom flask with additional MeOH and concentrated under reduced pressure. The brown oil was redissolved in DCM (50 mL) and filtered through a pad of Celite® (3 cm) to facilitate loading the material onto a column. The Celite® pad was rinsed with DCM (3×50 mL). The brown filtrate was concentrated under reduced pressure and purified by flash column chromatography (100-g Biotage column, eluent: gradient, 0 to 35% 3:1 EtOAc/EtOH in heptane with DCM as a 10% additive) to afford (Rac)-tert-butyl 1-(4-bromo-2-methoxy-5-methylphenyl)-2-oxo-1,2,7,8-tetrahydro-1,6-naphthyridine-6(5H)-carboxylate (1.87 g, 4.16 mmol, 37.9% yield) as a tan foam. $^1$H NMR (400 MHz, DMSO-$d_6$) δ=7.42 (s, 1H), 7.39-7.32 (m, 1H), 7.39-7.32 (m, 1H), 7.39-7.32 (m, 1H), 7.25-7.18 (m, 1H), 7.25-7.18 (m, 1H), 7.22 (s, 1H), 6.37 (d, J=9.4 Hz, 1H), 4.27 (s, 2H), 3.73 (s, 3H), 3.57-3.36 (m, 2H), 2.35-2.17 (m, 4H), 2.08-1.89 (m, 1H), 1.41 (s, 9H). m/z (ESI) 449.0 (M+H)$^+$.

Step 2: (Rac)-1-(4-Bromo-2-Methoxy-5-Methylphenyl)-5,6,7,8-Tetrahydro-1,6-Naphthyridin-2(1H)-One A 40-mL vial was charged with (Rac)-tert-butyl 1-(4-bromo-2-methoxy-5-methylphenyl)-2-oxo-1,2,7,8-tetrahydro-1,6-naphthyridine-6(5H)-carboxylate (1.87 g, 4.16 mmol) and trifluoroacetic acid (20.8 mL) then stirred for 30 min at ambient temperature. The reaction mixture was concentrated under reduced pressure, dissolved in DCM (50 mL) and carefully poured into saturated aqueous sodium bicarbonate solution (50 mL). The layers were separated and the aqueous layer extracted with additional DCM (3×50 mL). The combined organic layers were dried over anhydrous magnesium sulfate, filtered, concentrated under reduced pressure to afford (Rac)-1-(4-bromo-2-methoxy-5-methylphenyl)-5,6,7,8-tetrahydro-1,6-naphthyridin-2(1H)-one (1.45 g, 4.15 mmol, quantitative) as a tan foam which was used without further purification. $^1$H NMR (400 MHz, DMSO-$d_6$) δ=7.41 (s, 1H), 7.23 (d, J=9.3 Hz, 1H), 7.15 (d, J=0.6 Hz, 1H), 6.30 (d, J=9.3 Hz, 1H), 3.73 (s, 3H), 3.66-3.49 (m, 2H), 2.80 (dt, J=1.9, 5.8 Hz, 2H), 2.29 (s, 3H), 2.15-1.98 (m, 1H), 1.87 (td, J=5.6, 17.4 Hz, 1H). m/z (ESI) 349.0 (M+H)$^+$.

Step 3: (Rac)-1-(4-Bromo-2-Methoxy-5-Methylphenyl)-2-Oxo-N-(Pyridazin-3-Yl)-1,2,7,8-Tetrahydro-1,6-Naphthyridine-6(5H)-Sulfonamide A 25-mL sealed tube was charged with 1-(4-bromo-2-methoxy-5-methylphenyl)-5,6,7,8-tetrahydro-1,6-naphthyridin-2(1H)-one (1.45 g, 4.15 mmol), 2-oxo-N-(pyridazin-3-yl)oxazolidine-3-sulfonamide (Preparation 7f, 2.028 g, 8.30 mmol), N,N-diisopropylethylamine (5.06 ml, 29.1 mmol), and benzonitrile (8.30 ml). The reaction vessel was sealed and warmed to 130° C. After 30 min, the reaction mixture was cooled to ambient temperature and transferred to a 100-mL round-bottomed flask and concentrated under reduced pressure (1 mbar at 80-90° C.). The resultant black oil was diluted with DCM (50 mL) and washed with a solution of aqueous HCl (1.0 M, 50 mL). The aqueous layer was back-extracted with DCM (3×25 mL). The combined organic layers were dried over magnesium sulfate, filtered, concentrated under reduced pressure, and purified (100-g silica gel Grace, 0 to 10% MeOH in DCM) to afford (Rac)-1-(4-bromo-2-methoxy-5-methylphenyl)-2-oxo-N-(pyridazin-3-yl)-1,2,7,8-tetrahydro-1,6-naphthyridine-6(5H)-sulfonamide (607 mg, 1.20 mmol, 28.9% yield) as a brown solid. $^1$H NMR (400 MHz, DMSO-$d_6$) δ=8.34 (d, J=2.9 Hz, 1H), 7.83 (dd, J=1.4, 9.6 Hz, 1H), 7.69 (dd, J=4.1, 9.5 Hz, 1H), 7.42 (s, 1H), 7.36 (d, J=9.4 Hz, 1H), 7.19 (d, J=0.6 Hz, 1H), 6.35 (d, J=9.3 Hz, 1H), 4.14-3.99 (m, 2H), 3.73 (s, 3H), 3.22 (t, J=6.0 Hz, 2H), 2.39-2.25 (m, 4H), 2.14-2.01 (m, 1H). m/z (ESI) 508.0 (M+H)$^+$.

Step 4: (Rac)-1-(4'-Fluoro-5-Methoxy-2,3'-Dimethyl-[1,1'-Biphenyl]-4-Yl)-2-Oxo-N-(Pyridazin-3-Yl)-1,2,7,8-Tetrahydro-1,6-Naphthyridine-6(5H)-Sulfonamide A 4-mL vial was charged with (Rac)-1-(4-bromo-2-methoxy-5-methylphenyl)-2-oxo-N-(pyridazin-3-yl)-1,2,7,8-tetrahydro-1,6-naphthyridine-6(5H)-sulfonamide (200 mg, 0.395 mmol), (4-fluoro-3-methylphenyl)boronic acid (Acros Organics, 182 mg, 1.185 mmol), cesium carbonate (515 mg, 1.58 mmol), copper chloride (117 mg, 1.19 mmol), and 1,1-bis[(di-t-butyl-p-methylaminophenyl]palladium(II) chloride (84 mg, 0.19 mmol), then purged with nitrogen. DMF (4.0 mL) was introduced, the vial was sealed with a PTFE line cap, and the resultant orange reaction mixture was warmed to 50° C. After 1.5 h, the reaction mixture was allowed to cool to ambient temperature and diluted with aqueous HCl solution (1.0 M, 5 mL) and EtOAc (5 mL). The layers were separated and the aqueous layer extracted with additional EtOAc (2×5 mL). The combined organic layers were dried over anhydrous magnesium sulfate, filtered, concentrated under reduced pressure and purified reverse phase HPLC in 2 separate injections (XBridge Prep Shield RP18 19×100 mm Mobile phase: 0.1% formic acid in water/acetonitrile Flow rate: 40 ml/min Inj: 1000 uL Gradient: 12 min 25-70%). The fractions containing product were frozen and lyophilized to afford (Rac)-1-(4'-fluoro-5-methoxy-2,3'-dimethyl-[1,1'-biphenyl]-4-yl)-2-oxo-N-(pyridazin-3-yl)-1,2,7,8-tetrahydro-1,6-naphthyridine-6(5H)-sulfonamide (15.2 mg, 0.028 mmol, 7.19% yield) as an off-white solid. $^1$H NMR (400 MHz, DMSO-$d_6$) δ ppm 14.24 (br. s., 1H) 8.25 (br. s., 1H) 7.87 (br. s., 1H) 7.67 (dd, J=9.59, 4.09 Hz, 1H) 7.33-7.42 (m, 2H) 7.17-7.32 (m, 2H) 7.08 (s, 1H) 6.99 (s, 1H) 6.37 (d, J=9.54 Hz, 1H) 4.06 (br. s., 2H) 3.73 (s, 3H) 3.23 (br. s., 2H) 2.30-2.44 (m, 4H) 2.18 (s, 3H). m/z (ESI) 536.2 (M+H)$^+$.

Separation Step: Racemic product of Example 93 was subjected to chiral SFC (Regis Whelk-O (s,s), 45% methanol) to give (Example 93-P) (peak 1) and (Example 93-M) (peak 2) as an off-white solids.

Example 94

(P)-1-(5-Fluoro-2-Methoxy-4-(3,3,3-Trifluoropropyl)Phenyl)-N-(Isoxazol-3-Yl)-2-Oxo-1,2,7,8-Tetrahydro-1,6-Naphthyridine-6(5H)-Sulfonamide

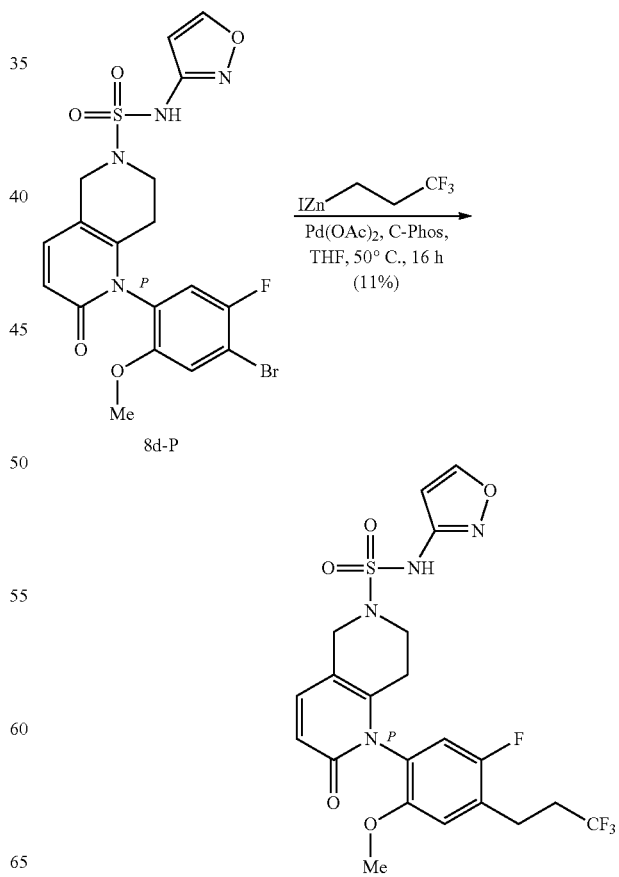

A 4-mL vial was charged with (P)-1-(4-bromo-5-fluoro-2-methoxyphenyl)-N-(isoxazol-3-yl)-2-oxo-1,2,7,8-tetrahydro-1,6-naphthyridine-6(5H)-sulfonamide (Preparation 8d-P, 85.0 mg, 0.17 mmol), palladium(II) acetate (2.29 mg, 10.2 μmol), and 2'-(dicyclohexylphosphino)-N2,N2,N6,N6-tetramethyl-[1,1'-biphenyl]-2,6-diamine (C-Phos) (8.92 mg, 0.02 mmol), then purged with nitrogen for 15 min. (3,3,3-Trifluoropropyl)zinc(II) iodide solution in THF (Rieke Metals, Inc., 0.5 M, 1.42 mL, 0.68 mmol) was introduced, the vial was sealed with a PTFE line cap, and the resultant reaction mixture was warmed to 50° C. After 16 h, the reaction mixture was allowed to cool to ambient temperature and diluted with aqueous HCl solution (1.0 M, 5 mL) and EtOAc (5 mL). The layers were separated and the aqueous layer extracted with additional EtOAc (2×5 mL). The combined organic layers were, dried over anhydrous magnesium sulfate, filtered, concentrated under reduced pressure, diluted with DMSO and filtered through a 0.45 micron filter. The filtrate was purified by reverse phase HPLC in 2 separate injections (XBridge Prep Shield RP18 19×100 mm Mobile phase: 0.1% formic acid in water/acetonitrile Flow rate: 40 ml/min Inj: 1000 uL Gradient: 12 min 25-70%). The fractions containing product were frozen and lyophilized to afford (P)-1-(5-fluoro-2-methoxy-4-(3,3,3-trifluoropropyl)phenyl)-N-(isoxazol-3-yl)-2-oxo-1,2,7,8-tetrahydro-1,6-naphthyridine-6(5H)-sulfonamide (10.0 mg, 0.02 mmol, 11.4% yield) as an orange solid. $^1$H NMR (400 MHz, DMSO-$d_6$) δ ppm 11.13 (s, 1H) 8.73 (d, J=1.71 Hz, 1H) 7.30 (d, J=9.48 Hz, 1H) 7.25 (d, J=6.74 Hz, 1H) 7.11 (d, J=9.64 Hz, 1H) 6.27-6.40 (m, 2H) 4.12-4.28 (m, 2H) 3.70 (s, 3H) 3.36-3.43 (m, 2H) 2.82-2.96 (m, 2H) 2.59-2.76 (m, 2H) 2.28-2.41 (m, 1H) 1.94-2.06 (m, 1H). m/z (ESI) 517.1 (M+H)$^+$.

Example 95

(P)-1-(5-Fluoro-2-Methoxy-4-(3,3,3-Trifluoropropyl)Phenyl)-2-Oxo-N-(Pyridazin-3-Yl)-1,2,7,8-Tetrahydro-1,6-Naphthyridine-6(5H)-Sulfonamide

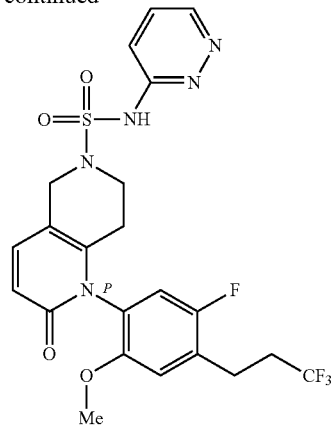

This compound was prepared analogous to the procedure of Example 94 from (P)-1-(4-bromo-5-fluoro-2-methoxyphenyl)-2-oxo-N-(pyridazin-3-yl)-1,2,7,8-tetrahydro-1,6-naphthyridine-6(5H)-sulfonamide (Preparation 8b-P, 200 mg, 0.392 mmol) and 2'-(dicyclohexylphosphino)-N2,N2,N6,N6-tetramethyl-[1,1'-biphenyl]-2,6-diamine (C-Phos) (20.5 mg, 0.05 mmol) to afford (P)-1-(5-fluoro-2-methoxy-4-(3,3,3-trifluoropropyl)phenyl)-2-oxo-N-(pyridazin-3-yl)-1,2,7,8-tetrahydro-1,6-naphthyridine-6(5H)-sulfonamide (12 mg, 0.023 mmol, 5.80% yield) as a off-white solid. $^1$H NMR (400 MHz, DMSO-$d_6$) δ ppm 8.27 (br. s., 1H) 7.83 (br. s., 1H) 7.65 (dd, J=9.59, 4.09 Hz, 1H) 7.34 (d, J=9.43 Hz, 1H) 7.26 (d, J=6.74 Hz, 1H) 7.17 (d, J=9.69 Hz, 1H) 6.34 (d, J=9.38 Hz, 1H) 3.94-4.17 (m, 2H) 3.72 (s, 3H) 3.22 (br. s., 2H) 2.83-2.97 (m, 2H) 2.59-2.77 (m, 2H) 2.35 (d, J=17.83 Hz, 1H) 2.06 (d, J=18.92 Hz, 1H). m/z (ESI) 528.0 (M+H)$^+$.

Example 96

(Rac)-; (P)-; and (M)-1-(5-Chloro-2-Methoxy-4-(3,3,3-Trifluoropropyl)Phenyl)-2-Oxo-N-(Pyridazin-3-Yl)-1,2,7,8-Tetrahydro-1,6-Naphthyridine-6(5H)-Sulfonamide

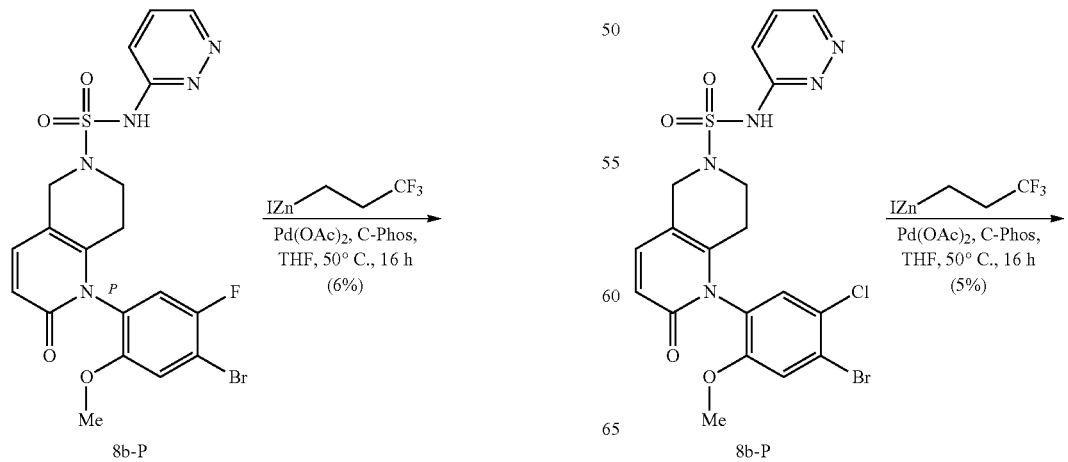

-continued

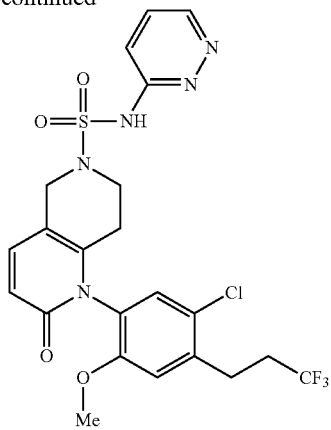

This compound was prepared analogous to the procedure of Example 94 from (Rac)-1-(4-bromo-5-chloro-2-methoxyphenyl)-2-oxo-N-(pyridazin-3-yl)-1,2,7,8-tetrahydro-1,6-naphthyridine-6(5H)-sulfonamide (Preparation 8e, 300 mg, 0.569 mmol) and 2'-(dicyclohexylphosphino)-N2,N2,N6,N6-tetramethyl-[1,1'-biphenyl]-2,6-diamine (C-Phos) (29.8 mg, 0.07 mmol) to afford (Rac)-1-(5-chloro-2-methoxy-4-(3,3,3-trifluoropropyl)phenyl)-2-oxo-N-(pyridazin-3-yl)-1,2,7,8-tetrahydro-1,6-naphthyridine-6(5H)-sulfonamide (15 mg, 0.028 mmol, 4.8% yield) as an off-white solid. $^1$H NMR (400 MHz, DMSO-d$_6$) δ ppm 8.71 (dd, J=4.09, 1.40 Hz, 1H) 8.09 (dd, J=9.43, 1.35 Hz, 1H) 7.94 (dd, J=9.49, 4.15 Hz, 1H) 7.74-7.82 (m, 2H) 7.69 (s, 1H) 6.91 (d, J=9.43 Hz, 1H) 4.61 (s, 2H) 4.30 (s, 3H) 3.80 (t, J=5.93 Hz, 2H) 3.53-3.64 (m, 1H) 3.36 (q, J=7.17 Hz, 1H) 3.00-3.21 (m, 1H) 2.82-2.97 (m, 1H) 2.63-2.77 (m, 1H). m/z (ESI) 544.0 (M+H)$^+$.

Separation Step: Racemic product of Example 96 was subjected to chiral SFC (Regis Whelk-O (s,s), 40% methanol) to give (Example 96-P) (peak 1) and (Example 96-M) (peak 2) as an off-white solids.

Biological Examples

The following assays were used in testing the exemplary compounds of the invention. Data for those examples tested in accordance with the procedures described below are presented in Table A below.

Nav 1.7 or Nav 1.5 IWQ In Vitro Assay

HEK293 cells stably transfected with either human Nav 1.7 or human Nav 1.5 were recorded in population patch-clamp mode with the IonWorks® Quattro automated electrophysiology system (Molecular Devices, LLC, Sunnyvale, Calif.). Cells were voltage clamped to −110 mV for three seconds (Nav 1.7) or half a second (Nav 1.5) and sodium currents were elicited by a train of 26 depolarizations of 150 msec duration to −20 mV (Nav 1.7) or 0 mV (Nav 1.5) at a frequency of 5 Hz. Cells were then left unclamped for a period of 5 to 8 minutes while a single concentration of test compound was added. Following this compound incubation period, cells were then reclamped to −110 mV for three seconds (Nav1.7) or half a second (Nav1.5) to recover unbound channels and put through the same 26 pulse voltage protocol as above. Peak inward current during the 26$^{th}$ pulse to −20 mV (Nav 1.7) or 0 mV (Nav 1.5) in the presence of compound was divided by the peak inward current evoked by the 26$^{th}$ pulse to −20 mV (Nav1.7) or 0 mV (Nav1.5) in the absence of compound to determine percent inhibition. Concentration-response curves of percent.

Nav 1.7 In Vitro PatchXpress (PX) Assay

HEK 293 cells stably transfected with human Nav1.7 were recorded in whole cell voltage clamp mode with the PatchXpress automated electrophysiology system (Molecular Devices, LLC, Sunnyvale, Calif.). Compound effects were measured on a partially inactivated state of the sodium channel. Cells were clamped to a holding potential yielding 20 to 50% inactivation. To elicit sodium current, channels were activated by pulsing to −10 mV for 20 msec. This voltage protocol was repeated at a rate of 0.1 Hz throughout the experiment. A single concentration of test compound was applied to cells for a duration of 3 minutes. Peak sodium current was measured at the end of the compound addition period to determine percent inhibition. Three to five cells were tested per concentration, and IC$_{50}$ curves were fitted to percent inhibition as a function of concentration. Data for compounds representative of the invention are presented in Table A herein.

Nav 1.5 In Vitro PX Assay 293 cells stably transfected with human Nav 1.5 were recorded in whole cell voltage clamp mode with the PatchXpress automated electrophysiology system according to the manufacturer's specifications (Molecular Devices, LLC, Sunnyvale, Calif.). Cells were held at a holding potential of −50 mV to inactivate sodium channels. To elicit sodium currents the voltage was changed to −120 mV to recover a portion of the channels, followed by delivery of test pulses of 20 msec duration to 0 mV, at 0.1 Hz. A single concentration of test compound was applied to cells for a duration of 5 minutes. Peak sodium current was measured at the end of the compound addition period to determine percent inhibition. A minimum of two cells were tested per concentration. IC$_{50}$ curves were fitted to percent inhibition as a function of concentration. Data for compounds representative of the invention are presented in the Table A herein.

The compounds of the present invention may also be tested in the following in vivo assays.

Rat Formalin Model of Persistent Pain

On the test day, animals (Naïve, male Sprague Dawley rats) weighing between 260-300 g at the start of testing can be obtained from Harlan (Indianapolis, Ind.). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hindpaw exposed. A dilute solution of formalin (2.5%) in phosphate buffered saline can be injected subcutaneously into the dorsal surface of the left hindpaw in a volume to 50 μL with a 30 g needle. Immediately following injection, a small metal band can be affixed to the plantar side of the left hindpaw with a drop of LOCTITE (adhesive). Animals may be then placed into the testing chambers and the number of flinches can be recorded between 10 to 40 minutes after formalin injection. A flinch is defined as a quick and spontaneous movement of the injected hindpaw not associated with ambulation. Flinches can be quantified with the aid of the Automated Nociception Analyzer built by the University of California, San Diego Department of Anesthesiology. Individual data can be expressed as a % maximal potential effect (% MPE) calculated with the following formula: (–(Individual score–Vehicle average score)/Vehicle average score))*100=% MPE Statistical analysis can be performed by analysis of variance (ANOVA), with post-hoc analysis using Bonferroni compared to the vehicle group for a significant main effect. Data can be represented as mean % MPE +/–standard error for each group.

Rat Open Field Assay

On the test day, animals (Naïve, male Sprague Dawley rats) weighing between 260-300 g at the start of testing may be obtained from Harlan (Indianapolis, Ind.). All animals can be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. In a room separate from the testing room, animals can be pretreated with the appropriate test compound either by oral gavage or intraperitoneal injection at the desired pretreatment time (typically two hours before test onset) and then can be returned to their home cages until the pretreatment has elapsed. At test time, animal can be transferred to the open field testing room in their home cages. Each animal may be placed in a separate testing chamber and the motion tracking system is started. The house lights in the testing room should be turned off and the animals can be allowed to explore the novel open field for 30 minutes. An automated motion tracker, made by San Diego Instruments, San Diego, Calif., can be used to capture animal exploration with the aid of infrared photo beams to detect animal movement. These behaviors include basic movement and vertical rearing, which can be used as the primary endpoints for this assay. At the end of the test, house lights can be turned on and the animals should be removed from the testing apparatus. Data can be expressed as a percent change from the vehicle control using the following equation.

(1–(Test mean/Vehicle mean))*100=% Change.

Statistical analysis can be performed by analysis of variance (ANOVA), with post-hoc analysis using Dunnett to follow up significant main effects.

Mouse Formalin Model of Persistent Pain

Mice (Naïve, male C57Bl/6) weighing between 22-30 g at the start of testing were obtained from Harlan (Indianapolis, Ind.). All animals were housed under a 12/12 h light/dark cycle with lights on at 0630. Mice were singly housed on solid bottom cages with corn cob bedding and had access to food and water ad libitum. Animals were allowed to habituate to the vivarium for at least five days before testing was begun and were brought into the testing room at least 30 minutes prior to dosing. Animals were pretreated with the appropriate test compound either by oral gavage or intraperitoneal injection at the desired pretreatment time (typically two hours before test onset) and then returned to their home cages. After dosing and at least 5 minutes prior to test onset, animals were acclimated to the individual testing chambers. At test time, each animal was gently wrapped in a cloth glove with the left hind paw exposed. A dilute solution of formalin (2%) in phosphate buffered saline was injected subcutaneously into the dorsal surface of the left hind paw in a volume to 20 μL with a 30 g needle. Animals were then placed into the observation chambers and the behaviors were recorded for 60 minutes following the formalin injection. A pain-like behavior was defined as licking and/or non-weight bearing of the injected hind paw not associated with ambulation.

Statistical analysis was performed by analysis of variance (ANOVA), with post-hoc analysis using the Dunnett post-hoc test compared to the vehicle group for any significant main effect. Data were represented as mean+/–standard error for each group.

Mouse Open Field Assay

Mice (Naïve, male C57Bl/6) weighing between 22-30 g at the start of testing were obtained from Harlan (Indianapolis, Ind.). All animals were housed under a 12/12 h light/dark cycle with lights on at 0630. Mice were singly housed on solid bottom cages with corn cob bedding and had access to food and water ad libitum. Animals were allowed to habituate to the vivarium for at least five days before testing was begun and were brought into the testing room at least 30 minutes prior to dosing. In a room separate from the testing room, animals were pretreated with the appropriate test compound either by oral gavage or intraperitoneal injection at the desired pretreatment time (typically two hours before test onset) and then returned to their home cages until the pretreatment has elapsed. At test time, animal were transferred to the open field testing room in their home cages. Each animal was placed in a separate testing chamber and the motion tracking system was started. The house lights in the testing room were turned off and the animals were allowed to explore the novel open field for 30 minutes. An automated motion tracker, made by Kinder Scientific, Poway, Calif., was used to capture animal exploration with the aid of infrared photo beams to detect animal movement. These behaviors include basic movement and vertical rearing, which were used as the primary endpoints for this assay. At the end of the test, house lights were turned on and the animals were removed from the testing apparatus.

Statistical analysis was performed by analysis of variance (ANOVA), with post-hoc analysis using the Dunnett post-hoc test compared to the vehicle group for any significant main effect. Data were represented as mean+/–standard error for each group. Data was also expressed as a percent change from the vehicle control using the following equation:

(1–(Test mean/Vehicle mean))*100=% Change.

CFA-Thermal Assay

Animals (Naïve, male Sprague Dawley rats) weighing between 260-300 g at the start of testing) can be obtained from Harlan (Indianapolis, Ind.). All animals can be housed under a 12/12 h light/dark cycle with lights on at 0600. Rodents may be housed two to a cage on solid bottom cages with corn cob bedding with access to food and water adlibitum. Animals can be allowed to habituate to the vivarium for at least five days before testing was begun and may be brought into the testing room at least 30 minutes prior to dosing. The Complete Freund's Adjuvant (CFA)-thermal assay may use a three continuous day testing schedule consisting of a habituation day, a baseline day, and a test day. On day 1, animals can be brought into the testing room, labeled, and placed in their individual testing boxes on the testing apparatus. Animals may be allowed to explore this environment for at least an hour without actually being tested. After habituating, animals can be placed back in their home cages and returned to the vivarium. On day 2, animals can be brought back into the testing room and placed on the testing apparatus and allowed to calm down (typically 30-45 minutes). A basal thermal threshold should be then taken with the following procedure: once calm, a Ugo Basile plantar device is placed under the animals left hindpaw; the start button is depressed turning on a steadily increasing thermal source and a timer; when the animal reaches its thermal threshold it will flinch its hindpaw, stopping the timer and the thermal stimulus. This latency to flinch can be recorded three times for each animal, with at least 5 minutes between trials, and the mean score can be used as the animal's baseline threshold. After testing, animals can be injected intraplantarly with a 25 µg/50 µl of complete Freund's adjuvant into the left hindpaw. Animals are then retuned to their home cages and returned to the vivarium. On test day, animals can be again placed on the thermal testing apparatus and their post-CFA baselines obtained with the procedure outlined above. Animals can be pretreated with the appropriate test compound either by oral gavage or intraperitoneal injection at the desired pretreatment time (typically two hours before test onset) and then can be returned to their home cages. Thirty minutes prior to testing, animals can be placed on the apparatus again. Once the pretreatment time has elapsed, animals can be again tested with the procedure above. Data may be expressed as a percent maximal potential effect with the following formula:

((Post-Drug Mean–Pre-Drug Mean)/(Baseline Mean–Pre-Drug Mean))*100=% MPE

Statistical analysis can be performed by analysis of variance (ANOVA), with post-hoc analysis using Bonferroni compared to the vehicle group for a significant main effect. Data can be represented as mean % MPE +/−standard error for each group.

Spinal Nerve Ligation (Chung)

Animals (Naïve, male Sprague Dawley rats) weighing between 150-200 g at the start of first time testing can be obtained from Harlan (Indianapolis, Ind.). All animals may be housed under a 12/12 h light/dark cycle with lights on at 0600. Rodents can be housed two to a cage on solid bottom cages with corn cob bedding with access to food and water ad libitum. Animals may be allowed to habituate to the vivarium for at least five days before testing is begun. Surgery may be then performed based on the method described by Kim and Chung (1992). Briefly, animals can be placed under isoflurane anesthesia and placed in a sterile surgical field. The area of the lumbar spine is excised and the spinal nerves at L4-L5 are exposed. The L5 spinal nerve is identified and tightly ligated with 5-0 silk suture. The muscle may be closed with absorbable suture and the skin with wound clip. Animals may be returned to the vivarium for 7-14 days and monitored daily. On test day, animals can be brought into the testing room and placed on a wire mesh floor in individual testing chambers. They may be allowed to acclimate to the chambers until they are calm. A series of Semmes-Weinstein monofilaments (von Frey hairs) with calibrated bending forces are then applied to determine a hyperalgesic baseline following the method set forth by Chaplan et al. (1994). Briefly, filaments are applied with an increasing force (if there was not reaction to the previous stimulus) or decreasing force (if there was a reaction to the previous stimulus) until a baseline value is reached. Animals are then pretreated with the appropriate test compound either by oral gavage or intraperitoneal injection at the desired pretreatment time (typically two hours before test onset) and then returned to their home cages. Thirty minutes prior to testing, animals are placed on the apparatus again. After the pretreatment time had elapsed, the procedure above is repeated to determine drug efficacy. Data can be expressed as the mean gram force to elicit a nociceptive behavior. Statistical analysis can be performed by analysis of variance (ANOVA), with post-hoc analysis using Bonferroni compared to the vehicle group for a significant main effect.

Nav 1.7 IWB In Vitro Assay

HEK293 cells stably transfected with human Nav 1.7 were recorded in population patch-clamp mode with the IonWorks© Barracuda (IWB) automated electrophysiology system (Molecular Devices, LLC, Sunnyvale, Calif.). From a holding potential of −110 mV, sodium currents were elicited by a train of 26 depolarizations of 150 ms duration to −20 mV at a frequency of 5 Hz. Cells were then clamped to −20 mV for a period of 4 minutes in the presence of a single concentration of test compound. Following this compound incubation period, cells were clamped to −110 mV for three seconds to recover unbound channels and put through the same 26 pulse voltage protocol as above. Peak inward current during the $26^{th}$ pulse to −20 mV in the presence of compound was divided by the peak inward current evoked by the $26^{th}$ pulse to −20 mV in the absence of compound to determine percent inhibition. Concentration-response curves of percent inhibition as a function of concentration were generated to calculate $IC_{50}$ values.

Table A provides data for compounds exemplified in the present application and priority document thereof, as representative compounds of the present invention, as follows: compound name (as named by ACD software, version 12; while the compound names in the written examples presented herein were named using ChemDraw Ultra version 12); and biological data including in-vitro Nav 1.7 PX data ($IC_{50}$ in uM), Nav 1.7 IWQ data ($IC_{50}$ in uM), Nav 1.7 IWB data ($IC_{50}$ in uM), Nav 1.5 PX data ($IC_{50}$ in uM, where available. Ex. # refers to Example No.

TABLE A

BIOLOGICAL DATA

| Ex. No. | COMPOUND NAME | hNav1.7 PX $IC_{50}$ (µM) | hNav1.7 IWQ $IC_{50}$ (µM) | hNav1.7 IWB $IC_{50}$ (µM) |
|---|---|---|---|---|
| 1-P | P-1-(4'-chloro-2-fluoro-5-methoxy-3'-methyl-4-biphenylyl)-2-oxo-N-4-pyrimidinyl-1,5,7,8-tetrahydro-1,6-naphthyridine-6(2H)-sulfonamide | 0.0296 | | |
| 2-P | P-1-(4'-chloro-2-fluoro-3',5-dimethoxy-4-biphenylyl)-2-oxo-N-3-pyridazinyl-1,5,7,8-tetrahydro-1,6-naphthyridine-6(2H)-sulfonamide | 0.2589 | <0.019 | 0.0066 |
| 2-M | M-1-(4'-chloro-2-fluoro-3',5-dimethoxy-4-biphenylyl)-2-oxo-N-3- | 5.5330 | 0.2550 | 0.1320 |

TABLE A-continued

BIOLOGICAL DATA

| Ex. No. | COMPOUND NAME | hNav1.7 PX IC$_{50}$ (μM) | hNav1.7 IWQ IC$_{50}$ (μM) | hNav1.7 IWB IC$_{50}$ (μM) |
|---|---|---|---|---|
| 3-A-P | pyridazinyl-1,5,7,8-tetrahydro-1,6-naphthyridine-6(2H)-sulfonamide P-(5R)-N-3-isoxazolyl-5-methyl-2-oxo-1-(2,3',5'-trifluoro-5-methoxy-4-biphenylyl)-1,5,7,8-tetrahydro-1,6-naphthyridine-6(2H)-sulfonamide | >1 | | 1.2000 |
| 3-A-M | M-(5R)-N-3-isoxazolyl-5-methyl-2-oxo-1-(2,3',5'-trifluoro-5-methoxy-4-biphenylyl)-1,5,7,8-tetrahydro-1,6-naphthyridine-6(2H)-sulfonamide | >1 | | 2.8000 |
| 3-B-M | M-(5S)-N-3-isoxazolyl-5-methyl-2-oxo-1-(2,3',5'-trifluoro-5-methoxy-4-biphenylyl)-1,5,7,8-tetrahydro-1,6-naphthyridine-6(2H)-sulfonamide | >1 | | >30.0 |
| 3b-P and 3d P mix | (5S)-N-3-isoxazolyl-5-methyl-2-oxo-1-(2,3',5'-trifluoro-5-methoxy-4-biphenylyl)-1,5,7,8-tetrahydro-1,6-naphthyridine-6(2H)-sulfonamide and (7R)-N-3-isoxazolyl-7-methyl-2-oxo-1-(2,3',5'-trifluoro-5-methoxy-4-biphenylyl)-1,5,7,8-tetrahydro-1,6-naphthyridine-6(2H)-sulfonamide | 0.3107 | | 0.0922 |
| 3-C-P | P-(7S)-N-3-isoxazolyl-7-methyl-2-oxo-1-(2,3',5'-trifluoro-5-methoxy-4-biphenylyl)-1,5,7,8-tetrahydro-1,6-naphthyridine-6(2H)-sulfonamide | >1 | | >30.0 |
| 3-C-M | M-(7S)-N-3-isoxazolyl-7-methyl-2-oxo-1-(2,3',5'-trifluoro-5-methoxy-4-biphenylyl)-1,5,7,8-tetrahydro-1,6-naphthyridine-6(2H)-sulfonamide | >1 | | 8.5200 |
| 3-D-M | M-(7R)-N-3-isoxazolyl-7-methyl-2-oxo-1-(2,3',5'-trifluoro-5-methoxy-4-biphenylyl)-1,5,7,8-tetrahydro-1,6-naphthyridine-6(2H)-sulfonamide | >1 | | >7.5 |
| 3-B-P | P-(5S)-N-3-isoxazolyl-5-methyl-2-oxo-1-(2,3',5'-trifluoro-5-methoxy-4-biphenylyl)-1,5,7,8-tetrahydro-1,6-naphthyridine-6(2H)-sulfonamide | 2.0760 | 0.2240 | 0.1970 |
| 3-D-P | P-(7R)-N-3-isoxazolyl-7-methyl-2-oxo-1-(2,3',5'-trifluoro-5-methoxy-4-biphenylyl)-1,5,7,8-tetrahydro-1,6-naphthyridine-6(2H)-sulfonamide | 0.2304 | 0.0405 | 0.0400 |
| 4-(Rac) | (Rac)-1-(3'-chloro-2,5'-difluoro-5-methoxy-4-biphenylyl)-N-(6-methyl-4-pyrimidinyl)-2-oxo-1,5,7,8-tetrahydro-1,6-naphthyridine-6(2H)-sulfonamide | 0.3864 | | 0.0459 |
| 4-P | P-1-(3'-chloro-2,5'-difluoro-5-methoxy-4-biphenylyl)-N-(6-methyl-4-pyrimidinyl)-2-oxo-1,5,7,8-tetrahydro-1,6-naphthyridine-6(2H)-sulfonamide | 0.0784 | 0.0243 | 0.0318 |
| 4-M | M-1-(3'-chloro-2,5'-difluoro-5-methoxy-4-biphenylyl)-N-(6-methyl-4-pyrimidinyl)-2-oxo-1,5,7,8-tetrahydro-1,6-naphthyridine-6(2H)-sulfonamide | | | 8.3000 |
| 5-(Rac) | (Rac)-1-(3'-chloro-2,5'-difluoro-5-methoxy-4-biphenylyl)-2-oxo-N-1,2,4-thiadiazol-5-yl-1,5,7,8-tetrahydro-1,6-naphthyridine-6(2H)-sulfonamide | 0.0546 | 0.0073 | 0.0067 |
| 5-P | P-1-(3'-chloro-2,5'-difluoro-5-methoxy-4-biphenylyl)-2-oxo-N-1,2,4-thiadiazol-5-yl-1,5,7,8-tetrahydro-1,6-naphthyridine-6(2H)-sulfonamide | 0.0123 | 0.0016 | 0.0015 |
| 5-M | M-1-(3'-chloro-2,5'-difluoro-5-methoxy-4-biphenylyl)-2-oxo-N-1,2,4-thiadiazol-5-yl-1,5,7,8-tetrahydro-1,6-naphthyridine-6(2H)-sulfonamide | | | 0.7260 |
| 6-(Rac) | (Rac)-1-(3'-chloro-2,5'-difluoro-5-methoxy-4-biphenylyl)-N-(2-methyl-4-pyrimidinyl)-2-oxo-1,5,7,8-tetrahydro-1,6-naphthyridine-6(2H)-sulfonamide | 0.6664 | | 0.1010 |

TABLE A-continued

BIOLOGICAL DATA

| Ex. No. | COMPOUND NAME | hNav1.7 PX IC$_{50}$ (μM) | hNav1.7 IWQ IC$_{50}$ (μM) | hNav1.7 IWB IC$_{50}$ (μM) |
|---|---|---|---|---|
| 6-P | P-1-(3'-chloro-2,5'-difluoro-5-methoxy-4-biphenylyl)-N-(2-methyl-4-pyrimidinyl)-2-oxo-1,5,7,8-tetrahydro-1,6-naphthyridine-6(2H)-sulfonamide | 0.2690 | 0.0254 | 0.0648 |
| 6-M | M-1-(3'-chloro-2,5'-difluoro-5-methoxy-4-biphenylyl)-N-(2-methyl-4-pyrimidinyl)-2-oxo-1,5,7,8-tetrahydro-1,6-naphthyridine-6(2H)-sulfonamide | | | 8.8200 |
| 7-(Rac) | (Rac)-1-(3'-chloro-5'-fluoro-3-methoxy-4-biphenylyl)-N-3-isoxazolyl-2-oxo-1,5,7,8-tetrahydro-1,6-naphthyridine-6(2H)-sulfonamide | 0.2537 | | 0.0167 |
| 7-P | P-1-(3'-chloro-5'-fluoro-3-methoxy-4-biphenylyl)-N-3-isoxazolyl-2-oxo-1,5,7,8-tetrahydro-1,6-naphthyridine-6(2H)-sulfonamide | 0.0763 | 0.0078 | 0.0143 |
| 7-M | M-1-(3'-chloro-5'-fluoro-3-methoxy-4-biphenylyl)-N-3-isoxazolyl-2-oxo-1,5,7,8-tetrahydro-1,6-naphthyridine-6(2H)-sulfonamide | | | 1.2100 |
| 8-(Rac) | (Rac)-1-(3'-chloro-5'-fluoro-3-methoxy-4-biphenylyl)-2-oxo-N-3-pyridazinyl-1,5,7,8-tetrahydro-1,6-naphthyridine-6(2H)-sulfonamide | 0.3495 | | 0.0317 |
| 8-P | P-1-(3'-chloro-5'-fluoro-3-methoxy-4-biphenylyl)-2-oxo-N-3-pyridazinyl-1,5,7,8-tetrahydro-1,6-naphthyridine-6(2H)-sulfonamide | 0.2408 | | 0.0259 |
| 8-M | M-1-(3'-chloro-5'-fluoro-3-methoxy-4-biphenylyl)-2-oxo-N-3-pyridazinyl-1,5,7,8-tetrahydro-1,6-naphthyridine-6(2H)-sulfonamide | | | 2.9500 |
| 9-(Rac) | (Rac)-1-(5'-chloro-2-fluoro-5-methoxy-2'-methyl-4-biphenylyl)-N-3-isoxazolyl-2-oxo-1,5,7,8-tetrahydro-1,6-naphthyridine-6(2H)-sulfonamide | 0.0307 | 0.0046 | 0.0054 |
| 9-P | P-1-(5'-chloro-2-fluoro-5-methoxy-2'-methyl-4-biphenylyl)-N-3-isoxazolyl-2-oxo-1,5,7,8-tetrahydro-1,6-naphthyridine-6(2H)-sulfonamide | 0.0180 | 0.0021 | 0.0031 |
| 9-M | M-1-(5'-chloro-2-fluoro-5-methoxy-2'-methyl-4-biphenylyl)-N-3-isoxazolyl-2-oxo-1,5,7,8-tetrahydro-1,6-naphthyridine-6(2H)-sulfonamide | 0.7718 | | 0.0550 |
| 10-(Rac) | (Rac)-N-(5-fluoro-2-pyrimidinyl)-2-oxo-1-(2,3',5'-trifluoro-5-methoxy-4-biphenylyl)-1,5,7,8-tetrahydro-1,6-naphthyridine-6(2H)-sulfonamide | 2.2800 | | 0.1630 |
| 10-P | P-N-(5-fluoro-2-pyrimidinyl)-2-oxo-1-(2,3',5'-trifluoro-5-methoxy-4-biphenylyl)-1,5,7,8-tetrahydro-1,6-naphthyridine-6(2H)-sulfonamide | 0.6436 | | 0.0529 |
| 10-M | M-N-(5-fluoro-2-pyrimidinyl)-2-oxo-1-(2,3',5'-trifluoro-5-methoxy-4-biphenylyl)-1,5,7,8-tetrahydro-1,6-naphthyridine-6(2H)-sulfonamide | 0.6122 | | 0.1020 |
| 11-(Rac) | (Rac)-1-(3'-chloro-2,5'-difluoro-5-methoxy-4-biphenylyl)-2-oxo-N-2-pyridinyl-1,5,7,8-tetrahydro-1,6-naphthyridine-6(2H)-sulfonamide | 0.3709 | | 0.0609 |
| 11-P | P-1-(3'-chloro-2,5'-difluoro-5-methoxy-4-biphenylyl)-2-oxo-N-2-pyridinyl-1,5,7,8-tetrahydro-1,6-naphthyridine-6(2H)-sulfonamide | 0.1662 | 0.0540 | 0.0553 |
| 11-M | M-1-(3'-chloro-2,5'-difluoro-5-methoxy-4-biphenylyl)-2-oxo-N-2-pyridinyl-1,5,7,8-tetrahydro-1,6-naphthyridine-6(2H)-sulfonamide | 4.5020 | | 0.8490 |
| 12-(Rac) | (Rac)-1-(3'-chloro-2,5'-difluoro-5-methoxy-4-biphenylyl)-N-(5-fluoro-2-pyridinyl)-2-oxo-1,5,7,8-tetrahydro-1,6-naphthyridine-6(2H)-sulfonamide | 0.1063 | 0.0815 | 0.0913 |

TABLE A-continued

BIOLOGICAL DATA

| Ex. No. | COMPOUND NAME | hNav1.7 PX IC$_{50}$ (μM) | hNav1.7 IWQ IC$_{50}$ (μM) | hNav1.7 IWB IC$_{50}$ (μM) |
| --- | --- | --- | --- | --- |
| 12-P | P-1-(3'-chloro-2,5'-difluoro-5-methoxy-4-biphenylyl)-N-(5-fluoro-2-pyridinyl)-2-oxo-1,5,7,8-tetrahydro-1,6-naphthyridine-6(2H)-sulfonamide | 0.0445 | 0.0566 | 0.0525 |
| 12-M | M-1-(3'-chloro-2,5'-difluoro-5-methoxy-4-biphenylyl)-N-(5-fluoro-2-pyridinyl)-2-oxo-1,5,7,8-tetrahydro-1,6-naphthyridine-6(2H)-sulfonamide | 9.3430 | | |
| 13-(Rac) | (Rac)-1-(3'-chloro-2,5'-difluoro-5-methoxy-4-biphenylyl)-N-(6-fluoro-2-pyridinyl)-2-oxo-1,5,7,8-tetrahydro-1,6-naphthyridine-6(2H)-sulfonamide | 0.1226 | 0.0332 | 0.0276 |
| 13-P | P-1-(3'-chloro-2,5'-difluoro-5-methoxy-4-biphenylyl)-N-(6-fluoro-2-pyridinyl)-2-oxo-1,5,7,8-tetrahydro-1,6-naphthyridine-6(2H)-sulfonamide | 0.0279 | 0.0284 | 0.0271 |
| 13-M | M-1-(3'-chloro-2,5'-difluoro-5-methoxy-4-biphenylyl)-N-(6-fluoro-2-pyridinyl)-2-oxo-1,5,7,8-tetrahydro-1,6-naphthyridine-6(2H)-sulfonamide | 7.5500 | | 0.9830 |
| 14-(Rac) | (Rac)-N-(6-fluoro-2-pyridinyl)-2-oxo-1-(2,3',5'-trifluoro-5-methoxy-4-biphenylyl)-1,5,7,8-tetrahydro-1,6-naphthyridine-6(2H)-sulfonamide | 0.0742 | 0.0444 | 0.0256 |
| 14-P | P-N-(6-fluoro-2-pyridinyl)-2-oxo-1-(2,3',5'-trifluoro-5-methoxy-4-biphenylyl)-1,5,7,8-tetrahydro-1,6-naphthyridine-6(2H)-sulfonamide | 0.1034 | 0.0260 | 0.0124 |
| 14-M | M-N-(6-fluoro-2-pyridinyl)-2-oxo-1-(2,3',5'-trifluoro-5-methoxy-4-biphenylyl)-1,5,7,8-tetrahydro-1,6-naphthyridine-6(2H)-sulfonamide | | | 0.4520 |
| 15-(Rac) | (Rac)-1-(4'-chloro-2-fluoro-3',5-dimethoxy-4-biphenylyl)-N-3-isoxazolyl-2-oxo-1,5,7,8-tetrahydro-1,6-naphthyridine-6(2H)-sulfonamide | 0.0218 | 0.1210 | 0.0081 |
| 15-P | P-1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide | 0.1065 | 0.0194 | 0.0092 |
| 15-M | M-1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide | | | 1.4800 |
| 15-P | P-1-(4'-chloro-2-fluoro-3',5-dimethoxy-4-biphenylyl)-N-3-isoxazolyl-2-oxo-1,5,7,8-tetrahydro-1,6-naphthyridine-6(2H)-sulfonamide | 0.0090 | 0.0061 | 0.0095 |
| 15-M | M-1-(4'-chloro-2-fluoro-3',5-dimethoxy-4-biphenylyl)-N-3-isoxazolyl-2-oxo-1,5,7,8-tetrahydro-1,6-naphthyridine-6(2H)-sulfonamide | 0.8514 | | 0.4450 |
| 16-(Rac) | (Rac)-1-(2-fluoro-5-methoxy-3'-(trifluoromethyl)-4-biphenylyl)-N-3-isoxazolyl-2-oxo-1,5,7,8-tetrahydro-1,6-naphthyridine-6(2H)-sulfonamide | 0.0388 | 0.0047 | 0.0053 |
| 16-P | P-1-(2-fluoro-5-methoxy-3'-(trifluoromethyl)-4-biphenylyl)-N-3-isoxazolyl-2-oxo-1,5,7,8-tetrahydro-1,6-naphthyridine-6(2H)-sulfonamide | 0.0158 | 0.0026 | 0.0024 |
| 16-M | M-1-(2-fluoro-5-methoxy-3'-(trifluoromethyl)-4-biphenylyl)-N-3-isoxazolyl-2-oxo-1,5,7,8-tetrahydro-1,6-naphthyridine-6(2H)-sulfonamide | | | 0.7200 |
| 17-(Rac) | (Rac)-N-1,2,4-oxadiazol-3-yl-2-oxo-1-(2,3',5'-trifluoro-5-methoxy-4-biphenylyl)-1,5,7,8-tetrahydro-1,6-naphthyridine-6(2H)-sulfonamide | 1.1240 | | 0.1910 |
| 17-P | P-N-1,2,4-oxadiazol-3-yl-2-oxo-1-(2,3',5'-trifluoro-5-methoxy-4-biphenylyl)-1,5,7,8-tetrahydro-1,6-naphthyridine-6(2H)-sulfonamide | >1 | | |

TABLE A-continued

| | | BIOLOGICAL DATA | | |
|---|---|---|---|---|
| Ex. No. | COMPOUND NAME | hNav1.7 PX IC$_{50}$ (μM) | hNav1.7 IWQ IC$_{50}$ (μM) | hNav1.7 IWB IC$_{50}$ (μM) |
| 17-M | M-N-1,2,4-oxadiazol-3-yl-2-oxo-1-(2,3',5'-trifluoro-5-methoxy-4-biphenylyl)-1,5,7,8-tetrahydro-1,6-naphthyridine-6(2H)-sulfonamide | 0.2919 | | 0.0343 |
| 18-(Rac) | (Rac)-1-(3'-chloro-2,5'-difluoro-5-methoxy-4-biphenylyl)-N-3-isoxazolyl-2-oxo-1,5,7,8-tetrahydro-1,6-naphthyridine-6(2H)-sulfonamide | 0.0399 | 0.0043 | 0.0069 |
| 18-P | P-1-(3'-chloro-2,5'-difluoro-5-methoxy-4-biphenylyl)-N-3-isoxazolyl-2-oxo-1,5,7,8-tetrahydro-1,6-naphthyridine-6(2H)-sulfonamide | 0.0175 | 0.0029 | 0.0039 |
| 18-M | M-1-(3'-chloro-2,5'-difluoro-5-methoxy-4-biphenylyl)-N-3-isoxazolyl-2-oxo-1,5,7,8-tetrahydro-1,6-naphthyridine-6(2H)-sulfonamide | 3.5630 | | 0.5670 |
| 19-(Rac) | (Rac)-1-(3'-(difluoromethoxy)-2-fluoro-5-methoxy-4-biphenylyl)-N-3-isoxazolyl-2-oxo-1,5,7,8-tetrahydro-1,6-naphthyridine-6(2H)-sulfonamide | 0.1169 | 0.0055 | 0.0156 |
| 19-P | P-1-(3'-(difluoromethoxy)-2-fluoro-5-methoxy-4-biphenylyl)-N-3-isoxazolyl-2-oxo-1,5,7,8-tetrahydro-1,6-naphthyridine-6(2H)-sulfonamide | 0.0333 | 0.0050 | 0.0074 |
| 19-M | M-1-(3'-(difluoromethoxy)-2-fluoro-5-methoxy-4-biphenylyl)-N-3-isoxazolyl-2-oxo-1,5,7,8-tetrahydro-1,6-naphthyridine-6(2H)-sulfonamide | 17.090 | | 1.9400 |
| 20-(Rac) | (Rac)-N-3-isoxazolyl-2-oxo-1-(2,3',4'-trifluoro-5-methoxy-4-biphenylyl)-1,5,7,8-tetrahydro-1,6-naphthyridine-6(2H)-sulfonamide | 0.1595 | 0.0067 | 0.0315 |
| 20-P | P-N-3-isoxazolyl-2-oxo-1-(2,3',4'-trifluoro-5-methoxy-4-biphenylyl)-1,5,7,8-tetrahydro-1,6-naphthyridine-6(2H)-sulfonamide | 0.0393 | 0.0036 | 0.0115 |
| 20-M | M-N-3-isoxazolyl-2-oxo-1-(2,3',4'-trifluoro-5-methoxy-4-biphenylyl)-1,5,7,8-tetrahydro-1,6-naphthyridine-6(2H)-sulfonamide | >30.0 | | 2.6700 |
| 21-(Rac) | (Rac)-1-(2,3'-difluoro-5-methoxy-4'-methyl-4-biphenylyl)-N-3-isoxazolyl-2-oxo-1,5,7,8-tetrahydro-1,6-naphthyridine-6(2H)-sulfonamide | 0.0913 | 0.0143 | 0.0178 |
| 21-P | P-1-(2,3'-difluoro-5-methoxy-4'-methyl-4-biphenylyl)-N-3-isoxazolyl-2-oxo-1,5,7,8-tetrahydro-1,6-naphthyridine-6(2H)-sulfonamide | 0.0243 | 0.0077 | 0.0095 |
| 21-M | M-1-(2,3'-difluoro-5-methoxy-4'-methyl-4-biphenylyl)-N-3-isoxazolyl-2-oxo-1,5,7,8-tetrahydro-1,6-naphthyridine-6(2H)-sulfonamide | 4.9390 | | 1.5500 |
| 22-(Rac) | (Rac)-1-(2,4'-difluoro-5-methoxy-3'-methyl-4-biphenylyl)-N-3-isoxazolyl-2-oxo-1,5,7,8-tetrahydro-1,6-naphthyridine-6(2H)-sulfonamide | 0.2550 | | |
| 22-P | P-1-(2,4'-difluoro-5-methoxy-3'-methyl-4-biphenylyl)-N-3-isoxazolyl-2-oxo-1,5,7,8-tetrahydro-1,6-naphthyridine-6(2H)-sulfonamide | 0.1064 | 0.0032 | 0.0080 |
| 22-M | M-1-(2,4'-difluoro-5-methoxy-3'-methyl-4-biphenylyl)-N-3-isoxazolyl-2-oxo-1,5,7,8-tetrahydro-1,6-naphthyridine-6(2H)-sulfonamide | >30.0 | | >10.0 |
| 23 | (Rac)-1-(5-fluoro-2-methoxy-4-(2-methoxy-5-(trifluoromethyl)-3-pyridinyl)phenyl)-N-3-isoxazolyl-2-oxo-1,5,7,8-tetrahydro-1,6-naphthyridine-6(2H)-sulfonamide | 0.0254 | 0.0070 | 0.0068 |
| 24-(Rac) | (Rac)-1-(4'-chloro-2-fluoro-5-methoxy-3'-methyl-4-biphenylyl)-N-3-isoxazolyl-2-oxo-1,5,7,8-tetrahydro-1,6-naphthyridine-6(2H)-sulfonamide | 0.0737 | 0.0067 | |

TABLE A-continued

BIOLOGICAL DATA

| Ex. No. | COMPOUND NAME | hNav1.7 PX IC$_{50}$ (μM) | hNav1.7 IWQ IC$_{50}$ (μM) | hNav1.7 IWB IC$_{50}$ (μM) |
|---|---|---|---|---|
| 24-P | P-1-(4'-chloro-2-fluoro-5-methoxy-3'-methyl-4-biphenylyl)-N-3-isoxazolyl-2-oxo-1,5,7,8-tetrahydro-1,6-naphthyridine-6(2H)-sulfonamide | 0.0209 | 0.0052 | 0.0038 |
| 24-M | M-1-(4'-chloro-2-fluoro-5-methoxy-3'-methyl-4-biphenylyl)-N-3-isoxazolyl-2-oxo-1,5,7,8-tetrahydro-1,6-naphthyridine-6(2H)-sulfonamide | | | 0.4620 |
| 25-(Rac) | (Rac)-N-3-isoxazolyl-2-oxo-1-(2,3',5'-trifluoro-5-methoxy-4-biphenylyl)-1,5,7,8-tetrahydro-1,6-naphthyridine-6(2H)-sulfonamide | 0.2093 | | |
| 25-P | P-N-3-isoxazolyl-2-oxo-1-(2,3',5'-trifluoro-5-methoxy-4-biphenylyl)-1,5,7,8-tetrahydro-1,6-naphthyridine-6(2H)-sulfonamide | 0.1757 | 0.0072 | |
| 25-M | M-N-3-isoxazolyl-2-oxo-1-(2,3',5'-trifluoro-5-methoxy-4-biphenylyl)-1,5,7,8-tetrahydro-1,6-naphthyridine-6(2H)-sulfonamide | >1 | | |
| 26-(Rac) | (Rac)-N-3-isoxazolyl-1-(2-methoxy-4-(trifluoromethyl)phenyl)-2-oxo-1,5,7,8-tetrahydro-1,6-naphthyridine-6(2H)-sulfonamide | >1 | | |
| 26-P | P-N-3-isoxazolyl-1-(2-methoxy-4-(trifluoromethyl)phenyl)-2-oxo-1,5,7,8-tetrahydro-1,6-naphthyridine-6(2H)-sulfonamide | >1 | | |
| 26-M | M-N-3-isoxazolyl-1-(2-methoxy-4-(trifluoromethyl)phenyl)-2-oxo-1,5,7,8-tetrahydro-1,6-naphthyridine-6(2H)-sulfonamide | >1 | | |
| 27 | (Rac)-N-3-isoxazolyl-1-(2-methoxyphenyl)-2-oxo-1,5,7,8-tetrahydro-1,6-naphthyridine-6(2H)-sulfonamide | >1 | | |
| 28-(Rac) | (Rac)-2-oxo-N-2-pyrimidinyl-1-(2,3',4'-trifluoro-5-methoxy-4-biphenylyl)-1,5,7,8-tetrahydro-1,6-naphthyridine-6(2H)-sulfonamide | 1.6800 | | 0.1990 |
| 28-P | P-2-oxo-N-2-pyrimidinyl-1-(2,3',4'-trifluoro-5-methoxy-4-biphenylyl)-1,5,7,8-tetrahydro-1,6-naphthyridine-6(2H)-sulfonamide | 0.4988 | | 0.0805 |
| 28-M | M-2-oxo-N-2-pyrimidinyl-1-(2,3',4'-trifluoro-5-methoxy-4-biphenylyl)-1,5,7,8-tetrahydro-1,6-naphthyridine-6(2H)-sulfonamide | >30.0 | | >10.0 |
| 29-(Rac) | (Rac)-1-(2,4'-difluoro-5-methoxy-3'-methyl-4-biphenylyl)-2-oxo-N-2-pyrimidinyl-1,5,7,8-tetrahydro-1,6-naphthyridine-6(2H)-sulfonamide | 1.1750 | | 0.1220 |
| 29-P | P-1-(2,4'-difluoro-5-methoxy-3'-methyl-4-biphenylyl)-2-oxo-N-2-pyrimidinyl-1,5,7,8-tetrahydro-1,6-naphthyridine-6(2H)-sulfonamide | 0.5684 | | 0.0555 |
| 29-M | M-1-(2,4'-difluoro-5-methoxy-3'-methyl-4-biphenylyl)-2-oxo-N-2-pyrimidinyl-1,5,7,8-tetrahydro-1,6-naphthyridine-6(2H)-sulfonamide | >30.0 | | >2.5 |
| 30-P | P-1-(4'-chloro-2-fluoro-5-methoxy-3'-methyl-4-biphenylyl)-2-oxo-N-2-pyrimidinyl-1,5,7,8-tetrahydro-1,6-naphthyridine-6(2H)-sulfonamide | 0.1970 | 0.0133 | 0.0375 |
| 30-M | M-1-(4'-chloro-2-fluoro-5-methoxy-3'-methyl-4-biphenylyl)-2-oxo-N-2-pyrimidinyl-1,5,7,8-tetrahydro-1,6-naphthyridine-6(2H)-sulfonamide | 24.890 | | 3.9100 |
| 30 | (Rac)-1-(4'-chloro-2-fluoro-5-methoxy-3'-methyl-4-biphenylyl)-2-oxo-N-2-pyrimidinyl-1,5,7,8-tetrahydro-1,6-naphthyridine-6(2H)-sulfonamide | 0.9934 | | 0.0443 |

TABLE A-continued

BIOLOGICAL DATA

| Ex. No. | COMPOUND NAME | hNav1.7 PX IC$_{50}$ (μM) | hNav1.7 IWQ IC$_{50}$ (μM) | hNav1.7 IWB IC$_{50}$ (μM) |
|---|---|---|---|---|
| 31 | (Rac)-1-(3'-chloro-2,5'-difluoro-5-methoxy-4-biphenylyl)-2-oxo-N-2-pyrimidinyl-1,5,7,8-tetrahydro-1,6-naphthyridine-6(2H)-sulfonamide | 0.1370 | 0.0281 | 0.0362 |
| 31-P | P-1-(3'-chloro-2,5'-difluoro-5-methoxy-4-biphenylyl)-2-oxo-N-2-pyrimidinyl-1,5,7,8-tetrahydro-1,6-naphthyridine-6(2H)-sulfonamide | 0.2050 | | 0.0369 |
| 31-M | M-1-(3'-chloro-2,5'-difluoro-5-methoxy-4-biphenylyl)-2-oxo-N-2-pyrimidinyl-1,5,7,8-tetrahydro-1,6-naphthyridine-6(2H)-sulfonamide | 5.0180 | | 2.7300 |
| 32-(Rac) | (Rac)-2-oxo-N-3-pyridazinyl-1-(2,3',4'-trifluoro-5-methoxy-4-biphenylyl)-1,5,7,8-tetrahydro-1,6-naphthyridine-6(2H)-sulfonamide | 0.1605 | 0.0237 | 0.0305 |
| 32-P | P-2-oxo-N-3-pyridazinyl-1-(2,3',4'-trifluoro-5-methoxy-4-biphenylyl)-1,5,7,8-tetrahydro-1,6-naphthyridine-6(2H)-sulfonamide | 0.1445 | 0.0184 | 0.0175 |
| 32-M | M-2-oxo-N-3-pyridazinyl-1-(2,3',4'-trifluoro-5-methoxy-4-biphenylyl)-1,5,7,8-tetrahydro-1,6-naphthyridine-6(2H)-sulfonamide | 20.560 | | 1.0000 |
| 33-(Rac) | (Rac)-1-(4'-chloro-2-fluoro-5-methoxy-3'-methyl-4-biphenylyl)-2-oxo-N-3-pyridazinyl-1,5,7,8-tetrahydro-1,6-naphthyridine-6(2H)-sulfonamide | 0.0533 | 0.0196 | 0.0261 |
| 33-P | P-1-(4'-chloro-2-fluoro-5-methoxy-3'-methyl-4-biphenylyl)-2-oxo-N-3-pyridazinyl-1,5,7,8-tetrahydro-1,6-naphthyridine-6(2H)-sulfonamide | 0.0213 | 0.0147 | 0.0126 |
| 33-M | M-1-(4'-chloro-2-fluoro-5-methoxy-3'-methyl-4-biphenylyl)-2-oxo-N-3-pyridazinyl-1,5,7,8-tetrahydro-1,6-naphthyridine-6(2H)-sulfonamide | | | >10.0 |
| 34-(Rac) | (Rac)-1-(4-(cyclopentylethynyl)-5-fluoro-2-methoxyphenyl)-N-3-isoxazolyl-2-oxo-1,5,7,8-tetrahydro-1,6-naphthyridine-6(2H)-sulfonamide | 0.4083 | 0.0888 | 0.0485 |
| 34-P | P-1-(4-(cyclopentylethynyl)-5-fluoro-2-methoxyphenyl)-N-3-isoxazolyl-2-oxo-1,5,7,8-tetrahydro-1,6-naphthyridine-6(2H)-sulfonamide | 0.1921 | 0.0092 | 0.0122 |
| 34-M | M-1-(4-(cyclopentylethynyl)-5-fluoro-2-methoxyphenyl)-N-3-isoxazolyl-2-oxo-1,5,7,8-tetrahydro-1,6-naphthyridine-6(2H)-sulfonamide | | | 9.7200 |
| 35 | (Rac)-1-(4'-chloro-3'-cyano-2-fluoro-5-methoxy-4-biphenylyl)-N-3-isoxazolyl-2-oxo-1,5,7,8-tetrahydro-1,6-naphthyridine-6(2H)-sulfonamide | 0.1771 | 0.0040 | 0.0180 |
| 36 | (Rac)-1-(6-(3-chloro-5-fluorophenyl)-5-fluoro-2-methoxy-3-pyridinyl)-N-3-isoxazolyl-2-oxo-1,5,7,8-tetrahydro-1,6-naphthyridine-6(2H)-sulfonamide | 0.4230 | | 0.1730 |
| 37 | (Rac)-1-(6-(3-chloro-5-fluorophenyl)-5-fluoro-2-methoxy-3-pyridinyl)-2-oxo-N-3-pyridazinyl-1,5,7,8-tetrahydro-1,6-naphthyridine-6(2H)-sulfonamide | 1.0300 | 0.1370 | 0.2690 |
| 38-(Rac) | (Rac)-1-(3'-chloro-2,5'-difluoro-5-methoxy-4-biphenylyl)-2-oxo-N-3-pyridazinyl-1,5,7,8-tetrahydro-1,6-naphthyridine-6(2H)-sulfonamide | 0.0878 | 0.0167 | 0.0102 |
| 38-P | P-1-(3'-chloro-2,5'-difluoro-5-methoxy-4-biphenylyl)-2-oxo-N-3-pyridazinyl-1,5,7,8-tetrahydro-1,6-naphthyridine-6(2H)-sulfonamide | 0.0561 | 0.0067 | 0.0109 |

TABLE A-continued

BIOLOGICAL DATA

| Ex. No. | COMPOUND NAME | hNav1.7 PX IC$_{50}$ (µM) | hNav1.7 IWQ IC$_{50}$ (µM) | hNav1.7 IWB IC$_{50}$ (µM) |
| --- | --- | --- | --- | --- |
| 38-M | M-1-(3'-chloro-2,5'-difluoro-5-methoxy-4-biphenylyl)-2-oxo-N-3-pyridazinyl-1,5,7,8-tetrahydro-1,6-naphthyridine-6(2H)-sulfonamide | 3.1220 | | 0.6620 |
| 39 | (Rac)-1-(4'-chloro-2-fluoro-5-methoxy-3'-methyl-4-biphenylyl)-2-oxo-N-1,3-thiazol-2-yl-1,5,7,8-tetrahydro-1,6-naphthyridine-6(2H)-sulfonamide | 0.0351 | 0.0152 | 0.0378 |
| 40 | (Rac)-1-(4'-chloro-2-fluoro-5-methoxy-3'-methyl-4-biphenylyl)-N-(6-methyl-4-pyrimidinyl)-2-oxo-1,5,7,8-tetrahydro-1,6-naphthyridine-6(2H)-sulfonamide | 0.2039 | | 0.0423 |
| 41 | P-1-(2,3'-difluoro-5-methoxy-5'-(trifluoromethyl)-4-biphenylyl)-2-oxo-N-3-pyridazinyl-1,5,7,8-tetrahydro-1,6-naphthyridine-6(2H)-sulfonamide | 0.0330 | | 0.0018 |
| 42 | P-1-(3'-cyclopropyl-2-fluoro-5-methoxy-4-biphenylyl)-2-oxo-N-3-pyridazinyl-1,5,7,8-tetrahydro-1,6-naphthyridine-6(2H)-sulfonamide | 0.0766 | | 0.0078 |
| 43 | P-1-(2'-chloro-2-fluoro-5-methoxy-5'-methyl-4-biphenylyl)-2-oxo-N-3-pyridazinyl-1,5,7,8-tetrahydro-1,6-naphthyridine-6(2H)-sulfonamide | 0.1557 | | 0.0038 |
| 44 | P-1-(3'-chloro-2-fluoro-5-methoxy-4'-methyl-4-biphenylyl)-2-oxo-N-3-pyridazinyl-1,5,7,8-tetrahydro-1,6-naphthyridine-6(2H)-sulfonamide | 0.0732 | | |
| 45 | P-1-(2-fluoro-5-methoxy-3'-(trifluoromethyl)-4-biphenylyl)-2-oxo-N-3-pyridazinyl-1,5,7,8-tetrahydro-1,6-naphthyridine-6(2H)-sulfonamide | 0.0298 | | |
| 46 | P-2-oxo-N-3-pyridazinyl-1-(2,3',4',5'-tetrafluoro-5-methoxy-4-biphenylyl)-1,5,7,8-tetrahydro-1,6-naphthyridine-6(2H)-sulfonamide | 0.1023 | | |
| 47 | P-1-(4'-chloro-2,3'-difluoro-5-methoxy-4-biphenylyl)-2-oxo-N-3-pyridazinyl-1,5,7,8-tetrahydro-1,6-naphthyridine-6(2H)-sulfonamide | 0.0951 | | |
| 48 | P-1-(3'-chloro-2,4'-difluoro-5-methoxy-4-biphenylyl)-2-oxo-N-3-pyridazinyl-1,5,7,8-tetrahydro-1,6-naphthyridine-6(2H)-sulfonamide | 0.0803 | | |
| 49 | P-1-(3'-chloro-2,2'-difluoro-5-methoxy-4-biphenylyl)-2-oxo-N-3-pyridazinyl-1,5,7,8-tetrahydro-1,6-naphthyridine-6(2H)-sulfonamide | 0.1684 | | |
| 50 | P-1-(4-(5-chloro-6-methoxy-3-pyridinyl)-5-fluoro-2-methoxyphenyl)-2-oxo-N-3-pyridazinyl-1,5,7,8-tetrahydro-1,6-naphthyridine-6(2H)-sulfonamide | 0.1716 | | |
| 51 | P-1-(2-chloro-3',4'-difluoro-5-methoxy-4-biphenylyl)-N-3-isoxazolyl-2-oxo-1,5,7,8-tetrahydro-1,6-naphthyridine-6(2H)-sulfonamide | 0.0451 | | <0.002 |
| 52 | P-1-(2,4'-dichloro-3',5-dimethoxy-4-biphenylyl)-N-3-isoxazolyl-2-oxo-1,5,7,8-tetrahydro-1,6-naphthyridine-6(2H)-sulfonamide | 0.0229 | | 0.0028 |
| 53 | P-1-(2,3'-dichloro-5'-fluoro-5-methoxy-4-biphenylyl)-N-3-isoxazolyl-2-oxo-1,5,7,8-tetrahydro-1,6-naphthyridine-6(2H)-sulfonamide | 0.0052 | | 0.0007 |
| 54 | P-1-(2-chloro-5-methoxy-3'-(trifluoromethyl)-4-biphenylyl)-N-3-isoxazolyl-2-oxo-1,5,7,8-tetrahydro-1,6-naphthyridine-6(2H)-sulfonamide | 0.0069 | | 0.0005 |
| 55-P | P-1-(3'-chloro-4-methoxy-4'-methyl-3-biphenylyl)-2-oxo-N-3-pyridazinyl- | 0.7098 | | |

TABLE A-continued

BIOLOGICAL DATA

| Ex. No. | COMPOUND NAME | hNav1.7 PX IC$_{50}$ (µM) | hNav1.7 IWQ IC$_{50}$ (µM) | hNav1.7 IWB IC$_{50}$ (µM) |
|---|---|---|---|---|
| | 1,5,7,8-tetrahydro-1,6-naphthyridine-6(2H)-sulfonamide | | | |
| 55-M | M-1-(3'-chloro-4-methoxy-4'-methyl-3-biphenylyl)-2-oxo-N-3-pyridazinyl-1,5,7,8-tetrahydro-1,6-naphthyridine-6(2H)-sulfonamide | >1 | | |
| 56-P | P-1-(4'-chloro-4-methoxy-3'-methyl-3-biphenylyl)-2-oxo-N-3-pyridazinyl-1,5,7,8-tetrahydro-1,6-naphthyridine-6(2H)-sulfonamide | 0.4933 | | |
| 56-M | M-1-(4'-chloro-4-methoxy-3'-methyl-3-biphenylyl)-2-oxo-N-3-pyridazinyl-1,5,7,8-tetrahydro-1,6-naphthyridine-6(2H)-sulfonamide | | | |
| 57-P | P-1-(3'-chloro-4-methoxy-2'-methyl-3-biphenylyl)-2-oxo-N-3-pyridazinyl-1,5,7,8-tetrahydro-1,6-naphthyridine-6(2H)-sulfonamide | 0.2317 | | |
| 57-M | M-1-(3'-chloro-4-methoxy-2'-methyl-3-biphenylyl)-2-oxo-N-3-pyridazinyl-1,5,7,8-tetrahydro-1,6-naphthyridine-6(2H)-sulfonamide | | | |
| 58-(Rac) | (Rac)-1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide | 0.0780 | 0.0123 | 0.0241 |
| 58-P | P-1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide | 0.1070 | 0.0194 | 0.0092 |
| 58-M | M-1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide | | | 1.4800 |
| 59 | P-1-(5'-chloro-2-fluoro-2',5-dimethoxy-[1,1'-biphenyl]-4-yl)-2-oxo-N-(pyridazin-3-yl)-1,2,7,8-tetrahydro-1,6-naphthyridine-6(5H)-sulfonamide | 0.0481 | | 0.0065 |
| 60 | P-1-(4-(5-chloro-2-methoxypyridin-3-yl)-5-fluoro-2-methoxyphenyl)-2-oxo-N-(pyridazin-3-yl)-1,2,7,8-tetrahydro-1,6-naphthyridine-6(5H)-sulfonamide | 0.4197 | | 0.0375 |
| 61 | P-1-(4'-chloro-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide | 0.1951 | | 0.0241 |
| 62 | P-1-(3'-chloro-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide | 0.0758 | | 0.0086 |
| 63 | P-1-(3'-chloro-2-fluoro-4',5-dimethoxy-[1,1'-biphenyl]-4-yl)-2-oxo-N-(pyridazin-3-yl)-1,2,7,8-tetrahydro-1,6-naphthyridine-6(5H)-sulfonamide | 0.3207 | | 0.0222 |
| 64 | P-1-(5-fluoro-2-methoxy-4-(2-methoxy-5-(trifluoromethyl)pyridin-3-yl)phenyl)-2-oxo-N-(pyridazin-3-yl)-1,2,7,8-tetrahydro-1,6-naphthyridine-6(5H)-sulfonamide | 0.0661 | | 0.0019 |
| 65 | P-1-(3'-chloro-2-fluoro-2',5-dimethoxy-[1,1'-biphenyl]-4-yl)-2-oxo-N-(pyridazin-3-yl)-1,2,7,8-tetrahydro-1,6-naphthyridine-6(5H)-sulfonamide | 0.2512 | | 0.0085 |
| 66 | P-1-(2-fluoro-5-methoxy-3'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide | 0.0371 | 0.0023 | 0.0038 |
| 67 | P-1-(2-fluoro-5-methoxy-4'-(trifluoromethyl)-[1,1'-biphenyl]-4-yl)- | 0.0758 | | 0.0205 |

TABLE A-continued

BIOLOGICAL DATA

| Ex. No. | COMPOUND NAME | hNav1.7 PX IC$_{50}$ (μM) | hNav1.7 IWQ IC$_{50}$ (μM) | hNav1.7 IWB IC$_{50}$ (μM) |
|---|---|---|---|---|
| | 2-oxo-N-(pyridazin-3-yl)-1,2,7,8-tetrahydro-1,6-naphthyridine-6(5H)-sulfonamide | | | |
| 68 | P-1-(2-fluoro-5-methoxy-3'-(2,2,2-trifluoroethoxy)-[1,1'-biphenyl]-4-yl)-2-oxo-N-(pyridazin-3-yl)-1,2,7,8-tetrahydro-1,6-naphthyridine-6(5H)-sulfonamide | 0.0742 | 0.0024 | 0.0053 |
| 69 | P-1-(3'-chloro-2-fluoro-5-methoxy-5'-methyl-[1,1'-biphenyl]-4-yl)-2-oxo-N-(pyridazin-3-yl)-1,2,7,8-tetrahydro-1,6-naphthyridine-6(5H)-sulfonamide | 0.0228 | | 0.0169 |
| 70 | P-1-(3'-chloro-2-fluoro-5,5'-dimethoxy-[1,1'-biphenyl]-4-yl)-2-oxo-N-(pyridazin-3-yl)-1,2,7,8-tetrahydro-1,6-naphthyridine-6(5H)-sulfonamide | 0.0200 | | 0.0062 |
| 71 | P-1-(2,4'-difluoro-5-methoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide | 0.0294 | 0.0028 | 0.0069 |
| 72 | P-1-(3'-(difluoromethyl)-2-fluoro-5-methoxy-[1,1'-biphenyl]-4-yl)-2-oxo-N-(pyridazin-3-yl)-1,2,7,8-tetrahydro-1,6-naphthyridine-6(5H)-sulfonamide | 0.2651 | | 0.0151 |
| 73 | P-1-(2,4'-difluoro-5-methoxy-3'-methyl-[1,1'-biphenyl]-4-yl)-2-oxo-N-(pyridazin-3-yl)-1,2,7,8-tetrahydro-1,6-naphthyridine-6(5H)-sulfonamide | 0.2319 | | 0.0180 |
| 74 | P-1-(2-fluoro-2',5-dimethoxy-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide | 0.0294 | | 0.0077 |
| 75 | P-1-(2-fluoro-5-methoxy-3'-methyl-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide | 0.0413 | | 0.0116 |
| 76 | P-1-(2-fluoro-3',5-dimethoxy-5'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide | 0.0388 | | 0.0042 |
| 77 | P-1-(3'-chloro-2-fluoro-5-methoxy-5'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide | 0.0405 | 0.0013 | 0.0044 |
| 78 | P-1-(2-fluoro-5-methoxy-3'-methyl-5'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide | 0.0445 | | 0.0053 |
| 79 | P-2-oxo-N-(pyridazin-3-yl)-1-(2,3',4'-trifluoro-5,5'-dimethoxy-[1,1'-biphenyl]-4-yl)-1,2,7,8-tetrahydro-1,6-naphthyridine-6(5H)-sulfonamide | | 0.0039 | 0.0026 |
| 80 | P-1-(5-fluoro-2-methoxy-4-(6-methoxy-5-(trifluoromethyl)pyridin-3-yl)phenyl)-2-oxo-N-(pyridazin-3-yl)-1,2,7,8-tetrahydro-1,6-naphthyridine-6(5H)-sulfonamide | | 0.0054 | 0.0139 |
| 81 | P-1-(2,4'-difluoro-5-methoxy-3'-(trifluoromethoxy)-[1,1'-biphenyl]-4-yl)-2-oxo-N-(pyridazin-3-yl)-1,2,7,8-tetrahydro-1,6-naphthyridine-6(5H)-sulfonamide | | 0.0039 | 0.0086 |
| 82 | P-1-(2-fluoro-4',5-dimethoxy-3'-(trifluoromethyl)-[1,1'-biphenyl]-4-yl)-2-oxo-N-(pyridazin-3-yl)-1,2,7,8- | | 0.0156 | 0.0258 |

TABLE A-continued

BIOLOGICAL DATA

| Ex. No. | COMPOUND NAME | hNav1.7 PX IC$_{50}$ (μM) | hNav1.7 IWQ IC$_{50}$ (μM) | hNav1.7 IWB IC$_{50}$ (μM) |
|---|---|---|---|---|
| 83 | P-1-(2-fluoro-3',5-dimethoxy-5'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide | | 0.0034 | 0.0051 |
| 84 | P-1-(3'-(difluoromethyl)-2,5'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide | | 0.0083 | 0.0171 |
| 85 | P-1-(3'-(difluoromethyl)-2,4'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide | | 0.0043 | 0.0174 |
| 86 | P-1-(3'-(difluoromethyl)-2,4',5'-trifluoro-5-methoxy-[1,1'-biphenyl]-4-yl)-2-oxo-N-(pyridazin-3-yl)-1,2,7,8-tetrahydro-1,6-naphthyridine-6(5H)-sulfonamide | | 0.0071 | 0.0143 |
| 87 | P-1-(4'-(difluoromethyl)-2,3'-difluoro-5-methoxy-[1,1'-biphenyl]-4-yl)-2-oxo-N-(pyridazin-3-yl)-1,2,7,8-tetrahydro-1,6-naphthyridine-6(5H)-sulfonamide | | 0.0124 | 0.0190 |
| 88 | P-2-oxo-N-(pyrimidin-4-yl)-1-(2,3',5'-trifluoro-5-methoxy-[1,1'-biphenyl]-4-yl)-1,2,7,8-tetrahydro-1,6-naphthyridine-6(5H)-sulfonamide | 0.4746 | | 0.0312 |
| 89 | P-1-(3'-chloro-2-fluoro-5,5'-dimethoxy-[1,1'-biphenyl]-4-yl)-N-(isoxazol-3-yl)-2-oxo-1,2,7,8-tetrahydro-1,6-naphthyridine-6(5H)-sulfonamide | 0.0199 | 0.0013 | 0.0088 |
| 90 | P-1-(2-fluoro-3',5,5'-trimethoxy-[1,1'-biphenyl]-4-yl)-N-(isoxazol-3-yl)-2-oxo-1,2,7,8-tetrahydro-1,6-naphthyridine-6(5H)-sulfonamide | 0.1637 | 0.0032 | 0.0365 |
| 91-(Rac) | (Rac)-1-(2-chloro-5-methoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide | 0.0299 | | 0.0112 |
| 91-P | P-1-(2-chloro-5-methoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide | 0.0169 | 0.0034 | 0.0035 |
| 91-M | M-1-(2-chloro-5-methoxy-3'-(trifluoromethyl)-[1,1'-biphenyl]-4-yl)-2-oxo-N-(pyridazin-3-yl)-1,2,7,8-tetrahydro-1,6-naphthyridine-6(5H)-sulfonamide | 0.6813 | | 0.1540 |
| 92-(Rac) | (Rac)-1-(2-chloro-4'-fluoro-5-methoxy-3'-methyl-[1,1'-biphenyl]-4-yl)-2-oxo-N-(pyridazin-3-yl)-1,2,7,8-tetrahydro-1,6-naphthyridine-6(5H)-sulfonamide | 0.0635 | | 0.0236 |
| 92-P | P-1-(2-chloro-4'-fluoro-5-methoxy-3'-methyl-[1,1'-biphenyl]-4-yl)-2-oxo-N-(pyridazin-3-yl)-1,2,7,8-tetrahydro-1,6-naphthyridine-6(5H)-sulfonamide | 0.0414 | | 0.0059 |
| 92-M | M-1-(2-chloro-4'-fluoro-5-methoxy-3'-methyl-[1,1'-biphenyl]-4-yl)-2-oxo-N-(pyridazin-3-yl)-1,2,7,8-tetrahydro-1,6-naphthyridine-6(5H)-sulfonamide | 3.0080 | | 0.2820 |
| 93-P | P-1-(4'-fluoro-5-methoxy-2,3'-dimethyl-[1,1'-biphenyl]-4-yl)-2-oxo-N-(pyridazin-3-yl)-1,2,7,8-tetrahydro-1,6-naphthyridine-6(5H)-sulfonamide | 0.1157 | | 0.0218 |

TABLE A-continued

BIOLOGICAL DATA

| Ex. No. | COMPOUND NAME | hNav1.7 PX IC$_{50}$ (μM) | hNav1.7 IWQ IC$_{50}$ (μM) | hNav1.7 IWB IC$_{50}$ (μM) |
|---|---|---|---|---|
| 93-M | M-1-(4'-fluoro-5-methoxy-2,3'-dimethyl-[1,1'-biphenyl]-4-yl)-2-oxo-N-(pyridazin-3-yl)-1,2,7,8-tetrahydro-1,6-naphthyridine-6(5H)-sulfonamide | 1.8010 | | 0.2700 |
| 94 | P-1-(5-fluoro-2-methoxy-4-(3,3,3-trifluoropropyl)phenyl)-N-(isoxazol-3-yl)-2-oxo-1,2,7,8-tetrahydro-1,6-naphthyridine-6(5H)-sulfonamide | | 0.0187 | 0.0335 |
| 95 | P-1-(5-fluoro-2-methoxy-4-(3,3,3-trifluoropropyl)phenyl)-2-oxo-N-(pyridazin-3-yl)-1,2,7,8-tetrahydro-1,6-naphthyridine-6(5H)-sulfonamide | | 0.0210 | 0.0365 |
| 96-P | P-1-(5-chloro-2-methoxy-4-(3,3,3-trifluoropropyl)phenyl)-2-oxo-N-(pyridazin-3-yl)-1,2,7,8-tetrahydro-1,6-naphthyridine-6(5H)-sulfonamide | | 0.0090 | 0.0339 |
| 96-M | M-1-(5-chloro-2-methoxy-4-(3,3,3-trifluoropropyl)phenyl)-2-oxo-N-(pyridazin-3-yl)-1,2,7,8-tetrahydro-1,6-naphthyridine-6(5H)-sulfonamide | | | 0.8560 |
| Preparation 8a | 1-(4-bromo-5-fluoro-2-methoxyphenyl)-2-oxo-N-2-pyrimidinyl-1,5,7,8-tetrahydro-1,6-naphthyridine-6(2H)-sulfonamide; | | | 4.2400 |
| Preparation 8b | 1-(4-bromo-5-fluoro-2-methoxyphenyl)-2-oxo-N-3-pyridazinyl-1,5,7,8-tetrahydro-1,6-naphthyridine-6(2H)-sulfonamide; | | | 1.1200 |
| Preparation 8c | 1-(4-bromo-5-chloro-2-methoxyphenyl)-N-3-isoxazolyl-2-oxo-1,5,7,8-tetrahydro-1,6-naphthyridine-6(2H)-sulfonamide | | | 2.8800 |
| Preparation 8c-P | P-1-(4-bromo-5-chloro-2-methoxyphenyl)-N-3-isoxazolyl-2-oxo-1,5,7,8-tetrahydro-1,6-naphthyridine-6(2H)-sulfonamide | | | 0.7680 |
| Preparation 8c-M | M-1-(4-bromo-5-chloro-2-methoxyphenyl)-N-3-isoxazolyl-2-oxo-1,5,7,8-tetrahydro-1,6-naphthyridine-6(2H)-sulfonamide | | | >25 |
| Preparation 8f-P | P-1-(4-bromo-5-fluoro-2-methoxyphenyl)-2-oxo-N-(pyrimidin-4-yl)-1,2,7,8-tetrahydro-1,6-naphthyridine-6(5H)-sulfonamide | | | 0.193 |
| Preparation 8f-M | M-1-(4-bromo-5-fluoro-2-methoxyphenyl)-2-oxo-N-(pyrimidin-4-yl)-1,2,7,8-tetrahydro-1,6-naphthyridine-6(5H)-sulfonamide | | | >25 |

The foregoing invention has been described in some detail by way of illustration and example, for purposes of clarity and understanding. Those skilled in the art understand that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited herein are hereby incorporated by reference in their entirety for all purposes to the same extent as if each individual patent, patent application or publication were so individually denoted.

What is claimed is:

1. A compound of Formula (I), an enantiomer, diastereomer, atropisomer thereof, or a mixture thereof, or a pharmaceutically acceptable salt thereof,

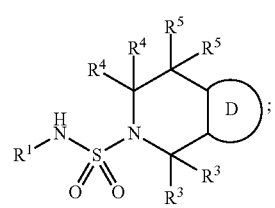

Wherein the group:

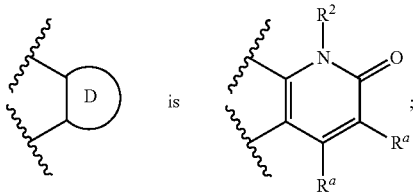 is 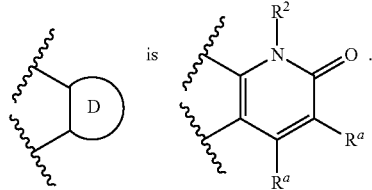 ;

$R^1$ is a 5-, 6-, 7-, 8-, 9-, or 10-membered aryl or heteroaryl, or a 3-, 4-, 5-, 6-, 7-, 8-, 9-, or 10-membered cycloalkyl or heterocycloalkyl group, wherein the heteroaryl or heterocycloalkyl group can have from 1 to 3 heteroatoms independently selected from O, N or S, or a carbon atom in the cycloalkyl or heterocycloalkyl group can be part of a C=O group, and the aryl, heteroaryl, cycloalkyl, or heterocycloalkyl group is substituted with 0, 1, 2, 3, or 4 substituents independently selected from halo, —CN, —$C_{1-6}$alkyl, halo$C_{1-6}$alkyl, —OH, —O—$C_{1-6}$alkyl, —O-halo$C_{1-6}$alkyl, —C(=O)$OR^a$, or —$(CR^bR^b)_n NR^aR^a$;

$R^2$ is $C_{1-6}$alkyl, or a 5-, 6-, 7-, 8-, 9-, or 10-membered aryl or heteroaryl, or a 3-, 4-, 5-, 6-, 7-, 8-, 9-, or 10-membered cycloalkyl or heterocycloalkyl group, where the heteroaryl or heterocycloalkyl group can have from 1 to 3 heteroatoms independently selected from O, N or S, or a carbon atom in the cycloalkyl or heterocycloalkyl group can be part of a C=O group, and the alkyl, aryl, heteroaryl, cycloalkyl or heterocycloalkyl group is optionally substituted with from 1 to 5 $R^6$ substituents independently selected from halo, —CN, —$C_{1-6}$alkyl, halo$C_{1-6}$alkyl, —OH, —O—$C_{1-6}$alkyl, —O-halo$C_{1-6}$alkyl, —$(CR^bR^b)_m$A, —$C_{2-6}$alkenyl-A, —$C_{2-6}$alkynyl-A, or —$O(CR^bR^b)_m$-A;

each $R^3$ is independently selected from H, —$C_{1-6}$alkyl, halo$C_{1-6}$alkyl, or halo;

each $R^4$ is independently selected from H, —$C_{1-6}$alkyl, halo$C_{1-6}$alkyl, or halo;

each $R^5$ is independently selected from H, —$C_{1-6}$alkyl, halo$C_{1-6}$alkyl, or halo;

A is a 4 to 9 membered aryl, heteroaryl, or heterocycloalkyl group, or a 3-, 4-, 5-, 6-, 7-, 8-, 9-, or 10-membered cycloalkyl group, where the heteroaryl or heterocycloalkyl group can have from 1 to 3 heteroatoms independently selected from O, N or S; and the aryl, heteroaryl, heterocycloalkyl, or cycloalkyl group is substituted with 0, 1, 2, 3, or 4 $R^7$ substituents independently selected from halo, —$NR^aR^a$, —$C_{1-6}$alkyl, —O—$C_{1-6}$alkyl, —$(CR^bR^b)_m$OH, hydroxy$C_{1-6}$alkyl, halo$C_{1-6}$alkyl, —O-halo$C_{1-6}$alkyl, —CN, —C(=O)$NR^aR^a$, —O—$(CR^bR^b)_m$B or —$(CR^bR^b)_m$B;

B is a 5 to 6 membered aryl, heteroaryl, or heterocycloalkyl group, or a 3 to 5 membered cycloalkyl group, where the heteroaryl or heterocycloalkyl group can have from 1 to 3 heteroatoms independently selected from O, N or S; and the aryl, heteroaryl, cycloalkyl or heterocycloalkyl group is substituted with 0, 1, 2, 3, or 4 $R^8$ substituents independently selected from halo, —$NR^aR^a$, —$C_{1-6}$alkyl, —O$C_{1-6}$alkyl, hydroxy$C_{1-6}$alkyl, —$CF_3$, —$CHF_2$, —$CH_2F$, —$OCF_3$, —$OCHF_2$, —$OCH_2F$, —CN or —C(=O)$NR^aR^a$;

each $R^a$ is independently H, halo, —CN, —$NR^bR^b$, —OH, —$C_{1-6}$alkyl, —$C_{1-6}$haloalkyl, —$OC_{1-6}$haloalkyl, or —$OC_{1-6}$alkyl;

each $R^b$ is independently H, halo, —CN, —$NR^bR^b$, —OH, —$C_{1-6}$alkyl, —$C_{1-6}$haloalkyl, —$OC_{1-6}$haloalkyl, or —$OC_{1-6}$alkyl;

each $R^c$ is independently H or —$C_{1-6}$alkyl;

each n is independently 0, 1, 2, 3 or 4; and each m is independently 0, 1, 2, 3 or 4.

2. The compound in accordance with claim 1, an enantiomer, diastereomer, atropisomer thereof, or a mixture thereof, or a pharmaceutically acceptable salt thereof, wherein the group

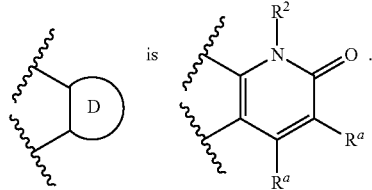 .

3. The compound in accordance claim 1, an enantiomer, diastereomer, atropisomer thereof, or a mixture thereof, or a pharmaceutically acceptable salt thereof, wherein $R^2$ is a 6 membered aryl or a 6 membered heteroaryl group.

4. The compound in accordance with claim 1, an enantiomer, diastereomer, atropisomer thereof, or a mixture thereof, or a pharmaceutically acceptable salt thereof, wherein $R^2$ is phenyl.

5. The compound in accordance claim 1, an enantiomer, diastereomer, atropisomer thereof, or a mixture thereof, or a pharmaceutically acceptable salt thereof, wherein $R^2$ is substituted with from 1 to 3 $R^6$ substituents independently selected from —$OC_{1-6}$alkyl, halo, —$C_{1-6}$alkyl, halo$C_{1-6}$alkyl, —$(CR^bR^b)_m$-A, or —$C_{2-6}$alkynyl-A.

6. The compound in accordance with claim 5, an enantiomer, diastereomer, atropisomer thereof, or a mixture thereof, or a pharmaceutically acceptable salt thereof, wherein in said $R^6$, which is —$(CR^bR^b)_m$-A group, A is a ring selected from phenyl, pyridyl, or pyrimidinyl, wherein the ring is substituted with 0, 1, 2, 3, or 4 $R^7$ substituents independently selected from chloro, fluoro, methyl, methoxy, —$CF_3$, —$CHF_2$, —$CH_2F$, —$OCF_3$, —$OCHF_2$, —$OCH_2F$, —$OCH_2CF_3$, or —CN; each $R^b$ is independently H or —$C_{1-6}$alkyl; and m is 0 or 1.

7. The compound in accordance with claim 5, an enantiomer, diastereomer, atropisomer thereof, or a mixture thereof, or a pharmaceutically acceptable salt thereof, wherein in said $R^6$—$C_{2-6}$alkynyl-A group, A is a $C_{3-8}$cycloalkyl ring substituted with 0, 1, 2, 3, or 4 $R^7$ substituents selected from chloro, fluoro, methyl, methoxy, —$CF_3$, —$CHF_2$, —$CH_2F$, —$OCF_3$, —$OCHF_2$, —$OCH_2F$, or —CN.

8. The compound in accordance with claim 1, an enantiomer, diastereomer, atropisomer thereof, or a mixture thereof, or a pharmaceutically acceptable salt thereof, wherein $R^2$ is phenyl or pyridinyl ring substituted with 3 $R^6$ substituents comprising:

(a) ortho to ring D: $R^6$ is selected from methyl, methoxy or ethoxy;

(b) meta to ring D: $R^6$ is selected from absent, methyl, F, or Cl; and (c) para to ring D: $R^6$ is selected from halo, phenyl ring, or pyridyl ring; wherein each of said phenyl ring or pyridyl ring is substituted with 0, 1, 2, 3, or 4 $R^7$ substituents selected from F, Cl, methyl, cyclopropyl, methoxy, ethoxy, —$CF_3$, —$CHF_2$, —$CH_2F$, —$OCF_3$, —$OCHF_2$, —$OCH_2F$, or —CN.

9. The compound in accordance with claim 8, an enantiomer, diastereomer, atropisomer thereof, or a mixture thereof, or a pharmaceutically acceptable salt thereof, wherein said $R^2$ is phenyl ring.

10. The compound in accordance with claim 1, an enantiomer, diastereomer, atropisomer thereof, or a mixture thereof, or a pharmaceutically acceptable salt thereof, wherein each of $R^3$, $R^4$, and $R^5$ is independently selected from H or methyl.

11. The compound in accordance with claim 1, an enantiomer, diastereomer, atropisomer thereof, or a mixture thereof, or a pharmaceutically acceptable salt thereof, wherein $R^1$ is a 5 to 6 membered heteroaryl group.

12. The compound in accordance with claim 1, an enantiomer, diastereomer, atropisomer thereof, or a mixture thereof, or a pharmaceutically acceptable salt thereof, wherein $R^1$ is isoxazolyl, thiazolyl, thiadiazolyl, pyridazinyl, pyridyl, or pyrimidinyl ring, wherein the ring is unsubstituted or is substituted with 0, 1, 2, 3, or 4 substituents independently selected from halo or —$C_{1-6}$alkyl.

13. The compound in accordance with claim 1, an enantiomer, diastereomer, atropisomer thereof, or a mixture thereof, or a pharmaceutically acceptable salt thereof, wherein $R^1$ is:

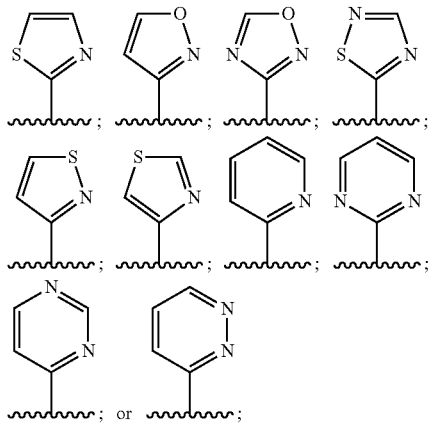

wherein the ring is unsubstituted or is substituted with 0, 1, 2, 3, or 4 substituents independently selected from halo or —$C_{1-6}$alkyl.

14. The compound in accordance with claim 1, an enantiomer, diastereomer, atropisomer thereof, or a mixture thereof, or a pharmaceutically acceptable salt thereof, selected from:
- 1-(4'-chloro-2-fluoro-3',5-dimethoxy-4-biphenylyl)-2-oxo-N-3-pyridazinyl-1,5,7,8-tetrahydro-1,6-naphthyridine-6(2H)-sulfonamide;
- 1-(4'-chloro-2-fluoro-3',5-dimethoxy-4-biphenylyl)-N-3-isoxazolyl-2-oxo-1,5,7,8-tetrahydro-1,6-naphthyridine-6(2H)-sulfonamide;
- 1-(2-fluoro-5-methoxy-3'-(trifluoromethyl)-4-biphenylyl)-N-3-isoxazolyl-2-oxo-1,5,7,8-tetrahydro-1,6-naphthyridine-6(2H)-sulfonamide;
- 1-(3'-chloro-2,5'-difluoro-5-methoxy-4-biphenylyl)-N-3-isoxazolyl-2-oxo-1,5,7,8-tetrahydro-1,6-naphthyridine-6(2H)-sulfonamide;
- 1-(5-fluoro-2-methoxy-4-(2-methoxy-5-(trifluoromethyl)-3-pyridinyl)phenyl)-N-3-isoxazolyl-2-oxo-1,5,7,8-tetrahydro-1,6-naphthyridine-6(2H)-sulfonamide;
- 1-(4'-chloro-2-fluoro-5-methoxy-3'-methyl-4-biphenylyl)-N-3-isoxazolyl-2-oxo-1,5,7,8-tetrahydro-1,6-naphthyridine-6(2H)-sulfonamide;
- 1-(4'-chloro-2-fluoro-5-methoxy-3'-methyl-4-biphenylyl)-2-oxo-N-2-pyrimidinyl-1,5,7,8-tetrahydro-1,6-naphthyridine-6(2H)-sulfonamide;
- 2-oxo-N-3-pyridazinyl-1-(2,3',4'-trifluoro-5-methoxy-4-biphenylyl)-1,5,7,8-tetrahydro-1,6-naphthyridine-6(2H)-sulfonamide;
- 1-(4'-chloro-2-fluoro-5-methoxy-3'-methyl-4-biphenylyl)-2-oxo-N-3-pyridazinyl-1,5,7,8-tetrahydro-1,6-naphthyridine-6(2H)-sulfonamide;
- 1-(3'-chloro-2,5'-difluoro-5-methoxy-4-biphenylyl)-2-oxo-N-3-pyridazinyl-1,5,7,8-tetrahydro-1,6-naphthyridine-6(2H)-sulfonamide;
- 1-(4'-chloro-2-fluoro-5-methoxy-3'-methyl-4-biphenylyl)-2-oxo-N-1,3-thiazol-2-yl-1,5,7,8-tetrahydro-1,6-naphthyridine-6(2H)-sulfonamide;
- 1-(2,3'-difluoro-5-methoxy-5'-(trifluoromethyl)-4-biphenylyl)-2-oxo-N-3-pyridazinyl-1,5,7,8-tetrahydro-1,6-naphthyridine-6(2H)-sulfonamide;
- 1-(3'-cyclopropyl-2-fluoro-5-methoxy-4-biphenylyl)-2-oxo-N-3-pyridazinyl-1,5,7,8-tetrahydro-1,6-naphthyridine-6(2H)-sulfonamide;
- 1-(2-fluoro-5-methoxy-3'-(trifluoromethyl)-4-biphenylyl)-2-oxo-N-3-pyridazinyl-1,5,7,8-tetrahydro-1,6-naphthyridine-6(2H)-sulfonamide;
- 2-oxo-N-3-pyridazinyl-1-(2,3',4',5'-tetrafluoro-5-methoxy-4-biphenylyl)-1,5,7,8-tetrahydro-1,6-naphthyridine-6(2H)-sulfonamide;
- 1-(2,4'-dichloro-3',5-dimethoxy-4-biphenylyl)-N-3-isoxazolyl-2-oxo-1,5,7,8-tetrahydro-1,6-naphthyridine-6(2H)-sulfonamide;
- 1-(2,3'-dichloro-5'-fluoro-5-methoxy-4-biphenylyl)-N-3-isoxazolyl-2-oxo-1,5,7,8-tetrahydro-1,6-naphthyridine-6(2H)-sulfonamide;
- 1-(2-chloro-5-methoxy-3'-(trifluoromethyl)-4-biphenylyl)-N-3-isoxazolyl-2-oxo-1,5,7,8-tetrahydro-1,6-naphthyridine-6(2H)-sulfonamide; and
- 1-(2-fluoro-3',5-dimethoxy-4'-methyl-4-biphenylyl)-N-3-isoxazolyl-2-oxo-1,5,7,8-tetrahydro-1,6-naphthyridine-6(2H)-sulfonamide.

15. The compound in accordance with claim 14, wherein the compound is a P atropisomer.

16. A pharmaceutical composition comprising the compound in accordance with claim 1, an enantiomer, diastereomer, atropisomer thereof, or a mixture thereof, or a pharmaceutically acceptable salt thereof, and a pharmaceutically acceptable excipient.

17. A method of treating pain, cough, or itch, comprising administering to a patient in need thereof a therapeutically effective amount of the compound in accordance with claim 1, or a pharmaceutically acceptable salt thereof, wherein the pain is selected from chronic pain, acute pain, neuropathic pain, pain associated with rheumatoid arthritis, pain associated with osteoarthritis, pain associated with cancer, or pain associated with diabetes; wherein the cough is selected from post viral cough, viral cough, or acute viral cough; and wherein the itch is selected from a) psoriatic pruritis, itch due to hemodyalisis, aguagenic pruritis, and itching caused by skin disorders, systemic disorders, neuropathy, psychogenic factors or a mixture thereof, b) itch caused by allergic reactions, insect bites, hypersensitivity, inflammatory conditions or injury, c) itch associated with vulvar vestibulitis, d) skin irritation or inflammatory effect from administration of another therapeutic selected from antibiotics, antivirals, or antihistamines, or e) itch due to activation of PAR-2 G-protein coupled receptors.

* * * * *